US012558415B2

(12) United States Patent
BenMohamed

(10) Patent No.: US 12,558,415 B2
(45) Date of Patent: *Feb. 24, 2026

(54) BROAD-SPECTRUM MULTI-ANTIGEN PAN-CORONAVIRUS VACCINE

(71) Applicant: THE REGENTS OF THE UNIVERSITY OF CALIFORNIA, Oakland, CA (US)

(72) Inventor: Lbachir BenMohamed, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/601,925

(22) Filed: Mar. 11, 2024

(65) Prior Publication Data

US 2024/0269266 A1 Aug. 15, 2024

Related U.S. Application Data

(63) Continuation-in-part of application No. PCT/US2023/068080, filed on Jun. 7, 2023, and a continuation-in-part of application No. 18/046,862, filed on Oct. 14, 2022, which is a continuation-in-part of application No. PCT/US2021/027341, filed on Apr. 14, 2021, application No. 18/601,925, filed on Mar. 11, 2024 is a continuation-in-part of application No. 18/046,875, filed on Oct. 14, 2022, which is a continuation-in-part of application No. PCT/US2021/027355, filed on Apr. 14, 2021, application No. 18/601,925, filed on Mar. 11, 2024 is a continuation-in-part of application No. 18/046,462, filed on Oct. 13, 2022, which is a continuation-in-part of application No. PCT/US2021/027340, filed on Apr. 14, 2021.

(60) Provisional application No. 63/626,937, filed on Jan. 30, 2024, provisional application No. 63/451,302, filed on Mar. 10, 2023, provisional application No. 63/349,799, filed on Jun. 7, 2022, provisional application No. 63/084,421, filed on Sep. 28, 2020, provisional application No. 63/009,907, filed on Apr. 14, 2020, provisional application No. 63/349,904, filed on Jun. 7, 2022, provisional application No. 63/302,454, filed on Jan. 24, 2022.

(51) Int. Cl.
| | |
|---|---|
| *A61K 39/215* | (2006.01) |
| *A61K 39/00* | (2006.01) |
| *A61K 39/295* | (2006.01) |
| *C12N 15/86* | (2006.01) |

(52) U.S. Cl.
CPC .......... *A61K 39/215* (2013.01); *A61K 39/295* (2013.01); *C12N 15/86* (2013.01); *A61K 2039/53* (2013.01); *A61K 2039/55555*

(2013.01); *A61K 2039/70* (2013.01); *C12N 2750/14143* (2013.01); *C12N 2770/20034* (2013.01)

(58) Field of Classification Search
CPC ................ A61K 39/215; A61K 39/295; A61K 2039/53; A61K 2039/55555; A61K 2039/70; C12N 15/86; C12N 2750/14143; C12N 2770/20034
See application file for complete search history.

(56) References Cited

U.S. PATENT DOCUMENTS

| | | | |
|---|---|---|---|
| 4,079,038 A | 3/1978 | Choi et al. | |
| 4,093,709 A | 6/1978 | Choi et al. | |
| 4,131,648 A | 12/1978 | Choi et al. | |

(Continued)

FOREIGN PATENT DOCUMENTS

| | | | | |
|---|---|---|---|---|
| CN | 101792491 B | * | 7/2012 | |
| KR | 20220132588 A | * | 9/2022 | |

(Continued)

OTHER PUBLICATIONS

Bartsch, S. M. et al. (2024). The potential epidemiologic, clinical, and economic value of a universal coronavirus vaccine: a modelling study. EClinicalMedicine, 68, 102369. (Year: 2024).*

(Continued)

*Primary Examiner* — Michael Allen
*Assistant Examiner* — Carey Alexander Stuart
(74) *Attorney, Agent, or Firm* — NGUYEN TARBET IP LAW

(57) ABSTRACT

Waning immunity induced by first-generation Spike-alone-based COVID-19 has failed to prevent immune escape by many variants of concern (VOCs) that emerged from 2020 to 2024, resulting in a prolonged COVID-19 pandemic. Thus, a next-generation Coronavirus (CoV) vaccine incorporating highly conserved non-Spike SARS-CoV-2 antigens is described herein. Conserved non-Spike T cell antigens in combination with a Spike antigen encapsulated in lipid nanoparticles: (i) Induced high frequencies of lung-resident antigen-specific CXCR5+CD4+ T follicular helper cells, GzmB+CD4+ and GzmB+CD8+ cytotoxic T cells, and CD69+IFN-γ+TNFα+CD4+ and CD69+IFN-γ+TNFα+CD8+ effector T cells; and (ii) Reduced viral load and COVID-19-like symptoms caused by various VOCs. The combined antigen/LNP-based pan-CoV vaccine could be rapidly adapted for clinical use to confer broader cross-protective immunity against emerging highly mutated and pathogenic VOCs.

15 Claims, 31 Drawing Sheets

Figures 1A, 1B, 1C:
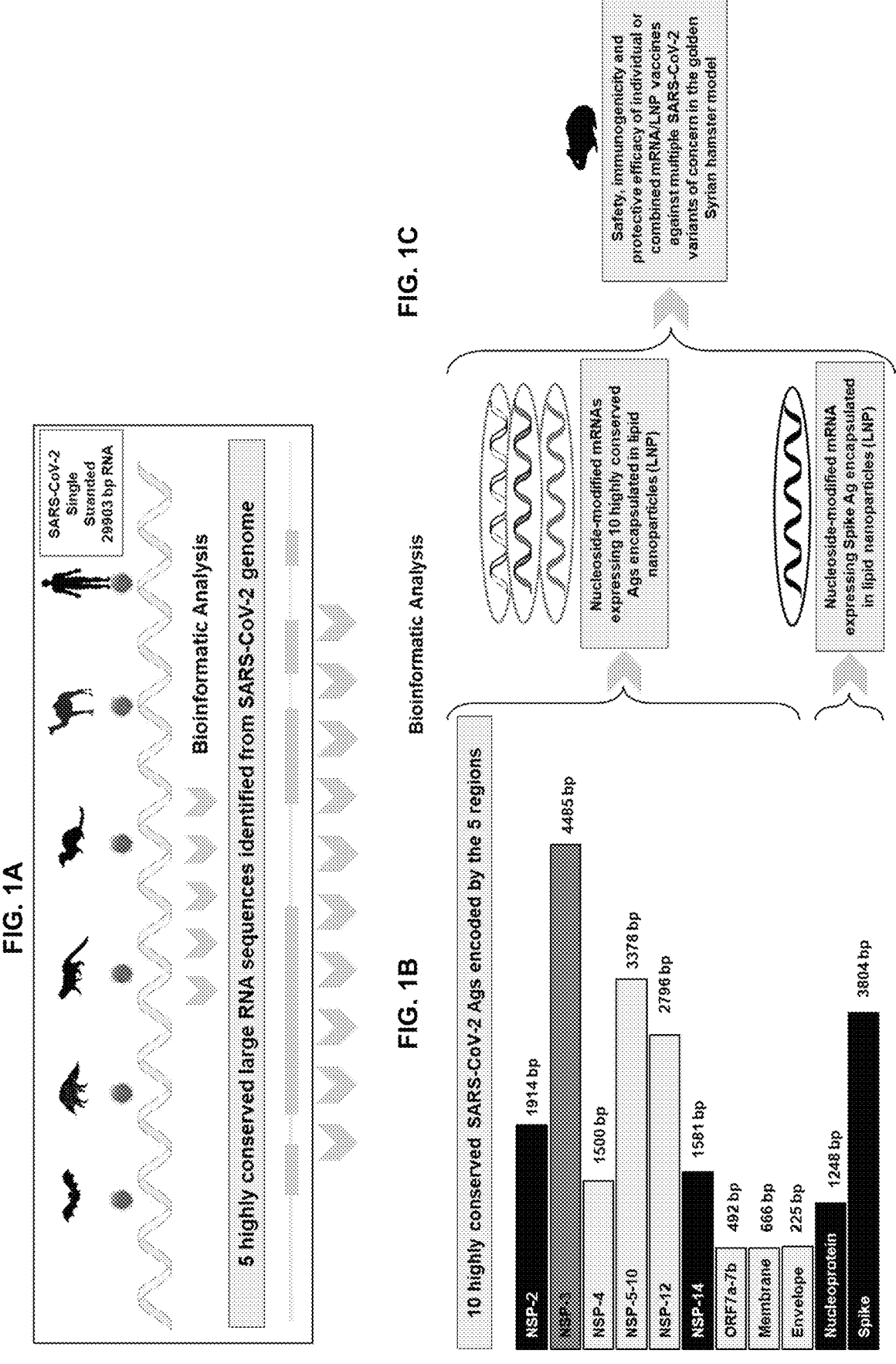

Specification includes a Sequence Listing.

(56) References Cited

U.S. PATENT DOCUMENTS

| | | | |
|---|---|---|---|
| 4,138,344 | A | 2/1979 | Choi et al. |
| 4,180,646 | A | 12/1979 | Choi et al. |
| 4,304,767 | A | 12/1981 | Heller et al. |
| 4,946,931 | A | 8/1990 | Heller et al. |
| 5,968,543 | A | 10/1999 | Heller et al. |
| 6,413,536 | B1 | 7/2002 | Gibson et al. |
| 6,596,296 | B1 | 7/2003 | Nelson et al. |
| 6,613,355 | B2 | 9/2003 | Ng et al. |
| 6,667,371 | B2 | 12/2003 | Ng et al. |
| 10,130,701 | B2 | 11/2018 | Bickerton et al. |
| 10,953,089 | B1* | 3/2021 | Smith .................. A61K 39/215 |
| 11,112,412 | B1 | 9/2021 | Wang |
| 11,253,587 | B2* | 2/2022 | Anderson .............. C12N 15/86 |
| 11,478,543 | B1* | 10/2022 | Schnell .................... A61P 31/14 |
| 11,684,669 | B2* | 6/2023 | Meinke .................. A61P 31/14 424/186.1 |
| 12,269,846 | B2 | 4/2025 | Chen |
| 2006/0121580 | A1 | 6/2006 | Ter et al. |
| 2006/0257944 | A1 | 11/2006 | Fridman et al. |
| 2007/0128217 | A1 | 6/2007 | Ter Meulen et al. |
| 2008/0241189 | A1* | 10/2008 | Wilson .................... A61P 37/00 424/233.1 |
| 2009/0317421 | A1 | 12/2009 | Missiakas et al. |
| 2010/0233204 | A1 | 9/2010 | Gill |
| 2011/0081377 | A1 | 4/2011 | Roederer et al. |
| 2012/0258126 | A1 | 10/2012 | Schoeller et al. |
| 2013/0023032 | A1 | 1/2013 | Wyeth et al. |
| 2013/0177639 | A1* | 7/2013 | Geall ................. A61K 31/7088 424/274.1 |
| 2013/0266640 | A1* | 10/2013 | de Fougerolles ....... A61P 25/28 424/94.64 |
| 2014/0227346 | A1* | 8/2014 | Geall ...................... A61K 39/12 424/186.1 |
| 2016/0106828 | A1* | 4/2016 | Toro ..................... A61K 39/215 435/237 |
| 2017/0275243 | A1* | 9/2017 | Beckwith .............. C07C 217/58 |
| 2017/0340725 | A1* | 11/2017 | Ciaramella .......... A61K 39/215 |
| 2018/0333479 | A1 | 11/2018 | Garcia-Sastre et al. |
| 2019/0314492 | A1 | 10/2019 | Barouch et al. |
| 2020/0030432 | A1* | 1/2020 | Ciaramella ............. A61P 31/16 |
| 2020/0046827 | A1 | 2/2020 | Benmohamed |
| 2020/0069784 | A1 | 3/2020 | Hodge et al. |
| 2021/0260180 | A1* | 8/2021 | Georges ................. A61P 31/14 |
| 2021/0290756 | A1* | 9/2021 | Sullivan ............. C07K 16/2827 |
| 2021/0290757 | A1 | 9/2021 | O'Dea et al. |
| 2021/0353761 | A1 | 11/2021 | Derosa et al. |
| 2023/0083931 | A1* | 3/2023 | Gaynor ................ C07K 14/005 424/186.1 |
| 2023/0108894 | A1* | 4/2023 | Stewart-Jones ......... A61P 31/14 424/221.1 |
| 2023/0141371 | A1* | 5/2023 | Gaynor .................. A61K 39/12 424/186.1 |
| 2023/0146932 | A1* | 5/2023 | BenMohamed ....... A61K 39/39 424/221.1 |
| 2023/0149535 | A1* | 5/2023 | Kulp ....................... A61P 37/04 424/221.1 |
| 2023/0173060 | A1* | 6/2023 | BenMohamed ..... C07K 14/005 424/186.1 |
| 2023/0190915 | A1* | 6/2023 | De Groot .............. C12N 15/63 424/221.1 |
| 2023/0226173 | A1* | 7/2023 | BenMohamed ........ A61P 37/04 424/221.1 |
| 2023/0270841 | A1* | 8/2023 | Shattock .............. C07K 14/005 424/186.1 |
| 2023/0324402 | A1* | 10/2023 | Felgner ............ G01N 33/56983 435/7.1 |
| 2024/0277830 | A1 | 8/2024 | Rauch et al. |

FOREIGN PATENT DOCUMENTS

| | | | |
|---|---|---|---|
| KR | 20220165731 A * | 12/2022 | |
| WO | 2005012337 A1 | 3/2006 | |
| WO | 2006/071896 A2 | 7/2006 | |
| WO | 2021/211748 A1 | 10/2021 | |
| WO | 2021211760 A1 | 10/2021 | |
| WO | 2022020460 A1 | 1/2022 | |
| WO | 2022071513 A1 | 4/2022 | |
| WO | 2022/167571 A1 | 8/2022 | |

OTHER PUBLICATIONS

Le Page M. (2021). Pre-existing immunity to covid-19 hints at universal coronavirus vaccine. New scientist (1971), 252(3361), 19. (Year: 2021).*

Zhou, F., Vahokoski, J., Bergen COVID-19 Research Group, Langeland, N., & Cox, R. J. (2024). Impact of ageing on homologous and human-coronavirus-reactive antibodies after SARS-CoV-2 vaccination or infection. NPJ vaccines, 9(1), 37. (Year: 2024).*

Gustiananda, M. et al. (2022). Immunoinformatics Identification of the Conserved and Cross-Reactive T-Cell Epitopes of SARS-CoV-2 with Human Common Cold Coronaviruses, SARS-CoV, MERS-CoV and Live Attenuated Vaccines Presented by HLA Alleles of Indonesian Population. Viruses, 14(11), 2328. (Year: 2022).*

Lim, C. P., Kok, B. H., Lim, H. T., Chuah, C., Abdul Rahman, B., Abdul Majeed, A. B., Wykes, M., Leow, C. H., & Leow, C. Y. (2023). Recent trends in next generation immunoinformatics harnessed for universal coronavirus vaccine design. Pathogens and global health, 117(2), 134-151. (Year: 2023).*

Piepenbrink, M. S. et al. (2022). Potent universal beta-coronavirus therapeutic activity mediated by direct respiratory administration of a Spike S2 domain-specific human neutralizing monoclonal antibody. PLoS pathogens, 18(7), e1010691. (Year: 2022).*

Vashishtha, V. M., & Kumar, P. (2022). Looking to the future: is a universal coronavirus vaccine feasible?. Expert review of vaccines, 21(3), 277-280. (Year: 2022).*

Martinez, D. R. et al. (2021). Chimeric spike mRNA vaccines protect against Sarbecovirus challenge in mice. Science (New York, N.Y.), 373(6558), 991-998. (Year: 2021).*

Li et al. (2012). CN 101792491 B. Machine Translation (Year: 2012).*

Fehr, A. R., & Perlman, S. (2015). Coronaviruses: an overview of their replication and pathogenesis. Methods in molecular biology (Clifton, N.J.), 1282, 1-23. (Year: 2015).*

Shah, R., Eldridge, D., Palombo, E., & Harding, I. (2015). Lipid Nanoparticles: Production, Characterization and Stability (1st ed. 2015.). Springer International Publishing. (Year: 2015).*

Tenchov, R., Bird, R., Curtze, A. E., & Zhou, Q. (2021). Lipid NanoparticlesFrom Liposomes to mRNA Vaccine Delivery, a Landscape of Research Diversity and Advancement. ACS Nano, 15(11), 16982-17015. (Year: 2021).*

Isaac, I., Shaikh, A., Bhatia, M., Liu, Q., Park, S., & Bhattacharya, C. (2024). Tetrahydropyrimidine Ionizable Lipids for Efficient mRNA Delivery. ACS Nano, 18(42), 29045-29058. (Year: 2024).*

Gurba-Bryśkiewicz, L., Maruszak, W., Smuga, D. A., Dubiel, K., & Wieczorek, M. (2023). Quality by Design (QbD) and Design of Experiments (DOE) as a Strategy for Tuning Lipid Nanoparticle Formulations for RNA Delivery. Biomedicines, 11(10), 2752. (Year: 2023).*

Kon, E., Elia, U., & Peer, D. (2022). Principles for designing an optimal mRNA lipid nanoparticle vaccine. Current Opinion in Biotechnology, 73, 329-336. (Year: 2022).*

Lederman et al., 2022. KR 20220165731 A. Machine translation. (Year: 2022).*

Mueller et al., 2022. KR 20220132588 A. Machine translation. (Year: 2022).*

Grifoni et al. "A sequence homology and bioinformatic approach can predict candidate targets for immune responses to SARS-CoV-2." Cell host & microbe 27.4 (2020): 671-680.

Slathia, Parvez, and Preeti Sharma. "Prediction of T and B cell epitopes in the proteome of SARS-CoV-2 for potential use in diagnostics and vaccine design." (2020).

Zhang et al. "Progress and prospects on vaccine development against SARS-CoV-2." Vaccines 8.2 (2020): 153.

(56)                    References Cited

OTHER PUBLICATIONS

Lan et al. "Structure of the SARS-CoV-2 spike receptor-binding domain bound to the ACE2 receptor." Nature 581.7807 (2020): 215-220.

Sun et al. "SARS-CoV-2 and SARS-CoV spike-RBD structure and receptor binding comparison and potential implications on neutralizing antibody and vaccine development." Biorxiv (2020).

Kibria et al. "The multi-epitope vaccine prediction to combat Pandemic SARS-CoV-2, an immunoinformatic approach." (2020).

Abdelmageed et al. "Design of multi epitope-based peptide vaccine against E protein of human 2019-nCoV: An immunoinformatics approach (preprint)." (2020).

Bojin et al. "Design of an epitope-based synthetic long peptide vaccine to counteract the novel China coronavirus (2019-nCoV)." (2020).

Ahmed, Syed Faraz, Ahmed A. Quadeer, and Matthew R. McKay. "Preliminary identification of potential vaccine targets for the COVID-19 coronavirus (SARS-CoV-2) based on SARS-CoV immunological studies." Viruses 12.3 (2020): 254.

Prakash et al. "Genome-wide B cell, CD4+, and CD8+ T cell epitopes that are highly conserved between human and animal coronaviruses, identified from SARS-CoV-2 as targets for preemptive pan-coronavirus vaccines." The Journal of Immunology 206.11 (2021): 2566-2582.

GenBank Accession No. M10298 "Influenza B/Hong Kong/8/73 hemagglutinin (HA) (seg 4) RNA, complete cds." Aug. 2, 1993 [online]. [Retrieved on Nov. 2, 2023]. Retrieved from the internet: <URL:https://www.ncbi.nlm.nih.gov/nuccore/M10298.1>; entire document.

Weinberg, Geoffrey A., and Peter G. Szilagyi. "Vaccine epidemiology: efficacy, effectiveness, and the translational research roadmap." The Journal of infectious diseases 201.11 (2010): 1607-1610.

International Search Report & Written Opinion for International Application PCT/US24/19443 dated Jul. 29, 2024.

Kirchdoerfer et al., "Stabilized Coronavirus Spikes Are Resistant to Conformational Changes Induced by Receptor Recognition or Proteolysis", Scientific Reports, vol. 8, No. 15701, Oct. 24, 2018, 11 pages.

CNPTO, "Office Action", issued in connection with Chinese Patent Application 202180042301.9, dated Mar. 30, 2025, 21 pages (10 pages of English Translation and 11 pages of official copy).

WIPO, "International Search Report and Written Opinion" issued in connection with PCT Patent Application PCT/US2025/018209, dated Jun. 16, 2025, 15 pages.

Miao et al., "Genetic Diversity of SARS-Co V-2 over a One-Year Period of the COVID-19 Pandemic: A Global Perspective", Biomedicines, vol. 9, No. 412, Apr. 11, 2021, 17 pages.

* cited by examiner

FIG. 2

| SARS-CoV-2 Antigen | Wuhan | Alpha | Beta | Gamma | Delta | Heavily Spike-Mutated Omicron Sub-Variants | | | | | | | Total Mutations |
|---|---|---|---|---|---|---|---|---|---|---|---|---|---|
| | | | | | | BA.2 | BA.5 | XBB.1.5 | BA.2.86 | EG.5 | HV.1 | JN.1 | |
| Spike | 0 | 10 | 10 | 12 | 10 | 42 | 34 | 31 | 60 | 43 | 42 | 52 | 346 |
| Membrane | 0 | 0 | 0 | 0 | 1 | 2 | 3 | 2 | 5 | 2 | 2 | 5 | 22 |
| Envelope | 0 | 0 | 0 | 0 | 1 | 1 | 1 | 2 | 1 | 2 | 2 | 1 | 11 |
| Nucleocapsid | 0 | 4 | 1 | 3 | 3 | 7 | 7 | 7 | 9 | 7 | 4 | 5 | 57 |
| NSP-2 | 0 | 1 | 2 | 1 | 2 | 1 | 1 | 2 | 2 | 3 | 3 | 3 | 21 |
| NSP-3 | 0 | 3 | 1 | 3 | 1 | 5 | 5 | 5 | 8 | 10 | 8 | 9 | 58 |
| NSP-4 | 0 | 0 | 0 | 0 | 0 | 3 | 0 | 3 | 4 | 5 | 5 | 3 | 18 |
| NSP-5-10 | 0 | 3 | 4 | 3 | 0 | 4 | 4 | 4 | 6 | 6 | 3 | 4 | 41 |
| NSP-12 | 0 | 0 | 0 | 0 | 0 | 0 | 0 | 0 | 0 | 0 | 0 | 0 | 0 |
| NSP-14 | 0 | 0 | 0 | 0 | 0 | 0 | 0 | 0 | 0 | 0 | 0 | 0 | 0 |
| ORF7a/b | 0 | 0 | 0 | 0 | 2 | 0 | 0 | 0 | 0 | 1 | 0 | 0 | 3 |

FIG. 3A

EXPERIMENTAL PLAN

Collecting blood samples from ASYMP and SYMP individuals tested SARS-CoV-2 PCR+ (early after the onset of symptoms: 4.8-day average)

HLA-A*02:01(+) and/or DRB1*01:01(+) COVID-19 Patients (SYMP)

HLA-A*02:01(+) and/or DRB1*01:01(+) COVID-19 Patients (ASYMP)

PBMCs extraction (Ficoll) and HLA screening and genotyping (PCR + FACS)

72h stimulation of 0.5x10^6 PBMCs with 10µg/ml of SARS-CoV-2-derived CD4+ and CD8+ T cell epitopes-peptides previously identified (Class-II HLA-DRB1*01:01 and Class-I HLA-A*02:01 -restricted, respectively)

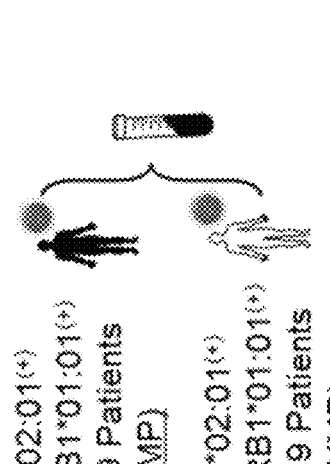

FIG. 3A
continued

IFN-γ ELISpot and FACS staining of CD8+/CD4+ T cells on various exhaustion markers (PD-1, TIGIT, TIM-3, CTLA-4) and functional markers (AIM: CD134/CD137). T-cells were gated on HLA-A*02:01 (for CD4+) and HLA-DRB1*01:01 (for CD8+) -restricted SARS-CoV-2 tetramers positive cells (Tet+)

Analysis & correlation with the disease severity (disease severity score assessed by clinicians after patient discharge)

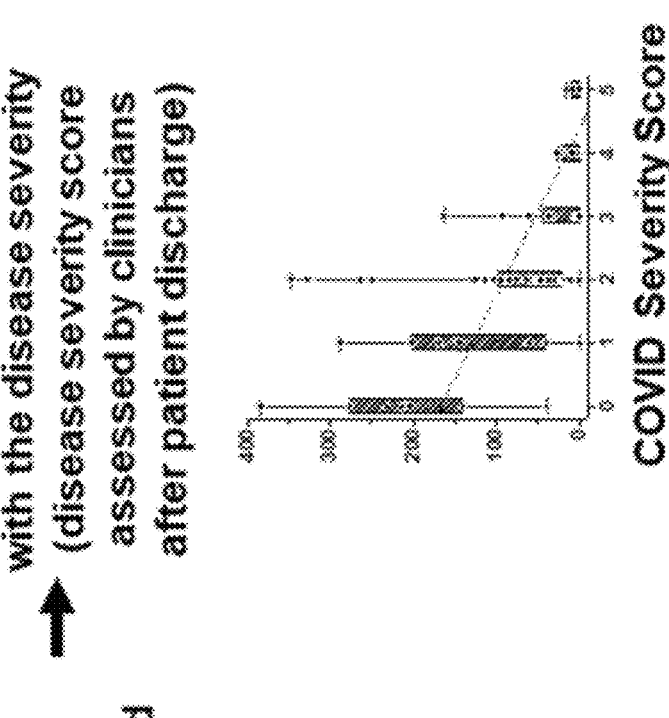

COVID Severity Score

ELISpot

Cytometry

FIG. 4A

Figure 4B:
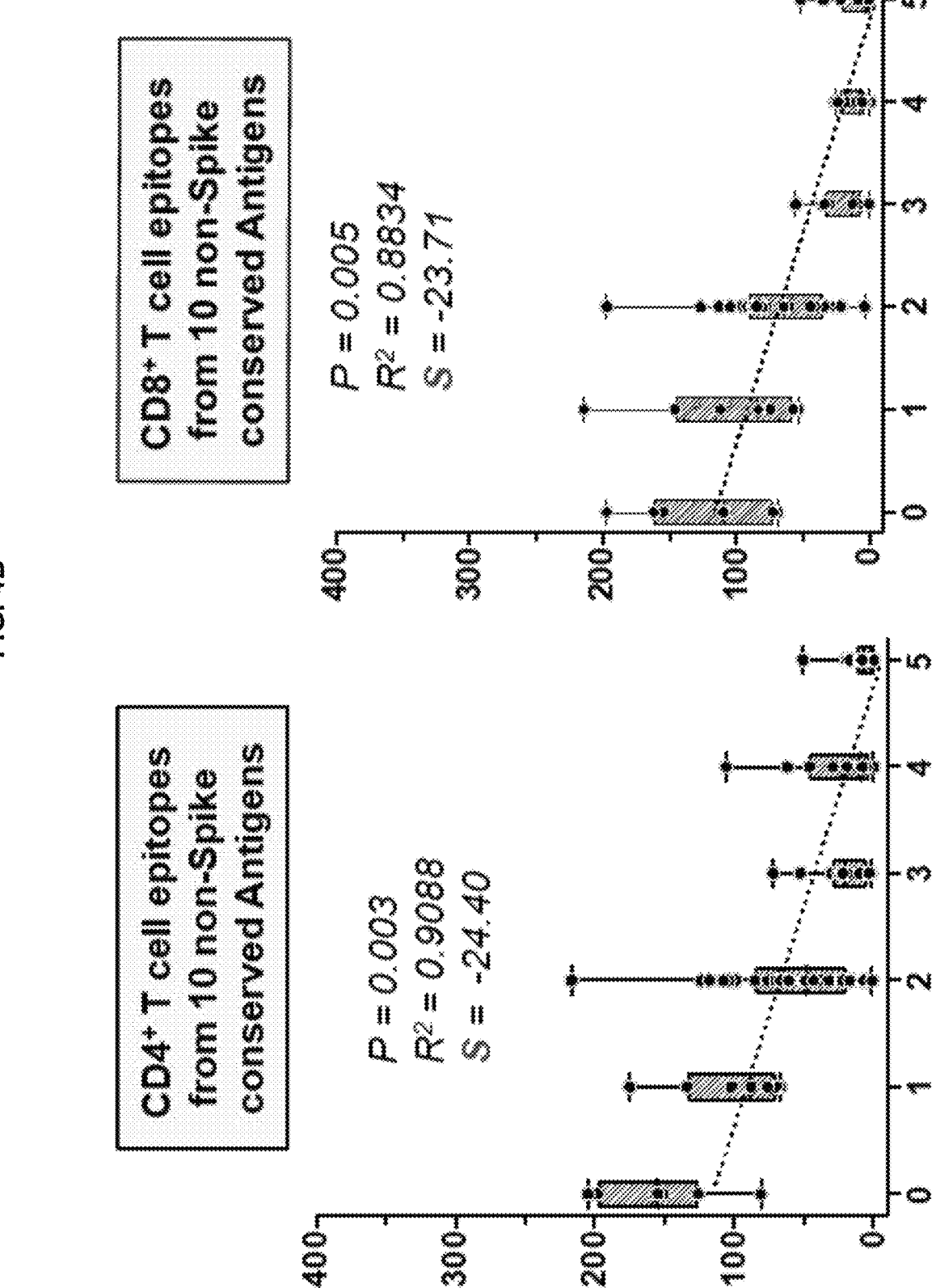
Figure 4C:
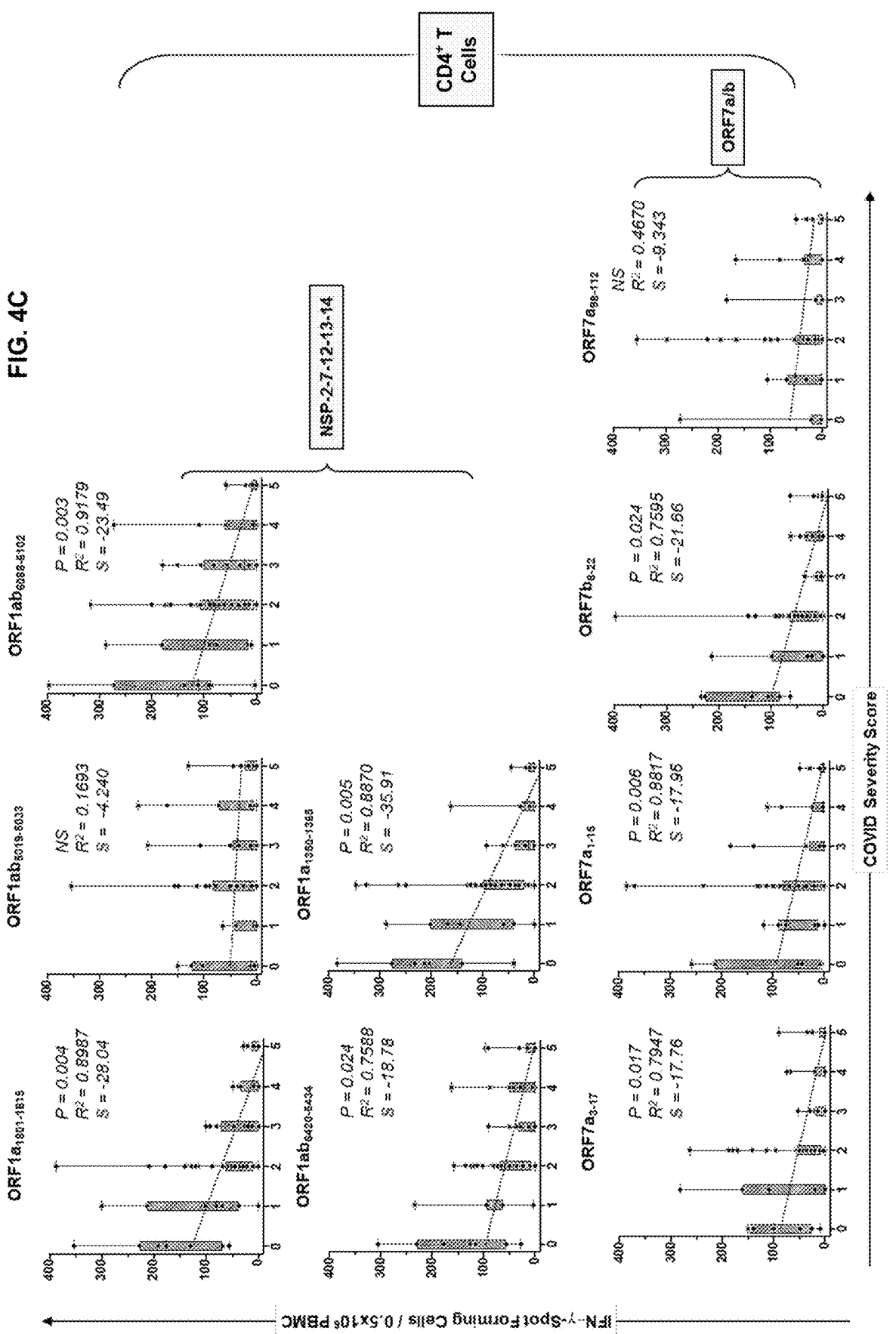

FIG. 4C (con't)
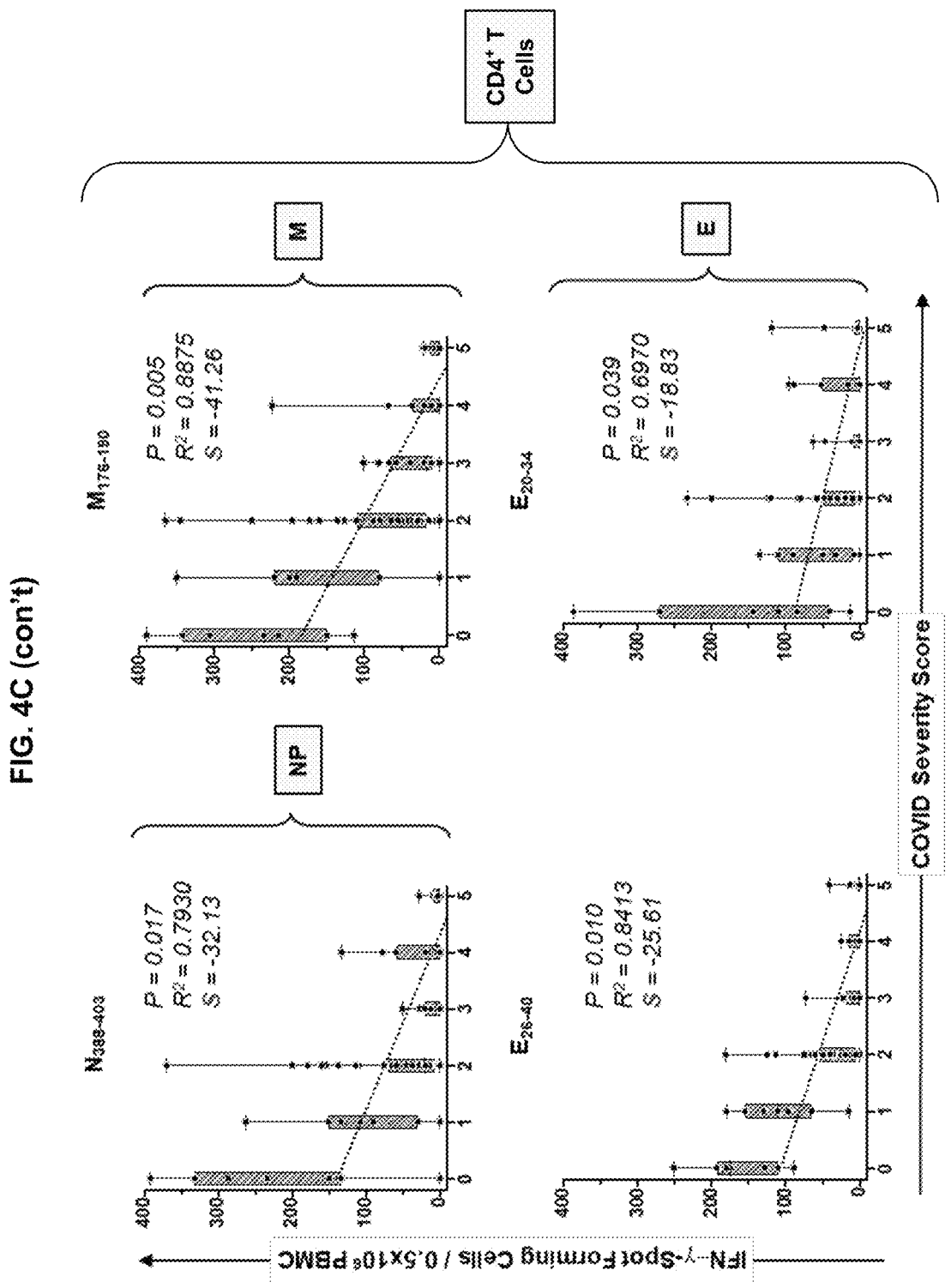

Figure 4D:
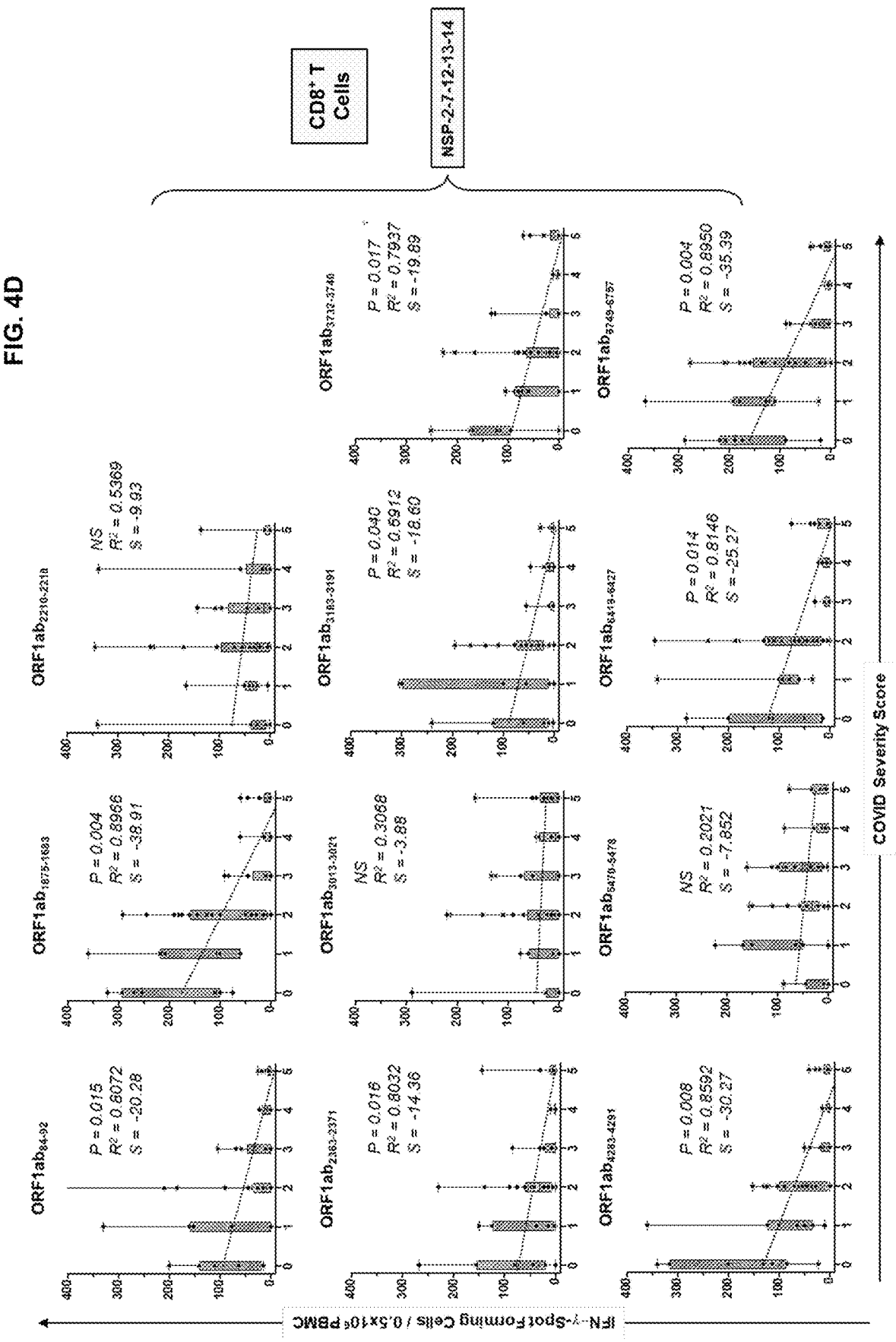

FIG. 4D (con't)
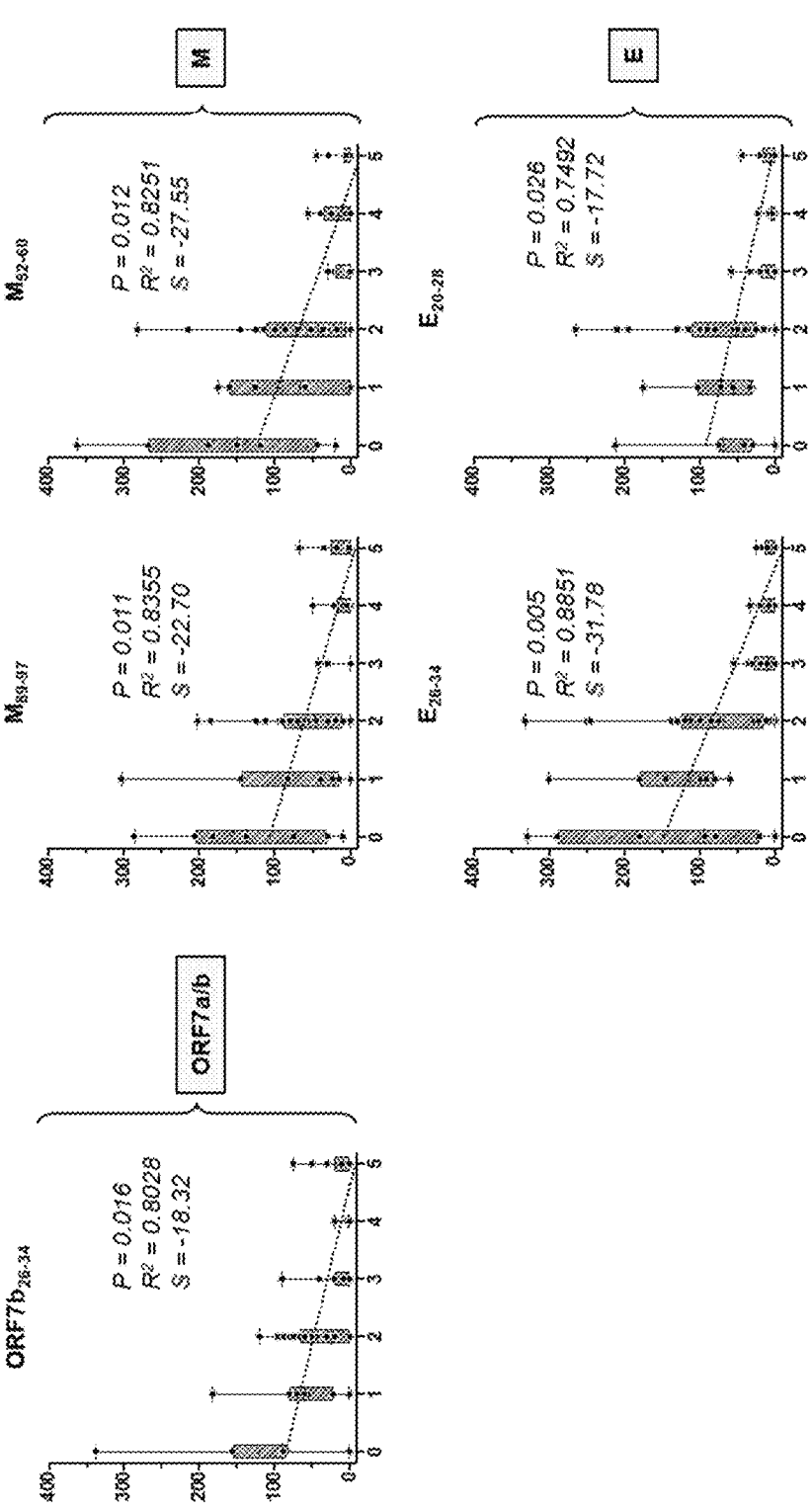

FIG. 6A mRNA/LNP expressing 1 T cell Ag
(i.e., NSP2, NSP-14 or Nucleoprotein)

CD4⁺ and CD8⁺ T cells

FIG. 6B

FIG. 7A

Combination of mRNA/LNP expressing 3 T cell Ags
(i.e., NSP2, NSP-14 and Nucleoprotein)

CD4+ & CD8+ T cells

FIG. 7B

Golden Syrian Hamsters

Days

Prime — 0

Boost — 21

Antibody assays — 42

57 — T cell Assays

Combined NSP-2, NSP-14, and Nucleoprotein mRNA/LNP-based vaccine

SARS-CoV-2 Variants and Sub-Variants

COVID-19-like symptoms, lung pathology, weight loss, and virus load

FIG. 7C

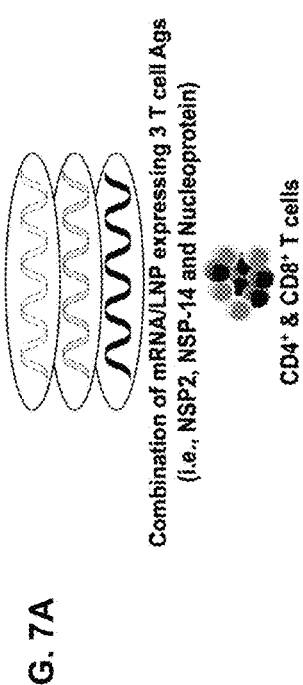

WA1/2020    Delta (B.1.617.2)    Omicron (XBB.1.5)

Vaccinated (3 T cell Ags)

Mock-Vaccinated

FIG. 7D
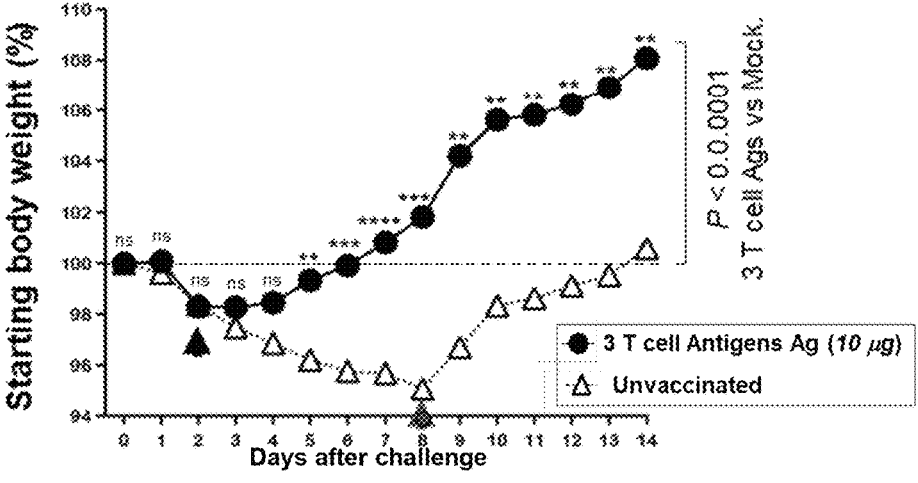
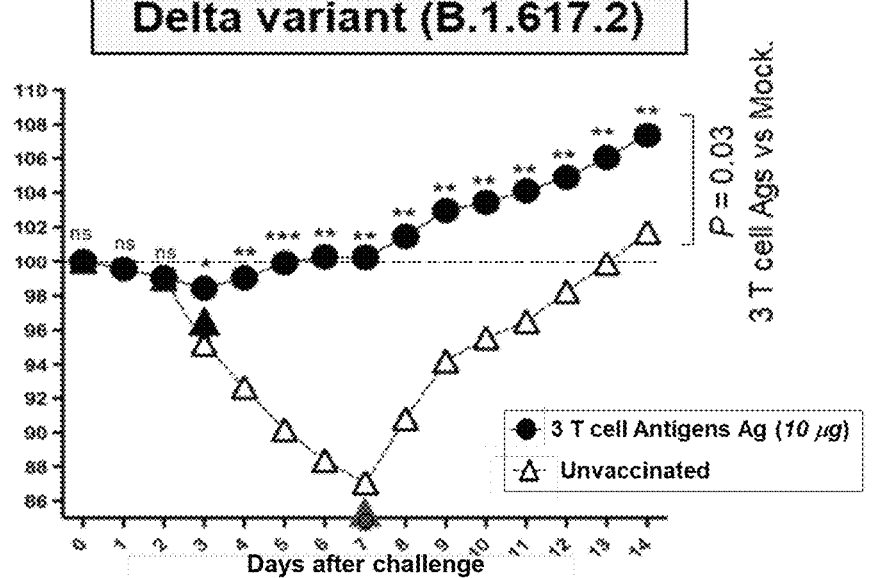
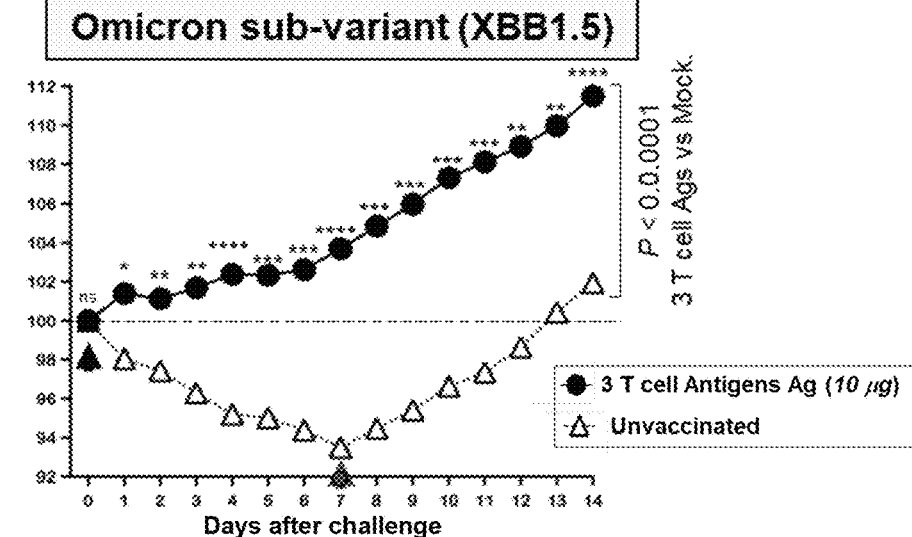

FIG. 7E
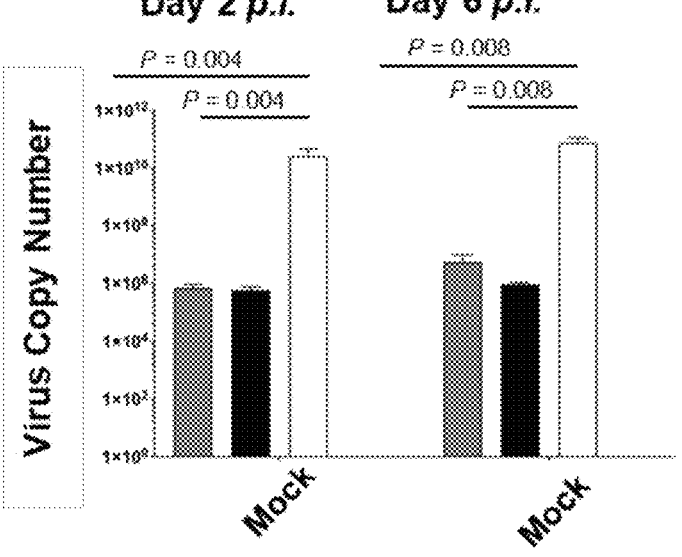
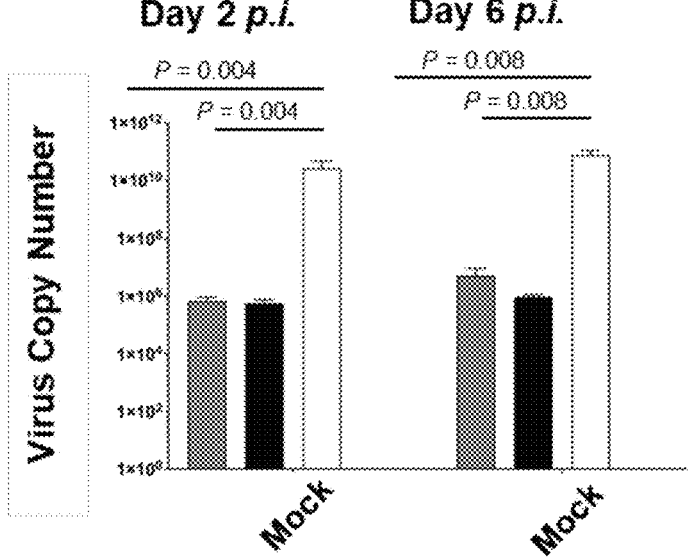

FIG. 8A
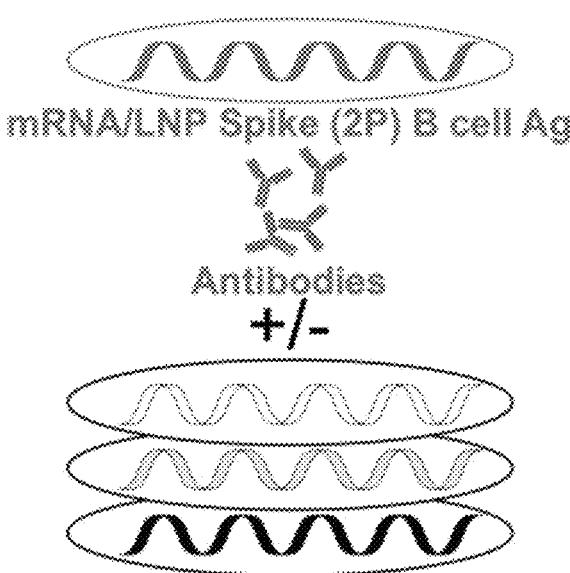
mRNA/LNP Spike (2P) B cell Ag
Antibodies
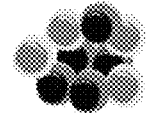
+/-
**Combination of mRNA/LNP expressing 3 T cell Ags
(i.e., NSP2, NSP-14 and Nucleoprotein)**
$CD4^+$ & $CD8^+$ T cells
FIG. 8B
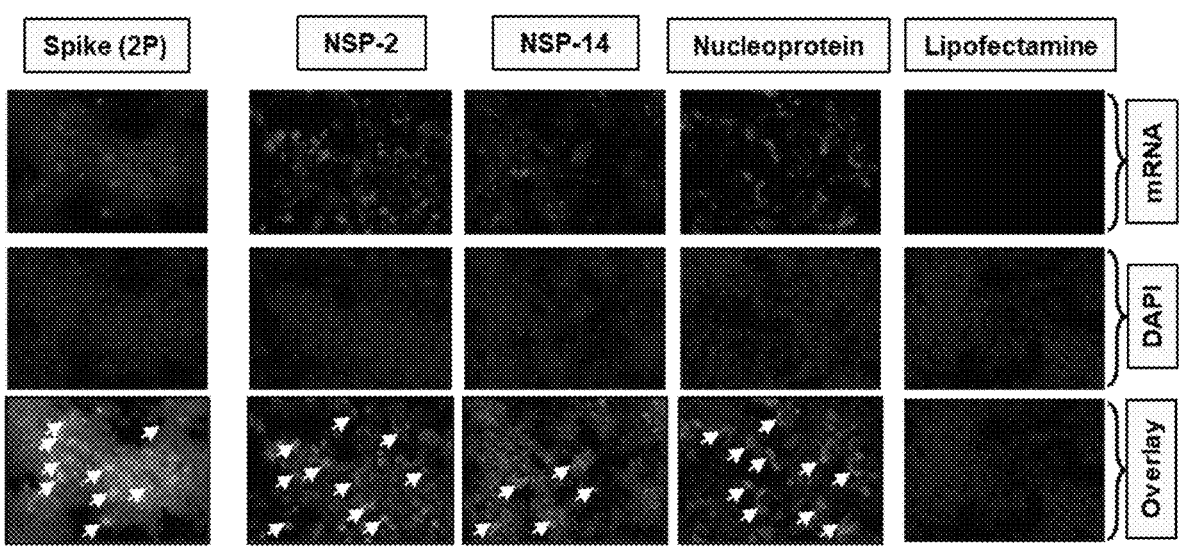

FIG. 8C

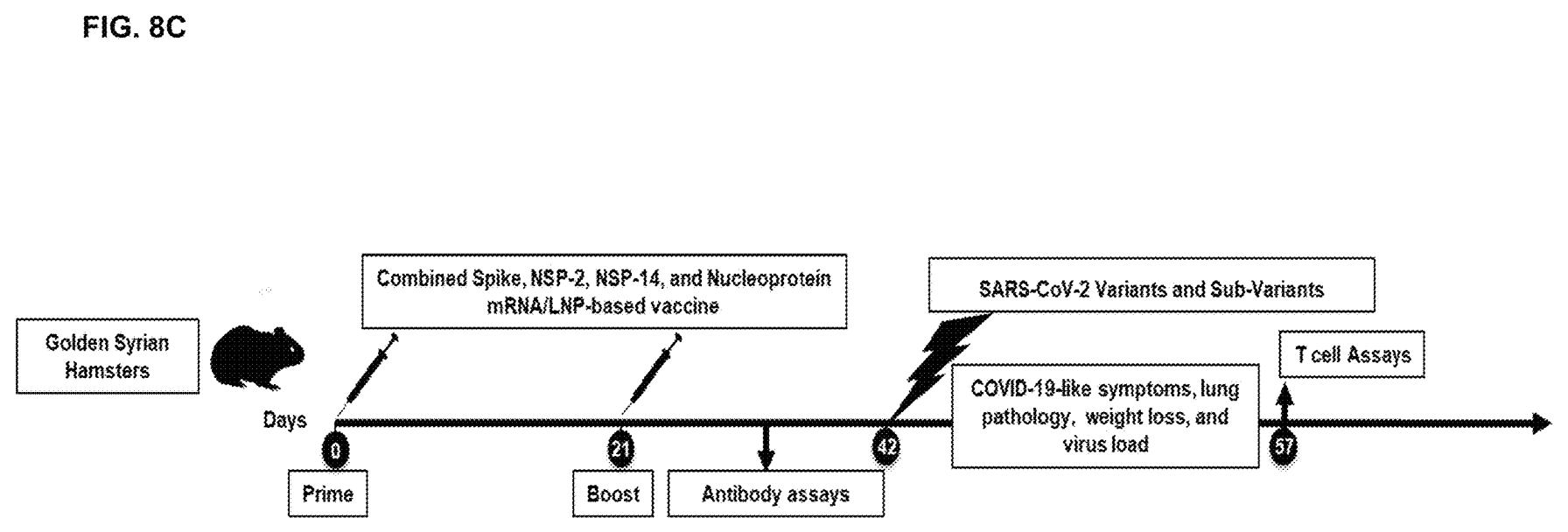

Golden Syrian Hamsters

Combined Spike, NSP-2, NSP-14, and Nucleoprotein mRNA/LNP-based vaccine

SARS-CoV-2 Variants and Sub-Variants

T cell Assays

COVID-19-like symptoms, lung pathology, weight loss, and virus load

Antibody assays

Days

Prime

Boost

FIG. 9A
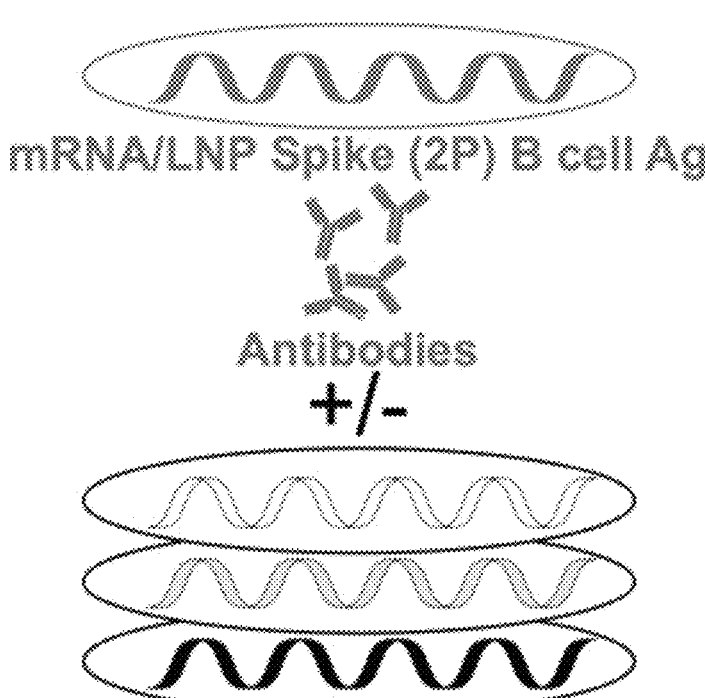
mRNA/LNP Spike (2P) B cell Ag
Antibodies
+/-
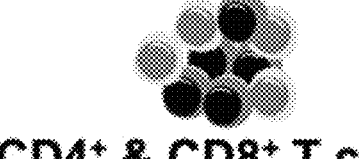
Combination of mRNA/LNP expressing 3 T cell Ags (i.e., NSP2, NSP-14 and Nucleoprotein)
CD4⁺ & CD8⁺ T cells

FIG. 9C

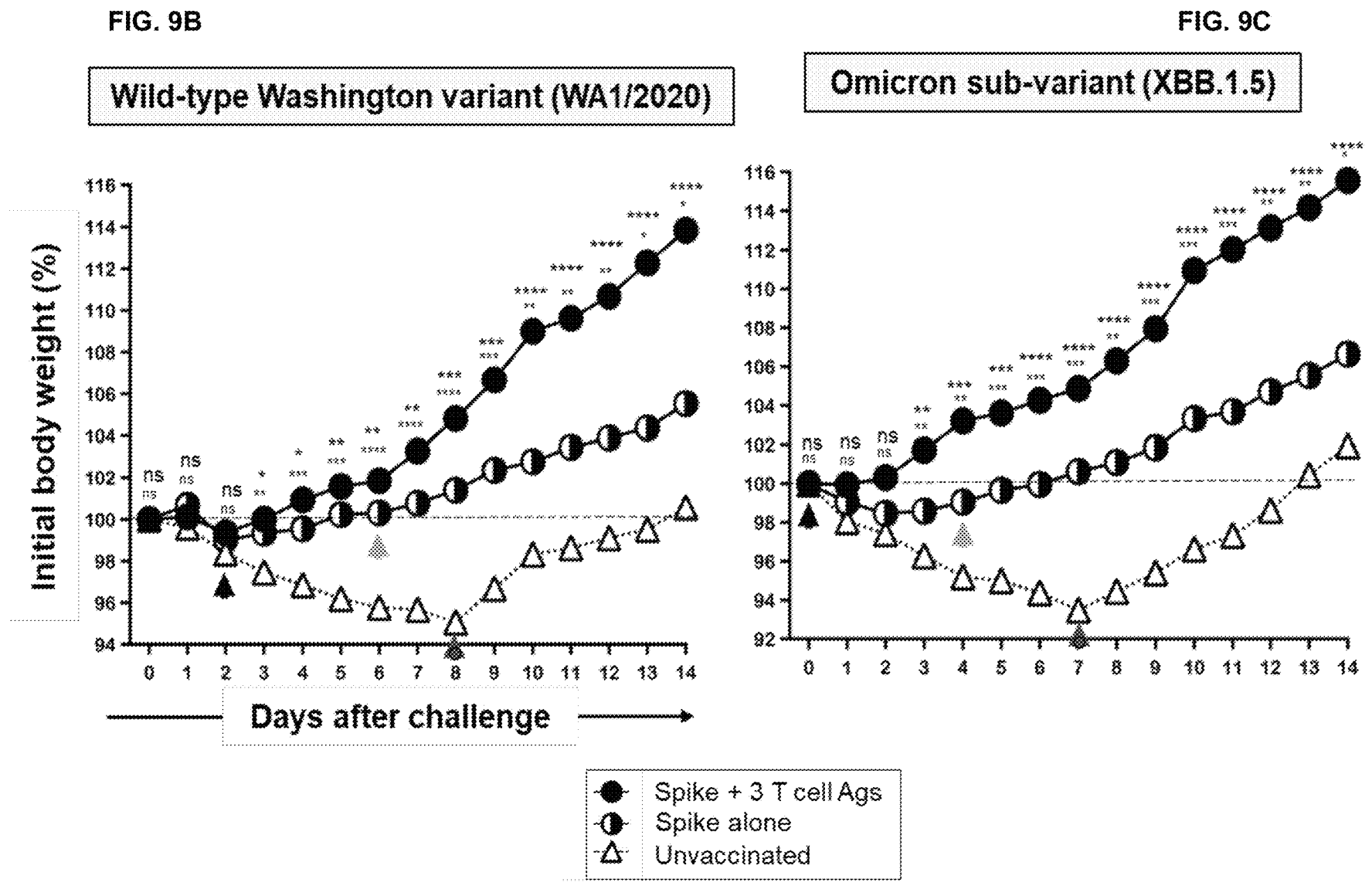

Omicron sub-variant (XBB.1.5)

FIG. 9B

Wild-type Washington variant (WA1/2020)

Initial body weight (%)

Days after challenge

Spike + 3 T cell Ags
Spike alone
Unvaccinated

FIG. 11

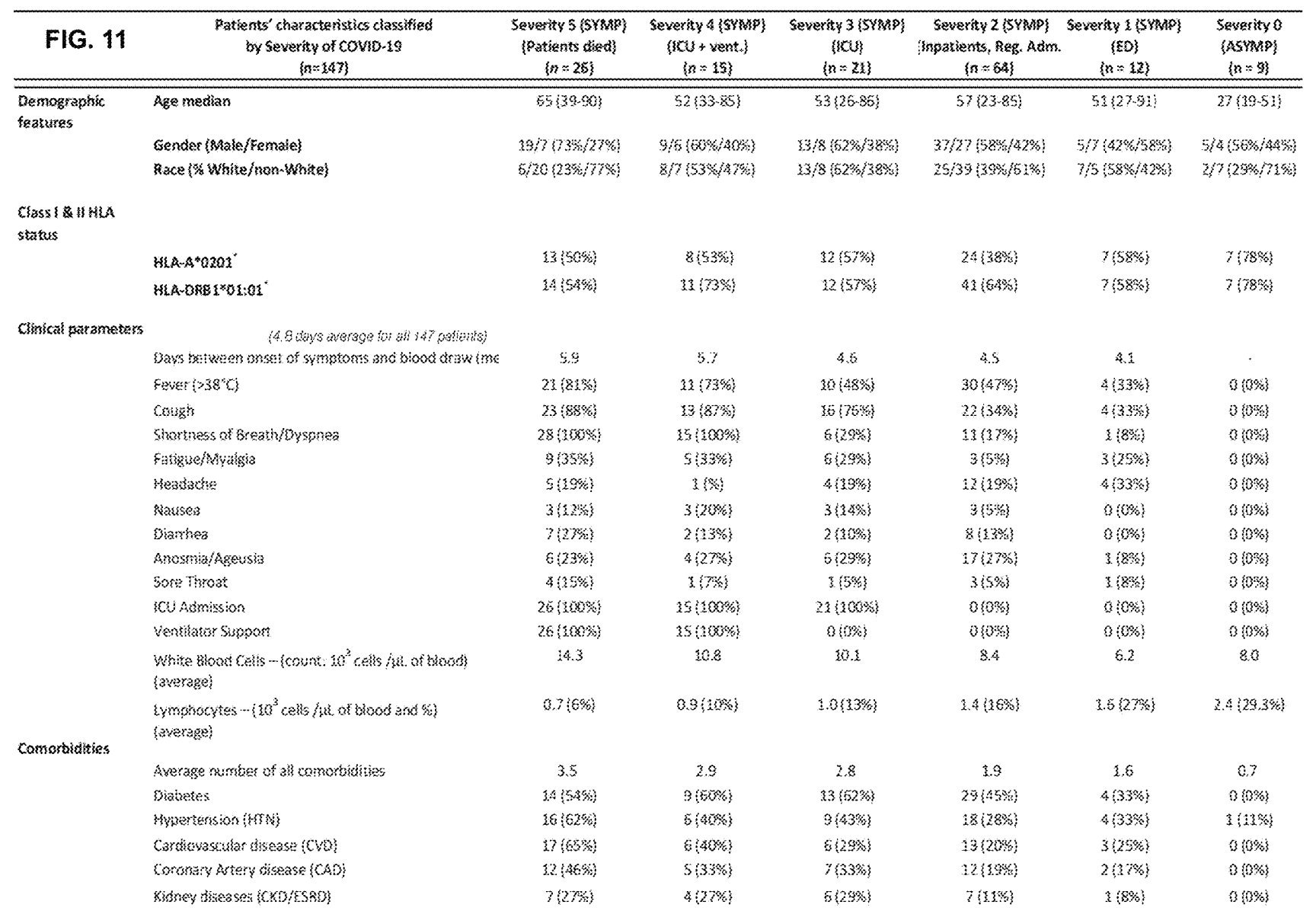

| Patients' characteristics classified by Severity of COVID-19 (n=147) | Severity 5 (SYMP) (Patients died) (n=26) | Severity 4 (SYMP) (ICU + vent.) (n=15) | Severity 3 (SYMP) (ICU) (n=21) | Severity 2 (SYMP) (Inpatients, Reg. Adm.) (n=64) | Severity 1 (SYMP) (ED) (n=12) | Severity 0 (ASYMP) (n=9) |
|---|---|---|---|---|---|---|
| Demographic features | | | | | | |
| Age median | 65 (39-90) | 52 (33-85) | 53 (26-85) | 57 (23-85) | 51 (27-91) | 27 (19-51) |
| Gender (Male/Female) | 19/7 (73%/27%) | 9/6 (60%/40%) | 13/8 (62%/38%) | 37/27 (58%/42%) | 5/7 (42%/58%) | 5/4 (56%/44%) |
| Race (% White/non-White) | 6/20 (23%/77%) | 8/7 (53%/47%) | 13/8 (62%/38%) | 25/39 (39%/61%) | 7/5 (58%/42%) | 2/7 (29%/71%) |
| Class I & II HLA status | | | | | | |
| HLA-A*0201` | 13 (50%) | 8 (53%) | 12 (57%) | 24 (38%) | 7 (58%) | 7 (78%) |
| HLA-DRB1*01.01` | 14 (54%) | 11 (73%) | 12 (57%) | 41 (64%) | 7 (58%) | 7 (78%) |
| Clinical parameters | | | | | | |
| Days between onset of symptoms and blood draw time *(4.9 days average for all 147 patients)* | 5.9 | 5.7 | 4.6 | 4.5 | 4.1 | · |
| Fever (>38°C) | 21 (81%) | 11 (73%) | 10 (48%) | 30 (47%) | 4 (33%) | 0 (0%) |
| Cough | 23 (88%) | 13 (87%) | 16 (76%) | 22 (34%) | 4 (33%) | 0 (0%) |
| Shortness of Breath/Dyspnea | 26 (100%) | 15 (100%) | 6 (29%) | 11 (17%) | 1 (8%) | 0 (0%) |
| Fatigue/Myalgia | 9 (35%) | 5 (33%) | 6 (29%) | 3 (5%) | 3 (25%) | 0 (0%) |
| Headache | 5 (19%) | 1 (8%) | 4 (19%) | 12 (19%) | 4 (33%) | 0 (0%) |
| Nausea | 3 (12%) | 3 (20%) | 3 (14%) | 3 (5%) | 0 (0%) | 0 (0%) |
| Diarrhea | 7 (27%) | 2 (13%) | 2 (10%) | 8 (13%) | 0 (0%) | 0 (0%) |
| Anosmia/Ageusia | 6 (23%) | 4 (27%) | 6 (29%) | 17 (27%) | 1 (8%) | 0 (0%) |
| Sore Throat | 4 (15%) | 1 (7%) | 1 (5%) | 3 (5%) | 1 (8%) | 0 (0%) |
| ICU Admission | 26 (100%) | 15 (100%) | 21 (100%) | 0 (0%) | 0 (0%) | 0 (0%) |
| Ventilator Support | 26 (100%) | 15 (100%) | 0 (0%) | 0 (0%) | 0 (0%) | 0 (0%) |
| White Blood Cells -- (count, $10^3$ cells /μL of blood) (average) | 14.3 | 10.8 | 10.1 | 8.4 | 6.2 | 8.0 |
| Lymphocytes -- ($10^3$ cells /μL of blood and %) (average) | 0.7 (6%) | 0.9 (10%) | 1.0 (13%) | 1.4 (16%) | 1.5 (27%) | 2.4 (29.3%) |
| Comorbidities | | | | | | |
| Average number of all comorbidities | 3.5 | 2.9 | 2.8 | 1.9 | 1.6 | 0.7 |
| Diabetes | 14 (54%) | 9 (60%) | 13 (62%) | 29 (45%) | 4 (33%) | 0 (0%) |
| Hypertension (HTN) | 16 (62%) | 6 (40%) | 9 (43%) | 18 (28%) | 4 (33%) | 1 (11%) |
| Cardiovascular disease (CVD) | 17 (65%) | 6 (40%) | 6 (29%) | 13 (20%) | 3 (25%) | 0 (0%) |
| Coronary Artery disease (CAD) | 12 (46%) | 5 (33%) | 7 (33%) | 12 (19%) | 2 (17%) | 0 (0%) |
| Kidney diseases (CKD/ESRD) | 7 (27%) | 4 (27%) | 6 (29%) | 7 (11%) | 1 (8%) | 0 (0%) |

FIG. 13A

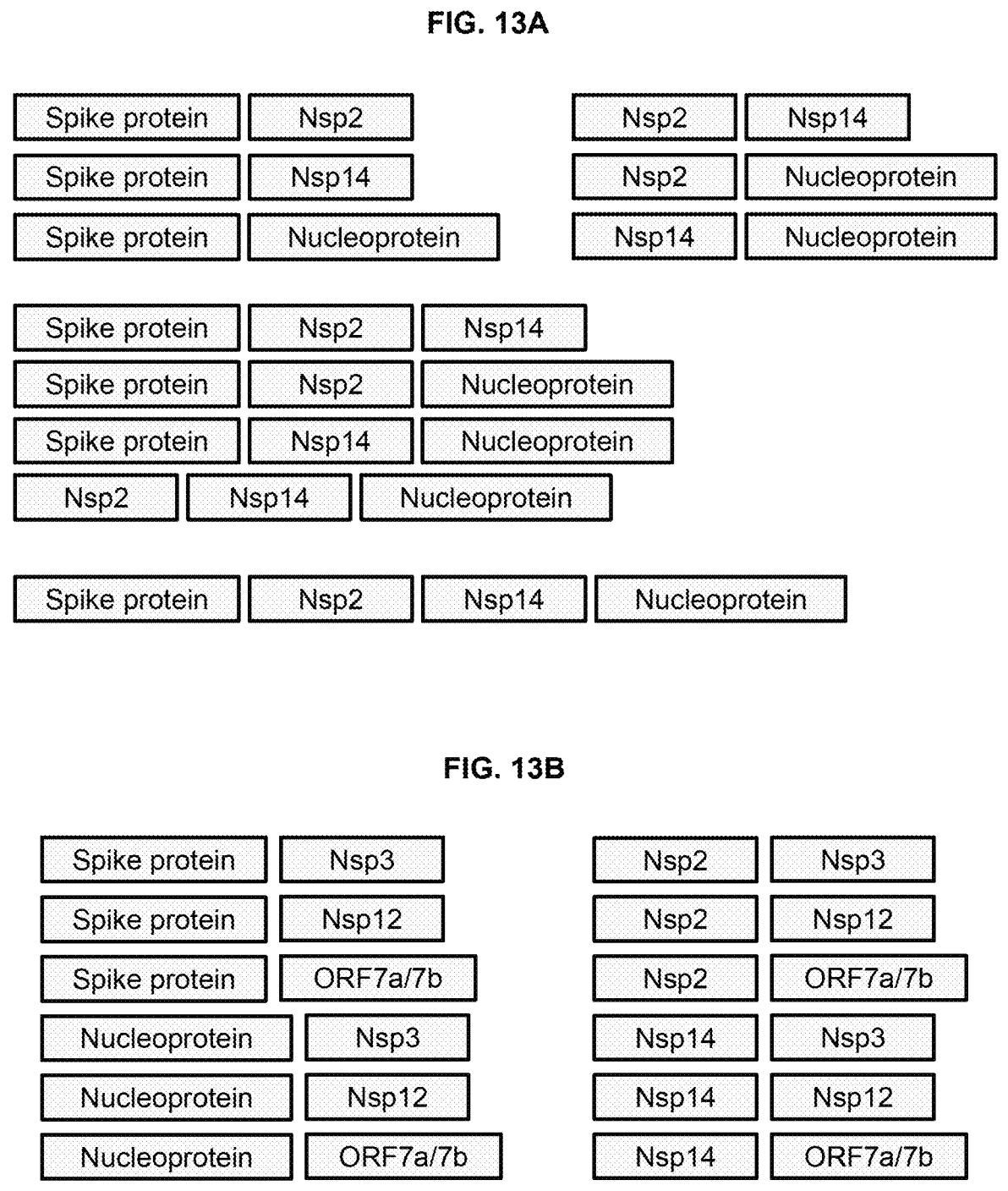

| Spike protein | Nsp2 |
| Spike protein | Nsp14 |
| Spike protein | Nucleoprotein |

| Nsp2 | Nsp14 |
| Nsp2 | Nucleoprotein |
| Nsp14 | Nucleoprotein |

| Spike protein | Nsp2 | Nsp14 |
| Spike protein | Nsp2 | Nucleoprotein |
| Spike protein | Nsp14 | Nucleoprotein |
| Nsp2 | Nsp14 | Nucleoprotein |

| Spike protein | Nsp2 | Nsp14 | Nucleoprotein |

FIG. 13B

| Spike protein | Nsp3 |
| Spike protein | Nsp12 |
| Spike protein | ORF7a/7b |
| Nucleoprotein | Nsp3 |
| Nucleoprotein | Nsp12 |
| Nucleoprotein | ORF7a/7b |

| Nsp2 | Nsp3 |
| Nsp2 | Nsp12 |
| Nsp2 | ORF7a/7b |
| Nsp14 | Nsp3 |
| Nsp14 | Nsp12 |
| Nsp14 | ORF7a/7b |

FIG. 13B (Con't)

| Nsp3 | Nsp2 | Nsp14 |

| Spike protein | Nsp3 | Nsp14 |

| Spike protein | Nsp2 | Nsp3 |

| Nsp12 | Nsp2 | Nucleoprotein |

| Spike protein | Nsp12 | Nucleoprotein |

| Spike protein | Nsp2 | Nsp12 |

| ORF7a/7b | Nsp14 | Nucleoprotein |

| Spike protein | ORF7a/7b | Nucleoprotein |

| Spike protein | Nsp14 | ORF7a/7b |

| Nsp3 | Nsp14 | Nucleoprotein |

| Nsp2 | Nsp3 | Nucleoprotein |

| Nsp2 | Nsp14 | Nsp3 |

| ORF7a/7b | Nsp14 | Nucleoprotein |

| Nsp2 | ORF7a/7b | Nucleoprotein |

| Nsp2 | Nsp14 | ORF7a/7b |

FIG. 13B (Con't)

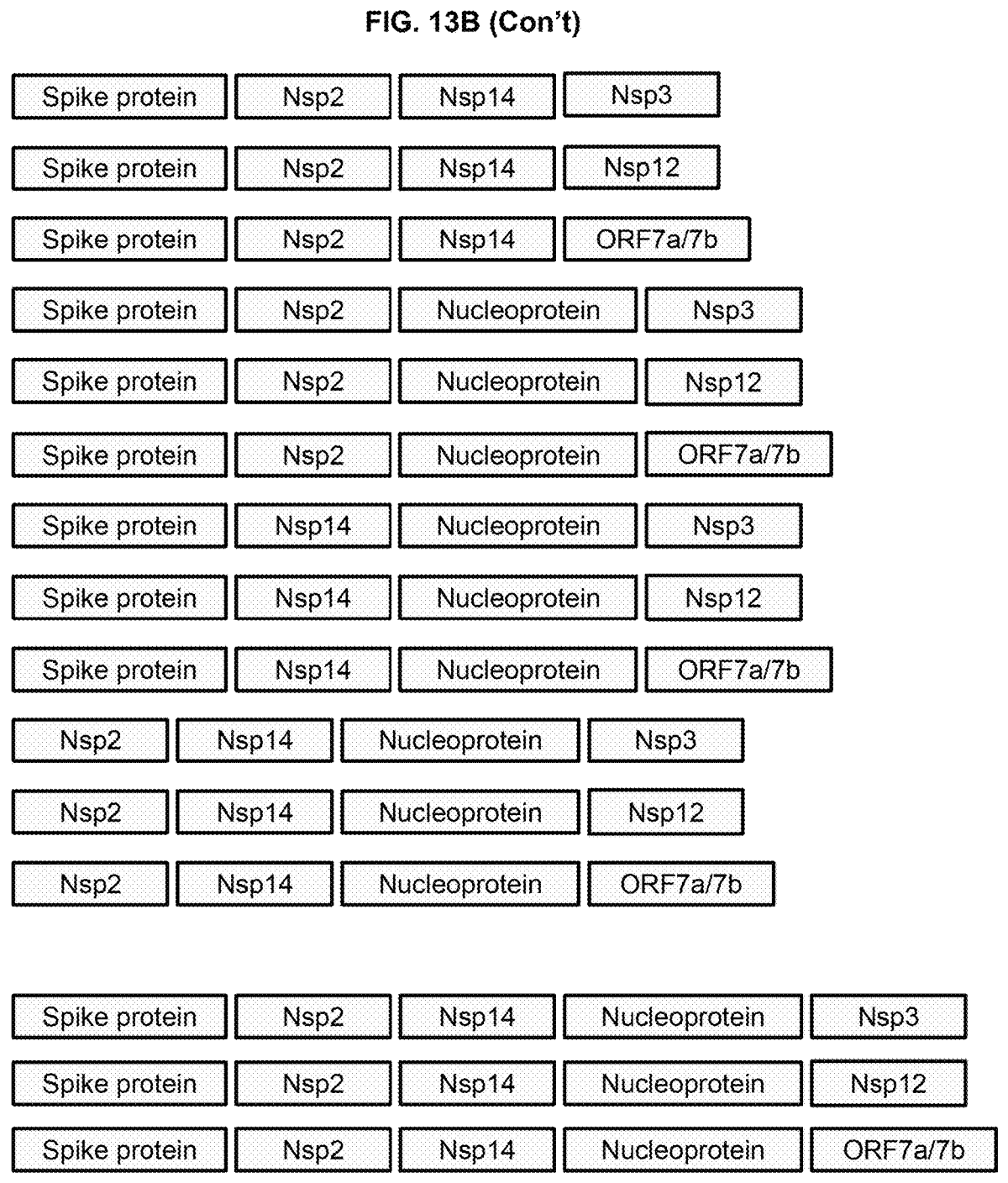

| Spike protein | Nsp2 | Nsp14 | Nsp3 |

| Spike protein | Nsp2 | Nsp14 | Nsp12 |

| Spike protein | Nsp2 | Nsp14 | ORF7a/7b |

| Spike protein | Nsp2 | Nucleoprotein | Nsp3 |

| Spike protein | Nsp2 | Nucleoprotein | Nsp12 |

| Spike protein | Nsp2 | Nucleoprotein | ORF7a/7b |

| Spike protein | Nsp14 | Nucleoprotein | Nsp3 |

| Spike protein | Nsp14 | Nucleoprotein | Nsp12 |

| Spike protein | Nsp14 | Nucleoprotein | ORF7a/7b |

| Nsp2 | Nsp14 | Nucleoprotein | Nsp3 |

| Nsp2 | Nsp14 | Nucleoprotein | Nsp12 |

| Nsp2 | Nsp14 | Nucleoprotein | ORF7a/7b |

| Spike protein | Nsp2 | Nsp14 | Nucleoprotein | Nsp3 |

| Spike protein | Nsp2 | Nsp14 | Nucleoprotein | Nsp12 |

| Spike protein | Nsp2 | Nsp14 | Nucleoprotein | ORF7a/7b |

BROAD-SPECTRUM MULTI-ANTIGEN PAN-CORONAVIRUS VACCINE

CROSS-REFERENCE TO RELATED APPLICATIONS

This application is a non-provisional and claims benefit of U.S. Provisional Application No. 63/626,937 filed Jan. 30, 2024 and U.S. Provisional Application No. 63/451,302 filed Mar. 10, 2023, the specifications of which are incorporated herein in their entirety by reference.

This application is also a continuation-in-part and claims benefit of PCT Application No. PCT/US23/68080 filed Jun. 7, 2023, which claims benefit to U.S. Provisional Application No. 63/349,799 filed Jun. 7, 2022, the specifications of which are incorporated herein in their entirety by reference.

This application is also a continuation-in-part and claims benefit of U.S. application Ser. No. 18/046,862 filed Oct. 14, 2022, which is a 371 of PCT Application No. PCT/US2021/027341 filed Apr. 14, 2021, which claims benefit of U.S. Provisional Application No. 63/009,907 filed Apr. 14, 2020, and U.S. Provisional Application No. 63/084,421 filed Sep. 28, 2020, the specifications of which are incorporated herein in their entirety by reference.

U.S. application Ser. No. 18/046,862 is a non-provisional and claims benefit of U.S. Provisional Application No. 63/302,454 filed Jan. 24, 2022, U.S. Provisional Application No. 63/349,799 filed Jun. 7, 2022, and U.S. Provisional Application No. 63/349,904 filed Jun. 7, 2022, the specifications of which are incorporated herein in their entirety by reference.

This application is also a continuation-in-part and claims benefit of U.S. application Ser. No. 18/046,875 filed Oct. 14, 2022, which is a 371 of PCT Application No. PCT/US2021/027355 filed Apr. 14, 2021, which claims benefit of U.S. Provisional Application No. 63/009,907 filed Apr. 14, 2020, and U.S. Provisional Application No. 63/084,421 filed Sep. 28, 2020, the specifications of which are incorporated herein in their entirety by reference.

U.S. application Ser. No. 18/046,875 is a non-provisional and claims benefit of U.S. Provisional Application No. 63/302,454 filed Jan. 24, 2022, U.S. Provisional Application No. 63/349,799 filed Jun. 7, 2022, and U.S. Provisional Application No. 63/349,904 filed Jun. 7, 2022, the specifications of which are incorporated herein in their entirety by reference.

This application is also a continuation-in-part and claims benefit of U.S. application Ser. No. 18/046,462 filed Oct. 13, 2022, which is a 371 of PCT Application No. PCT/2021/027340 filed Apr. 14, 2021, which claims benefit of U.S. Provisional Application No. 63/009,907 filed Apr. 14, 2020, and U.S. Provisional Application No. 63/084,421 filed Sep. 28, 2020, the specifications of which are incorporated herein in their entirety by reference.

STATEMENT REGARDING FEDERALLY SPONSORED RESEARCH OR DEVELOPMENT

This invention was made with government support under Grant No. A1158060, A1150091, A1143348, A1147499, A1143326, A1138764, A1124911, and A1110902 awarded by National Institutes of Allergy and Infectious Diseases (NIAID). The government has certain rights in the invention.

REFERENCE TO AN ELECTRONIC SEQUENCE LISTING

The contents of the electronic sequence listing, Name: UCI_23_02_NP1.xml; Size: 77,824 bytes; and Date of Creation: Aug. 12, 2025, is herein incorporated by reference in its entirety.

FIELD OF THE INVENTION

The present invention relates to vaccines, for example, viral vaccines, such as those directed to coronaviruses, e.g., pan-coronavirus vaccines.

BACKGROUND OF THE INVENTION

The Coronavirus disease 2019 (COVID-19) pandemic has created one of the largest global health crises in nearly a century. As of January 2024, the number of confirmed SARS-CoV-2 cases has reached over 770 million, and COVID-19 disease caused nearly 7 million deaths. Since early 2020, the world has continued to contend with successive waves of COVID-19, fueled by the emergence of over 20 variants of concern (VOCs) with continued enhanced transmissibility. While the Wuhan strain Hu1 is the ancestral variant of SARS-CoV-2 that emerged in late 2019 in China, Alpha (B.1.1.7), Beta (B.1.351), and Gamma (B.1.1.28) VOCs subsequently emerged between 2020 to 2021 in the United Kingdom, South Africa, and Brazil, respectively. The most pathogenic Delta variant (B. 1.617. 2) was identified in India in mid-2021, where it led to a deadly wave of infections. The fast and heavily Spike-mutated Omicron variants and sub-variants (i.e., B.1.1.529, XBB1.5, EG.5, HV.1, BA.2.86, and JN.1) that emerged from 2021-2023 are less pathogenic but are more immune-evasive. Over the last four years, breakthrough infections by these VOCs contributed to repetitive seasonal surges that often strain the world's healthcare systems, causing sustained hospitalizations, illnesses, and deaths.

While the first-generation Spike-based COVID-19 vaccines have contributed to reducing the burden of COVID-19, vaccine-waning immunity against heavily Spike-mutating emerging variants and sub-variants contributed to a prolonged COVID-19 pandemic. The first-generation COVID-19 vaccines were subject to regular updates to incorporate the Spike mutations of the new VOCs that emerged throughout the pandemic. This "copy-passed" vaccine strategy that "chased" the emerged VOC into a new batch of "improved" bivalent COVID-19 vaccines was often surpassed by fast-emerging and rapidly mutating Omicron lineages. The sequences of Spike protein in the recently circulating EG.5, HV.1, and JN.1 Omicron subvariants have already undergone over 100 accumulated mutations, away from the recent XBB1.5-adapted bivalent vaccine. The "improved" bivalent vaccine was only effective 4 to 29% against the Omicron subvariants, circulating in Winter 2022, and its effectiveness decreased even further against the more recent divergent and highly transmissible EG.5, HV.1, and JN.1 Omicron subvariants, circulating in Winter 2023. These observations highlight the need for an alternative and superior next-generation pan-CoV vaccine strategy incorporating highly conserved non-Spike antigens to induce broad, cross-protective immunity against past, present, and future VOCs. Such a pan-Coronavirus vaccine may put an end to and eradicate an apparent prolonged COVID-19 pandemic.

BRIEF SUMMARY OF THE INVENTION

It is an objective of the present invention to provide systems, compositions and methods, featuring a universal pre-emptive coronavirus vaccine as specified in the independent claims. Embodiments of the invention are given in the dependent claims. Embodiments of the present invention can be freely combined with each other if they are not mutually exclusive.

The present invention features a universal pre-emptive pan-Coronavirus vaccine composition. In some embodiments, the composition may comprise two (or three) or more Coronavirus antigens derived from a) at least a portion of an NSP2 protein; b) at least a portion of an NSP14 protein; and c) at least a portion of a Nucleoprotein protein. In other embodiments, the composition comprises a sequence encoding two (or three) or more Coronavirus antigens derived from a) at least a portion of an NSP2 protein; b) at least a portion of an NSP14 protein; and c) at least a portion of a Nucleoprotein protein. The aforementioned composition may further comprise Coronavirus antigen derived from at least a portion of a Spike protein. For example, the composition may comprise two (or three) Coronavirus antigens derived from a) at least a portion of an NSP2 protein; b) at least a portion of an NSP14 protein; c) at least a portion of a Nucleoprotein protein and d) at least a portion of a Spike protein. In some embodiments, the composition may comprises a sequence encoding two (or three) Coronavirus antigens derived from a) at least a portion of an NSP2 protein; b) at least a portion of an NSP14 protein; c) at least a portion of a Nucleoprotein protein and d) at least a portion of a Spike protein.

Likewise, the present invention features a universal pre-emptive pan-Coronavirus vaccine composition. In some embodiments, the composition may comprise two (or three) or more Coronavirus antigens derived from a) an NSP2 protein; b) an NSP14 protein; and c) a Nucleoprotein protein. In other embodiments, the composition comprises a sequence encoding two (or three) or more Coronavirus antigens derived from a) an NSP2 protein; b) an NSP14 protein; and c) a Nucleoprotein protein. The aforementioned composition may further comprise Coronavirus antigen derived from a Spike protein. For example, the composition may comprise two (or three) Coronavirus antigens derived from a) an NSP2 protein; b) an NSP14 protein; c) Nucleoprotein protein and d) a Spike protein. In some embodiments, the composition may comprise a sequence encoding two (or three) Coronavirus antigens derived from a) an NSP2 protein; b) an NSP14 protein; c) a Nucleoprotein protein and a Spike protein.

The present invention may also feature a pan-Coronavirus recombinant vaccine composition. In some embodiments, the composition comprising a delivery system encoding two (or three) or more Coronavirus antigens derived from: a) at least a portion of an NSP2 protein; b) at least a portion of an NSP14 protein; and c) at least a portion of a Nucleoprotein protein. The aforementioned delivery system may further encode a Coronavirus antigen derived from at least a portion of a Spike protein. Alternatively, the aforementioned delivery system may further comprise an additional delivery system encoding a Coronavirus antigens derived from at least a portion of a Spike protein. For example, the composition may comprise a delivery system encoding two (or three) or more Coronavirus antigens derived from: a) at least a portion of an NSP2 protein; b) at least a portion of an NSP14 protein; c) at least a portion of a Nucleoprotein protein; and d) at least a portion of a Spike protein. The delivery system may comprise a single delivery system or may comprise two or more delivery systems.

Moreover, the present invention may feature a pan-Coronavirus recombinant vaccine composition. In some embodiments, the composition comprises a delivery system encoding two (or three) or more Coronavirus antigens derived from: a) an NSP2 protein; b) an NSP14 protein; and c) a Nucleoprotein protein. The aforementioned delivery system may further encode a Coronavirus antigen derived from a Spike protein. Alternatively, the aforementioned delivery system may further comprise an additional delivery system encoding a Coronavirus antigens derived from a Spike protein. For example, the composition may comprise a delivery system encoding two (or three) or more Coronavirus antigens derived from: a) an NSP2 protein; b) an NSP14 protein; c) a Nucleoprotein protein; and d) a Spike protein. The delivery system may comprise a single delivery system or may comprise two or more delivery systems.

Referring to FIG. 13A, the aforementioned Coronavirus antigens may be the Spike protein or a portion thereof and the NSP2 protein or a portion thereof. In some embodiments, the Coronavirus antigens may be the Spike protein or a portion thereof and the NSP14 protein or a portion thereof. In some embodiments, the Coronavirus antigens may be the Spike protein or a portion thereof and the Nucleoprotein or a portion thereof. In some embodiments, the Coronavirus antigens may be the Spike protein or a portion thereof, the NSP2 protein or a portion thereof, and the NSP14 protein or a portion thereof. In some embodiments, the Coronavirus antigens may be the Spike protein or a portion thereof, the NSP2 protein or a portion thereof, and the Nucleoprotein or a portion thereof. In some embodiments, the Coronavirus antigens may be the Spike protein or a portion thereof, the NSP14 protein or a portion thereof, and the Nucleoprotein or a portion thereof. In some embodiments, the Coronavirus antigens may be the Spike protein; the NSP2 protein or a portion thereof; the NSP14 protein or a portion thereof; and the Nucleoprotein or a portion thereof.

Referring to FIG. 13B, the aforementioned composition, in certain embodiments, may further comprise one or more Coronavirus antigens derived from an NSP3 protein or portion thereof, a NSP12 protein or portion thereof, or a protein encoded by ORF7a/b or portion thereof. In some embodiments, the aforementioned composition may further comprise two or more Coronavirus antigens derived from an NSP3 protein or portion thereof, a NSP12 protein or portion thereof, or a protein encoded by ORF7a/b or portion thereof. In other embodiments, the aforementioned composition may further comprise three or more Coronavirus antigens derived from an NSP3 protein or portion thereof, a NSP12 protein or portion thereof, or a protein encoded by ORF7a/b or portion thereof. The present invention is not limited to the aforestated Coronavirus antigens.

In some embodiments, the aforementioned compositions may further comprise T cell attracting chemokine, e.g., CCL5, CXCL9, CXCL10, CXCL11, or a combination thereof. Alternatively, or in addition to, the composition may also comprise a composition that promotes T cell proliferation and T-cell memory, e.g., IL-7, IL-2, IL-15, or a combination thereof.

The vaccine compositions described herein may protect against disease caused by one or more coronavirus variants or coronavirus subvariants. The coronavirus variants or coronavirus subvariants may comprise past or currently circulating coronavirus variants (e.g., alpha, beta, gamma, delta, and omicron) or coronavirus subvariants. Additionally, the coronavirus variants or coronavirus subvariants may comprise future variants or future subvariants of human and animal coronavirus. In some embodiments, the vaccine compositions herein protect against infection and re-infection of coronavirus variants or coronavirus subvariants. For example, the vaccine composition may protect against infection or reinfection of one or more coronavirus variant or coronavirus subvariant. Alternatively, the vaccine compositions may protect against infection or reinfection of multiple coronavirus variants or coronavirus subvariants. Furthermore, the vaccine composition protects against infection or re-infection of one coronavirus variants or coronavirus subvariants.

The vaccine compositions described herein may induce strong and long-lasting protection mediated by antibodies (Abs), CD4+ T helper (Th1) cells, and/or CD8+ cytotoxic T-cells (CTL).

The present invention may further feature a composition comprising two (or three) or more ribonucleic acids (mRNAs) comprising an open reading frame encoding at least a portion of a Coronavirus protein selected from a group consisting of: an NSP2 protein, an NSP14 protein, and a Nucleoprotein protein. The two or three mRNAs may be formulated in a lipid nanoparticle. Alternatively, the composition may comprise two (or three) or more mRNAs comprising an open reading frame encoding an entire Coronavirus protein selected from a group consisting of: an NSP2 protein, an NSP14 protein, and a Nucleoprotein protein. The composition may further comprise an mRNA comprising an open reading frame encoding a Coronavirus Spike protein or portion thereof formulated in a lipid nanoparticle. For example, the composition may comprise two (or three) or more mRNAs comprising an open reading frame encoding at least a portion of a Coronavirus protein selected from a group consisting of: an NSP2 protein, an NSP14 protein, a Nucleoprotein protein; and a Spike protein. Alternatively, the composition may comprise two (or three) or more mRNAs comprising an open reading frame encoding an entire Coronavirus protein selected from a group consisting of: an NSP2 protein, an NSP14 protein, a Nucleoprotein protein; and a Spike protein. In some embodiments, the two (or three) or more mRNAs are formulated in a lipid nanoparticle.

Additionally, the present invention may feature a pharmaceutical composition. In some embodiments, the pharmaceutical composition may comprise a plurality of lipid nanoparticles; where a first lipid nanoparticle comprises three messenger ribonucleic acids (mRNAs) encapsulated therein, and each mRNA comprises an open reading frame encoding a Coronavirus protein selected from a group consisting of: an NSP2 protein, an NSP14 protein, and a Nucleoprotein, and a second lipid nanoparticle comprising an mRNA comprising an open reading frame encoding a Coronavirus Spike protein or portion thereof encapsulated therein. Likewise, the pharmaceutical composition may comprise a plurality of lipid nanoparticles; where a first lipid nanoparticle comprises three messenger ribonucleic acids (mRNAs) encapsulated therein, and each mRNA comprises an open reading frame encoding an entire Coronavirus protein selected from a group consisting of: an NSP2 protein, an NSP14 protein, and a Nucleoprotein, and a second lipid nanoparticle comprising an mRNA comprising an open reading frame encoding a Coronavirus Spike protein or portion thereof encapsulated therein.

The mRNAs may further comprise a 5' untranslated region (UTR) and a 3' UTR. In some embodiments, the mRNAs further comprise a 3' poly(A) tail and/or a 5' cap or cap analog.

One of the unique and inventive technical features of the present invention is the use of both B cell antigens and T cell antigens within a single composition (e.g., a vaccine composition, a pharmaceutical composition, etc.). Without wishing to limit the invention to any theory or mechanism, it is believed that the technical feature of the present invention advantageously provides for a universal vaccine composition that will protect from future human outbreaks and deter future zoonosis. None of the presently known prior references or work has the unique inventive technical feature of the present invention.

Likewise, the present invention may feature a universal pre-emptive pan-Coronavirus vaccine composition comprising a B cell antigen and two (or three) or more T-cell antigens. In some embodiments, the universal pre-emptive pan-Coronavirus vaccine composition comprises a sequence encoding a B cell antigen and two (or three) or more T-cell antigens. In some embodiments, the universal pre-emptive pan-Coronavirus vaccine composition comprises a B cell antigen and three T-cell antigens. In other embodiments, the universal pre-emptive pan-Coronavirus vaccine composition comprises a sequence encoding a B cell antigen and three T-cell antigens. The B cell antigens may be derived from a Coronavirus Spike protein or portion thereof. Whereas, the T cell antigens may be derived from an NSP2 protein or portion thereof, an NSP14 protein or portion thereof, a Nucleoprotein or portion thereof, or a combination thereof. In certain embodiments, the T cell antigens may be derived from an NSP3 protein or portion thereof, an NSP12 protein or portion thereof, or a protein encoded by ORF7a/b or portion thereof.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 1A, 1B, and 1C shows highly conserved non-spike, structural, non-structural, and accessory protein antigens identified in the SARS-CoV-2 genome: FIG. 1A shows bioinformatic analysis and alignment of the 29903 bp single strand RNA of 8.7 million genome sequences of SARS-CoV-2 strains that circulated worldwide over the last 4 years, including 20 VOCs; SARS-CoV; MERS-CoV; common cold Coronaviruses; and twenty-five animal's SARS-like Coronaviruses (SL-CoVs) genome sequences isolated from bats (*Rhinolophus affinis, Rhinolophus malayanus*), pangolins (*Manis javanica*), civet cats (*Paguma larvata*), and camels (*Camelus dromedaries*). FIG. 1B depicts 10 highly conserved non-Spike antigens that comprise 3 structural (Membrane, Envelope, and Nucleoprotein), 12 non-structural (NSP-2, NSP-3, NSP-4, NSP-5-10, NSP-12, and NSP-14) and 1 accessory protein (ORF7a/b) as T cell antigens (top) and Spike as the B cell antigen (bottom) used to construct the individual and combined mRNA/LNP vaccines. FIG. 1C illustrates the individual and combined mRNA/LNP vaccines that consist of modified mRNAs expressing the B and T cell antigens encapsulated in lipid nanoparticles (LNPs), as detailed herein, and delivery intramuscularly in the outbreed golden Syrian hamsters.

FIG. 2 shows a comparison of cumulative mutation frequencies between Spike B cell antigen and ten conserved non-Spike T cell antigens among 12 SARS-CoV-2 variants and sub-variants of concern, including the recent highly mutated COVID variants 'Pirola' BA.2.86 and JN.1 that may cause more severe disease.

Figure 3B:
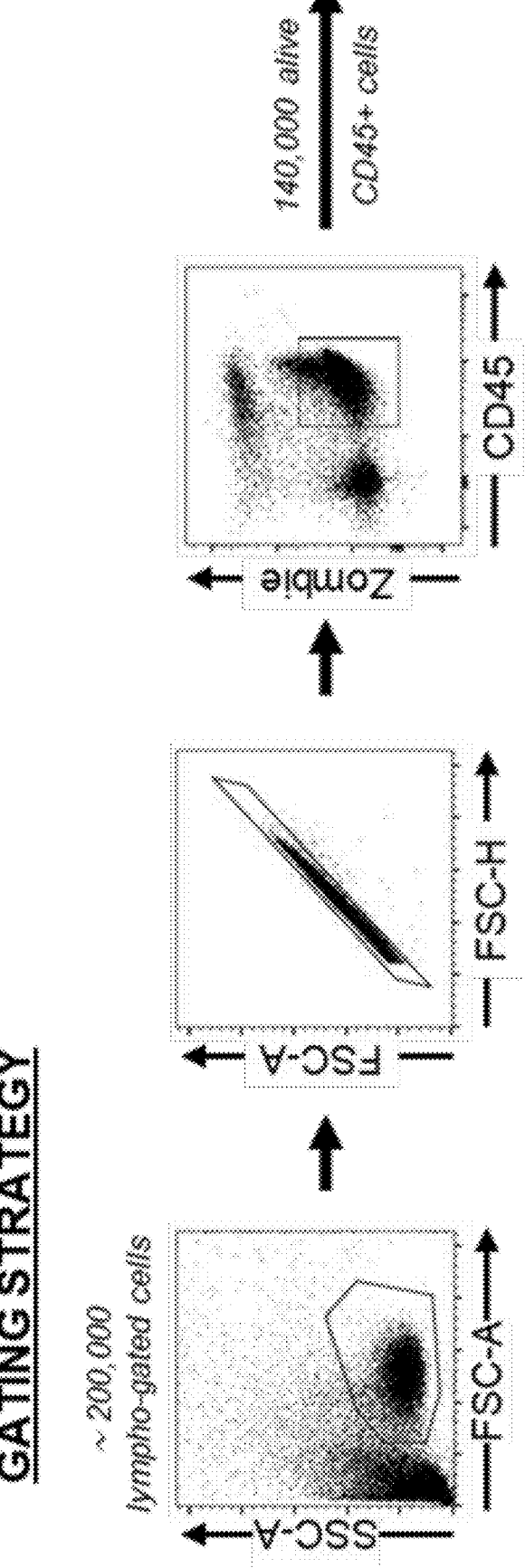
Figure 3B:
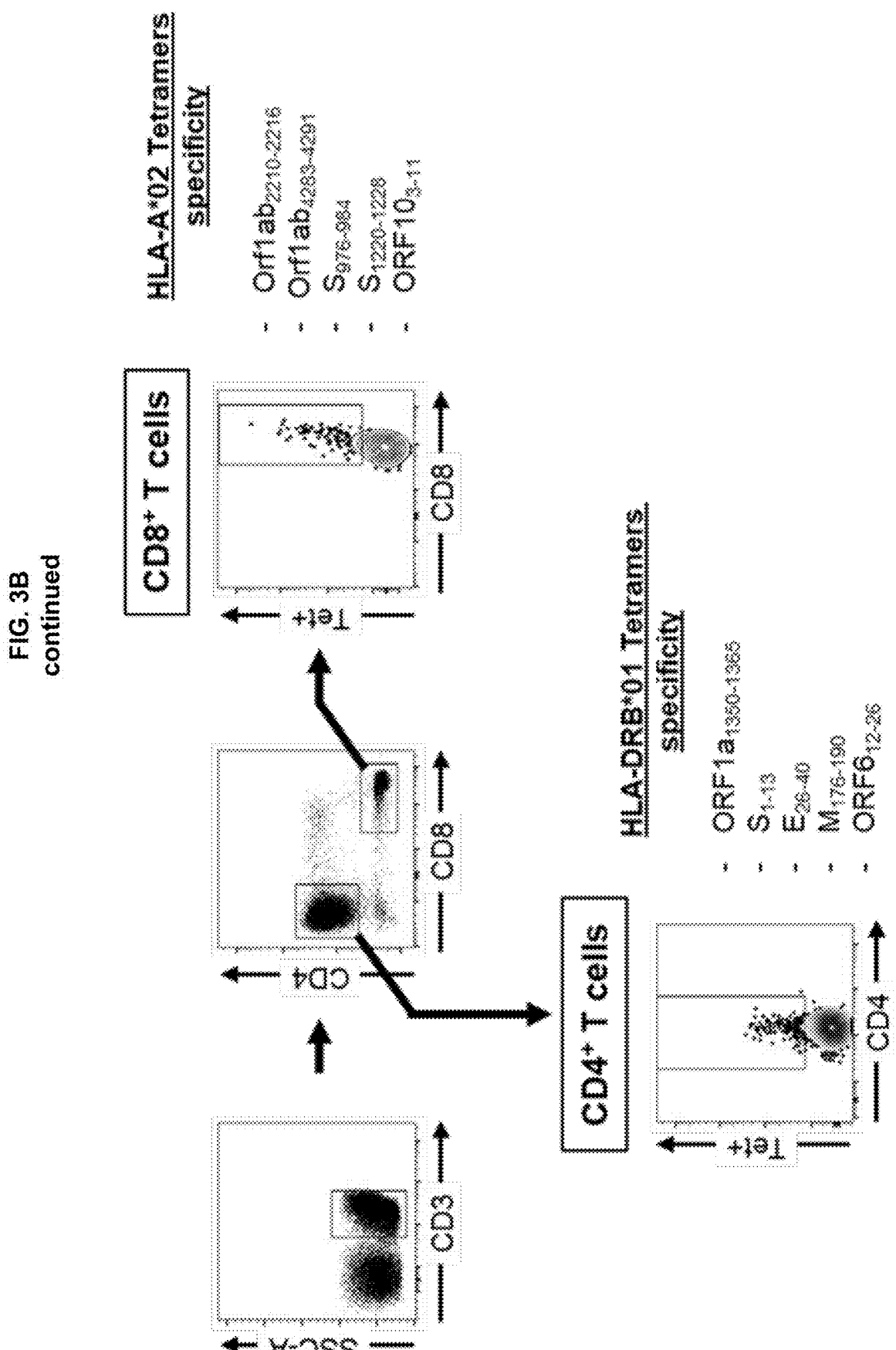

FIGS. 3A and 3B shows experimental plan and gating strategy: FIG. 3A shows the experimental plan followed for the flow-cytometry experiments and the ELISpot experiments presented in FIGS. 4A, 4B, 4C, and 4D, starting with the COVID-19 blood samples collection, patient genotyping, PBMCs extraction, and peptide stimulation. FIG. 3B shows the gating strategy applied when analyzing the flow cytometry data. Fresh peripheral blood mononuclear cells (PBMCs) were used in this study as they generally have higher viability and functionality compared to frozen PBMCs. Freezing and thawing can lead to cell damage and loss of T-cell functionality, which may affect the accuracy and reliability of experimental results. Frozen PBMCs may exhibit altered activation status compared to fresh cells. Cryopreservation can induce stress responses in cells, leading to changes in their activation state and potentially affecting immune response assays. In the context of COVID-19 research, where precise characterization of immune responses is crucial for understanding disease pathogenesis, vaccine development, and treatment strategies, using fresh PBMCs ensures the accuracy and reliability of experimental results. A side-by-side comparison of frozen and fresh PBMCs and pre-pandemic healthy control PBMCs yielded no significant difference.

Figure 4A:
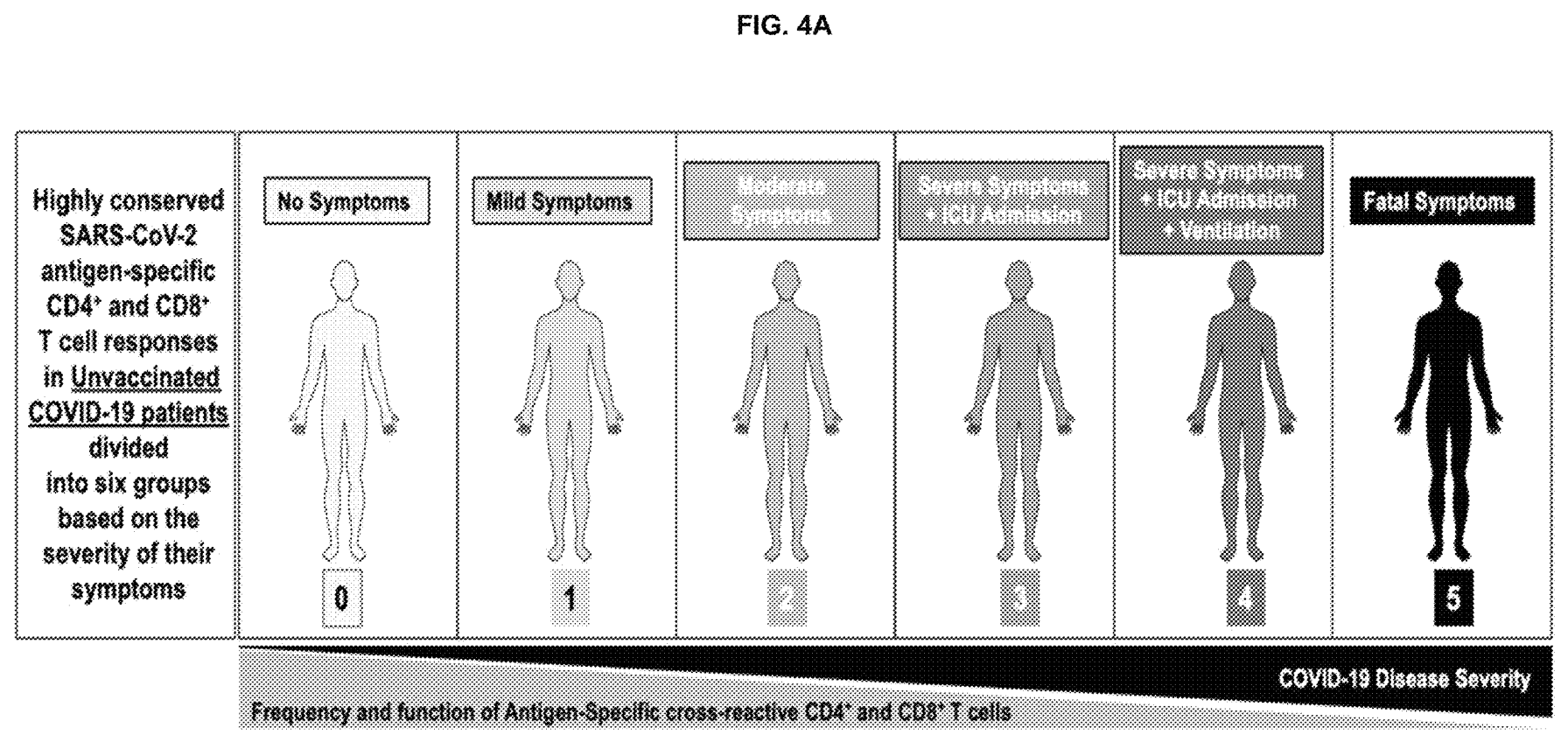

FIGS. 4A, 4B, 4C, and 4D shows IFN-γ-producing CD4$^+$ and CD8$^+$ T cell responses to highly conserved antigens in unvaccinated COVID-19 patients with various degrees of disease severity: FIG. 4A illustrates a positive correlation between the severity of COVID-19 and the magnitude of SARS-CoV-2 common antigens-specific CD4$^+$ and CD8$^+$ T cell responses in 71 COVID-19 patients. COVID-19 patients (n=71) are divided into six groups based on disease severity scored 0 to 5, as described in Materials and Methods, and as identified by six colors on a grayscale (Black=severity 5, to white=severity 0). PBMCs from HLA-DR- and HLA-A*0201-positive COVID-19 patients (n=71) were isolated and stimulated for a total of 72 hours with 10 μg/ml of each of the previously identified. The magnitude of CD4$^+$ and CD8$^+$ T cell responses specific to CD4$^+$ and CD8$^+$ T cell epitopes from all the ten selected conserved antigens (FIG. 4B), the 13 individual cross-reactive CD4$^+$ T cell epitope peptides (FIG. 4C); and the 16 individual cross-reactive CD8$^+$ T cell epitopes that belong to the selected 10 highly conserved antigens (i.e., NSP-2, NSP-3, NSP-4, NSP-5-10, NSP-12, NSP-14, ORF7a/b, Membrane, Envelope, and Nucleoprotein) (FIG. 4D) are shown. The number of IFN-γ-producing CD8$^+$ T cells was quantified in each of the 71 patients using ELISpot assay. Shown are the average/mean numbers (±SD) of IFN-γ-spot forming cells (SFCs) after CD4$^+$ T cell peptide stimulation detected in each of the 71 COVID-19 patients divided into six groups based on disease severity scored 0 to 5. A mean SFCs between 25 and 50 SFCs corresponds to a medium/intermediate response, whereas a strong response is defined for mean SFCs>50 per $0.5 \times 10^6$ stimulated PBMCs. PHA was used as a positive control of T-cell activation. Unstimulated negative control SFCs (DMSO—no peptide stimulation) were subtracted from the SFC counts of peptides-stimulated cells. Shown is the correlation between the overall number of IFN-γ-producing CD4$^+$ T cells induced by each of the 14 cross-reactive CD4$^+$ T cell epitope peptides (FIG. 4C); and IFN- γ-producing CD8$^+$ T cells induced by each of the 16 cross-reactive CD8$^+$ T cell epitope peptides (FIG. 4D) in each of the six groups of COVID-19 patients with various disease severity. For all graphs: the coefficient of determination ($R^2$) is calculated from the Pearson correlation Coefficients®. The associated P-value and the slope (S) of the best-fitted line (dotted line) are calculated by linear regression analysis is indicated. The gray-hatched boxes in the correlation graphs extend from the 25$^{th}$ to 75th percentiles (hinges of the plots) with the median represented as a horizontal line in each box and the extremity of the vertical bars showing the minimum and maximum values. Results are representative of two independent experiments and were considered statistically significant at P≤0.05 using either the Mann-Whitney test (two groups) or the Kruskal-Wallis test (more than two groups).

Figures 5A, 5B, 5C, 5D:
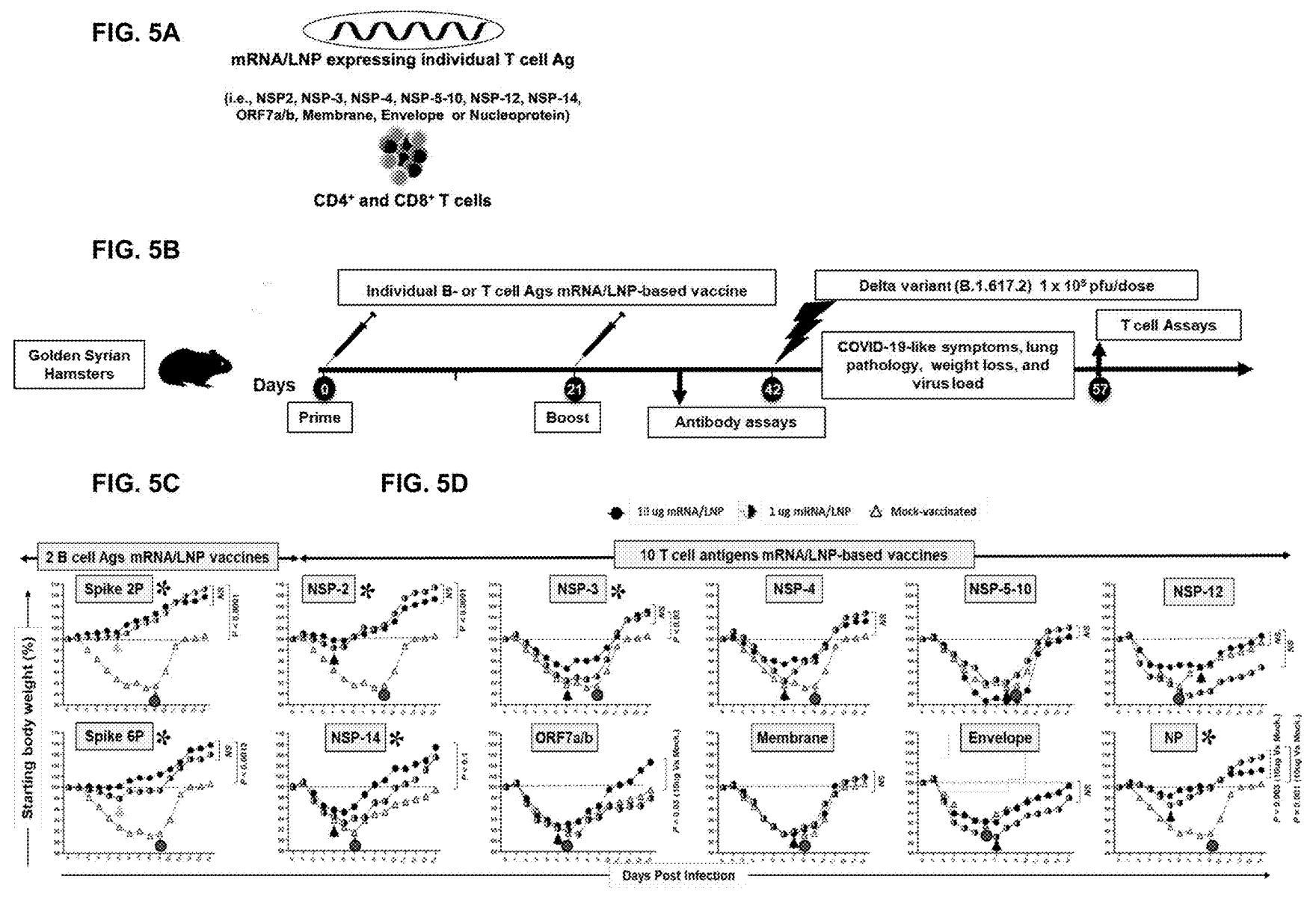

FIGS. 5A, 5B, 5C, and 5D shows the screening of 10 highly conserved T cell antigens for protection against the highly pathogenic Delta variant (B.1.617.2) in golden Syrian hamsters: FIG. 5A shows Omicron sub-variant BA.2.75-based sequences of 10 highly conserved non-Spike T-cell antigens (i.e., NSP-2, NSP-3, NSP-4, NSP-5-10, NSP-12, NSP-14, ORF7a/b, Membrane, Envelope, and Nucleoprotein) are used to construct methyl-pseudouridine-modified (m1Ψ) mRNA and capped using CleanCap technology. Modified mRNAs expressing the prefusion Spike proteins, stabilized by either two (Spike 2P) or six (Spike 6P) prolines, were expressed as B cell antigens. The 12 modified mRNAs were then encapsulated in lipid nanoparticles (LNPs) as the delivery system. FIG. 5B shows the experimental plan to screen the vaccine efficacy of the 10 highly conserved T-cell Ags. Female hamsters (n=5 per group) were immunized intramuscularly twice on day 0 (prime) and day 21 (boost) with 1 μg/dose or 10 μg/dose of the mRNA/LNP-based Coronavirus vaccine expressing each of the 10 highly conserved non-Spike T-cell antigens. Hamsters that received phosphate-buffered saline alone were used as mock-immunized controls (Saline, Mock, n=5). Three weeks after booster vaccination (day 42), vaccinated and mock-vaccinated hamsters were intranasally challenged (both nostrils) with $1 \times 10^5$ pfu of SARS-CoV-2 highly pathogenic Delta variant (B.1.617.2). Weight losses were assessed for 14- or 24-days post-challenge. FIG. 5C shows percent weight change for 14 days post-challenge normalized to the initial body weight on the day of infection in hamsters immunized with mRNA/LNP expressing Spike 2P and Spike 6P. FIG. 5D shows percent weight change for 14 days post-challenge normalized to the initial body weight on the day of infection in hamsters immunized with mRNA/LNP expressing individual NSP-2, NSP-3, NSP-4, NSP-5-10, NSP-12, NSP-14, ORF7a/b, Membrane, Envelope, and Nucleoprotein at 1 μg/dose or 10 μg/dose. The dashed line indicates the 100% starting body weight. The arrows indicate the first-day post-challenge when the weight loss is reversed in T cell antigen (black arrow), Spike (grey arrow), and mock (circle) vaccinated hamsters. The data represent two independent experiments; the graphed values and bars represent the SD between the two experiments. The Mann-Whitney test (two groups) or the Kruskal-Wallis test (more than two groups) were used for statistical analysis. ns P>0.05, *P<0.05, P<0.01, *P<0.001, ****P<0.0001.

Figures 6A, 6B, 6C:
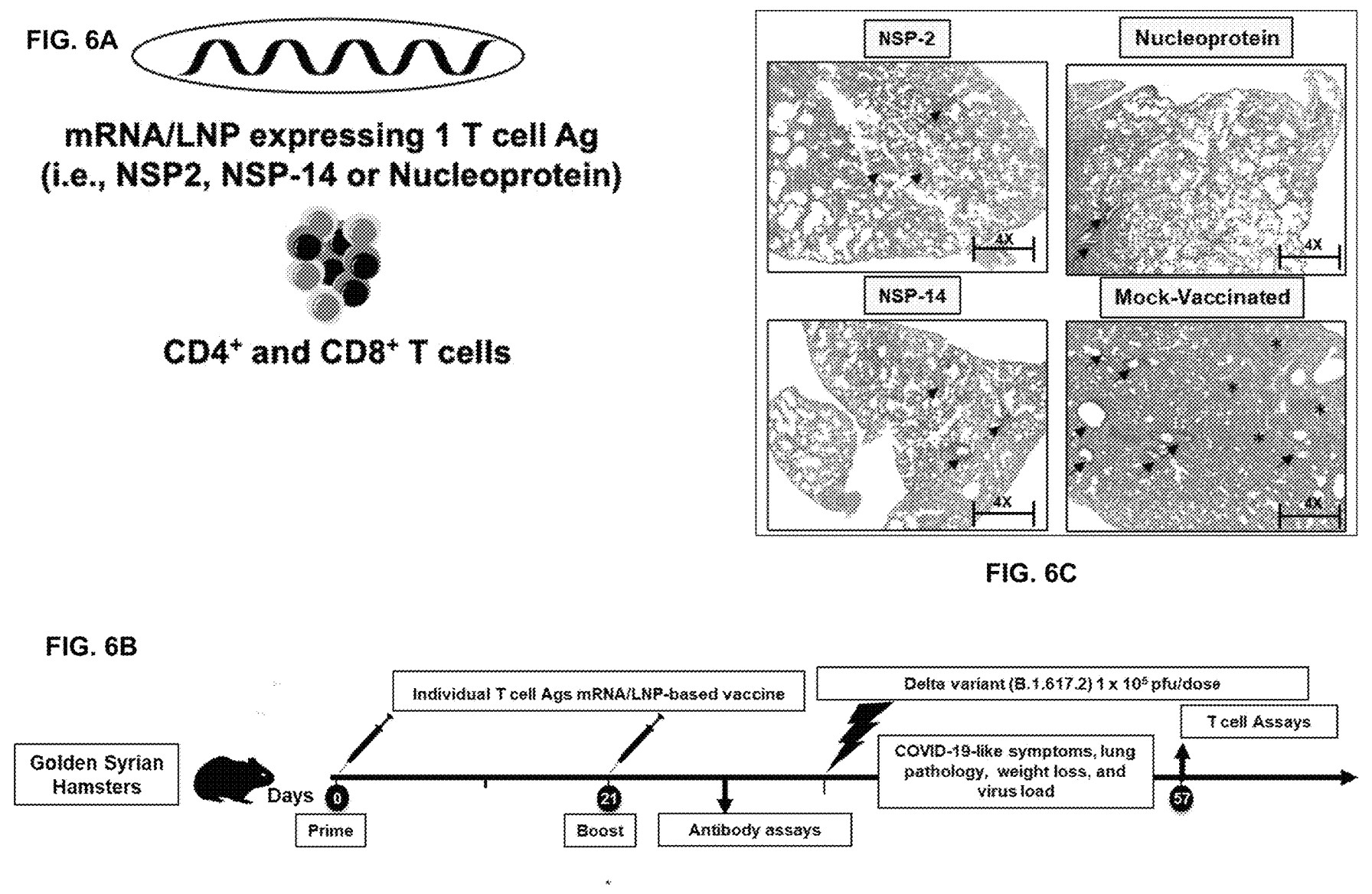
Figure 6D:
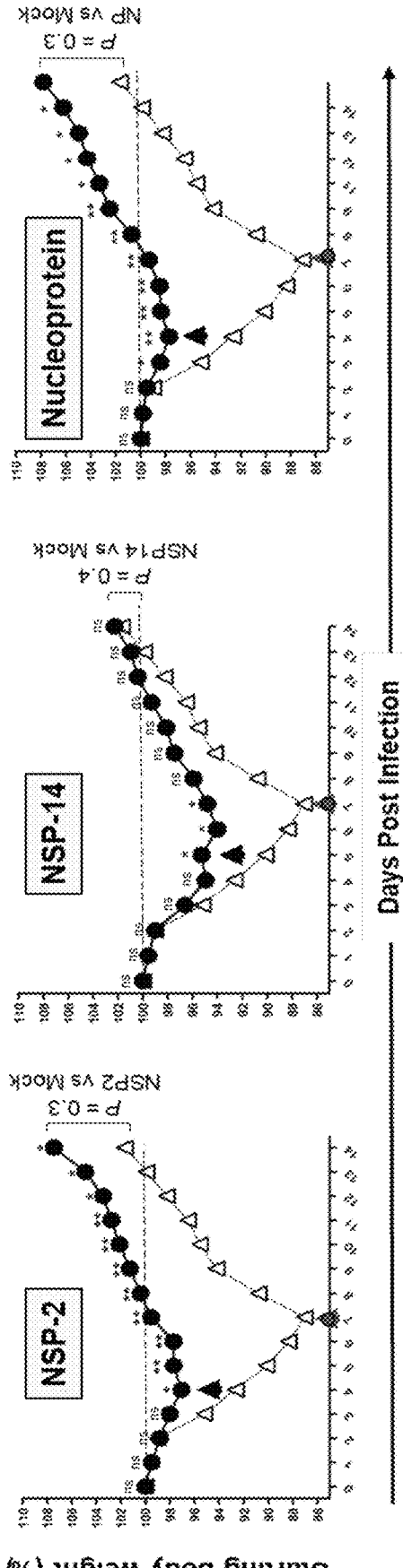
Figure 6E:
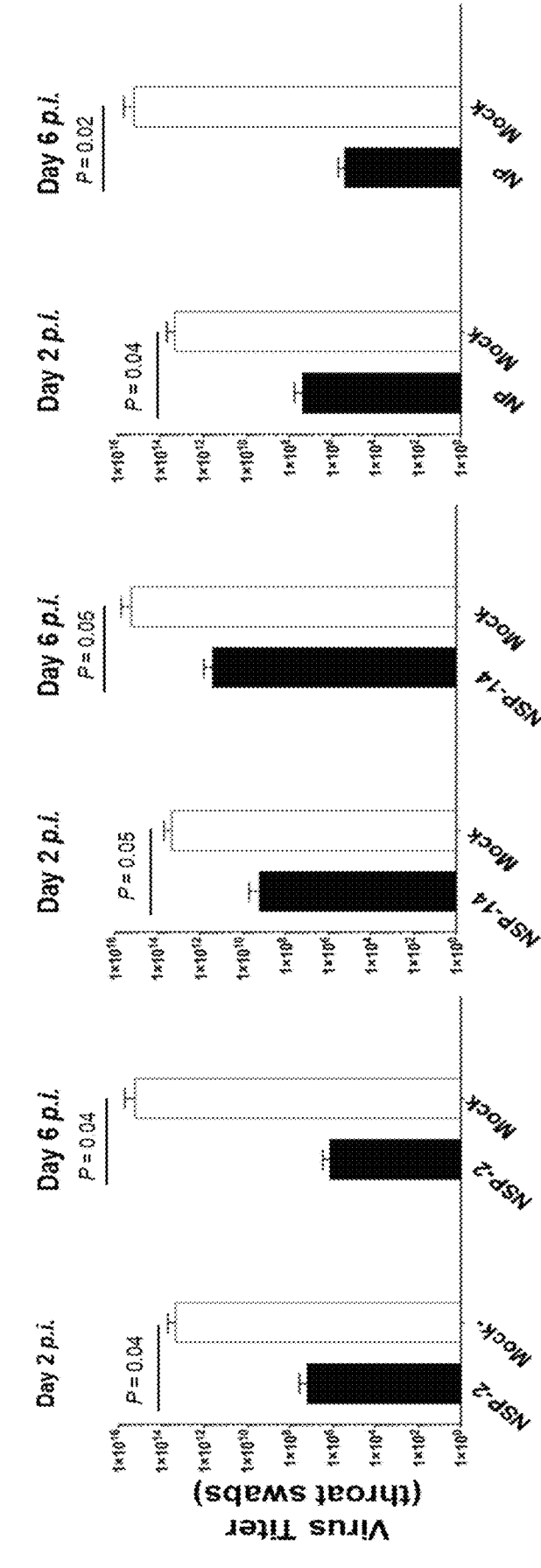

FIGS. 6A, 6B, 6C, 6D, and 6E shows protection against the highly pathogenic Delta variant (B.1.617.2) induced by individual NSP-2, NSP-14, and Nucleoprotein T cell antigen-based mRNA/LNP vaccines in golden Syrian hamsters: FIG. 6A illustrates the three mRNA/LNP vaccines that consist of highly conserved T-cell Ags, NSP-2, NSP-14, and Nucleoprotein expressed as nucleoside-modified mRNA sequences derived from BA.2.75 Omicron sub-variant (BA2) and encapsulated in lipid nanoparticles (LNP). FIG. 6B shows the experimental plan to screen the vaccine efficacy of the 10 highly conserved T-cell Ags (i.e., NSP-2, NSP-3, NSP-4, NSP-5-10, NSP-12, NSP-14, ORF7a/b, Membrane, Envelope, and Nucleoprotein). Female hamsters (n=5 per group) were immunized intramuscularly twice on day 0 (prime) and day 21 (boost) with each mRNA/LNP-based Coronavirus vaccine expressing each of the 10 highly conserved non-Spike T-cell antigens. Hamsters that received phosphate-buffered saline alone were used as mock-immunized controls (Saline, Mock, n=5). Three weeks after booster vaccination (day 42), vaccinated and mock-vaccinated hamsters were intranasally challenged (both nostrils) with 1×10⁵ pfu of SARS-CoV-2 highly pathogenic Delta variant (B.1.617.2). COVID-19-like symptoms, lung pathology, weight loss, and virus load were assessed for 14 days post-challenge. FIG. 6C shows representative H & E staining images of lung pathology at day 14 p.i. of SARS-CoV-2 infected hamsters mock vaccinated or vaccinated with three protective NSP-2, NSP-14, and Nucleoprotein-based mRNA/LNP vaccines at 4× magnifications. Fourteen days post-challenge, the lung tissues were collected and fixed, and 5-μm sections were cut from hamsters and stained with hematoxylin and eosin. The lung of mock-vaccinated hamsters demonstrates many bronchi with bronchiolitis (arrows) and adjacent marked interstitial pneumonia (asteria). Lungs of hamsters immunized with NSP2, NSP-14, or NP mRNA/LNP show few bronchiolitis (arrow) and normal bronchial, bronchiolar, and alveolar architecture. Scale bars, 1 mm. FIG. 6D shows percent weight change for 14 days post-challenge normalized to the initial body weight on the day of infection. The dashed line indicates the 100% starting body weight. The arrows indicate the first-day post-challenge when the weight loss is reversed in T cell antigen (black arrow) and mock (circle) vaccinated hamsters. FIG. 6E shows two- and 6 days post-infection (p.i.), viral loads were analyzed, to evaluate vaccine-induced protection against virus replication, by comparing viral RNA copies in the hamster's throats and lungs between mock and vaccine groups. Viral RNA copies were quantified by RT-PCR and expressed as log, copies per milligram of throat or lung tissue. The graphs show a comparison of viral titers in the hamster lungs between vaccinated vs. mock-vaccinated hamsters. The data represent two independent experiments; the graphed values and bars represent the SD between the two experiments. The Mann-Whitney test (two groups) or the Kruskal-Wallis test (more than two groups) were used for statistical analysis. ns P>0.05, *P<0.05, P<0.01, *P<0.001, ****P<0.0001.

FIGS. 7A, 7B, 7C, 7D, and 7E shows the protection against multiple SARS-CoV-2 variants and sub-variants of concern induced by combined NSP-2, NSP-14, and Nucleoprotein-based mRNA/LNP vaccine in the hamster model: FIG. 7A illustrates the combination of three vaccines that consist of highly conserved protective T-cell Ags, NSP-2, NSP-14, and Nucleoprotein expressed as nucleoside-modified mRNA sequences derived from BA.2.75 Omicron sub-variant (BA2) and encapsulated in lipid nanoparticles (LNP). FIG. 7B shows the hamster experimental design and timeline to study the vaccine efficacy in golden Syrian hamsters of 10 individual T cell antigen-based mRNA/LNP vaccines on COVID-19-like symptoms detected. Female hamsters were immunized intramuscularly twice on day 0 (prime) and day 21 (boost) with the combined NSP-2, NSP-14, and Nucleoprotein-based mRNA/LNP vaccine (n=15 per group) or mock-vaccinated (Mock, n=15 per group). Three weeks after booster vaccination (day 42), vaccinated and mock-vaccinated hamsters were intranasally challenged (both nostrils) with, 2×10⁵ pfu of the wild-type Washington variant (WA1/2020), 1×10⁵ pfu of the highly pathogenic Delta variant (B.1.617.2) or 2×10⁵ pfu of the highly transmissible Omicron sub-variant (XBB1.5). COVID-19-like symptoms, lung pathology, weight loss, and virus load were assessed for 14 days post-challenge. FIG. 7C shows representative H & E staining images of lung pathology at day 14 p.i. of SARS-CoV-2 infected hamsters mock vaccinated or vaccinated with the combined NSP-2, NSP-14, and Nucleoprotein-based mRNA/LNP vaccines at 4× magnifications. Fourteen days post-challenge, the lung tissues were collected and fixed, and 5-μm sections were cut from hamsters and stained with hematoxylin and eosin. The lung of mock-vaccinated hamsters demonstrates many bronchi with bronchiolitis (arrows) and adjacent marked interstitial pneumonia (asteria). Lungs of hamsters that received combined T cell antigens mRNA/LNP vaccine demonstrate mostly normal bronchial, bronchiolar, and alveolar architecture. Scale bars, 1 mm. FIG. 7D shows percent weight change for 14 days post-challenge normalized to the initial body weight on the day of infection for each variant and sub-variant. The dashed line indicates the 100% starting body weight. The arrows indicate the first-day post-challenge when the weight loss is reversed in T cell antigen (black arrow), Spike (grey arrow), and mock (circle) vaccinated hamsters. FIG. 7E show two- and 6-days post-infection (p.i.) with the wild-type Washington variant (WA1/2020), the highly pathogenic Delta variant (B.1.617.2), or the highly transmissible Omicron sub-variant (XBB1.5), viral loads were analyzed, to evaluate vaccine-induced protection against virus replication, by comparing viral RNA copies in the hamster's throats and lungs between mock and vaccine groups. Viral RNA copies were quantified by RT-PCR and expressed as log 10 copies per milligram of throat or lung tissue. The graphs show a comparison of viral titers in the hamster lungs between vaccinated vs. mock-vaccinated hamsters. Viral titration data showing viral RNA copy number in the throats of vaccinated vs. mock-vaccinated hamsters detected at days 2 and 6 post-challenge. The data represent two independent experiments; the graphed values and bars represent the SD between the two experiments. The Mann-Whitney test (two groups) or the Kruskal-Wallis test (more than two groups) were used for statistical analysis. ns P>0.05, *P<0.05, P<0.01, *P<0.001, ****P<0.0001.

Figures 8D, 8E:
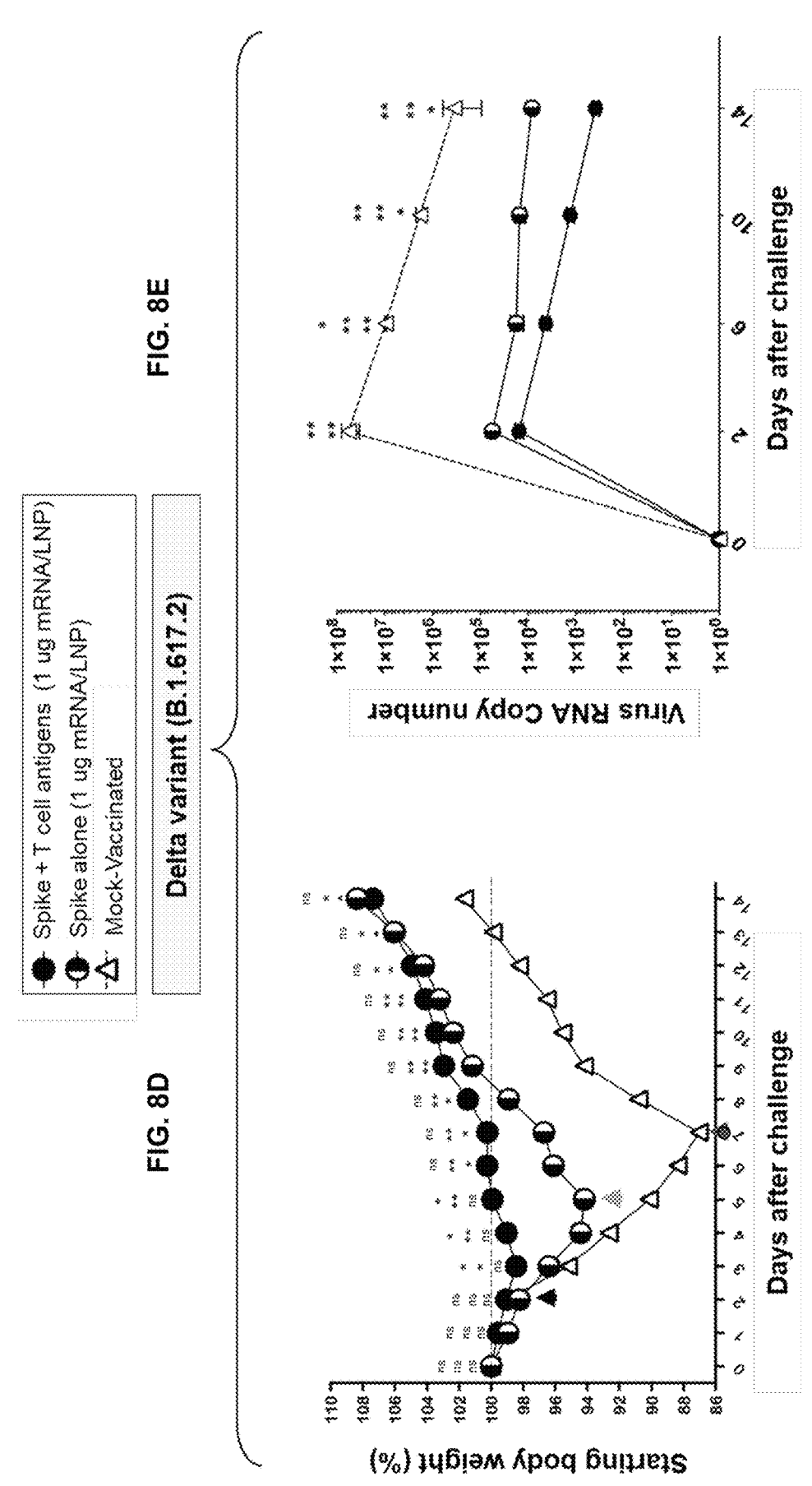

FIGS. 8A, 8B, 8C, 8D, and 8E shows protection induced by combined Spike, NSP-2, NSP-14, and Nucleoprotein-based mRNA/LNP vaccine against the highly pathogenic Delta variant (B.1.617.2): FIG. 8A illustrates combined Spike, NSP-2, NSP-14, and Nucleoprotein-based mRNA/LNP vaccine that consists of Spike mRNA/LNP vaccine combined to highly conserved protective T-cell Ags, NSP-2, NSP-14, and Nucleoprotein mRNA/LNP vaccines. All sequences are derived from BA.2.75 Omicron sub-variant (BA2). FIG. 8B shows the transfection of Spike, NSP-2, NSP-14, and Nucleoprotein mRNA and protein expression in vitro in the human epithelial HEK293T cells. FIG. 8C the hamster experimental design and timeline to study the beneficial effect in golden Syrian hamsters of adding the Spike mRNA/LNP vaccine to the combined NSP-2, NSP-14, and Nucleoprotein-based mRNA/LNP vaccine on the protection against the highly pathogenic Delta variant (B.1.617.2). Female hamsters were immunized intramuscularly twice on day 0 (prime) and day 21 (boost) with the combined Spike, NSP-2, NSP-14, and Nucleoprotein-based mRNA/LNP vaccine (1 μg/dose, n=5 per group), the Spike mRNA/LNP vaccine alone (1 μg/dose, n=5 per group), or mock-vaccinated (n=5 per group). Three weeks after booster vaccination (day 42), vaccinated and mock-vaccinated hamsters were intranasally challenged (both nostrils) vaccinated and mock-vaccinated hamsters were subsequently intranasally challenged (both nostrils) with $1 \times 10^5$ pfu of the highly pathogenic Delta variant (B.1.617.2). COVID-19-like symptoms, lung pathology, weight loss, and virus load were assessed for 14 days post-challenge. FIG. 8D shows percent weight change for 14 days post-challenge normalized to the initial body weight on the day of infection with the highly pathogenic Delta variant (B.1.617.2). The dashed line indicates the 100% starting body weight. FIG. 8E shows six days post-infection (p.i.), with the highly pathogenic Delta variant (B.1.617.2), the viral loads were analyzed, to evaluate vaccine-induced protection against virus replication, by comparing viral RNA copies in the hamster's throats and lungs between mock and vaccine groups. Viral RNA copies were quantified by RT-PCR and expressed as $\log_{10}$ copies per milligram of throat or lung tissue. The graphs show a comparison of viral titers in the hamster lungs between vaccinated vs. mock-vaccinated hamsters. The data represent two independent experiments; the graphed values and bars represent the SD between the two experiments. The Mann-Whitney test (two groups) or the Kruskal-Wallis test (more than two groups) were used for statistical analysis. ns P>0.05, *P<0.05, P<0.01, *P<0.001, **P<0.0001.

Figure 9D:
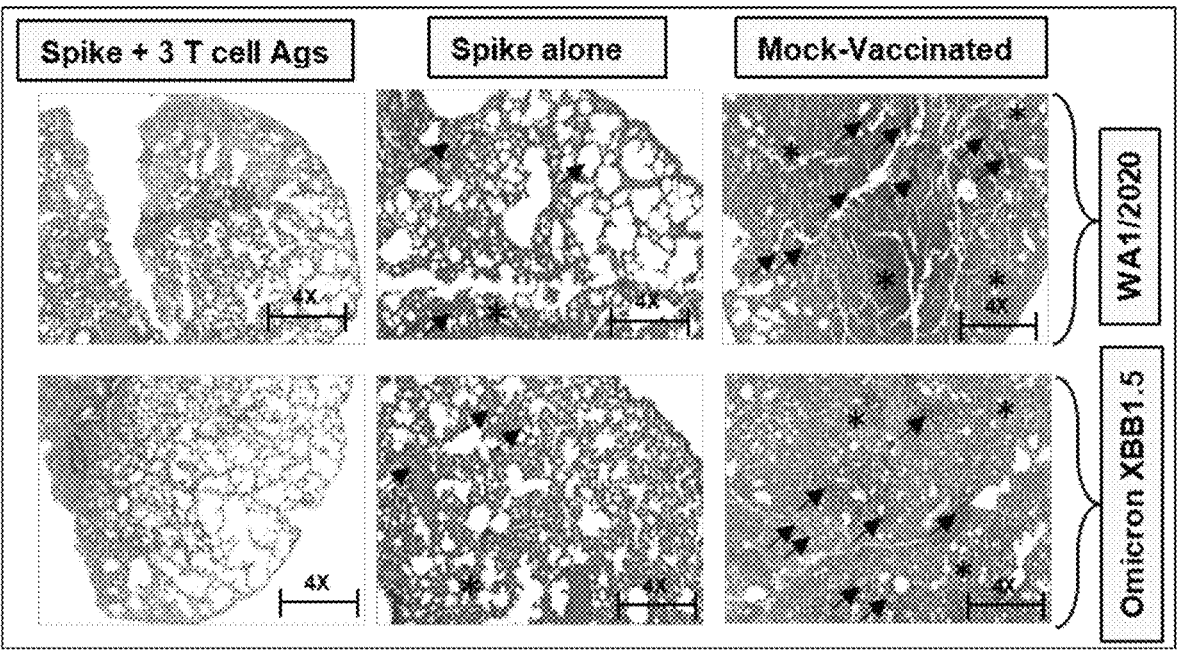
Figure 9E:
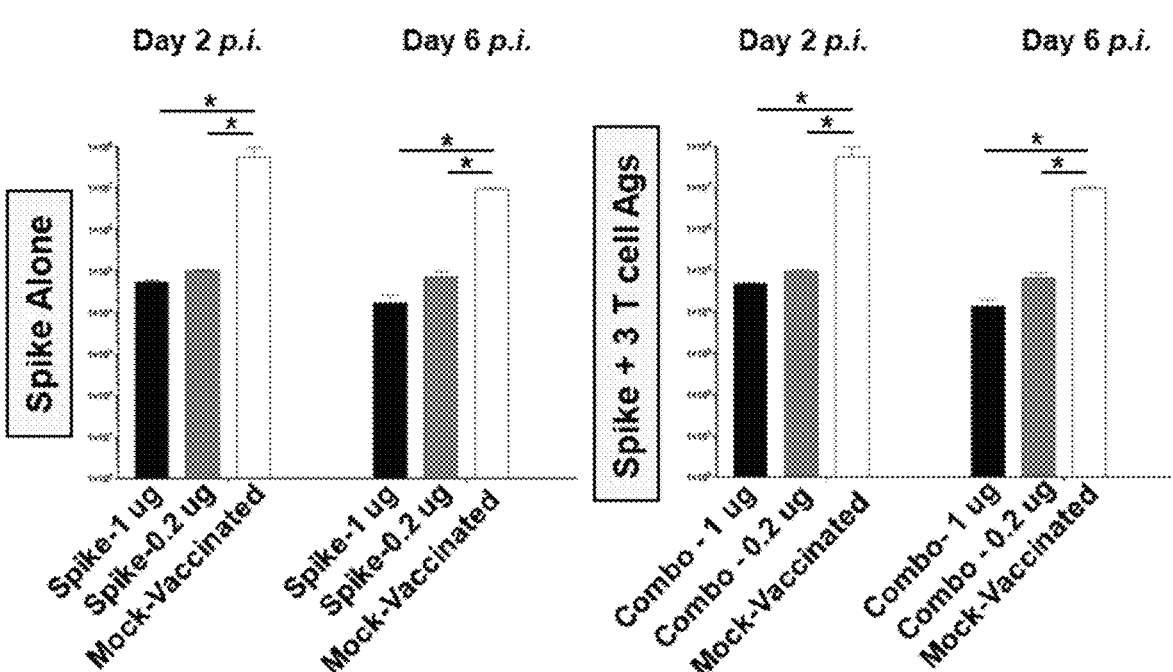
Figure 9F:
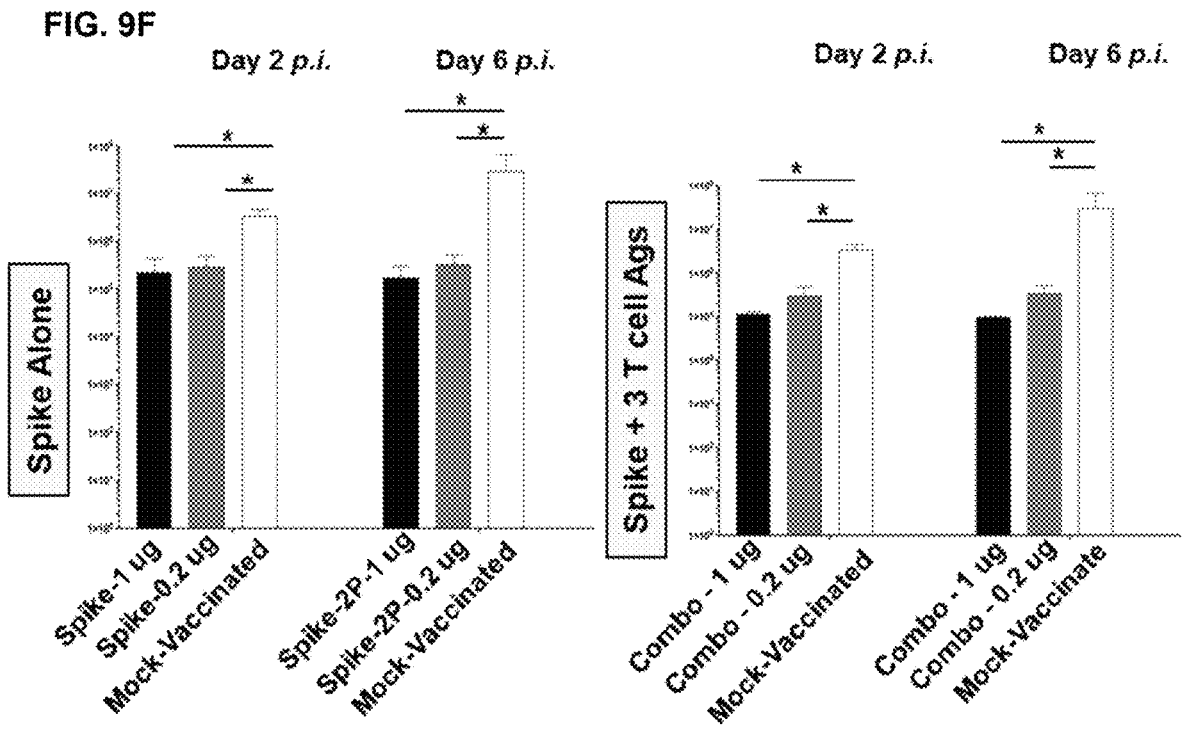

FIGS. 9A, 9B, 9C, 9D, 9E, and 9F shows protection induced by the combined Spike, NSP-2, NSP-14, and Nucleoprotein-based mRNA/LNP vaccine against the wild-type Washington variant (WA1/2020) and the highly transmissible Omicron sub-variant (XBB1.5). FIG. 9A illustrates combined Spike, NSP-2, NSP-14, and Nucleoprotein-based mRNA/LNP vaccine. FIGS. 9B and 9C shows percent weight change for 14 days post-challenge normalized to the initial body weight on the day of challenge with the wild-type Washington variant (WA1/2020) at $2 \times 10^5$ pfu/hamster and the highly transmissible Omicron sub-variant (XBB1.5) at $2 \times 10^5$ pfu/hamster, respectively. The dashed line indicates the 100% starting body weight. The arrows indicate the first-day post-challenge when the weight loss is reversed in T cell antigen (black arrow), Spike (grey arrow), and mock (circle) vaccinated hamsters. FIG. 9D shows representative H & E staining images of lung pathology at day 14 p.i. of SARS-CoV-2 infected hamsters mock vaccinated or vaccinated with the combined Spike, NSP-2, NSP-14, and Nucleoprotein-based mRNA/LNP vaccine (1 μg/dose), or the Spike mRNA/LNP vaccine alone (1 μg/dose) at 4× magnifications. Hamster lung histopathology is shown. Fourteen days post-challenge, the lung tissues were collected and fixed, and 5-μm sections were cut from hamsters and stained with hematoxylin and eosin. The lung of mock-immunized hamsters demonstrates many bronchi with bronchiolitis (arrows) and adjacent marked interstitial pneumonia (asteria). Lungs of hamsters immunized with Spike mRNA/LNP alone show peri bronchiolitis (arrow), perivasculitis (asterisk), and multifocal interstitial pneumonia. Lungs of hamsters that received a combination Spike mRNA/LNP vaccine and combined T cell antigens mRNA/LNP vaccine demonstrate mostly normal bronchial, bronchiolar (arrows), and alveolar architecture. Scale bars, 1 mm. FIGS. 9E and 9F shows viral titration data showing viral RNA copy number in the throats of vaccinated vs. mock-vaccinated hamsters detected at days 2 and 6 post-challenge with the wild-type Washington variant (WA1/2020) and the highly transmissible Omicron sub-variant (XBB1.5), respectively. The data represent two independent experiments; the graphed values and bars represent the SD between the two experiments. The Mann-Whitney test (two groups) or the Kruskal-Wallis test (more than two groups) were used for statistical analysis. ns P>0.05, *P<0.05, P<0.01, *P<0.001, ****P<0.0001.

Figure 10:
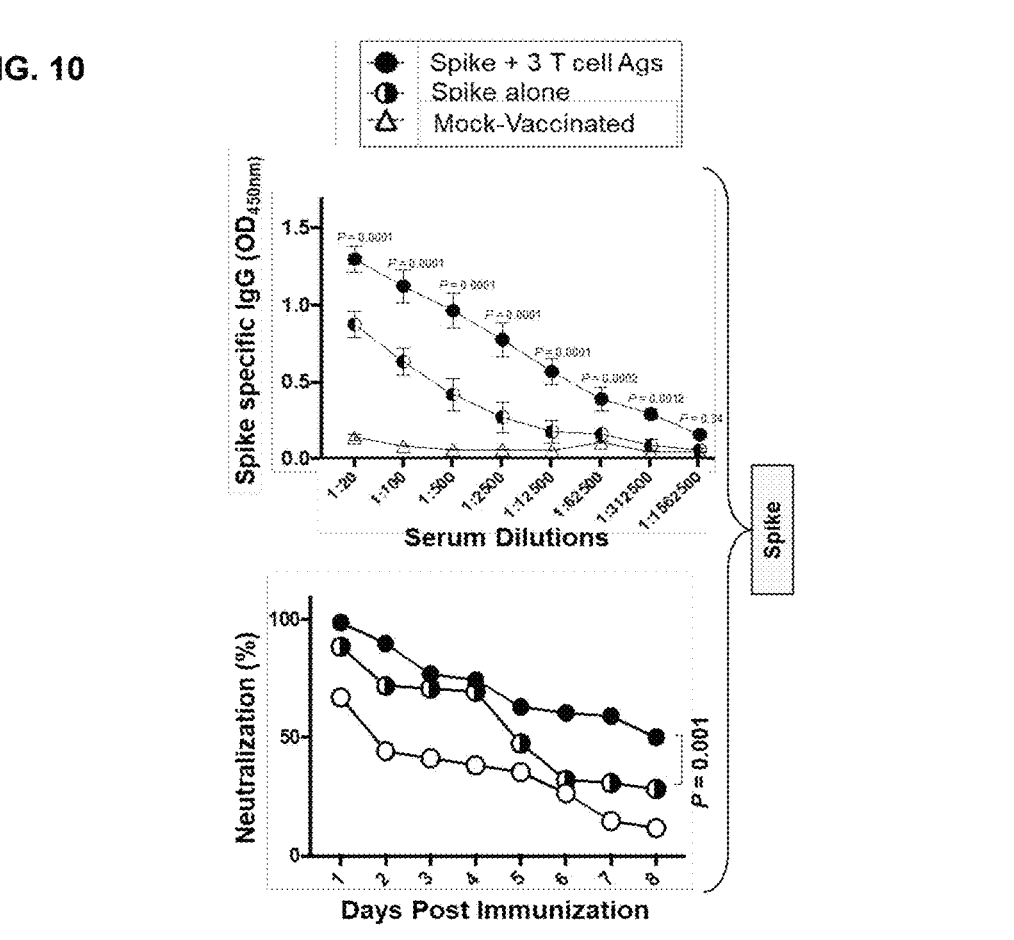

FIG. 10 shows a graph of the IgG level among hamsters vaccinated with a combination of NSP-2, NSP-14, and Nucleoprotein-based mRNA/LNP vaccines, spike alone vaccine, and mock vaccination (Top Panel). Neutralization assay data among the vaccinated and mock-vaccinated groups showing vaccine-induced serum-neutralizing activities (Bottom Panel). Comparison of the neutralizing antibodies induced by the combination of Spike mRNA/LNP vaccine and highly conserved protective T-cell Ags, NSP-2, NSP-14, and Nucleoprotein expressed as nucleoside-modified mRNA sequences derived from BA.2.75 Omicron sub-variant (BA2) and encapsulated in lipid nanoparticles (LNP). The data represent two independent experiments; the graphed values and bars represent the SD between the two experiments. Data are presented as median and IQR where appropriate. Data were analyzed by multiple t-tests. Results were considered statistically significant at P<0.05. The Mann-Whitney test (two groups) or the Kruskal-Wallis test (more than two groups) were used for statistical analysis. ns P>0.05, *P<0.05, P<0.01, *P<0.001, ****P<0.0001.

FIG. 11 shows Patient selection based on HLA-A*02:01 and HLA-DRB1*01:01 alleles: All the 600 patients enrolled in our study for were genotyped class I HLA-A*02:01 and class II HLA-DRB1*01:01 by PCR. Out of the 600 COVID-19 patients, 147 patients were positive for HLA-A*02:01 or/and HLA-DRB1*01:01 and were considered in this study. The 147 patients were from mixed ethnicities (Hispanic (28%), Hispanic Latino (22%), Asian (16%), Caucasian (13%), mixed Afro-American and Hispanic (8%), Afro-American (5%), mixed Afro-American and Caucasian (2%), Native Hawaiian and Other Pacific Islander descent (1%). Six percent of the patients did not reveal their race/ethnicity. The detailed demographic and clinical data for the 147 patients enrolled in this study are shown.

Symptomatic and Asymptomatic COVID-19 patient stratification based on disease severity: Following patient discharge, they were divided into six groups depending on the severity of their symptoms and their intensive care unit (ICU) and intubation (mechanical ventilation) status by medical practitioners. The scoring criteria were as follows: Severity 5: patients who died from COVID-19 complications; Severity 4: infected COVID-19 patients with severe disease who were admitted to the intensive care unit (ICU) and required ventilation support; Severity 3: infected COVID-19 patients with severe disease that required enrollment in ICU, but without ventilation support; Severity 2: infected COVID-19 patients with moderate symptoms that involved a regular hospital admission; Severity 1: infected COVID-19 patients with mild symptoms; and Severity 0: infected individuals with no symptoms. Among the 147 COVID-19 Patients, subjects with a Severity score of 0 were defined as Asymptomatic and subjects with a severity score of 1-5 were defined as Symptomatic.

Pre-Pandemic Healthy Controls: Subsequently, 15 liquid-nitrogen frozen PBMCs samples (blood collected pre-COVID-19 in 2018) from HLA-A*02:01+/HLA-DRB1*01:01+ unexposed pre-pandemic healthy individuals ((UPPHI) were used—8 males, 7 females; median age: 54 (20-76)) as controls to measure recalled SARS-CoV-2 cross-reactive T cell responses. The class-II HLA status of each patient was first screened for HLA-DRB1*01:01 by PCR. For class-I HLA, the screening was first performed (two-digit level) by HLA-A*02 flow cytometry staining (data not shown, mAbs clone BB7.2, BioLegend, San Diego, CA). The four-digit class-I HLA-A*02:01 subtype was subsequently screened by PCR on blood samples.

Figure 12A:
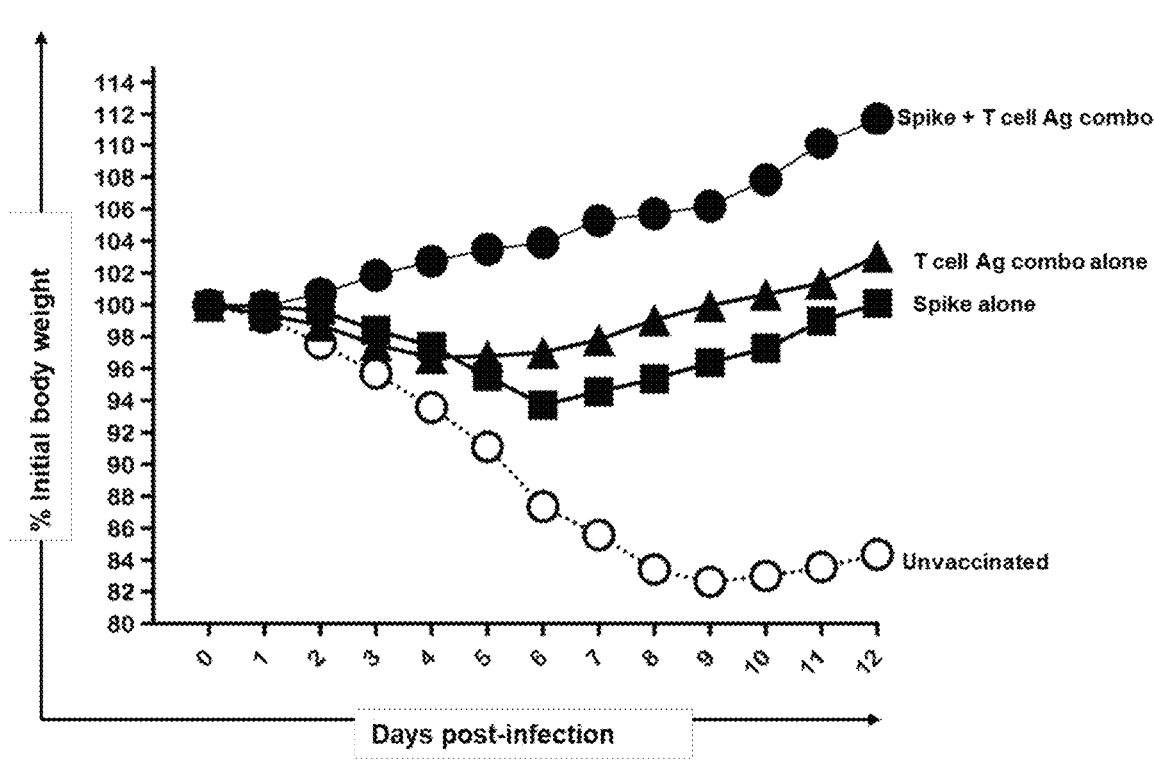

FIG. 12A show pre-clinical superiority of the mRNA-LNP Encoding Spike+T Cell Antigens Combination Vaccine described herein Versus mRNA-LNP Encoding Spike Protein Alone Against SARS-CoV-2 Delta (B.1.617.2) variant in hACE2 mice. The pre-Clinical protective efficacy of the Techlmmune mRNA-LNP encoding Spike+T Cell antigens combination vaccine versus Spike alone was assessed by measuring body weight loss of mRNA-LNP immunized hACE2 mice and challenged with $1 \times 10^5$ pfu of SARS-CoV-2 Delta (B.1.617.2) variant. The mice were followed-up for fourteen days post intranasal infection and their body weight was measured daily. The graph show the body weight of mice immunized with mRNA-LNP encoding for Spike 2P protein alone (Square), the body weight of mice immunized with mRNA-LNP encoding for T cell Ag (Nucleoprotein, NSP2 and NSP14) proteins (triangle); the body weight of mice immunized with mRNA-LNP encoding for Spike SP2+ T cell Ag (Nucleoprotein, NSP2 and NSP14) proteins (Black circle) and the Body weight of mock immunized (unvaccinated) mice (empty circle). Mice were followed-up for fourteen days for changes in body weight in each group of mice after challenge with SARS-CoV-2 Delta (B.1.617.2) variant. A two-tailed unpaired t-test was applied in the comparison of weight loss and survival rates between groups assuming Gaussian distribution. P<0.05 was statistically significant at a 95% confidence interval.

Figure 12B:
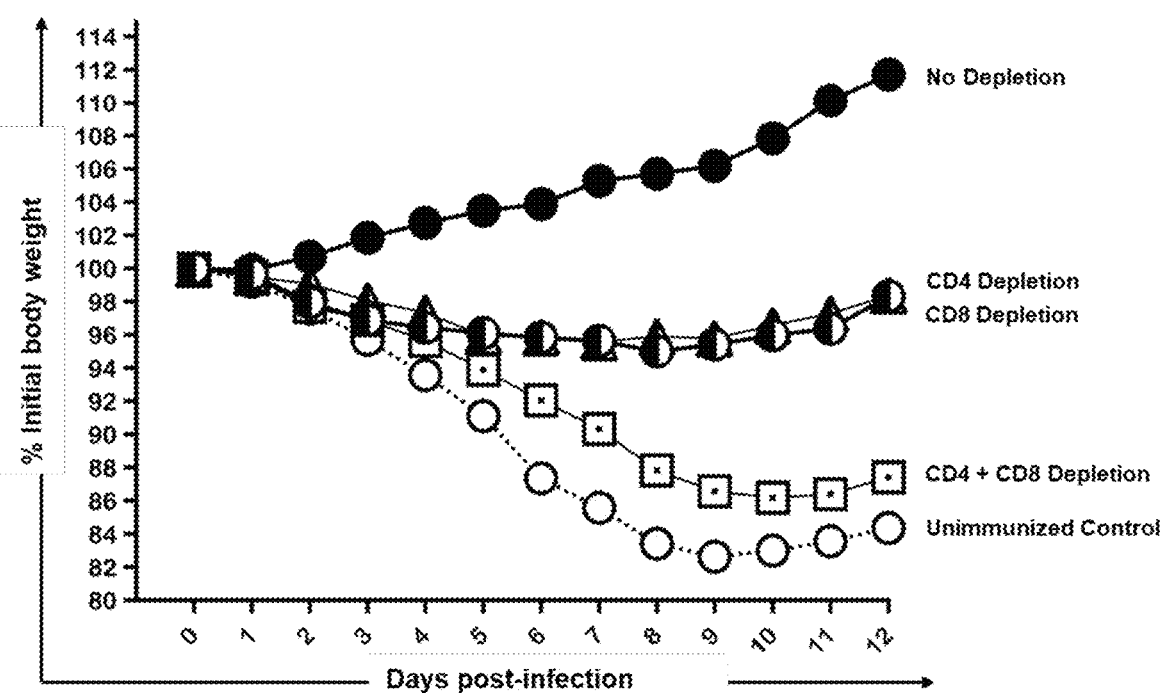

FIG. 12B shows the mRNA-LNP Encoding Spike+T Cell Antigens Combination Vaccine Protection is Mediated by CD4+ and CD8+ T-Cells. The effects of CD4+ and CD8+ T cell depletion on body weight loss against intranasal infection with SARS-CoV-2 Delta (B.1.617.2) variant were analyzed in Techlmmune mRNA-LNP encoding Spike+T cell antigens vaccinated hACE2 mice, CD4+ and/or CD8+ T cell depleted and challenged with $1 \times 10^5$ pfu of SARS-CoV-2 Delta (B.1.617.2) variant. The mice were followed-up for fourteen days post intranasal infection and their weight was measured daily. The graph show the body weight of mice immunized with the mRNA-LNP encoding for Spike SP2+ T cell Ag (Nucleoprotein, NSP2 and NSP14) proteins without depleted CD4+ and CD8+ T-cells (Black circle), or with depletion of CD4+ T cells (Triangle), depletion of CD8+ T-cell (circle half with half black), with both depletion of CD4+ and CD8+ T cells (empty square) and the Body weight of mock immunized (unvaccinated) mice (empty circle). CD4+ or CD8+ T cell depletion in mice immunized with mRNA-LNP was conducted by intraperitoneal injection (2 times) of 300 μg of anti-CD4 Ab (GK1.5) and/or anti-CD8a Ab (2.43). 2 days after the last depletion with anti-CD4 and/or anti-CD8 mAb injections, mice were followed-up for fourteen days for changes in body weight in each group of mice after challenge with SARS-CoV-2 Delta (B.1.617.2) variant. A two-tailed unpaired t-test was applied in the comparison of weight loss and survival rates between groups assuming Gaussian distribution. P<0.05 was statistically significant at a 95% confidence interval.

FIGS. 13A and 13B shows non-limiting examples of antigen combinations that may be used for the vaccine compositions described herein. The proteins may be covalently or non-covalently linked together for administration of the vaccine composition. Note: "Spike protein" may refer to a portion of the spike protein or a spike protein with one or more mutations (e.g., a spike protein with two or six proline substitutions). Additionally, proteins denoted in the figures may include only a portion of said protein. In some embodiments, the antigen combinations may be synthesized and delivered in a single delivery system. In other embodiments, the antigen combinations may be synthesized and delivered in different delivery systems.

TERMS

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessarily solely." Furthermore, variations of the word "comprising," such as "comprise" and "comprises," have correspondingly the same meanings. In one respect, the technology described herein is related to the herein described compositions, methods, and respective component(s) thereof, as essential to the invention, yet open to the inclusion of unspecified elements, essential or not ("comprising").

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999, Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), and the Ambion 1998 Catalog (Ambion, Austin, Tex.), the disclosures of which are incorporated in their entirety herein by reference.

Although methods and materials similar or equivalent to those described herein can be used to practice or test the disclosed technology, suitable methods and materials are described below. The materials, methods, and examples are illustrative only and are not intended to be limiting.

As used herein, the terms "immunogenic protein, polypeptide, or peptide" or "antigen" refer to polypeptides or other molecules (or combinations of polypeptides and other molecules) that are immunologically active in the sense that once administered to the host, it is able to evoke an immune response of the humoral and/or cellular type directed against the protein. In embodiments, the protein fragment has substantially the same immunological activity as the total protein. Thus, a protein fragment according to the disclosure can comprises or consists essentially of or consists of at least one epitope or antigenic determinant. An "immunogenic" protein or polypeptide, as used herein, may include the full-length sequence of the protein, analogs thereof, or immunogenic fragments thereof. "Immunogenic fragment" refers to a fragment of a protein that includes one or more epitopes and thus elicits the immunological response described above.

Synthetic antigens are also included within the definition, for example, poly-epitopes, flanking epitopes, and other recombinant or synthetically derived antigens. Immunogenic fragments for purposes of the disclosure may feature at least about 1 amino acid, at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or the full-length of the protein sequence, or even a fusion protein comprising at least one epitope of the protein.

As used herein, the term "epitope" refers to the site on an antigen or hapten to which specific B cells and/or T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

As used herein, the term "immunological response" to a composition or vaccine refers to the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. The host may display either a therapeutic or protective immunological response, so resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "variant" refers to a substantially similar sequence. For polynucleotides, a variant comprises a deletion and/or addition and/or change of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or an amino acid sequence, respectively. Variants of a particular polynucleotide of the disclosure (e.g., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present disclosure are biologically active; that is, they have the ability to elicit an immune response.

As used herein, the terms "treat" or "treatment" or "treating" refer to both therapeutic treatment and prophylactic or preventative measures, wherein the object is to prevent or slow the development of the disease, such as slow down the development of a disorder, or reducing at least one adverse effect or symptom of a condition, disease or disorder, e.g., any disorder characterized by insufficient or undesired organ or tissue function. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" also includes ameliorating a disease, lessening the severity of its complications, preventing it from manifesting, preventing it from recurring, merely preventing it from worsening, mitigating an inflammatory response included therein, or a therapeutic effort to affect any of the aforementioned, even if such therapeutic effort is ultimately unsuccessful.

As used herein, the term "carrier," or "pharmaceutically acceptable carrier," or "pharmaceutically acceptable vehicle" refers to any appropriate or useful carrier or vehicle for introducing a composition to a subject. Pharmaceutically acceptable carriers or vehicles may be conventional but are not limited to conventional vehicles. For example, E. W. Martin, Remington's Pharmaceutical Sciences, Mack Publishing Co., Easton, PA, 15th Edition (1975) and D. B. Troy, ed. Remington: The Science and Practice of Pharmacy, Lippincott Williams & Wilkins, Baltimore MD and Philadelphia, PA, 21st Edition (2006) describe compositions and formulations suitable for pharmaceutical delivery of one or more therapeutic compounds or molecules. Carriers (e.g., pharmaceutical carriers, pharmaceutical vehicles, pharmaceutical compositions, pharmaceutical molecules, etc.) are materials generally known to deliver molecules, proteins, cells and/or drugs and/or other appropriate material into the body. In general, the nature of the carrier will depend on the nature of the composition being delivered as well as the particular mode of administration being employed. In addition to biologically-neutral carriers, pharmaceutical compositions administered may contain minor amounts of non-toxic auxiliary substances, such as wetting or emulsifying agents, preservatives, and pH buffering agents and the like. Patents that describe pharmaceutical carriers include, but are not limited to: U.S. Pat. Nos. 6,667,371; 6,613,355; 6,596, 296; 6,413,536; 5,968,543; 4,079,038; 4,093,709; 4,131, 648; 4,138,344; 4,180,646; 4,304,767; 4,946,931, the disclosures of which are incorporated in their entirety by reference herein. The carrier may, for example, be solid, liquid (e.g., a solution), foam, a gel, the like, or a combination thereof. In some embodiments, the carrier comprises a biological matrix (e.g., biological fibers, etc.). In some embodiments, the carrier comprises a synthetic matrix (e.g., synthetic fibers, etc.). In certain embodiments, a portion of the carrier may comprise a biological matrix and a portion may comprise synthetic matrix.

As used herein, "coronavirus" may refer to a group of related viruses such as but not limited to severe acute respiratory syndrome (SARS), Middle East respiratory syndrome (MERS), and severe acute respiratory syndrome coronavirus 2 (SARS-CoV-2). All the coronaviruses cause respiratory tract infections that range from mild to lethal in mammals. Several non-limiting examples of Coronavirus strains are described herein. In some embodiments, the compositions may protect against any Sarbecoviruses, including but not limited to SARS-CoV1 or SARS-CoV2. As used herein, "severe acute respiratory syndrome coronavirus 2 (SARS-CoV2)" is a betacoronavirus that causes Coronavirus Disease 19 (COVID-19).

A "subject" is an individual and includes, but is not limited to, a mammal (e.g., a human, horse, pig, rabbit, dog, sheep, goat, non-human primate, cow, cat, guinea pig, or rodent), a fish, a bird, a reptile, or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects The terms "administering" and "administration" refer to methods of providing a pharmaceutical preparation to a subject. Such methods are well known to those skilled in the art and include, but are not limited to, administering the compositions orally, parenterally (e.g., intravenously and subcutaneously), by intramuscular injection, by intraperitoneal injection, intrathecally, transdermally, extracorporeally, topically or the like.

A composition can also be administered by topical intranasal administration (intranasally) or administration by inhalant. As used herein, "topical intranasal administration" means delivery of the compositions into the nose and nasal passages through one or both of the nares and can comprise delivery by a spraying mechanism (device) or droplet mechanism (device), or through aerosolization of the composition. Administration of the compositions by inhalant can be through the nose or mouth via delivery by a spraying or droplet mechanism. As used herein, "an inhaler" can be a spraying device or a droplet device for delivering a composition comprising the vaccine composition, in a pharmaceutically acceptable carrier, to the nasal passages and the upper and/or lower respiratory tracts of a subject. Delivery can also be directly to any area of the respiratory system (e.g., lungs) via intratracheal intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

A composition can also be administered by buccal delivery or by sublingual delivery. As used herein "buccal delivery" may refer to a method of administration in which the compound is delivered through the mucosal membranes lining the cheeks. In some embodiment, for a buccal delivery the vaccine composition is placed between the gum and the cheek of a patient. As used herein "sublingual delivery" may refer to a method of administration in which the compound is delivered through the mucosal membrane under the tongue. In some embodiments, for a sublingual delivery the vaccine composition is administered under the tongue of a patient.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves the use of a slow-release or sustained-release system such that a constant dosage is maintained. See, for example, U.S. Pat. No. 3,610,795, which is incorporated by reference herein.

DETAILED DESCRIPTION OF THE INVENTION

Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting. Embodiments of the present invention can be freely combined with each other if they are not mutually exclusive.

Pre-Emptive Pan-Coronavirus Vaccines

The present invention features pre-emptive pan-coronavirus vaccines, methods of use, methods of producing said vaccines, methods of preventing coronavirus infections, etc. The present invention also provides methods of testing said vaccines, e.g., using particular animal models and clinical trials. The vaccine compositions herein can induce efficient and powerful protection against the coronavirus disease or infection, e.g., by inducing the production of antibodies (Abs), $CD4^+$ T helper (Th1) cells, and $CD8^+$ cytotoxic T-cells (CTL).

The present invention features a universal pre-emptive pan-coronavirus vaccine composition. In some embodiments, the composition may comprise two (or more) Coronavirus antigens derived from a) at least a portion of an NSP2 protein; b) at least a portion of an NSP14 protein; and c) at least a portion of a Nucleoprotein protein. In other embodiments, the composition may comprise three (or more) Coronavirus antigens derived from a) at least a portion of an NSP2 protein; b) at least a portion of an NSP14 protein; and c) at least a portion of a Nucleoprotein protein. In some embodiments, the composition comprises a sequence encoding two (or more) Coronavirus antigens derived from a) at least a portion of an NSP2 protein; b) at least a portion of an NSP14 protein; and c) at least a portion of a Nucleoprotein protein. In some embodiments, the composition comprises a sequence encoding three (or more) Coronavirus antigens derived from a) at least a portion of an NSP2 protein; b) at least a portion of an NSP14 protein; and c) at least a portion of a Nucleoprotein protein. The aforementioned composition may further comprise Coronavirus antigen derived from at least a portion of a Spike protein. For example, the composition may comprise two (or more) Coronavirus antigens derived from a) at least a portion of an NSP2 protein; b) at least a portion of an NSP14 protein; c) at least a portion of a Nucleoprotein protein and d) at least a portion of a Spike protein. In other embodiments, the composition may comprise three (or more) Coronavirus antigens derived from a) at least a portion of an NSP2 protein; b) at least a portion of an NSP14 protein; c) at least a portion of a Nucleoprotein protein and d) at least a portion of a Spike protein In some embodiments, the composition may comprise a sequence encoding two (or more) Coronavirus antigens derived from a) at least a portion of an NSP2 protein; b) at least a portion of an NSP14 protein; c) at least a portion of a Nucleoprotein protein and d) at least a portion of a Spike protein. In some embodiments, the composition may comprise a sequence encoding three (or more) Coronavirus antigens derived from a) at least a portion of an NSP2 protein; b) at least a portion of an NSP14 protein; c) at least a portion of a Nucleoprotein protein and d) at least a portion of a Spike protein.

Likewise, the present invention features a universal pre-emptive pan-Coronavirus vaccine composition. In some embodiments, the composition may comprise two (or more) Coronavirus antigens derived from a) an NSP2 protein; b) an NSP14 protein; and c) a Nucleoprotein protein. In some embodiments, the composition may comprise three (or more) Coronavirus antigens derived from a) an NSP2 protein; b) an NSP14 protein; and c) a Nucleoprotein protein. In some embodiments, the composition comprises a sequence encoding two (or more) Coronavirus antigens derived from a) an NSP2 protein; b) an NSP14 protein; and c) a Nucleoprotein protein. In some embodiments, the composition comprises a sequence encoding three (or more) Coronavirus antigens derived from a) an NSP2 protein; b) an NSP14 protein; and c) a Nucleoprotein protein. The aforementioned composition may further comprise Coronavirus antigen derived from a Spike protein. For example, the composition may comprise two (or more) Coronavirus antigens derived from a) an NSP2 protein; b) an NSP14 protein; c) Nucleoprotein protein and d) a Spike protein. In some embodiments, the composition may comprise three (or more) Coronavirus antigens derived from a) an NSP2 protein; b) an NSP14 protein; c) Nucleoprotein protein and d) a Spike protein. In some embodiments, the composition may comprise a sequence encoding two (or more) Coronavirus antigens derived from a) an NSP2 protein; b) an NSP14 protein; c) a Nucleoprotein protein and a Spike protein. In other embodiments, the composition may comprise a sequence encoding three (or more) Coronavirus antigens derived from a) an NSP2 protein; b) an NSP14 protein; c) a Nucleoprotein protein and a Spike protein.

Additionally, the present invention may also feature a pan-Coronavirus recombinant vaccine composition. In some embodiments, the composition comprising a delivery system encoding two (or more) Coronavirus antigens derived from a) at least a portion of an NSP2 protein; b) at least a portion of an NSP14 protein; and c) at least a portion of a Nucleoprotein protein. In other embodiments, the composition comprising a delivery system encoding three (or more) Coronavirus antigens derived from a) at least a portion of an NSP2 protein; b) at least a portion of an NSP14 protein; and c) at least a portion of a Nucleoprotein protein. The aforementioned delivery system may further encode a Coronavirus antigen derived from at least a portion of a Spike protein. Alternatively, the aforementioned delivery system may further comprise an additional delivery system encoding a Coronavirus antigens derived from at least a portion of a Spike protein. For example, the composition may comprise a delivery system encoding two (or more) Coronavirus antigens derived from: a) at least a portion of an NSP2 protein; b) at least a portion of an NSP14 protein; c) at least a portion of a Nucleoprotein protein; and d) at least a portion of a Spike protein. In some embodiments, the composition may comprise a delivery system encoding three (or more) Coronavirus antigens derived from: a) at least a portion of an NSP2 protein; b) at least a portion of an NSP14 protein; c)

at least a portion of a Nucleoprotein protein; and d) at least a portion of a Spike protein. The delivery system may comprise a single delivery system or may comprise two or more delivery systems.

Moreover, the present invention may feature a pan-Coronavirus recombinant vaccine composition. In some embodiments, the composition comprises a delivery system encoding two (or more) Coronavirus antigens derived from: a) an NSP2 protein; b) an NSP14 protein; and c) a Nucleoprotein protein. In some embodiments, the composition comprises a delivery system encoding three (or more) Coronavirus antigens derived from: a) an NSP2 protein; b) an NSP14 protein; and c) a Nucleoprotein protein. The aforementioned delivery system may further encode a Coronavirus antigen derived from a Spike protein. Alternatively, the aforementioned delivery system may further comprise an additional delivery system encoding a Coronavirus antigens derived from a Spike protein. For example, the composition may comprise a delivery system encoding two (or more) Coronavirus antigens derived from: a) an NSP2 protein; b) an NSP14 protein; c) a Nucleoprotein protein; and d) a Spike protein. In other embodiments, the composition may comprise a delivery system encoding three (or more) Coronavirus antigens derived from: a) an NSP2 protein; b) an NSP14 protein; c) a Nucleoprotein protein; and d) a Spike protein. The delivery system may comprise a single delivery system or may comprise two or more delivery systems.

Likewise, the present invention may feature a universal pre-emptive pan-Coronavirus vaccine composition comprising a B cell antigen and two (or three) or more T-cell antigens. In some embodiments, the universal pre-emptive pan-Coronavirus vaccine composition comprises a sequence encoding a B cell antigen and two (or three) or more T-cell antigens. In some embodiments, the universal pre-emptive pan-Coronavirus vaccine composition comprising a B cell antigen and three T-cell antigens. In other embodiments, the universal pre-emptive pan-Coronavirus vaccine composition comprises a sequence encoding a B cell antigen and three T-cell antigens. The B cell antigens may be derived from a Coronavirus Spike protein or portion thereof. Whereas, the T cell antigens may be derived from an NSP2 protein or portion thereof, an NSP14 protein or portion thereof, a Nucleoprotein or portion thereof, or a combination thereof. In certain embodiments, the T cell antigens may be derived from an NSP3 protein or portion thereof, an NSP12 protein or portion thereof, or a protein encoded by ORF7a/b or portion thereof.

The present invention features may further universal pre-emptive pan-Coronavirus vaccine composition comprising two or more large sequences derived from at least a portion of an NSP2 protein; at least a portion of an NSP14 protein; at least a portion of a Nucleoprotein protein; and at least a portion of a Spike protein. In some embodiments, the universal pre-emptive pan-Coronavirus vaccine composition comprises at least three or more large sequences derived from at least a portion of an NSP2 protein; at least a portion of an NSP14 protein; at least a portion of a Nucleoprotein protein; and at least a portion of a Spike protein.

Referring to FIG. 13A, the aforementioned Coronavirus antigens may be the Spike protein (or a portion thereof) and the NSP2 protein (or a portion thereof). In some embodiments, the Coronavirus antigens may be the Spike protein (or a portion thereof) and the NSP14 protein (or a portion thereof). In some embodiments, the Coronavirus antigens may be the Spike protein (or a portion thereof) and the Nucleoprotein (or a portion thereof). In some embodiments, the Coronavirus antigens may be the Spike protein (or a portion thereof), the NSP2 protein (or a portion thereof), and the NSP14 protein (or a portion thereof). In some embodiments, the Coronavirus antigens may be the Spike protein (or a portion thereof), the NSP2 protein (or a portion thereof), and the Nucleoprotein (or a portion thereof). In some embodiments, the Coronavirus antigens may be the Spike protein (or a portion thereof), the NSP14 protein (or a portion thereof), and the Nucleoprotein (or a portion thereof). In some embodiments, the Coronavirus antigens may be the Spike protein (or portion thereof); the NSP2 protein (or a portion thereof); the NSP14 protein (or a portion thereof); and the Nucleoprotein (or a portion thereof). In some embodiments, the Spike protein (or a portion thereof) comprises one or more proline substitutions. Portions of the aforementioned may comprise immunogenic fragments.

Referring to FIG. 13B, the aforementioned composition, in certain embodiments, may further comprise one or more Coronavirus antigens derived from an NSP3 protein or portion thereof, a NSP12 protein or portion thereof, or a protein encoded by ORF7a/b or portion thereof. In some embodiments, the aforementioned composition may further comprise two or more Coronavirus antigens derived from an NSP3 protein or portion thereof, a NSP12 protein or portion thereof, or a protein encoded by ORF7a/b or portion thereof. In other embodiments, the aforementioned composition may further comprise three or more Coronavirus antigens derived from an NSP3 protein or portion thereof, a NSP12 protein or portion thereof, or a protein encoded by ORF7a/b or portion thereof. The present invention is not limited to the aforestated Coronavirus antigens.

The vaccine compositions herein may feature multiple antigens, e.g., large sequences, which may comprise multiple conserved epitopes, that help provide multiple opportunities for the body to develop an immune response for preventing infection. Further, the vaccines herein may be designed to be effective against past, current, and future coronavirus outbreaks.

The vaccine composition comprises multiple antigens. In certain embodiments, the antigens are conserved antigens, e.g., antigens that are highly conserved among human coronaviruses and/or animal coronaviruses (e.g., coronaviruses isolated from animals susceptible to coronavirus infections). In certain embodiments, the vaccine composition comprises multiple large sequences. In certain embodiments, the large sequences are conserved large sequences, e.g., sequences that are highly conserved among human coronaviruses and/ or animal coronaviruses (e.g., coronaviruses isolated from animals susceptible to coronavirus infections).

Coronaviruses used for determining conserved antigens may include human SARS-CoVs as well as animal CoVs (e.g., bats, pangolins, civet cats, minks, camels, etc.) as described herein. A phylogenetic analysis was performed between SARS-CoV-2 strains (obtained from humans (*Homo Sapiens*), along with the animal's SARS-like Coronaviruses genome sequence (SL-CoVs) sequences obtained from bats (*Rhinolophus affinis, Rhinolophus malayanus*), pangolins (*Manis javanica*), civet cats (*Paguma larvata*), and camels (*Camelus dromedarius*). The included SARS-CoV/MERS-CoV strains are from previous outbreaks (obtained from humans (Urbani, MERS-CoV, OC43, NL63, 229E, HKU1-genotype-B), bats (WIV16, WIV1, YNLF-31C, Rs672, recombinant strains), camel (*Camelus dromedarius*, (KT368891.1, MN514967.1, KF917527.1, NC_028752.1), and civet (Civet007, A022, B039)). The human SARS-CoV-2 genome sequences are represented from six continents. An evolutionary analysis performed among the human-SARS-CoV-2 genome sequences reported from six continents and SARS-CoV-2 genome sequences obtained from bats (*Rhinolophus* affinis, *Rhinolophus malayanus*), and pangolins (*Manis javanica*).

Additionally, other coronaviruses may be used for determining conserved antigens (including human SARS-CoVs as well as animal CoVs (e.g., bats, pangolins, civet cats, minks, camels, etc.)) that meet the criteria to be classified as "variants of concern" or "variants of interest." Coronavirus variants that appear to meet one or more of the undermentioned criteria may be labeled "variants of interest" or "variants under investigation" pending verification and validation of these properties. In some embodiments, the criteria may include increased transmissibility, increased morbidity, increased mortality, increased risk of "long COVID," ability to evade detection by diagnostic tests, decreased susceptibility to antiviral drugs (if and when such drugs are available), decreased susceptibility to neutralizing antibodies, either therapeutic (e.g., convalescent plasma or monoclonal antibodies) or in laboratory experiments, ability to evade natural immunity (e.g., causing reinfections), ability to infect vaccinated individuals, increased risk of particular conditions such as multisystem inflammatory syndrome or long-haul COVID or Increased affinity for particular demographic or clinical groups, such as children or immunocompromised individuals. Once validated, variants of interest are renamed "variant of concern" by monitoring organizations, such as the CDC.

The antigens, e.g., conserved antigens may be derived from structural (e.g., spike glycoprotein, or Nucleoprotein) or non-structural proteins of the coronaviruses (e.g., any of the 16 NSPs, e.g., NSP2 and NSP14, encoded by ORF a/b).

In some embodiments, the antigens, e.g., large sequences are each highly conserved among one or a combination of: SARS-CoV-2 human strains, SL-CoVs isolated from bats, SL-CoVs isolated from pangolin, SL-CoVs isolated from civet cats, and MERS strains isolated from camels. For example, in certain embodiments, the antigens, e.g., large sequences are each highly conserved among one or a combination of: at least 50,000 SARS-CoV-2 human strains, five SL-CoVs isolated from bats, five SL-CoVs isolated from pangolin, three SL-CoVs isolated from civet cats, and four MERS strains isolated from camels. In certain embodiments, the antigens, e.g., large sequences are each highly conserved among one or a combination of: at least 80,000 SARS-CoV-2 human strains, five SL-CoVs isolated from bats, five SL-CoVs isolated from pangolin, three SL-CoVs isolated from civet cats, and four MERS strains isolated from camels. In certain embodiments, the antigens, e.g., large sequences are each highly conserved among one or a combination of: at least 50,000 SARS-CoV-2 human strains in circulation during the COVID-19 pandemic, at least one CoV that caused a previous human outbreak, five SL-CoVs isolated from bats, five SL-CoVs isolated from pangolin, three SL-CoVs isolated from civet cats, and four MERS strains isolated from camels. In certain embodiments, the antigens, e.g., large sequences are each highly conserved among at least 1 SARS-CoV-2 human strain in current circulation, at least one CoV that has caused a previous human outbreak, at least one SL-CoV isolated from bats, at least one SL-CoV isolated from pangolin, at least one SL-CoV isolated from civet cats, and at least one MERS strain isolated from camels. In certain embodiments, the antigens, e.g., large sequences are each highly conserved among at least 1,000 SARS-CoV-2 human strains in current circulation, at least two CoVs that have caused a previous human outbreak, at least two SL-CoVs isolated from bats, at least two SL-CoVs isolated from pangolin, at least two SL-CoVs isolated from civet cats, and at least two MERS strains isolated from camels. In certain embodiments, the antigens, e.g., large sequences are each highly conserved among one or a combination of: at least one SARS-CoV-2 human strain in current circulation, at least one CoV that has caused a previous human outbreak, at least one SL-CoV isolated from bats, at least one SL-CoV isolated from pangolin, at least one SL-CoV isolated from civet cats, and at least one MERS strain isolated from camels. The present invention is not limited to the aforementioned coronavirus strains that may be used to identify conserved antigens, e.g., large sequences.

In certain embodiments, one or more of the conserved antigens, e.g., large sequences are derived from one or more SARS-CoV-2 human strains or variants in current circulation; one or more coronaviruses that have caused a previous human outbreak; one or more coronaviruses isolated from animals selected from a group consisting of bats, pangolins, civet cats, minks, camels, and other animal receptive to coronaviruses; and/or one or more coronaviruses that cause the common cold. SARS-CoV-2 human strains and variants in current circulation may include the original SARS-CoV-2 strain (SARS-CoV-2 isolate Wuhan-Hu-1), and several variants of SARS-CoV-2 including but not limited to variant B.1.177 (Spain); variant B.1.160 (Australia), variant B.1.1.7 (UK), variant P.1 (Japan/Brazil), variant B.1.351 (South Africa), variant B.1.427 (California), variant B.1.429 (California), variant B.1.258 (Scotland); variant B.1.221 (Belgium/Netherlands); variant B.1.367 (Norway/France); variant B.1.1.277 (UK); variant B.1.1.302 (Sweden); variant B.1.525 (North America, Europe, Asia, Africa, and Australia); variant B.1.526 (New York), variant S:677H; variant S:677P; B.1.617.2-Delta, variant B.1.1.529-Omicron (BA.1); sub-variant Omicron (BA.1); sub-variant Omicron (BA.2); sub-variant Omicron (BA.3); sub-variant Omicron (BA.4); sub-variant Omicron (BA.5). The present invention is not limited to the aforementioned variants of SARS-CoV-2 and encompasses variants identified in the future. The one or more coronaviruses that cause the common cold may include but are not limited to strains 229E (alpha coronavirus), NL63 (alpha coronavirus), OC43 (beta coronavirus), HKU1 (beta coronavirus).

As used herein, the term "conserved" refers to an antigen or large sequence that is among the most highly conserved antigen or large sequences identified in a sequence alignment and analysis. For example, the conserved antigen or large sequences may be the 2 most highly conserved sequences identified. In some embodiments, the conserved antigen or large sequences may be the 3 most highly conserved sequences identified. In some embodiments, the conserved antigen or large sequences may be the 4 most highly conserved sequences identified. In some embodiments, the conserved antigen or large sequences may be the 5 most highly conserved sequences identified. In some embodiments, the conserved antigen or large sequences may be the 6 most highly conserved sequences identified. In some embodiments, the conserved antigen or large sequences may be the 7 most highly conserved sequences identified. In some embodiments, the conserved antigen or large sequences may be the 8 most highly conserved sequences identified. In some embodiments, the conserved antigen or large sequences may be the 9 most highly conserved sequences identified. In some embodiments, the conserved antigen or large sequences may be the 10 most highly conserved sequences identified. In some embodiments, the conserved antigen or large sequences may be the 15 most highly conserved sequences identified. In some embodiments, the conserved antigen or large sequences may be the 20 most highly conserved sequences identified. In some embodiments, the conserved antigen or large sequences may be the 25 most highly conserved sequences identified. In some embodiments, the conserved antigen or large sequences may be the 30 most highly conserved sequences identified. In some embodiments, the conserved antigen or large sequences may be the 40 most highly conserved sequences identified. In some embodiments, the conserved antigen or large sequences may be the 50 most highly conserved sequences identified. In some embodiments, the conserved sequences may be the 50% most highly conserved antigen or large sequences identified. In some embodiments, the conserved antigen or large sequences may be the 60% most highly conserved sequences identified. In some embodiments, the large conserved sequences may be the 70% most highly conserved sequences identified. In some embodiments, the conserved antigen or large sequences may be the 80% most highly conserved sequences identified. In some embodiments, the conserved antigen or large sequences may be the 90% most highly conserved sequences identified. In some embodiments, the conserved antigen or large sequences may be the 95% most highly conserved sequences identified. In some embodiments, the conserved antigen or large sequences may be the 99% most highly conserved sequences identified. The present invention is not limited to the aforementioned thresholds.

In some embodiments, the composition comprises one or more antigens. In some embodiments, the one or more antigens comprise at least one of one or more conserved coronavirus B-cell target epitopes; one or more conserved coronavirus CD4+ T cell target epitopes; and one or more conserved coronavirus CD8+ T cell target epitopes. In other embodiments, the vaccine composition comprises two or more antigens. In some embodiments, the two or more antigens comprise at least one of one or more conserved coronavirus B-cell target epitopes; one or more conserved coronavirus CD4+ T cell target epitopes; and one or more conserved coronavirus CD8+ T cell target epitopes.

In some embodiments, the composition comprises one or more large sequences. In some embodiments, the one or more large sequences comprise at least one of one or more conserved coronavirus B-cell target epitopes; one or more conserved coronavirus CD4+ T cell target epitopes; and one or more conserved coronavirus CD8+ T cell target epitopes. In other embodiments, the vaccine composition comprises two or more large sequences. In some embodiments, the two or more large sequences comprise at least one of one or more conserved coronavirus B-cell target epitopes; one or more conserved coronavirus CD4+ T cell target epitopes; and one or more conserved coronavirus CD8+ T cell target epitopes.

The antigens may be each separated by a linker. In certain embodiments, the linker allows for an enzyme to cleave between the antigens. The present invention is not limited to particular linkers or particular lengths of linkers. As an example, in certain embodiments, one or more antigens may be separated by a linker 2 amino acids in length, or a linker 3 amino acids in length, or a linker 4 amino acids in length, or a linker 5 amino acids in length, or a linker 6 amino acids in length, or a linker 7 amino acids in length, or a linker 8 amino acids in length, or a linker 9 amino acids in length, or a linker 10 amino acids in length. In certain embodiments, one or more antigens may be separated by a linker from 2 to 10 amino acids in length.

Linkers are well known to one of ordinary skill in the art. Non-limiting examples of linkers include AAY, KK, and GPGPG (SEQ ID NO: 40).

The antigens, e.g., large sequences may be derived from structural proteins, non-structural proteins, or a combination thereof. For example, structural proteins may include spike proteins (S) or Nucleoproteins (N), and non-structural proteins may include NSP2 and NSP14, encoded by ORF1a/b.

In some embodiments, the antigens are derived from at least one SARS-CoV-2 protein. The SARS-CoV-2 proteins may include ORF1ab protein, Spike glycoprotein, ORF3a protein, Envelope protein, Membrane glycoprotein, ORF6 protein, ORF7a protein, ORF7b protein, ORF8 protein, Nucleoprotein protein, and ORF10 protein. The ORF1ab protein provides nonstructural proteins (Nsp) such as Nsp1, Nsp2, Nsp3 (Papain-like protease), Nsp4, Nsp5 (3C-like protease), Nsp6, Nsp7, Nsp8, Nsp9, Nsp10, Nsp11, Nsp12 (RNA polymerase), Nsp13 (5' RNA triphosphatase enzyme), Nsp14 (guanosineN7-methyltransferase), Nsp15 (endoribonuclease), and Nsp16 (2'-O-ribose-methyltransferase). In certain embodiments, the SARS-CoV-2 proteins include Spike glycoprotein, Nucleoprotein protein, Nsp2, Nsp14, or a combination thereof.

The SARS-CoV-2 has a genome length of 29,903 base pairs (bps) ssRNA. Generally, the region between 266-21555 bps codes for ORF1ab polypeptide; the region between 21563-25384 bps codes for one of the structural proteins (spike protein or surface glycoprotein); the region between 25393-26220 bps codes for the ORF3a gene; the region between 26245-26472 bps codes for the envelope protein; the region between 26523-27191 codes for the membrane glycoprotein (or membrane protein); the region between 27202-27387 bps codes for the ORF6 gene; the region between 27394-27759 bps codes for the ORF7a gene; the region between 27894-28259 bps codes for the ORF8 gene; the region between 28274-29533 bps codes for the Nucleoprotein phosphoprotein (or the Nucleoprotein protein); and the region between 29558-29674 bps codes for the ORF10 gene.

The antigens may comprise a T-cell epitope restricted to a large number of human class 1 and class 2 HLA haplotypes and not restricted to HLA-0201 for class 1 or HLA-DR for class 2. The conserved antigens may be restricted to human HLA class 1 and 2 haplotypes. In some embodiments, the conserved epitopes are restricted to cat and dog MHC class 1 and 2 haplotypes.

The vaccine compositions described herein protects against disease caused by one or more coronavirus variants or coronavirus subvariants. In some embodiments, the coronavirus variants or coronavirus subvariants comprise past or currently circulating coronavirus variants or coronavirus subvariants, including, but not limited to, alpha, beta, gamma, delta, and omicron. In other embodiments, the coronavirus variants or coronavirus subvariants comprise future variants or future subvariants of human and animal coronavirus.

The vaccine compositions described herein may also protect against infection and reinfection of coronavirus variants or coronavirus subvariants. In some embodiments, the coronavirus variants or coronavirus subvariants comprise past or currently circulating coronavirus variants or coronavirus subvariants, including but not limited to alpha, beta, gamma, delta, and omicron. In other embodiments, the coronavirus variants or coronavirus subvariants comprise future variants or future subvariants of human and animal coronavirus.

The vaccine compositions described herein protects against infection or reinfection of one or more coronavirus variants or coronavirus subvariants. In some embodiments, the vaccine composition described herein against infection or reinfection of multiple coronavirus variants or coronavirus subvariants. In other embodiments, the vaccine composition described herein composition protects against infection or re-infection caused by one coronavirus variant or coronavirus subvariant.

In some embodiments, the vaccine composition induces strong and long-lasting protection mediated by antibodies (Abs), CD4+ T helper (Th1) cells, and/or CD8+ cytotoxic T-cells (CTL).

Antigens/Large Sequences:

The antigen may comprise large sequences, such as conserved large sequences that are highly conserved among human and animal coronaviruses. As used herein, the term large sequence refers to a sequence having at least 25 amino acids or at least 75 nucleotides. The large sequences comprise epitopes, such as the conserved epitopes described herein.

In some embodiments, the large sequence has at least 75 nt. In some embodiments, the large sequence has at least 150 nt. In some embodiments, the large sequence has at least 200 nt. In some embodiments, the large sequence has at least 250 nt. In some embodiments, the large sequence has at least 300 nt. In some embodiments, the large sequence has at least 400 nt. In some embodiments, the large sequence has at least 500 nt. In some embodiments, the large sequence has at least 600 nt. In some embodiments, the large sequence has at least 700 nt. In some embodiments, the large sequence has at least 800 nt. In some embodiments, the large sequence has at least 900 nt. In some embodiments, the large sequence has at least 1000 nt. In some embodiments, the large sequence has at least 1500 nt. In some embodiments, the large sequence has at least 2000 nt.

In some embodiments, the vaccine composition comprises one antigen. In some embodiments, the vaccine composition comprises one or more antigens. In some embodiments, the vaccine composition comprises two antigens. In some embodiments, the vaccine composition comprises two or more antigens.

In some embodiments, the vaccine composition comprises three antigens. In some embodiments, the vaccine composition comprises three or more antigens. In some embodiments, the vaccine composition comprises four antigens. In some embodiments, the vaccine composition comprises four or more antigens. In some embodiments, the vaccine composition comprises five or more antigens, e.g., 5, 6, 7, 8, etc. In some embodiments, the vaccine composition comprises one antigen.

In some embodiments, the vaccine composition comprises one large sequence. In some embodiments, the vaccine composition comprises one or more large sequences. In some embodiments, the vaccine composition comprises two or more large sequences. In some embodiments, the vaccine composition comprises three or more large sequences. In some embodiments, the vaccine composition comprises four or more large sequences. In some embodiments, the vaccine composition comprises five or more large sequences, e.g., 5, 6, 7, 8, etc.

In some embodiments, the antigens, e.g., large sequences are derived from a whole protein sequence expressed by SARS-CoV-2. In other embodiments, the antigens, e.g., large sequences are derived from a partial protein sequence expressed by SARS-CoV-2. In some embodiments, the antigens, e.g., large sequence of said proteins comprises B cell epitopes and T-cell epitopes that are restricted to a large number, e.g., from 3 to 10, different haplotypes that encompass 100% of the population regardless of race and ethnicity) of human class 1 and class 2 HLA haplotypes, so they are not restricted only to HLA-0201 for class 1 or HLA-DR1 for class 2.

As previously discussed, the antigens, e.g., large sequences may be highly conserved among human and animal coronaviruses. In some embodiments, the antigens, e.g., large sequences are derived from one or a combination of: one or more SARS-CoV-2 human strains or variants in current circulation; one or more coronaviruses that have caused a previous human outbreak; one or more coronaviruses isolated from animals selected from a group consisting of bats, pangolins, civet cats, minks, camels, and other animal receptive to coronaviruses; and/or one or more coronaviruses that cause the common cold.

As previously discussed, the SARS-CoV-2 human strains or variants in current circulation may include variant B.1.177; variant B.1.160, variant B.1.1.7 (UK), variant P.1 (Japan/Brazil), variant B.1.351 (South Africa), variant B.1.427 (California), variant B.1.429 (California), variant B.1.258; variant B.1.221; variant B.1.367; variant B.1.1.277; variant B.1.1.302; variant B.1.525; variant B.1.526, variant S:677H; variant S:677P; B.1.617.2-Delta, variant B.1.1.529-Omicron (BA.1); sub-variant Omicron (BA.1); sub-variant Omicron (BA.2); sub-variant Omicron (BA.3); sub-variant Omicron (BA.4); sub-variant Omicron (BA.5). In some embodiments, the one or more coronaviruses that cause the common cold are selected from 229E alpha coronavirus, NL63 alpha coronavirus, OC43 beta coronavirus, and HKU1 beta coronavirus.

The antigen(s), e.g., large sequence(s) may be derived from structural proteins, non-structural proteins, or a combination thereof. The large sequence(s) may be selected from ORF1ab protein, Spike glycoprotein (e.g., the RBD), ORF3a protein, Envelope protein, Membrane glycoprotein, ORF6 protein, ORF7a protein, ORF7b protein, ORF8 protein, Nucleoprotein protein, and/or an ORF10 protein. Note the ORF1ab protein comprises nonstructural protein (Nsp) 1, Nsp2, Nsp3, Nsp4, Nsp5, Nsp6, Nsp7, Nsp8, Nsp9, Nsp10, Nsp11, Nsp12, Nsp13, Nsp14, Nsp15 and Nsp16. In certain embodiments, the large sequence(s) may be selected from ORF1ab protein (encoding Nsp2 and Nsp14), Spike glycoprotein (e.g., the RBD), Nucleoprotein protein, or a combination thereof.

In some embodiments, the present invention features a universal pre-emptive pan-coronavirus vaccine composition. In some embodiments, the composition may comprise a sequence encoded by or comprises two (or three) or more Coronavirus antigens derived from a) at least a portion of an NSP2 protein; b) at least a portion of an NSP14 protein; and c) at least a portion of a Nucleoprotein protein. The aforementioned composition may further comprise Coronavirus antigen derived from at least a portion of a Spike protein. For example, the composition may comprise a sequence encoded by or comprises two (or three) Coronavirus antigens derived from a) at least a portion of an NSP2 protein; b) at least a portion of an NSP14 protein; c) at least a portion of a Nucleoprotein protein and d) at least a portion of a Spike protein. See Table 1.

In some embodiments, the present invention features a universal pre-emptive pan-Coronavirus vaccine composition comprising two or more large sequences derived from at least a portion of an NSP2 protein, at least a portion of an NSP14 protein, at least a portion of a Nucleoprotein protein, and at least a portion of a Spike protein (See Table 1).

TABLE 1

| SARS-CoV-2 Omicron sub-variant BA.2 | | |
| --- | --- | --- |
| Antigens | Sequence | SEQ ID NO: |
| NSP2 | ATGGCATACACTCGCTATGTCGATAACAACTTCTGTGGC CCTGATGGCTACCCTCTTGAGTGCATTAAAGACCTTCTA GCACGTGCTGGTAAAGCTTCATGCACTTTGTCCGAACAA CTGGACTTTATTGACACTAAGAGGGGTGTATACTGCTGC CGTGAACATGAGCATGAAATTGCTTGGTACACGGAACG TTCTGAAAAGAGCTATGAATTGCAGACACCTTTTGAAAT TAAATTGGCAAAGAAATTTGACACCTTCAATGGGGAAT GTCCAAATTTTGTATTTCCCTTAAATTCCATAATCAAGAC TATTCAACCAAGGGTTGAAAAGAAAAAGCTTGATGGCT TTATGGGTAGAATTCGATCTGTCTATCCAGTTGCGTCAC CAAATGAATGCAACCAAATGTGCCTTTCAACTCTCATGA AGTGTGATCATTGTGGTGAAACTTCATGGCAGACGGGCG ATTTTGTTAAAGCCACTTGCGAATTTTGTGGCACTGAGA ATTTGACTAAAGAAGGTGCCACTACTTGTGGTTACTTAC CCCAAAATGCTGTTGTTAAAATTTATTGTCCAGCATGTC ACAATTCAGAAGTAGGACCTGAGCATAGTCTTGCCGAAT ACCATAATGAATCTGGCTTGAAAACCATTCTTCGTAAGG GTGGTCGCACTATTGCCTTTGGAGGCTGTGTGTTCTCTTA TGTTGGTTGCCATAACAAGTGTGCCTATTGGGTTCCACG TGCTAGCGCTAACATAGGTTGTAACCATACAGGTGTTGT TGGAGAAGGTTCCGAAGGTCTTAATGACAACCTTCTTGA AATACTCCAAAAAGAGAAAGTCAACATCAATATTGTTG GTGACTTTAAACTTAATGAAGAGATCGCCATTATTTTGG CATCTTTTTCTGCTTCCACAAGTGCTTTTGTGGAAACTGT GAAAGGTTTGGATTATAAAGCATTCAAACAAATTGTTGA ATCCTGTGGTAATTTTAAAGTTACAAAAGGAAAAGCTAA AAAAGGTGCCTGGAATATTGGTGAACAGAAATCAATAC TGAGTCCTCTTTATGCATTTGCATCAGAGGCTGCTCGTGT TGTACGATCAATTTTCTCCCGCACTCTTGAAACTGCTCA AAATTCTGTGCGTGTTTTACAGAAGGCCGCTATAACAAT ACTAGATGGAATTTCACAGTATTCACTGAGACTCATTGA TGCTATGATGTTCACATCTGATTTGGCTACTAACAATCT | 1 |

TABLE 1-continued

| SARS-CoV-2 Omicron sub-variant BA.2 | | |
|---|---|---|
| Antigens | Sequence | SEQ ID NO: |
| | AGTTGTAATGGCCTACATTACAGGTGGTGTTGTTCAGTT GACTTCGCAGTGGCTAACTAACATCTTTGGCACTGTTTA TGAAAAACTCAAACCCGTCCTTGATTGGCTTGAAGAGAA GTTTAAGGAAGGTGTAGAGTTTCTTAGAGACGGTTGGGA AATTGTTAAATTTATCTCAACCTGTGCTTGTGAAATTGTC GGTGGACAAATTGTCACCTGTGCAAAGGAAATTAAGGA GAGTGTTCAGACATTCTTTAAGCTTGTAAATAAATTTTT GGCTTTGTGTGCTGACTCTATCATTATTGGTGGAGCTAA ACTTAAAGCCTTGAATTTAGGTGAAACATTTGTCACGCA CTCAAAGGGATTGTACAGAAAGTGTGTTAAATCCAGAG AAGAAACTGGCCTACTCATGCCTCTAAAAGCCCCAAAA GAAATTATCTTCTTAGAGGGAGAAACACTTCCCACAGAA GTGTTAACAGAGGAAGTTGTCTTGAAAACTGGTGATTTA CAACCATTAGAACAACCTACTAGTGAAGCTGTTGAAGCT CCATTGGTTGGTACACCAGTTTGTATTAACGGGCTTATG TTGCTCGAAATCAAAGACACAGAAAAGTACTGTGCCCTT GCACCTAATATGATGGTAACAAACAATACCTTCACACTC AAAGGCGGTTGATGA | |
| NSP2 (Codon Optimized) | ATGGCCTATACCAGGTACGTGGATAATAATTTCTGTGGG CCTGACGGCTACCCTCTGGAATGCATCAAAGACCTGTTG GCTAGGGCAGGAAAAGCTTCATGCACCCTGTCTGAGCA ACTTGACTTCATTGACACAAAGCGGGGAGTCTACTGCTG CCGCGAACATGAGCACGAGATTGCTTGGTACACAGAGC GAAGCGAAAAATCTTATGAACTGCAGACACCCTTTGAA ATCAAGTTAGCAAAGAAGTTCGACACCTTTAATGGCGA GTGCCCAAACTTTGTGTTCCCTCTGAATTCGATCATTAA AACCATCCAGCCTAGAGTAGAAAAAAAAAAGCTCGATG GTTTCATGGGCCGCATAAGATCTGTGTATCCTGTGGCTA GCCCCAACGAGTGTAACCAGATGTGTTTGTCAACCCTGA TGAAATGTGATCACTGTGGAGAAACGAGTTGGCAGACT GGAGACTTTGTTAAAGCTACTTGCGAATTCTGCGGGACA GAGAACCTCACCAAGGAGGGAGCAACCACGTGCGGTTA CCTGCCCCAAAATGCTGTAGTCAAAATCTACTGTCCGGC ATGCCATAACTCAGAGGTTGGGCCAGAGCATAGCTTGG CAGAGTACCATAATGAATCGGGACTTAAAACAATCCTG CGGAAGGGTGGCCGTACGATTGCCTTTGGAGGGTGCGTT TTCAGCTATGTGGGCTGCCACAACAAGTGCGCCTACTGG GTGCCCAGAGCCAGTGCCAACATTGGATGTAACCACAC AGGCGTCGTTGGGGAGGGCAGTGAGGGCTTGAATGACA ATCTTCTGGAGATTCTACAAAAGGAAAAGGTCAACATC AACATAGTTGGGGATTTCAAGCTGAACGAGGAGATTGC CATCATTTTAGCGTCCTTTTCTGCCTCAACAAGTGCCTTC GTGGAAACTGTGAAAGGGCTTGACTACAAGGCATTTAA GCAGATCGTGGAGTCCTGTGGCAACTTTAAAGTGACTAA GGGCAAGGCCAAAAAGGGGGCCTGGAATATAGGCGAAC AGAAGTCCATCCTGAGCCCTCTCTATGCTTTTGCTAGTG AAGCTGCCCGCGTTGTCCGGTCTATCTTCAGCCGAACTT TGGAGACTGCTCAGAACTCTGTCAGAGTCCTGCAGAAG GCAGCCATTACCATACTTGATGGGATATCTCAATACAGC CTCCGTCTGATTGATGCCATGATGTTTACTTCAGATCTCG CAACCAACAATCTCGTTGTGATGGCTTATATCACTGGGG GTGTGGTACAGCTGACGTCCCAGTGGCTGACTAATATAT TCGGGACCGTATATGAGAAGCTCAAGCCAGTGCTGGAC TGGCTGGAAGAGAAATTCAAGGAAGGTGTGGAATTTTT GAGGGACGGCTGGGAGATTGTGAAGTTTATTAGCACCT GTGCATGTGAGATTGTTGGCGGACAGATCGTGACATGTG CTAAGGAAATAAAAGAGAGTGTACAAACGTTCTTCAAA CTCGTGAATAAATTTTTAGCGCTATGTGCTGACTCCATC ATAATTGGCGGAGCCAAGTTAAAAGCGCTCAACTTGGG AGAGACATTTGTCACCCACTCCAAAGGTCTGTATAGGAA GTGTGTAAAGTCCAGAGAGGAGATCATCTTCTTAGAAGGA GAGACACTTCCGACTGAGGTCCTTACAGAAGAAGTGGT CCTCAAAACTGGTGATCTCCAGCCCCTAGAGCAGCCCAC ATCCGAGGCAGTCGAAGCCCCACTGGTGGGCACACCTG TGTGCATCAATGGACTCATGTTACTCGAAATCAAGGATA CCGAGAAGTACTGCGCACTGGCCCCTAACATGATGGTA ACCAATAACACATTCACCCTGAAAGGTGGTTGATAA | 2 |
| NSP2 (aa) | AYTRYVDNNFCGPDGYPLECIKDLLARAGKASCTLSEQLD FIDTKRGVYCCREHEHEIAWYTERSEKSYELQTPFEIKLAK KFDTFNGECPNFVFPLNSIIKTIQPRVEKKKLDGFMGRIRSV YPVASPNECNQMCLSTLMKCDHCGETSWQTGDFVKATCE FCGTENLTKEGATTCGYLPQNAVVKIYCPACHNSEVGPEH | 3 |

TABLE 1-continued

SARS-CoV-2 Omicron sub-variant BA.2

| Antigens | Sequence | SEQ ID NO: |
|---|---|---|
| | SLAEYHNESGLKTILRKGGRTIAFGGCVFSYVGCHNKCAY WVPRASANIGCNHTGVVGEGSEGLNDNLLEILQKEKVNINI VGDFKLNEEIAIILASFSASTSAFVETVKGLDYKAFKQIVES CGNFKVTKGKAKKGAWNIGEQKSILSPLYAFASEAARVVR SIFSRTLETAQNSVRVLQKAAITILDGISQYSLRLIDAMMFT SDLATNNLVVMAYITGGVVQLTSQWLTNIFGTVYEKLKPV LDWLEEKFKEGVEFLRDGWEIVKFISTCACEIVGGQIVTCA KEIKESVQTFFKLVNKFLALCADSIIIGGAKLKALNLGETFV THSKGLYRKCVKSREETGLLMPLKAPKEIIFLEGETLPTEVL TEEVVLKTGDLQPLEQPTSEAVEAPLVGTPVCINGLMLLEI KDTEKYCALAPNMMVTNNTFTLKGG | |
| NSP14 | ATGGCTGAAAATGTAACAGGACTCTTTAAAGATTGTAGT AAGGTAATCACTGGGTTACATCCTACACAGGCACCTACA CACCTCAGTGTTGACACTAAATTCAAAACTGAAGGTTTA TGTGTTGACGTACCTGGCATACCTAAGGACATGACCTAT AGAAGACTCATCTCTATGATGGGTTTTAAAATGAATTAT CAAGTTAATGGTTACCCTAACATGTTTATCACCCGCGAA GAAGCTATAAGACATGTACGTGCATGGATTGGCTTCGAT GTCGAGGGGTGTCATGCTACTAGAGAAGCTGTTGGTACC AATTTACCTTTACAGCTAGGTTTTTCTACAGGTGTTAACC TAGTTGCTGTACCTACAGGTTATGTTGATACACCTAATA ATACAGATTTTTCCAGAGTTAGTGCTAAACCACCGCCTG GAGATCAATTTAAACACCTCATACCACTTATGTACAAAG GACTTCCTTGGAATGTAGTGCGTATAAAGATTGTACAAA TGTTAAGTGACACACTTAAAAATCTCTCTGACAGAGTCG TATTTGTCTTATGGGCACATGGCTTTGAGTTGACATCTAT GAAGTATTTTGTGAAAATAGGACCTGAGCGCACCTGTTG TCTATGTGATAGACGTGCCACATGCTTTTCCACTGCTTCA GACACTTATGCCTGTTGGCATCATTCTATTGGATTTGATT ACGTCTATAATCCGTTTATGATTGATGTTCAACAATGGG GTTTTACAGGTAACCTACAAAGCAACCATGATCTGTATT GTCAAGTCCATGGTAATGCACATGTAGCTAGTTGTGATG CAATCATGACTAGGTGTCTAGCTGTCCACGAGTGCTTTG TTAAGCGTGTTGACTGGACTATTGAATATCCTATAATTG GTGATGAACTGAAGATTAATGCGGCTTGTAGAAAGGTTC AACACATGGTTGTTAAAGCTGCATTATTAGCAGACAAAT TCCCAGTTCTTCACGACATTGGTAACCCTAAAGCTATTA AGTGTGTACCTCAAGCTGATGTAGAATGGAAGTTCTATG ATGCACAGCCTTGTAGTGACAAAGCTTATAAAATAGAA GAATTATTCTATTCTTATGCCACACATTCTGACAAATTCA CAGATGGTGTATGCCTATTTTGGAATTGCAATGTCGATA GATATCCTGCTAATTCCATTGTTTGTAGATTTGACACTAG AGTGCTATCTAACCTTAACTTGCCTGGTTGTGATGGTGG CAGTTTGTATGTAAATAAACATGCATTCCACACACCAGC TTTTGATAAAAGTGCTTTTGTTAATTTAAAACAATTACC ATTTTTCTATTACTCTGACAGTCCATGTGAGTCTCATGGA AAACAAGTAGTGTCAGATATAGATTATGTACCACTAAA GTCTGCTACGTGTATAACACGTTGCAATTTAGGTGGTGC TGTCTGTAGACATCATGCTAATGAGTACAGATTGTATCT CGATGCTTATAACATGATGATCTCAGCTGGCTTTAGCTT GTGGGTTTACAAACAATTTGATACTTATAACCTCTGGAA CACTTTTACAAGACTTCAGTGATGA | 4 |
| NSP14 (Codon Optimized) | ATGGCTGAGAATGTCACAGGGCTGTTTAAGGACTGTTCC AAGGTGATAACAGGACTGCACCCAACACAGGCCCCTAC GCACTTGTCTGTTGACACAAAATTCAAAACAGAAGGACT CTGTGTGGATGTACCCGGCATCCCTAAAGACATGACCTA TCGCAGGCTCATCAGTATGATGGGCTTCAAGATGAACTA CCAGGTCAATGGCTACCCAAATATGTTCATCACCAGGGA GGAAGCTATTAGGCATGTGAGGGCCTGGATTGGTTTTGA CGTGGAAGGCTGTCATGCAACAAGAGAAGCAGTGGGGA CCAACTTACCTCTGCAGCTGGGGTTCAGCACTGGGGTCA ACCTGGTTGCTGTCCCAACTGGATATGTTGATACCCCCA ACAACACAGACTTCTCACGGGTCTCTGCAAAGCCTCCAC CTGGGGATCAGTTCAAGCACCTGATCCCATTAATGTATA AAGGTCTGCCCCTGGAATGTGGTAAGGATCAAAATTGTTC AGATGCTGAGTGACACTCTGAAGAACTTGAGTGACAGA GTTGTGTTTGTCCTGTGGGCTCATGGCTTTGAGCTGACC AGCATGAAGTACTTTGTGAAAATTGGACCAGAGAGAAC GTGCTGCCTGTGTGACCGACGGGCAACTTGTTTTTTCTAC CGCATCAGATACTTACGCCTGCTGGCACCATAGTATCGG CTTTGACTATGTCTACAACCCTTTCATGATTGATGTCCAG CAATGGGGCTTCACAGGAAATTTGCAGTCCAACCACGA CCTGTACTGCCAGGTCCATGGGAATGCTCACGTGGCCTC | 5 |

TABLE 1-continued

| SARS-CoV-2 Omicron sub-variant BA.2 | | |
|---|---|---|
| Antigens | Sequence | SEQ ID NO: |
| | CTGCGATGCTATCATGACACGATGTCTGGCTGTGCATGA GTGCTTTGTGAAGCGTGTCGACTGGACCATCGAATACCC CATTATTGGCGACGAGCTAAAAATAAATGCAGCGTGTA GAAAAGTGCAGCACATGGTGGTCAAGGCAGCACTCCTT GCTGACAAGTTTCCAGTATTACATGACATCGGCAACCCA AAGGCCATTAAGTGTGTTCCTCAAGCGGATGTGGAGTGG AAGTTCTATGATGCCCAGCCGTGCTCTGATAAAGCCTAC AAGATAGAAGAACTCTTTTATTCTTACGCTACTCACAGC GACAAATTTACAGATGGAGTTTGCCTCTTCTGGAACTGC AATGTCGATAGATATCCGGCCAACAGCATAGTGTGCCGC TTTGATACGCGCGTGCTATCCAACTTGAACCTCCCGGGT TGTGATGGCGGTTCGCTTTATGTAAATAAACATGCTTTC CACACACCTGCCTTCGACAAGTCCGCCTTTGTGAATCTG AAACAACTTCCCTTCTTCTACTACAGCGACAGCCCCTGC GAGTCCCACGGGAAGCAGGTGGTGAGTGATATTGACTA TGTCCCCCTTAAGTCAGCGACTTGCATCACTCGCTGTAA CCTTGGAGGAGCTGTTTGTCGGCACCACGCGAATGAGTA CCGACTCTACCTGGACGCCTATAACATGATGATCTCTGC CGGTTTCTCACTATGGGTATATAAGCAGTTTGATACCTA CAATTTGTGGAACACCTTCACCCGGCTCCAATGATAA | |
| NSP14 (aa) | AENVTGLFKDCSKVITGLHPTQAPTHLSVDTKFKTEGLCV DVPGIPKDMTYRRLISMMGFKMNYQVNGYPNMFITREEAI RHVRAWIGFDVEGCHATREAVGTNLPLQLGFSTGVNLVA VPTGYVDTPNNTDFSRVSAKPPPGDQFKHLIPLMYKGLPW NVVRIKIVQMLSDTLKNLSDRVVFVLWAHGFELTSMKYFV KIGPERTCCLCDRRATCFSTASDTYACWHHSIGFDYVYNPF MIDVQQWGFTGNLQSNHDLYCQVHGNAHVASCDAIMTR CLAVHECFVKRVDWTIEYPIIGDELKINAACRKVQHMVVK AALLADKFPVLHDIGNPKAIKCVPQADVEWKFYDAQPCSD KAYKIEELFYSYATHSDKFTDGVCLFWNCNVDRYPANSIV CRFDTRVLSNLNLPGCDGGSLYVNKHAFHTPAFDKSAFVN LKQLPFFYYSDSPCESHGKQVVSDIDYVPLKSATCITRONL GGAVCRHHANEYRLYLDAYNMMISAGFSL WVYKQFDTY NLWNTFTRLQ | 6 |
| Nucleoprotein | ATGTCTGATAATGGACCCCAAAATCAGCGAAATGCACTC CGCATTACGTTTGGTGGACCCTCAGATTCAACTGGCAGT AACCAGAATGGTGGGGCGCGATCAAAACAACGTCGGCC CCAAGGTTTACCCAATAATACTGCGTCTTGGTTCACCGC TCTCACTCAACATGGCAAGGAAGACCTTAAATTCCCTCG AGGACAAGGCGTTCCAATTAACACCAATAGCAGTCCAG ATGACCAAATTGGCTACTACCGAAGAGCTACCAGACGA ATTCGTGGTGGTGACGGTAAAATGAAAGATCTCAGTCCA AGATGGTATTTCTACTACCTAGGAACTGGGCCAGAAGCT GGACTTCCCTATGGTGCTAACAAAGACGGCATCATATGG GTTGCAACTGAGGGAGCCTTGAATACACCAAAAGATCA CATTGGCACCCGCAATCCTGCTAACAATGCTGCAATCGT GCTACAACTTCCTCAAGGAACAACATTGCCAAAAGGCTT CTACGCAGAAGGGAGCAGAGGCGGCAGTCAAGCCTCTT CTCGTTCCTCATCACGTAGTCGCAACAGTTCAAGAAATT CAACTCCAGGCAGCAGTAAACGAACTTCTCCTGCTAGAA TGGCTGGCAATGGCGGTGATGCTGCTCTTGCTTTGCTGC TGCTTGACAGATTGAACCAGCTTGAGAGCAAAATGTCTG GTAAAGGCCAACAACAACAAGGCCAAACTGTCACTAAG AAATCTGCTGCTGAGGCTTCTAAGAAGCCTCGGCAAAA ACGTACTGCCACTAAAGCATACAATGTAACACAAGCTTT CGGCAGACGTGGTCCAGAACAAACCCAAGGAAATTTTG GGGACCAGGAACTAATCAGACAAGGAACTGATTACAAA CATTGGCCGCAAATTGCACAATTTGCCCCCAGCGCTTCA GCGTTCTTCGGAATGTCGCGCATTGGCATGGAAGTCACA CCTTCGGGAACGTGGTTGACCTACACAGGTGCCATCAAA TTGGATGACAAAGATCCAAATTTCAAAGATCAAGTCATT TTGCTGAATAAGCATATTGACGCATACAAAACATTCCCA CCAACAGAGCCTAAAAAGGACAAAAAGAAGAAGGCTG ATGAAACTCAAGCCTTACCGCAGAGACAGAAGAAACAG CAAACTGTGACTCTTCTTCCTGCTGCAGATTTGGATGATT TCTCCAAACAATTGCAACAATCCATGAGCCGTGCTGACT CAACTCAGGCCTAATGATGA | 7 |
| Nucleoprotein (codon optimized) | ATGTCAGACAATGGGCCCCAGAACCAGAGAAATGCCCT TCGCATCACGTTTGGTGGCCCTAGTGACAGCACCGGCAG CAATCAGAATGGAGGTGCCCGCAGTAAACAAAGGAGAC CACAGGGACTGCCAAACAACACAGCATCCTGGTTTACTG CACTTACGCAGCATGGTAAGGAGGACCTGAAGTTCCCA | 8 |

TABLE 1-continued

| SARS-CoV-2 Omicron sub-variant BA.2 | | |
|---|---|---|
| Antigens | Sequence | SEQ ID NO: |
| | AGAGGACAGGGAGTCCCCATCAACACCAACAGCTCACC<br>AGATGATCAGATCGGCTATTACCGGCGGGCTACTCGCCG<br>CATACGAGGGGGCGATGGCAAGATGAAGGATCTAAGTC<br>CGCGTTGGTACTTCTACTATCTGGGCACAGGGCCTGAAG<br>CTGGCCTGCCTTATGGGGCCAATAAGGATGGCATCATCT<br>GGGTGGCCACTGAGGGGGCTTTGAATACCCCAAAAGAC<br>CACATCGGGACTCGAAACCCTGCCAACAATGCAGCCATT<br>GTCCTTCAGCTCCCACAAGGGACAACATTACCCAAGGGC<br>TTCTATGCAGAGGGCTCCAGGGGAGGTTCTCAAGCCAGC<br>AGCCGGAGCAGCTCGCGGTCCCGGAACTCAAGCCGAAA<br>TTCCACTCCTGGCAGCTCCAAGAGAACATCACCTGCGAG<br>GATGGCTGGAAATGGAGGCGATGCTGCTCTGGCCCTCCT<br>TTTGCTGGACAGGCTCAACCAGCTGGAGAGTAAAATGA<br>GTGGAAAGGGGCAGCAGCAACAGGGCCAGACTGTGACC<br>AAGAAGTCTGCAGCAGAAGCGTCCAAGAAACCCAGGCA<br>GAAAAGGACAGCCACAAAAGCCTATAATGTGACACAAG<br>CCTTTGGGAGAAGAGGGCCAGAGCAGACCCAGGGAAAC<br>TTTGGAGACCAGGAGCTGATTCGTCAAGGTACAGACTAC<br>AAGCACTGGCCACAGATTGCTCAGTTTGCTCCCTCTGCA<br>TCAGCCTTCTTCGGCATGAGCAGGATAGGTATGGAGGTG<br>ACTCCGAGCGGAACCTGGCTGACCTACACCGGAGCCAT<br>CAAGCTGGATGACAAGGATCCCAACTTCAAGGACCAGG<br>TAATTCTCTTAAACAAGCATATTGATGCCTACAAAACCT<br>TTCCTCCAACAGAACCCAAAAAGGACAAAAAAAAAAAA<br>GCTGATGAAACTCAGGCCCTACCTCAGCGGCAAAAGAA<br>ACAACAGACGGTTACCCTACTCCCGGCTGCAGATTTGGA<br>CGACTTCTCTAAGCAGCTGCAGCAGTCCATGTCCAGAGC<br>TGACTCTACCCAAGCATGATAATGA | |
| Nucleoprotein (aa) | MSDNGPQNQRNALRITFGGPSDSTGSNQNGGARSKQRRPQ<br>GLPNNTASWFTALTQHGKEDLKFPRGQGVPINTNSSPDDQI<br>GYYRRATRRIRGGDGKMKDLSPRWYFYYLGTGPEAGLPY<br>GANKDGIIWVATEGALNTPKDHIGTRNPANNAAIVLQLPQ<br>GTTLPKGFYAEGSRGGSQASSRSSSRSRNSSRNSTPGSSKRT<br>SPARMAGNGGDAALALLLLDRLNQLESKMSGKGQQQQG<br>QTVTKKSAAEASKKPRQKRTATKAYNVTQAFGRRGPEQT<br>QGNFGDQELIRQGTDYKHWPQIAQFAPSASAFFGMSRIGM<br>EVTPSGTWLTYTGAIKLDDKDPNFKDQVILLNKHIDAYKTF<br>PPTEPKKDKKKKADETQALPQRQKKQQTVTLLPAADLDDF<br>SKQLQQSMSRADSTQA | 9 |

In some embodiments, the portion of the NSP2 protein is encoded by a sequence that is 100%, 98%, 95%, 90%, 85%, 80%, 75%, or 50% identical to SEQ ID NO: 1 or SEQ ID NO: 2. In some embodiments, the portion of the NSP2 protein comprises a sequence that is 100%, 98%, 95%, 90%, 85%, 80%, 75%, or 50% identical to SEQ ID NO: 3. In some embodiments, the portion of the NSP14 protein is encoded by a sequence that is 100%, 98%, 95%, 90%, 85%, 80%, 75%, or 50% identical to SEQ ID NO: 4 or SEQ ID NO: 5. In some embodiments, the portion of the NSP14 protein comprises a sequence that is 100%, 98%, 95%, 90%, 85%, 80%, 75%, or 50% identical to SEQ ID NO: 6. In some embodiments, the portion of the Nucleoprotein is encoded by a sequence that is 100%, 98%, 95%, 90%, 85%, 80%, 75%, or 50% identical to SEQ ID NO: 7 or SEQ ID NO: 8.

In some embodiments, the portion of the Nucleoprotein protein comprises a sequence that is 100%, 98%, 95%, 90%, 85%, 80%, 75%, or 50% identical to SEQ ID NO: 9.

In other embodiments, one or more antigens are derived from a full-length spike glycoprotein. In some embodiments, one or more antigens is derived from a partial spike glycoprotein. In some embodiments, the spike (S) protein comprises at least one proline substitution, or at least two proline substitutions, or at least four proline substitutions, or at least six proline substitutions. The spike (5) protein may comprise two consecutive proline substitutions at amino acid positions 986 and 987. The proline substitutions may comprise K986P and V987P mutations. In further embodiments, the spike (5) protein is receptor-binding domain (RBD). In some embodiments, the RBD comprises a trimerized SARS-CoV-2 receptor-binding domain (RBD). See Table 2.

TABLE 2

| Shows non-limiting examples of Coronavirus Spike (S) protein that may be used in accordance with the present invention. | | |
|---|---|---|
| Antigen | Sequence | SEQ ID NO: |
| spike glycoprotein | TACCAAGCTACTAGAGTAGTGGTACTTTCATTTGAGCTTCTAAATGCA<br>CCTGCCACAGTGTGTGGACCAAAATTGTCCACATCACTAATTAAGAA<br>CCAGTGTGTCAATTTTAATTTCAATGGACTCAAGGGTACTGGTGTGTT | 10 |

TABLE 2-continued

Shows non-limiting examples of Coronavirus Spike (S) protein that may be used in
accordance with the present invention.

| Antigen | Sequence | SEQ ID NO: |
|---|---|---|
| | GACTGACTCGTCCAAAAAGTTTCAGTCTTTTCAACAATTTGGAAGGGA<br>TGCATCTGATTTTACTGACTCAGTACGCGACCCTCAGACACTTCAAAT<br>ACTTGACATTTCACCATGTTCATTTGGTGGTGTGAGTGTAATAACACC<br>AGGAACAAATGCTTCATCTGAAGTAGCCGTTCTATACCAAGATGTAAA<br>CTGCACTGATGTTCCCACGGCCATACGTGCTGACCAACTCACACCTG<br>CTTGGCGTGTTTACTCTGCTGGAGTAAATGTGTTTCAAACTCAGGCT<br>GGCTGTTTAATAGGAGCGGAACATGTCAATGCTTCATATGAGTGTGA<br>CATTCCCATTGGTGCAGGCATTTGTGCTAGTTACCATACAGCTTCCCT<br>TTTACGTAATACAGGCCAGAAATCAATTGTGGCCTATACTATGTCACT<br>TGGTGCTGAAAACTCAATTGCTTATGCTAATAACTCAATTGCCATACC<br>TACAAATTTTCAATCAGTGTCACAACTGAAGTGATGCCTGTTTCAAT<br>GGCTAAGACATCAGTAGATTGTACAATGTACATCTGTGGTGACTCTCA<br>GGAGTGCAGCAACTTACTACTTCAGTATGGTAGCTTTTGCACACAATT<br>AAATCGTGCCCTTTCAGGCATTGCTGTTGAACAGGACAAAAACACTC<br>AAGAGGTTTTTGCCCAAGTTAAACAAATGTATAAGACACCAGCCATAA<br>AAGATTTTGGTGGCTTTAATTTCTCACAAATATTGCCTGACCCTTCTAA<br>GCCAACAAAAAGATCATTTATTGAGGATTTACTCTTCAACAAAGTGAC<br>TCTCGCTGATGCTGGCTTTATGAAGCAATACGGCGAATGCCTAGGCG<br>ATATTAGTGCTAGAGATCTCATTTGTGCGCAGAAGTTCAATGGACTCA<br>CTGTCCTTCCACCTCTACTCACGGATGAAATGATTGCTGCTTACACC<br>GCCGCTCTTGTCAGCGGTACTGCTACTGCTGGTTGGACATTTGGTGC<br>AGGTGCTGCTCTACAAATACCTTTTGCTATGCAAATGGCTTATAGGTT<br>CAATGGCATTGGAGTTACTCAAAATGTTCTCTATGAGAACCAGAAGCA<br>GATCGCTAACCAATTTAACAAGGCGATCAGTCAAATTCAAGAATCACT<br>TACTACTACTTCAACTGCATTGGGCAAGCTGCAAGACGTCGTCAACC<br>AGAATGCTCAAGCATTGAACACACTTGTTAAACAACTAAGTTCTAACT<br>TTGGTGCAATTTCAAGTGTTTTAAATGACATTCTGTCTCGACTYGACA<br>AAGTTGAGGCTGAAGTGCAAATTGATAGGTTGATTACTGGCAGATTA<br>CAAAGCCTTCAGACCTATGTAACACAACAACTAATCAGAGCTGCTGA<br>AATCAGAGCTTCTGCCAATCTTGCTGCCACTAAGATGTCCGAGTGTG<br>TTCTTGGACAATCAAAAAGAGTTGACTTTTGTGGAAAAGGCTATCATC<br>TTATGTCTTTCCCTCAAGCAGCCCCACATGGTGTCGTCTTCTTACATG<br>TCACATACGTGCCATCGCAAGAAAGAAACTTCACCACTGCCCCAGCA<br>ATCTGCCATCAAGGCAAGGCACACTTCCCTCGTGAAGGTGTTTTTGT<br>ATCTAATGGCACTTCTTGGTTTATCACACAGAGGAACTTCTTTTCACC<br>ACAAATAATTACAACAGACAATACATTTGTCTCTGGAAATTGTGATGT<br>CGTTATTGGCATCATCAACAATACTGTTTATGATCCTCTGCAACCTGA<br>GCTTGACTCATTTAAAGAAGAGCTGGACAAGTACTTCAAAAACCACAC<br>GTCACCTGATGTRGATCTTGGCGACATCTCAGGCATTAATGCTTCAG<br>TCGTCAATATTCAAAAAGAAATTGACCGCCTCAATGAGGTTGCCAAA<br>ATCTAAATGAATCGCTCATCGATCTTCAAGAACTTGGAAAATATGAGC<br>A | |
| spike<br>glycoprotein<br>with two proline<br>substitutions<br>(K986P,<br>V987P) | MFVFLVLLPLVSSQCVNLTTRTQLPPAYTNSFTRGVYYPDKVFRSSVLH<br>STQDLFLPFFSNVTWFHAIHVSGTNGTKRFDNPVLPFNDGVYFASTEKS<br>NIIRGWIFGTTLDSKTQSLLIVNNATNVVIKVCEFQFCNDPFLGVYYHKNN<br>KSWMESEFRVYSSANNCTFEYVSQPFLMDLEGKQGNFKNLREFVFKNI<br>DGYFKIYSKHTPINLVRDLPQGFSALEPLVDLPIGINITRFQTLLALHRSYL<br>TPGDSSSGWTAGAAAYYVGYLQPRTFLLKYNENGTITDAVDCALDPLSE<br>TKCTLKSFTVEKGIYQTSNFRVQPTESIVRFPNITNLCPFGEVFNATRFAS<br>VYAWNRKRISNCVADYSVLYNSASFSTFKCYGVSPTKLNDLCFTNVYAD<br>SFVIRGDEVRQIAPGQTGKIADYNYKLPDDFTGCVIAWNSNNLDSKVGG<br>NYNYLYRLFRKSNLKPFERDISTEIYQAGSTPCNGVEGENCYFPLQSYG<br>FQPTNGVGYQPYRVVVLSFELLHAPATVCGPKKSTNLVKNKCVNFNFN<br>GLTGTGVLTESNKKFLPFQQFGRDIADTTDAVRDPQTLEILDITPCSFGG<br>VSVITPGTNTSNQVAVLYQDVNCTEVPVAIHADQLTPTWRVYSTGSNVF<br>QTRAGCLIGAEHVNNSYECDIPIGAGICASYQTQTNSPRRARSVASQSIIA<br>YTMSLGAENSVAYSNNSIAIPTNFTISVTTEILPVSMTKTSVDCTMYICGD<br>STECSNLLLQYGSFCTQLNRALTGIAVEQDKNTQEVFAQVKQIYKTPPIK<br>DFGGFNFSQILPDPSKPSKRSFIEDLLFNKVTLADAGFIKQYGDCLGDIAA<br>RDLICAQKFNGLTVLPPLLTDEMIAQYTSALLAGTITSGWTFGAGAALQIP<br>FAMQMAYRFNGIGVTQNVLYENQKLIANQFNSAIGKIQDSLSSTASALGK<br>LQDVVNQNAQALNTLVKQLSSNFGAISSVLNDILSRLDPPEAEVQIDRLIT<br>GRLQSLQTYVTQQLIRAAEIRASANLAATKMSECVLGQSKRVDFCGKGY<br>HLMSFPQSAPHGVVFLHVTYVPAQEKNFTTAPAICHDGKAHFPREGVFV<br>SNGTHWFVTQRNFYEPQIITTDNTFVSGNCDVVIGIVNNTVYDPLQPELD<br>SFKEELDKYFKNHTSPDVDLGDISGINASVVNIQKEIDRLNEVAKNLNESL<br>IDLQELGKYEQYIKWPWYIWLGFIAGLIAIVMVTIMLCCMTSCCSCLKGCC<br>SCGSCCKFDEDDSEPVLKGVKLHYT | 11 |
| spike<br>glycoprotein<br>with six proline<br>substitutions | MFVFLVLLPLVSSQCVNLTTRTQLPPAYTNSFTRGVYYPDKVFRSSVLH<br>STQDLFLPFFSNVTWFHAIHVSGTNGTKRFDNPVLPFNDGVYFASTEKS<br>NIIRGWIFGTTLDSKTQSLLIVNNATNVVIKVCEFQFCNDPFLGVYYHKNN<br>KSWMESEFRVYSSANNCTFEYVSQPFLMDLEGKQGNFKNLREFVFKNI | 12 |

TABLE 2-continued

Shows non-limiting examples of Coronavirus Spike (S) protein that may be used in accordance with the present invention.

| Antigen | Sequence | SEQ ID NO: |
|---|---|---|
| (F817P, A892P, A899P, A942P, K986P, V987P) | DGYFKIYSKHTPINLVRDLPQGFSALEPLVDLPIGINITRFQTLLALHRSYL TPGDSSSGWTAGAAAYYVGYLQPRTFLLKYNENGTITDAVDCALDPLSE TKCTLKSFTVEKGIYQTSNFRVQPTESIVRFPNITNLCPFGEVENATRFAS VYAWNRKRISNCVADYSVLYNSASFSTFKCYGVSPTKLNDLCFTNVYAD SFVIRGDEVRQIAPGQTGKIADYNYKLPDDFTGCVIAWNSNNLDSKVGG NYNYLYRLFRKSNLKPFERDISTEIYQAGSTPCNGVEGENCYFPLQSYG FQPTNGVGYQPYRVVVLSFELLHAPATVCGPKKSTNLVKNKCVNFNFN GLTGTGVLTESNKKFLPFQQFGRDIADTTDAVTRAGCLIGAEHVNNSYE CDIPIGAGICASYQTQTNRDPQTLEILDITPCSFGGVSVITPGTNTSNQVA VLYQDVNCTEVPVAIHADQLTPTWRVYSTGSNVFQSPRRARSVASQSII AYTMSLGAENSVAYSNNSIAIPTNFTISVTTEILPVSMTKTSVDCTMYICG DSTECSNLLLQYGSFCTQLNRALTGIAVEQDKNTQEVFAQVKQIYKTPPI KDFGGFNFSQILPDPSKPSKRSPIEDLLFNKVTLADAGFIKQYGDCLGDIA ARDLICAQKFNGLTVLPPLLTDEMIAQYTSALLAGTITSGWTFGAGPALQI PFPMQMAYRFNGIGVTQNVLYENQKLIANQFNSAIGKIQDSLSSTPSALG KLQDVVNQNAQALNTLVKQLSSNFGAISSVLNDILSRLDPPEAEVQIDRLI TGRLQSLQTYVTQQLIRAAEIRASANLAATKMSECVLGQSKRVDFCGKG YHLMSFPQSAPHGVVFLHVTYVPAQEKNFTTAPAICHDGKAHFPREGVF VSNGTHWFVTQRNFYEPQIITTDNTFVSGNCDVVIGIVNNTVYDPLQPEL DSFKEELDKYFKNHTSPDVDLGDISGINASVVNIQKEIDRLNEVAKNLNES LIDLQELGKYEQYIKWPWYIWLGFIAGLIAIVMVTIMLCCMTSCCSCLKGC CSCGSCCKFDEDDSEPVLKGVKLHYT | |

In some embodiments, the Spike protein is encoded by a sequence that is 100%, 98%, 95%, 90%, 85%, 80%, 75%, or 50% identical to SEQ ID NO: 10. In some embodiments, the portion of the Spike protein comprises a sequence that is 100%, 98%, 95%, 90%, 85%, 80%, 75%, or 50% identical to SEQ ID NO: 11 or SEQ ID NO: 12.

In some embodiments, the Coronavirus antigens may further comprise NSP 3, NSP12, ORF7a/b, or a combination thereof (see Table 3).

TABLE 3

| Antigens | Sequence | SEQ ID NO: |
|---|---|---|
| NSP3 | ATGCTCTTGTTAGTGACATTGACATCACTTTCTTAAAGAAAGATGCTCC ATATATAGTGGGTGATGTTGTTCAAGAGGGTGTTTTAACTGCTGTGGT TATACCTACTAAAAAGGCTAGTGGCACTACTGAAATGCTAGCGAAAGC TTTGAGAAAAGTGCCAACAGACAATTATATAACCACTTACCCGGGTCA GGGTTTAAATGGTTACACTGTAGAGGAGGCAAAGACAGTGCTTAAAAA GTGTAAAAGTGCTTTTTACATTCTACCATCTATTATCTCTAATGAGAAG CAAGAAATTCTTGGAACTGTTTCTTGGAATTTGCGAGAAATGCTTGCA CATGCAGAAGAAACACGCAAATTAATGCCTGTCTGTGTGGAAACTAAA GCCATAGTTTCAACTATACAGCGTAAATATAAGGGTATTAAAATACAAG AGGGTGTGGTTGATTATGGTGCTAGATTTTACTTTTACACCAGTAAAA CAACTGTAGCGTCACTTATCAACACACTTAACGATCTAAATGAAACTCT TGTTACAATGCCACTTGGCTATGTAACACATGGCTTAAATTTGGAAGA AGCTGCTCGGTATATGAGATCTCTCAAAGTGCCAGCTACAGTTTCTGT TTCTTCACCTGATGCTGTTACAGCGTATAATGGTTATCTTACTTCTTCT TCTAAAACACCTGAAGAACATTTTATTGAAACCATCTCACTTGCTGGTT CCTATAAAGATTGGTCCTATTCTGGACAATCTACACAACTAGGTATAG AATTTCTTAAGAGAGGTGATAAAAGTGTATATTACACTAGTAATCCTAC CACATTCCACCTAGATGGTGAAGTTATCACCTTTGACAATCTTAAGAC ACTTCTTTCTTTGAGAGAAGTGAGGACTATTAAGGTGTTTACAACAGT AGACAACATTAACCTCCACACGCAAGTTGTGGACATGTCAATGACATA TGGACAACAGTTTGGTCCAACTTATTTGGATGGAGCTGATGTTACTAA AATAAAACCTCATAATTCACATGAAGGTAAAACATTTTATGTTTTACCT AATGATGACACTCTACGTGTTGAGGCTTTTGAGTACTACCACACAACT GATCCTAGTTTTCTGGGTAGGTACATGTCAGCATTAAATCACACTAAA AAGTGGAAATACCCACAAGTTAATGGTTTAACTTCTATTAAATGGGCA GATAACAACTGTTATCTTGCCACTGCATTGTTAACACTCCAACAAATAG AGTTGAAGTTTAATCCACCTGCTCTACAAGATGCTTATTACAGAGCAA GGGCTGGTGAAGCTGCTAACTTTTGTGCACTTATCTTAGCCTACTGTA ATAAGACAGTAGGTGAGTTAGGTGATGTTAGAGAAACAATGAGTTACT TGTTTCAACATGCCAATTTAGATTCTTGCAAAAGAGTCTTGAACGTGG TGTGTAAAACTTGTGGACAACAGCAGACAACCCTTAAGGGTGTAGAA GCTGTTATGTACATGGGCACACTTTCTTATGAACAATTTAAGAAAGGT | 13 |

TABLE 3-continued

| Antigens | Sequence | SEQ ID NO: |
|---|---|---|
| | GTTCAGATACCTTGTACGTGTGGTAAACAAGCTACAAAATATCTAGTA<br>CAACAGGAGTCACCTTTTGTTATGATGTCAGCACCACCTGCTCAGTAT<br>GAACTTAAGCATGGTACATTTACTTGTGCTAGTGAGTACACTGGTAAT<br>TACCAGTGTGGTCACTATAAACATATAACTTCTAAAGAAACTTTGTATT<br>GCATAGACGGTGCTTTACTTACAAAGTCCTCAGAATACAAAGGTCCTA<br>TTACGGATGTTTTCTACAAAGAAAACAGTTACACAACAACCATAAAACC<br>AGTTACTTATAAATTGGATGGTGTTGTTTGTACAGAAATTGACCCTAAG<br>TTGGACAATTATTATAAGAAAGACAATTCTTATTTCACAGAGCAACCAA<br>TTGATCTTGTACCAAACCAACCATATCCAAACGCAAGCTTCGATAATTT<br>TAAGTTTGTATGTGATAATATCAAATTTGCTGATGATTTAAACCAGTTA<br>ACTGGTTATAAGAAACCTGCTTCAAGAGAGCTTAAAGTTACATTTTTCC<br>CTGACTTAAATGGTGATGTGGTGGCTATTGATTATAAACACTACACAC<br>CCTCTTTTAAGAAAGGAGCTAAATTGTTACATAAACCTATTGTTTGGCA<br>TGTTAACAATGCAACTAATAAAGCCACGTATAAACCAAATACCTGGTG<br>TATACGTTGTCTTTGGAGCACAAAACCAGTTGAAACATCAAATTCGTTT<br>GATGTACTGAAGTCAGAGGACGCGCAGGGAATGGATAATCTTGCCTG<br>CGAAGATCTAAAACCAGTCTCTGAAGAAGTAGTGGAAAATCCTACCAT<br>ACAGAAAGACGTTCTTGAGTGTAATGTGAAAACTACCGAAGTTGTAGG<br>AGACATTATACTTAAACCAGCAAATAATAGTTTAAAAATTACAGAAGAG<br>GTTGGCCACACAGATCTAATGGCTGCTTATGTAGACAATTCTAGTCTT<br>ACTATTAAGAAACCTAATGAATTATCTAGAGTATTAGGTTTGAAAACCC<br>TTGCTACTCATGGTTTAGCTGCTGTTAATAGTGTCCCTTGGGATACTA<br>TAGCTAATTATGCTAAGCCTTTTCTTAACAAAGTTGTTAGTACAACTAC<br>TAACATAGTTACACGGTGTTTAAACCGTGTTTGTACTAATTATATGCCT<br>TATTTCTTTACTTTATTGCTACAATTGTGTACTTTTACTAGAAGTACAAA<br>TTCTAGAATTAAAGCATCTATGCCGACTACTATAGCAAAGAATACTGTT<br>AAGAGTGTCGGTAAATTTTGTCTAGAGGCTTCATTTAATTATTTGAAGT<br>CACCTAATTTTTCTAAACTGATAAATATTATAATTTGGTTTTTACTATTA<br>AGTGTTTGCCTAGGTTCTTTAATCTACTCAACCGCTGCTTTAGGTGTTT<br>TAATGTCTAATTTAGGCATGCCTTCTTACTGTACTGGTTACAGAGAAG<br>GCTATTTGAACTCTACTAATGTCACTATTGCAACCTACTGTACTGGTTC<br>TATACCTTGTAGTGTTTGTCTTAGTGGTTTAGATTCTTTAGACACCTAT<br>CCTTCTTTAGAAACTATACAAATTACCATTTCATCTTTTAAATGGGATTT<br>AACTGCTTTTGGCTTAGTTGCAGAGTGGTTTTTGGCATATATTCTTTTC<br>ACTAGGTTTTCTATGTACTTGGATTGGCTGCAATCATGCAATTGTTTT<br>TCAGCTATTTTGCAGTACATTTTATTAGTAATTCTTGGCTTATGTGGTT<br>AATAATTAATCTTGTACAAATGGCCCCGATTTCAGCTATGGTTAGAATG<br>TACATCTTCTTTGCATCATTTTATTATGTATGGAAAAGTTATGTGCATG<br>TTGTAGACGGTTGTAATTCATCAACTTGTATGATGTGTTACAAACGTAA<br>TAGAGCAACAAGAGTCGAATGTACAACTATTGTTAATGGTGTTAGAAG<br>GTCCTTTTATGTCTATGCTAATGGAGGTAAAGGCTTTTGCAAACTACA<br>CAATTGGAATTGTGTTAATTGTGATACATTCTGTGCTGGTAGTACATTT<br>ATTAGTGATGAAGTTGCGAGAGACTTGTCACTACAGTTTAAAAGACCA<br>ATAAATCCTACTGACCAGTCTTCTTACATCGTTGATAGTGTTACAGTGA<br>AGAATGGTTCCATCCATCTTTACTTTGATAAAGCTGGTCAAAAGACTTA<br>TGAAAGACATTCTCTCTCTCATTTTGTTAACTTAGACAACCTGAGAGCT<br>AATAACACTAAAGGTTCATTGCCTATTAATGTTATAGTTTTTTGATGGTA<br>AATCAAAATGTGAAGAATCATCTGCAAAATCAGCGTCTGTTTACTACA<br>GTCAGCTTATGTGTCAACCTATACTGTTACTAGATCAGGCATTAGTGT<br>CTGATGTTGGTGATAGTGCGGAAGTTGCAGTTAAAATGTTTGATGCTT<br>ACGTTAATACGTTTTCATCAACTTTTAACGTACCAATGGAAAAACTCAA<br>AACACTAGTTGCAACTGCAGAAGCTGAACTTGCAAAGAATGTGTCCTT<br>AGACAATGTCTTATCTACTTTTATTTCAGCAGCTCGGCAAGGGTTTGTT<br>GATTCAGATGTAGAAACTAAAGATGTTGTTGAATGTCTTAAATTGTCAC<br>ATCAATCTGACATAGAAGTTACTGGCGATAGTTGTAATAACTATATGCT<br>CACCTATAACAAAGTTGAAAACATGACACCCCGTGACCTTGGTGCTTG<br>TATTGACTGTAGTGCGCGTCATATTAATGCGCAGGTAGCAAAAAGTCA<br>CAACATTGCTTTGATATGGAACGTTAAAGATTTCATGTCATTGTCTGAA<br>CAACTACGAAACAAATACGTAGTGCTGCTAAAAAGAATAACTTACCT<br>TTTAAGTTGACATGTGCAACTACTAGACAAGTTGTTAATGTTGTAACAA<br>CAAAGATAGCACTTAAGGGTGGTTGATGA | |
| NSP13 codon optimized | ATGCTCTTACTTGTTATTGACATCACCTTTCTAAAGAAAGATGCCCCTT<br>ATATTGTGGGAGACGTTGTCCAGGAGGGAGTCCTTACGGCCGTGGTG<br>ATTCCAACAAAGAAGGCTAGTGGCACCACAGAAATGCTGGCCAAGGC<br>CTTGCGCAAGGTGCCGACAGACAACTACATCACTACATATCCTGGAC<br>AAGGCCTGAACGGATATACAGTGGAAGAGGCAAAGACTGTGCTAAAG<br>AAGTGCAAGTCTGCCTTTTACATCCTTCCAAGCATTATTAGCAACGAG<br>AAGCAGGAAATACTCGGAACCGTAAGCTGGAACCTTAGAGAGATGCT<br>TGCGCATGCTGAGGAAACCCGAAAACTGATGCCTGTGTGTGTTGAAA<br>CCAAAGCCATCGTTTCTACCATCCAGCGAAAGTATAAGGGTATCAAGA<br>TCCAAGAGGGAGTGGTAGACTATGGCGCTAGATTCTACTTCTATACCT<br>CTAAAACAACTGTCGCCTCTCTTATCAATACTCTGAATGACCTGAATG<br>AGACTCTTGTGACCATGCCCCTGGGATACGTAACCCATGGGCTTAAC<br>TTGGAAGAAGCCGCTCGCTACATGCGTAGCCTGAAGGTCCCTGCTAC<br>TGTTAGTGTCTCTTCCCCCGATGCCGTCACAGCTTACAACGGGTATCT<br>GACGTCAAGCTCCAAAACTCCTGAAGAGCACTTCATCGAGACCATTA | 14 |

TABLE 3-continued

| Antigens | Sequence | SEQ ID NO: |
|---|---|---|
| | GTCTAGCAGGATCCTATAAAGACTGGAGTTACTCAGGCCAGAGCACC | |
| | CAGCTGGGGATAGAGTTCTTGAAACGTGGAGACAAGTCCGTCTACTA | |
| | CACATCAAATCCCACGACGTTCCACCTGGATGGGGAAGTGATAACCT | |
| | TTGATAACTTAAAAACCCTGCTGAGCCTGAGGGAAGTCCGGACTATCA | |
| | AGGTTTTTACTACAGTGGATAATATTAACCTTCACACACAGGTGGTGG | |
| | ACATGTCCATGACCTATGGGCAGCAGTTCGGTCCTACCTACCTGGAC | |
| | GGAGCTGACGTTACCAAAATCAAACCCCACAACTCTCATGAGGGAAA | |
| | GACGTTCTACGTGCTGCCCAATGATGACACCTTGCGAGTGGAGGCAT | |
| | TTGAGTATTACCACACTACCGATCCGTCTTTCTTAGGCCGCTATATGT | |
| | CCGCTTTAAATCATACAAAGAAGTGGAAGTACCCTCAGGTAAACGGC | |
| | CTGACATCTATTAAATGGGCCGACAACAACTGCTATCTGGCAACTGCT | |
| | TTGCTCACACTTCAGCAGATTGAGTTGAAATTTAACCCTCCCGCACTG | |
| | CAGGACGCTTATTATCGGGCAAGGGCCGGTGAGGCGGCTAACTTCT | |
| | GTGCTCTCATCCTTGCTTACTGTAACAAAACAGTGGGCGAGCTAGGA | |
| | GATGTCAGGGAGACAATGTCTTACTTGTTTCAGCACGCCAACTTAGAC | |
| | TCCTGCAAAGAGTGCTCAATGTAGTCTGCAAAACCTGCGGTCAGCA | |
| | GCAGACTACCTTGAAGGGGGTCGAAGCAGTGATGTACATGGGTACAC | |
| | TATCCTATGAGCAATTTAAAAAGGGTGTTCAGATCCCCTGCACATGTG | |
| | GCAAGCAGGCAACAAAATACCTCGTGCAGCAAGAATCCCCATTTGTTA | |
| | TGATGAGCGCACCTCCAGCCCAGTACGAACTGAAACATGGAACATTT | |
| | ACCTGCGCTTCGGAGTACACTGGCAATTACCAGTGTGGGCATTACAA | |
| | GCACATCACGTCAAAGAAACACTCTACTGCATAGATGGAGCCCTGTT | |
| | GACCAAGTCCAGCGAATATAAAGGCCCTATCACAGATGTTTTCTACAA | |
| | GGAGAATTCATATACAACCACCATCAAGCCCGTGACATACAAGTTAGA | |
| | CGGCGTGGTATGTACAGAAATTGACCCCAAGCTGGACAATTACTACA | |
| | AAAAAGACAATAGCTATTTTACTGAACAACCAATCGATCTTGTCCCTAA | |
| | TCAGCCCTACCCCAATGCGTCATTTGATAACTTTAAGTTTGTGTGTGA | |
| | TAATATTAAATTTGCAGATGATCTAAACCAGTTGACGGGATACAAGAA | |
| | ACCCGCCTCGCGCGAACTGAAAGTGACTTTTTTTCCAGATCTGAATGG | |
| | GGATGTCGTGGCCATAGATTATAAGCATTATACTCCAAGTTTCAAGAA | |
| | AGGCGCTAAGTTATTACATAAGCCTATTGTCTGGCATGTCAACAATGC | |
| | TACAAATAAAGCCACTTATAAGCCAAACACATGGTGTATTAGGTGCCT | |
| | GTGGAGCACAAAACCAGTGGAGACTAGCAATTCCTTTGACGTCCTGA | |
| | AGAGTGAAGATGCACAAGGCATGGATAACTTGGCCTGTGTGAGGACCTG | |
| | AAACCAGTCTCAGAGGAAGTGGTGGAAAATCCAACCATCCAGAAAGA | |
| | CGTACTGGAGTGTAACGTGAAAACCACTGAGGTTGTGGGGGACATTA | |
| | TCTTAAAACCTGCTAACAACAGCCTGAAGATTACCGAGGAGGTAGGA | |
| | CACACTGATTTAATGGCAGCTTACGTAGATAACTCCAGTCTGACCATC | |
| | AAGAAGCCTAACGAGCTGAGTCGGGTGCTAGGCCTCAAAACTCTGGC | |
| | CACCCACGGCCTAGCGGCCGTTAATTCTGTACCGTGGGATACAATCG | |
| | CTAATTATGCCAAGCCCTTCCTCAACAAGGTTGTCAGCACGACCACCA | |
| | ACATCGTGACCCGATGCTTGAACCGTGTGTGCACGAACTATATGCCC | |
| | TATTTCTTTACCCTTCTACTCCAGCTGTGTACTTTCACCCGGTCTACAA | |
| | ACAGTCGGATCAAGGCCAGCATGCCAACCACAATTGCCAAGAACACC | |
| | GTTAAATCCGTTGGGAAGTTCTGCCTTGAGGCTAGCTTCAACTACCTG | |
| | AAATCACCCAAACTTCTCGAAGCTGATTAACATTATAATATGGTTCCTGC | |
| | TCCTGTCCGTGTGTCTTGGAAGCCTTATCTACTCCACAGCTGCCCTG | |
| | GGCGTCCTCATGTCTAATCTGGGTATGCCTAGTTACTGCACAGGCTA | |
| | CCGGGAAGGTTATTTGAATAGCACTAACGTTACAATCGCCACATACTG | |
| | CACAGGGAGCATTCCTTGCTCCGTTTGTTTGTCAGGTTTGGATTCTCT | |
| | CGATACTTATCCCTCTCTGGAAACTATTCAGATCACGATTTCTAGTTTC | |
| | AAATGGGACCTCACGGCATTTGGGCTCGTGGCCGAGTGGTTCCTGG | |
| | CCTATATACTCTTCACTAGGTTCTTCTATGTCCTGGGGCTGGCTGCCA | |
| | TCATGCAGCTCTTTTTCAGTTATTTCGCAGTCCATTTTATCAGCAATAG | |
| | CTGGCTCATGTGGCTCATAATAAATTTAGTACAGATGGCACCAATCTC | |
| | GGCCATGGTGAGGATGTATATCTTTTTCGCATCCTTTTACTATGTGTG | |
| | GAAATCATATGTCCACGTGGTGGACGGATGCAATAGTAGCACGTGCA | |
| | TGATGTGCTACAAACGGAATAGAGCGACCCGCGTGGAATGTACCACC | |
| | ATTGTGAATGGGGTTCGCAGATCATTCTACGTGTATATGCCAACGGCGG | |
| | CAAGGGCTTCTGCAAGCTCCATAACTGGAACTGTGTCAATTGTGACAC | |
| | ATTTTGTGCAGGATCAACTTTCATCAGTGACGAGGTCGCGCGGGACC | |
| | TCAGTCTGCAATTCAAGAGACCGATCAACCCTACCGACCAGTCATCTT | |
| | ACATCGTGGATTCAGTTACCGTCAAGAATGGATCCATTCACTTATACT | |
| | TCGATAAAGCAGGCCAAAAGACTTACGAGAGGCACTCTCTCAGCCAC | |
| | TTTGTGAACCTGGACAATCTGAGGGCAAATAACACCAAGGGGTCTCTT | |
| | CCCATTAATGTGATAGTGTTTGACGGGAAGAGCAAGTGTGAGGAGAG | |
| | CAGCGCCAAATCTGCCTCAGTGTACTACAGCCAGCTCATGTGTCAAC | |
| | CAATACTCCTTCTAGACCAAGCCCTGGTCTCAGACGTTGGGGACAGT | |
| | GCTGAAGTGGCTGTGAAGATGTTCGATGCTTATGTGAACACATTTTCT | |
| | TCCACTTTCAACGTCCCTATGGAGAAACTAAAGACGCTGGTGGCAAC | |
| | GGCCGAGGCCGAGCTGGCCAAGAACGTTTCATTGGACAATGTGCTCT | |
| | CGACATTCATCTCCGCTGCAAGACAGGGCTTTGTGGACTCAGATGTA | |
| | GAAACCAAGGATGTGGTCGAGTGCTTGAAGTTGTCGCACCAGAGCGA | |
| | CATCGAAGTCACAGGTGACAGCTGCAATAATTACATGCTGACCTATAA | |
| | CAAGGTAGAGAACATGACACCACGCGATTTGGGAGCCTGCATAGACT | |
| | GTAGTGCTAGGCACATTAATGCACAGGTCGCAAAATCTCATAACATCG | |
| | CGCTAATCTGGAATGTCAAAGATTTCATGAGCCTGTCTGAGCAATTGA | |

TABLE 3-continued

| Antigens | Sequence | SEQ ID NO: |
|---|---|---|
| | GAAAGCAAATCAGGAGTGCAGCTAAAAAAAAATAACCTCCCGTTCAAGC<br>TAACATGTGCCACAACTAGACAGGTGGTGAACGTGGTAACTACTAAAA<br>TTGCGCTGAAGGGTGGTTGATAA | |
| NSP 12 | ATGTCAGCTTGCACAATCGTTTTTAAACGGGTTTGCGGTGTAAGTGCA<br>GCCCGTCTTACACCGTGCGGCACAGGCACTAGTACTGATGTCGTATA<br>CAGGGCTTTTGACATCTACAATGATAAAGTAGCTGGTTTTGCTAAATT<br>CCTAAAAACTAATTGTTGTCGCTTCCAAGAAAAGGACGAAGATGACAA<br>TTTAATTGATTCTTACTTTGTAGTTAAGAGACACACTTTCTCTAACTAC<br>CAACATGAAGAAACAATTTATAATTTACTTAAGGATTGTCCAGCTGTTG<br>CTAAACATGACTTCTTTAAGTTTAGAATAGACGGTGACATGGTACCAC<br>ATATATCACGTCAACGTCTTACTAAATACACAATGGCAGACCTCGTCT<br>ATGCTTTAAGGCATTTTGATGAAGGTAATTGTGACACATTAAAAGAAAT<br>ACTTGTCACATACAATTGTTGTGATGATTATTTCAATAAAAAGGAC<br>TGGTATGATTTTGTAGAAAACCCAGATATATTACGCGTATACGCCAAC<br>TTAGGTGAACGTGTACGCCAAGCTTTGTTAAAAACAGTACAATTCTGT<br>GATGCCATGCGAAATGCTGGTATTGTTGGTGTACTGACATTAGATAAT<br>CAAGATCTCAATGGTAACTGGTATGATTTCGGTGATTTCATACAAACC<br>ACGCCAGGTAGTGGAGTTCCTGTTGTAGATTCTTATTATTCATTGTTAA<br>TGCCTATATTAACCTTGACCAGGGCTTTAACTGCAGAGTCACATGTTG<br>ACACTGACTTAACAAAGCCTTACATTAAGTGGGATTTGTTAAAATATGA<br>CTTCACGGAAGAGAGGTTAAAACTCTTTGACCGTTATTTTAAATATTGG<br>GATCAGACATACCACCCAAATTGTGTTAACTGTTTGGATGACAGATGC<br>ATTCTGCATTGTGCAAACTTTAATGTTTTATTCTCTACAGTGTTCCCAC<br>TTACAAGTTTTGGACCACTAGTGAGAAAAATATTTGTTGATGGTGTTCC<br>ATTTGTAGTTTCAACTGGATACCACTTCAGAGAGCTAGGTGTTGTACA<br>TAATCAGGATGTAAACTTACATAGCTCTAGACTTAGTTTTAAGGAATTA<br>CTTGTGTATGCTGCTGACCCTGCTATGCACGCTGCTTCTGGTAATCTA<br>TTACTAGATAAACGCACTACGTGCTTTTCAGTAGCTGCACTTACTAAC<br>AATGTTGCTTTTCAAACTGTCAAACCCGGTAATTTTAACAAAGACTTCT<br>ATGACTTTGCTGTGTCTAAGGGTTTCTTTAAGGAAGGAAGTTCTGTTG<br>AATTAAAACACTTCTTCTTTGCTCAGGATGGTAATGCTGCTATCAGCG<br>ATTATGACTACTATCGTTATAATCTACCAACAATGTGTGATATCAGACA<br>ACTACTATTTGTAGTTGAAGTTGTTGATAAGTACTTTGATTGTTACGAT<br>GGTGGCTGTATTAATGCTAACCAAGTCATCGTCAACAACCTAGACAAA<br>TCAGCTGGTTTTCCATTTAATAAATGGGGTAAGGCTAGACTTTATTATG<br>ATTCAATGAGTTATGAGGATCAAGATGCACTTTTCGCATATACAAAC<br>GTAATGTCATCCCTACTATAACTCAAATGAATCTTAAGTATGCCATTAG<br>TGCAAAGAATAGAGCTCGCACCGTAGCTGGTGTCTCTATCTGTAGTAC<br>TATGACCAATAGACAGTTTCATCAAAAATTATTGAAATCAATAGCCGCC<br>ACTAGAGGAGCTACTGTAGTAATTGGAACAAGCAAATTCTATGGTGGT<br>TGGCACAACATGTTAAAAACTGTTTATAGTGATGTAGAAAACCCTCAC<br>CTTATGGGTTGGGATTATCCTAAATGTGATAGAGCCATGCCTAACATG<br>CTTAGAATTATGGCCTCACTTGTTCTTGCTCGCAAACATACAACGTGT<br>TGTAGCTTGTCACACCGTTTCTATAGATTAGCTAATGAGTGTGCTCAA<br>GTATTGAGTGAAATGGTCATGTGTGGCGGTTCACTATATGTTAAACCA<br>GGTGGAACCTCATCAGGAGATGCCACAACTGCTTATGCTAATAGTGTT<br>TTTAACATTTGTCAAGCTGTCACGGCCAATGTTAATGCACTTTTATCTA<br>CTGATGGTAACAAAATTGCCGATAAGTATGTCCGCAATTTACAACACA<br>GACTTTATGAGTGTCTCTATAGAAATAGAGATGTTGACACAGACTTTG<br>TGAATGAGTTTTACGCATATTTGCGTAAACATTTCTCAATGATGATACT<br>TTCTGACGATGCTGTTGTGTGTTTCAATAGCACTTATGCATCTCAAGG<br>TCTAGTGGCTAGCATAAAGAACTTTAAGTCAGTTCTTTATTATCAAAAC<br>AATGTTTTTATGTCTGAAGCAAAATGTTGGACTGAGACTGACCTTACTA<br>AAGGACCTCATGAATTTTGCTCTCAACATACAATGCTAGTTAAACAGG<br>GTGATGATTATGTGTACCTTCCTTACCCAGATCCATCAAGAATCCTAG<br>GGGCCGGCTGTTTTGTAGATGATATCGTAAAAACAGATGGTACACTTA<br>TGATTGAACGGTTCGTGTCTTTAGCTATAGATGCTTACCCACTTACTAA<br>ACATCCTAATCAGGAGTATGCTGATGTCTTTCATTTGTACTTACAATAC<br>ATAAGAAAGCTACATGATGAGTTAACAGGACACATGTTAGACATGTAT<br>TCTGTTATGCTTACTAATGATAACACTTCAAGGTATTGGGAACCTGAG<br>TTTTATGAGGCTATGTACACACCGCATACAGTCTTACAGTGATGA | 15 |
| NSP12 codon optimized | ATGTCTGCCTGCACAATTGTGTTCAAGCGGGTGTGTGGAGTGTCTGC<br>AGCGCGATTAACTCCCTGTGGAACCGGCACCTCAACAGACGTAGTGT<br>ACCGTGCCTTCGATATTTACAATGATAAGGTGGCCGGGTTCGCGAAA<br>TTCCTAAAGACGAACTGTTGCAGGTTCCAGGAGAAGGATGAAGATGA<br>CAATCTCATAGATTCTTATTTCGTGGTTAAACGGCATACATTTAGTAAT<br>TACCAACATGAAGAAACAATCTACAACCTCCTCAAAGACTGTCCTGCT<br>GTGGCAAAACATGACTTCTTCAAGTTCCGGATTGACGGCGACATGGT<br>TCCACACATCTCTCGGCAGAGATTAACAAAGTACACCATGGCTGACCT<br>TGTATATGCACTGCGACACTTTGATGAAGGAAATTGCGATACTGTAA<br>AGAGATTCTTGTTACCTACAACTGCTGTGATGACGACTACTTCAACAA<br>GAAAGACTGGTACGACTTTGTAGAAAACCCAGATATCCTCAGAGTTTA<br>CGCCAACTTAGGAGAGCGCGTAAGACAAGCCCTGTTAAAAACAGTTC<br>AGTTCTGTGATGCCATGAGGAATGCAGGAATCGTGGGAGTCTTGACC<br>CTGGACAACCAGGACTTGAATGGGAACTGGTATGACTTCGGGGATTT | 16 |

TABLE 3-continued

| Antigens | Sequence | SEQ ID NO: |
|---|---|---|
| | CATCCAGACTACACCCGGCAGCGGAGTGCCAGTGGTGGATAGCTATT ACTCCTTGCTGATGCCCATCCTTACGTTGACAAGAGCCCTGACAGCA GAGAGCCATGTGGACACTGACCTTACCAAACCCTACATCAAGTGGGA CTTACTCAAGTATGACTTCACAGAAGAGCGGCTAAAGTTGTTCGATCG CTACTTTAAATATTGGGATCAGACCTATCATCCCAACTGTGTGAATTGT CTGGATGACAGGTGCATATTGCACTGTGCAAACTTCAACGTTCTTTTT TCCACGGTTTTCCCCCTGACCAGCTTTGGGCCTCTGGTGAGAAAGAT CTTTGTCGACGGGGTACCATTTGTTGTCAGTACCGGCTACCATTTCAG GGAACTCGGTGTCGTGCACAATCAGGATGTAAACCTGCACAGCAGCC GGCTAAGCTTTAAAGAACTGCTTGTTTATGCTGCTGATCCAGCCATGC ACGCTGCCAGCGGAAATTTACTCCTGGACAAGCGTACTACCTGTTTCA GTGTGGCAGCCCTCACCAACAACGTAGCCTTCCAAACCGTGAAACCA GGCAACTTTAACAAAGATTTCTACGACTTTGCCGTTTCAAAGGGGTTT TTTAAGGAGGGGAGTTCCGTGGAACTGAAGCATTTTTTCTTTGCACAA GACGGTAATGCTGCTATAAGCGACTATGATTATTACCGGTATAATCTG CCAACGATGTGTGATATTAGGCAACTGCTCTTCGTGGTAGAGGTCGT GGACAAATACTTTGACTGCTACGATGGCGGCTGCATCAATGCTAATCA GGTGATTGTCAACAATCTCGACAAGAGTGCGGGCTTTCCTTTCAATAA ATGGGGCAAGGCCCGCCTCTACTATGACAGCATGAGCTACGAGGAC CAAGATGCTCTGTTTGCTTATACAAAGAGAAATGTGATCCCTACCATC ACACAGATGAACCTTAAATATGCCATCTCCGCGAAGAACCGTGCCCG AACAGTTGCTGGTGTCTCCATTTGTTCTACCATGACAAACCGCCAGTT CCACCAGAAGCTGTTGAAGAGCATAGCAGCTACTAGGGGCGCCACC GTCGTAATCGGGACATCCAAGTTTTATGGAGGGTGGCACAACATGCT TAAAACGGTTTACTCAGATGTGGAGAATCCCCACCTAATGGGCTGGG ACTACCCCAAGTGTGACCGAGCAATGCCGAACATGCTCCGCATTATG GCAAGTCTGGTCCTCGCCAGAAAACACACGACTTGCTGCTCATTGTC ACACAGGTTTTATCGTCTGGCCAATGAATGTGCCCAGGTCCTGTCAG AGATGGTCATGTGCGGAGGATCCTTATATGTGAAGCCAGGTGGCACT AGTTCTGGTGATGCCACAACTGCGTACGCAAATAGTGTGTTCAACATC TGCCAGGCTGTCACTGCGAATGTTAATGCGTTGCTGTCCACTGATGG AAACAAAATTGCAGACAAATACGTGCGCAACCTGCAGCATCGTTTATA TGAGTGCCTATACAGAAACAGAGATGTGGACACCGATTTTGTGAACG AGTTCTATGCCTACCTGAGGAAGCATTTCTCAATGATGATCCTGTCGG ATGATGCCGTTGTCTGCTTTAATTCTACTTATGCTTCACAGGGCCTGG TGGCTTCCATAAAAAACTTCAAGTCTGTGCTGTATTACCAGAACAATG TGTTTATGTCTGAAGCTAAGTGCTGGACCGAGACGGACCTCACCAAG GGTCCCCATGAGTTCTGCTCCCAGCACACAATGCTTGTGAAGCAGGG GGACGATTATGTGTATCTCCCTTACCCTGACCCTTCGAGGATACTGG GCGCCGGGTGTTTTGTAGACGACATTGTCAAAACTGACGGTACTCTA ATGATCGAGCGGTTCGTGAGCCTGGCTATTGATGCTTACCCACTGAC CAAGCACCCGAATCAAGAGTACGCAGATGTCTTTCACCTTTACCTTCA GTACATTCGGAAGCTTCATGATGAGCTGACCGGCCACATGCTGGACA TGTATTCAGTGATGCTGACAAATGACAATACATCTAGGTACTGGGAGC CTGAATTTTATGAAGCTATGTATACTCCTCATACCGTGTTGCAGTGATA A | |
| ORF7a/7b | ATGAAAATTATTCTTTTCTTGGCACTGATAACACTCGCTACTTGTGAGC TTTATCACTACCAAGAGTGTGTTAGAGGTACAACAGTACTTTTAAAAGA ACCTTGCTCTTCTGGAACATACGAGGGCAATTCACCATTTCATCCTCT AGCTGATAACAAATTTGCACTGACTTGCTTTAGCACTCAATTTGCTTTT GCTTGTCCTGACGGCGTAAAACACGTCTATCAGTTACGTGCCAGATC AGTTTCACCTAAACTGTTCATCAGACAAGAGGAAGTTCAAGAACTTTA CTCTCCAATTTTTCTTATTGTTGCGGCAATAGTGTTTATAACACTTTGC TTCACACTCAAAAGAAAGACAGAATGTGAACTTTCATTAATTGACTTCT ATTTGTGCTTTTTAGCCTTTCTGTTATTCCTTGTTTTAATTATGCTTATT ATCTTTTGGTTCTCACTTGAACTGCAAGATCATAATGAAACTTGTCACG CCTAATGATGA | 17 |
| ORF7a/7b codon optimized | ATGAAGATCATTTTGTTTCTAGCATTAATAACTCTAGCCACCTGTGAGC TCTACCACTACCAGGAGTGTGTGAGGGGTACCACTGTACTGCTGAAG GAGCCCTGCAGCTCTGGAACATATGAAGGCAACAGCCCTTTCCACCC TTTGGCTGATAACAAGTTTGCTCTTACGTGCTTTTCTACTCAGTTTGCA TTTGCCTGCCCAGATGGGGTGAAGCATGTGTATCAGCTGCGAGCGCG CAGTGTTTCCCCAAAACTCTTCATTCGGCAAGAAGAGGTCCAAGAACT GTATAGTCCCATCTTTCTCATTGTGGCTGCCATCGTGTTCATCACACT ATGTTTCACCCTGAAAAGAAAAACAGAATGTGAACTTTCATTGATTGAC TTCTACCTGTGCTTCCTGGCCTTCCTCTTATTTCTTGTTCTCATCATGC TGATCATCTTCTGGTTCTCCCTGGAGCTGCAGGACCACAATGAGACC TGCCATGCATGATAATGA | 18 |

In some embodiments, the portion of the NSP3 protein is encoded by a sequence that is 100%, 98%, 95%, 90%, 85%, 80%, 75%, or 50% identical to SEQ ID NO: 13 or SEQ ID NO: 14. In some embodiments, the portion of the NSP12 protein is encoded by a sequence that is 100%, 98%, 95%, 90%, 85%, 80%, 75%, or 50% identical to SEQ ID NO: 15 or SEQ ID NO: 16. In some embodiments, the portion of the ORF7a/b is encoded by a sequence that is 100%, 98%, 95%, 90%, 85%, 80%, 75%, or 50% identical to SEQ ID NO: 17 or SEQ ID NO: 18.

Molecular Adjuvants and T Cell Enhancements

In certain embodiments, the vaccine composition comprises a molecular adjuvant and/or one or more T cell enhancement compositions. The adjuvant and/or enhancement compositions may help improve the immunogenicity and/or long-term memory of the vaccine composition. Non-limiting examples of molecular adjuvants include CpG, such as a CpG polymer, and flagellin.

In some embodiments, the vaccine composition comprises a T cell attracting chemokine. The T cell attracting chemokine helps pull the T cells from the circulation to the appropriate tissues, e.g., the lungs, heart, kidney, and brain. Non-limiting examples of T cell attracting chemokines include CCL5, CXCL9, CXCL10, CXCL11, CCL25, CCL28, CXCL14, CXCL17, or a combination thereof.

In some embodiments, the vaccine composition comprises a composition that promotes T cell proliferation. Non-limiting examples of compositions that promote T cell proliferation include IL-7, IL-15, IL-2, or a combination thereof.

In some embodiments, the vaccine composition comprises a composition that promotes T cell homing in the lungs. Non-limiting examples of compositions that promote T cell homing include CCL25, CCL28, CXCL14, CXCL17, or a combination thereof.

In certain embodiments, the molecular adjuvant and/or the T cell attracting chemokine and/or the composition that promotes T cell proliferation are delivered with a separate antigen delivery system from the large sequences.

Table 4 shows non-limiting examples of T-cell enhancements that may be used to create a vaccine composition described herein.

| T-cell enhancement | Sequence | SEQ ID NO: |
|---|---|---|
| CXCL11 | ATGAACAGGAAGGTGACCGCCATCGCCCTGGCCGCCATCATCTGGG CCACCGCCGCCCAGGGCTTCCTGATGTTCAAGCAGGGCAGGTGCCT GTGCATCGGCCCCGGCATGAAGGCCGTGAAGATGGCCGAGATCGA GAAGGCCAGCGTGATCTACCCCAGCAACGGCTGCGACAAGGTGGA GGTGATCGTGACCATGAAGGCCCACAAGAGGCAGAGGTGCCTGGA CCCCAGGAGCAAGCAGGCCAGGCTGATCATGCAGGCCATCGAGAA GAAGAACTTCCTGAGGAGGCAGAACATGTGA | 19 |
| CCL5 | ATGAAGGTCTCCGCGGCAGCCCTCGCTGTCATCCTCATTGCTACTG CCCTCTGCGCTCCTGCATCTGCCTCCCCATATTCCTCGGACACCACA CCCTGCTGCTTTGCCTACATTGCCCGCCCACTGCCCCGTGCCCACA TCAAGGAGTATTTCTACACCAGTGGCAAGTGCTCCAACCCAGCAGTC GTCCACAGGTCAAGGATGCCAAAGAGAGAGGGACAGCAAGTCTGGC AGGATTTCCTGTATGACTCCCGGCTGAACAAGGGCAAGCTTTGTCAC CCGAAAGAACCGCCAAGTGTGTGCCAACCCAGAGAAGAAATGGGTT CGGGAGTACATCAACTCTTTGGAGATGAGCTAGGATGGAGAGTCCTT GAACCTGAACTTACACAAATTTGCCTGTTTCTGCTTGCTCTTGTCCTA GCTTGGGAGGCTTCCCCTCACTATCCTACCCCACCCGCTCCTTGA | 20 |
| CXCL9 | ATGAAGAAAAGTGGTGTTCTTTTCCTCTTGGGCATCATCTTGCTGGTT CTGATTGGAGTGCAAGGAACCCCAGTAGTGAGAAAGGGTCGCTGTT CCTGCATCAGCACCAACCAAGGGACTATCCACCTACAATCCTTGAAA GACCTTAAACAATTTGCCCCAAGCCCTTCCTGCGAGAAAATTGAAAT CATTGCTACACTGAAGAATGGAGTTCAAACATGTCTAAACCCAGATT CAGCAGATGTGAAGGAACTGATTAAAAAGTGGGAGAAACAGGTCAG CCAAAAGAAAAAGCAAAAGAATGGGAAAAAACATCAAAAAAAGAAAG TTCTGAAAGTTCGAAAATCTCAACGTTCTCGTCAAAAGAAGACTACAT AA | 21 |
| CXCL10 | ATGAATCAAACTGCCATTCTGATTTGCTGCCTTATCTTTCTGACTCTA AGTGGCATTCAAGGAGTACCTCTCTCTAGAACTGTACGCTGTACCTG CATCAGCATTAGTAATCAACCTGTTAATCCAAGGTCTTTAGAAAAACT TGAAATTATTCCTGCAAGCCAATTTTGTCCACGTGTTGAGATCATTGC TACAATGAAAAAGAAGGGTGAGAAGAGATGTCTGAATCCAGAATCGA AGGCCATCAAGAATTTACTGAAAGCAGTTAGCAAGGAAAGGTCTAAA AGATCTCCTTAA | 22 |
| CXCL14 | ATGAGGCTCCTGGCGGCCGCGCTGCTCCTGCTGCTGCTGGCGCTG TACACCGCGCGTGTGGACGGGTCCAAATGCAAGTGCTCCCGGAAGG GACCCAAGATCCGCTACAGCGACGTGAAGAAGCTGGAAATGAAGCC AAAGTACCCGCACTGCGAGGAGAAGATGGTTATCATCACCACCAAG AGCGTGTCCAGGTACCGAGGTCAGGAGCACTGCCTGCACCCCAAGC TGCAGAGCACCAAGCGCTTCATCAAGTGGTACAACGCCTGGAACGA GAAGCGCAGGGTCTACGAAGAATAG | 23 |
| CXCL17 | ATGAAAGTTCTAATCTCTTCCCTCCTCCTGTTGCTGCCACTAATGCTG ATGTCCATGGTCTCTAGCAGCCTGAATCCAGGGGTCGCCAGAGGCC ACAGGGACCGAGGCCAGGCTTCTAGGAGATGGCTCCAGGAAGGCG GCCAAGAATGTGAGTGCAAAGATTGGTTCCTGAGAGCCCCGAGAAG AAAATTCATGACAGTGTCTGGGCTGCCAAAGAAGCAGTGCCCCTGT GATCATTTCAAGGGCAATGTGAAGAAAACAAGACACCAAAGGCACCA | 24 |

-continued

| T-cell enhancement | Sequence | SEQ ID NO: |
|---|---|---|
| | CAGAAAGCCAAACAAGCATTCCAGAGCCTGCCAGCAATTTCTCAAAC<br>AATGTCAGCTAAGAAGCTTTGCTCTGCCTTTGTAG | |
| CCL25 | ATGAACCTGTGGCTCCTGGCCTGCCTGGTGGCCGGCTTCCTGGGAG<br>CCTGGGCCCCCGCTGTCCACACCCAAGGTGTCTTTGAGGACTGCTG<br>CCTGGCCTACCACTACCCCATTGGGTGGGCTGTGCTCCGGCGCGCC<br>TGGACTTACCGGATCCAGGAGGTGAGCGGGAGCTGCAATCTGCCTG<br>CTGCGATATTCTACCTCCCCAAGAGACACAGGAAGGTGTGTGGGAA<br>CCCCAAAAGCAGGGAGGTGCAGAGAGCCATGAAGCTCCTGGATGCT<br>CGAAATAAGGTTTTTGCAAAGCTCCACCACAACACGCAGACCTTCCA<br>AGCAGGCCCTCATGCTGTAAAGAAGTTGAGTTCTGGAAACTCCAAGT<br>TATCATCGTCCAAGTTTAGCAATCCCATCAGCAGCAGTAAGAGGAAT<br>GTCTCCCTCCTGATATCAGCTAATTCAGGACTGTGA | 25 |
| CCL28 | ATGCAGCAGAGAGGACTCGCCATCGTGGCCTTGGCTGTCTGTGCGG<br>CCCTACATGCCTCAGAAGCCATACTTCCCATTGCCTCCAGCTGTTGC<br>ACGGAGGTTTCACATCATATTTCCAGAAGGCTCCTGGAAAGAGTGAA<br>TATGTGTCGCATCCAGAGAGCTGATGGGGATTGTGACTTGGCTGCT<br>GTCATCCTTCATGTCAAGCGCGAAGAATCTGTGTCAGCCCGCCACAA<br>CCATACTGTTAAGCAGTGGATGAAAGTGCAAGCTGCCAAGAAAAATG<br>GTAAAGGAAATGTTTGCCACACAGGAAGAAACACCATGGCAAGAGGAA<br>CAGTAACAGGGCACATCAGGGGAAACACGAAACATACGGCCATAAA<br>ACTCCTTATTAG | 26 |
| IL-7 | ATGTTCCACGTGAGCTTCAGGTACATCTTCGGCATCCCCCCCCTGAT<br>CCTGGTGCTGCTGCCCGTGACCAGCAGCGAGTGCCACATCAAGGAC<br>AAGGAGGGCAAGGCCTACGAGAGCGTGCTGATGATCAGCATCGACG<br>AGCTGGACAAGATGACCGGCACCGACAGCAACTGCCCCAACAACGA<br>GCCCAACTTCTTCAGGAAGCACGTGTGCGACGACACCAAGGAGGCC<br>GCCTTCCTGAACAGGGCCGCCAGGAAGCTGAAGCAGTTCCTGAAGA<br>TGAACATCAGCGAGGAGTTCAACGTGCACCTGCTGACCGTGAGCCA<br>GGGCACCCAGACCCTGGTGAACTGCACCAGCAAGGAGGAGAAGAA<br>CGTGAAGGAGCAGAAGAAGAACGACGCCTGCTTCCTGAAGAGGCTG<br>CTGAGGGAGATCAAGACCTGCTGGAACAAGATCCTGAAGGGCAGCA<br>TCTGA | 27 |
| IL-15 | ATGAGAATTTCGAAACCACATTTGAGAAGTATTTCCATCCAGTGCTAC<br>TTGTGTTTACTTCTAAACAGTCATTTTCTAACTGAAGCTGGCATTCAT<br>GTCTTCATTTTGGGCTGTTTCAGTGCAGGGCTTCCTAAAACAGAAGC<br>CAACTGGGTGAATGTAATAAGTGATTTGAAAAAAATTGAAGATCTTAT<br>TCAATCTATGCATATTGATGCTACTTTATATACGGAAAGTGATGTTCA<br>CCCCAGTTGCAAAGTAACAGCAATGAAGTGCTTTCTCTTGGAGTTAC<br>AAGTTATTTCACTTGAGTCCGGAGATGCAAGTATTCATGATACAGTAG<br>AAAATCTGATCATCCTAGCAAACAACAGTTTGTCTTCTAATGGGAATG<br>TAACAGAATCTGGATGCAAAGAATGTGAGGAACTGGAGGAAAAAAAT<br>ATTAAAGAATTTTTGCAGAGTTTTGTACATATTGTCCAAATGTTCATCA<br>ACACTTCTTGA | 28 |
| IL-2 | ATGTACAGGATGCAACTCCTGTCTTGCATTGCACTAAGTCTTGCACTT<br>GTCACAAACAGTGCACCTACTTCAAGTTCTACAAAGAAAACACAGCT<br>ACAACTGGAGCATTTACTGCTGGATTTACAGATGATTTTGAATGGAAT<br>TAATAATTACAAGAATCCCAAACTCACCAGGATGCTCACATTTAAGTT<br>TTACATGCCCAAGAAGGCCACAGAACTGAAACATCTTCAGTGTCTAG<br>AAGAAGAACTCAAACCTCTGGAGGAAGTGCTAAATTTAGCTCAAAGC<br>AAAAACTTTCACTTAAGACCCAGGGACTTAATCAGCAATATCAACGTA<br>ATAGTTCTGGAACTAAAGGGATCTGAAACAACATTCATGTGTGAATAT<br>GCTGATGAGACAGCAACCATTGTAGAATTTCTGAACAGATGGATTAC<br>CTTTTGTCAAAGCATCATCTCAACACTGACTTGA | 29 |

In preferred embodiments, the T-cell enhancement compositions described herein (e.g. CXCL9, CXCL10, IL-7, IL-2) may be integrated into a separate delivery system from the vaccine compositions. In some embodiments, the T-cell enhancement compositions described herein (e.g. CXCL9, CXCL10, IL-7, IL-2) may be integrated into the same delivery system as the vaccine compositions.

In certain embodiments, the vaccine composition comprises a tag. For example, in some embodiments, the vaccine composition comprises a His tag. The present invention is not limited to a His tag and includes other tags such as those known to one of ordinary skill in the art, such as a fluorescent tag (e.g., GFP, YFP, etc.), etc.

Delivery System

The present invention also features vaccine compositions in the form of a delivery system (e.g., an antigen delivery system). Any appropriate antigen delivery system may be considered for delivery of the antigens described herein. The present invention is not limited to the antigen delivery systems described herein.

In certain embodiments, the antigen delivery system is for targeted delivery of the vaccine composition, e.g., for targeting to the tissues of the body where the virus replicates.

In certain embodiments, the antigen delivery system comprises adenoviruses such as but not limited to Ad5, Ad26, Ad35, etc., as well as carriers such as lipid nanoparticles, polymers, peptides, etc. In other embodiments, the antigen delivery system comprises a vesicular stomatitis virus (VSV) vector.

The present invention is not limited to adenovirus vector-based antigen delivery systems. In certain embodiments, the antigen delivery system comprises an adeno-associated virus vector-based antigen delivery system, such as but not limited to the adeno-associated virus vector type 9 (AAV9 serotype), AAV type 8 (AAV8 serotype), etc. In certain embodiments, the adeno-associated virus vectors used are tropic, e.g., tropic to lungs, brain, heart, and kidney, e.g., the tissues of the body that express ACE2 receptors. For example, AAV9 is known to be neurotropic, which would help the vaccine composition to be expressed in the brain.

In the antigen delivery system, the one or more antigens are operatively linked to a promoter. In certain embodiments, the one or more large sequences are operatively linked to a generic promoter. For example, in certain embodiments, the one or more antigens are operatively linked to a CMV promoter. In certain embodiments, the one or more antigens are operatively linked to a CAG, EFIA, EFS, CBh, SFFV, MSCV, mPGK, hPGK, SV40, UBC, or another appropriate promoter.

In some embodiments, the one or more antigens are operatively linked to a tissue-specific promoter (e.g., a lung-specific promoter). For example, the antigen may be operatively linked to a SpB promoter or a CD144 promoter.

As discussed, in certain embodiments, the vaccine composition comprises a molecular adjuvant. In certain embodiments, the molecular adjuvant is operatively linked to a generic promoter, e.g., as described above. In certain embodiments, the molecular adjuvant is operatively linked to a tissue-specific promoter, e.g., a lung-specific promoter, e.g., SpB or CD144.

As discussed, in certain embodiments, the vaccine composition comprises a T cell attracting chemokine. In certain embodiments, the T cell attracting chemokine is operatively linked to a generic promoter, e.g., as described above. In certain embodiments, the T cell attracting chemokine is operatively linked to a tissue-specific promoter, e.g., a lung-specific promoter, e.g., SpB or CD144.

As discussed, in certain embodiments, the vaccine composition comprises a composition for promoting T cell proliferation. In certain embodiments, the composition for promoting T cell proliferation is operatively linked to a generic promoter, e.g., as described above. In certain embodiments, the composition for promoting T cell proliferation is operatively linked to a tissue-specific promoter, e.g., a lung-specific promoter, e.g., SpB or CD144.

Table 5 shows non-limiting examples of promoters that may be used to create a vaccine composition described herein.

| Promoter | Sequence | SEQ ID NO: |
|---|---|---|
| CAG | CTCGACATTGATTATTGACTAGTTATTAATAGTAATCAATTACGGGGTCATT<br>AGTTCATAGCCCATATATGGAGTTCCGCGTTACATAACTTACGGTAAATGG<br>CCCGCCTGGCTGACCGCCCAACGACCCCCGCCCATTGACGTCAATAATG<br>ACGTATGTTCCCATAGTAACGCCAATAGGGACTTTCCATTGACGTCAATG<br>GGTGGAGTATTTACGGTAAACTGCCCACTTGGCAGTACATCAAGTGTATC<br>ATATGCCAAGTACGCCCCCTATTGACGTCAATGACGGTAAATGGCCCGCC<br>TGGCATTATGCCCAGTACATGACCTTATGGGACTTTCCTACTTGGCAGTAC<br>ATCTACGTATTAGTCATCGCTATTACCATGGTCGAGGTGAGCCCCACGTT<br>CTGCTTCACTCTCCCCATCTCCCCCCCCTCCCCACCCCCAATTTTGTATTT<br>ATTTATTTTTTAATTATTTTGTGCAGCGATGGGGGCGGGGGGGGGGGGGG<br>GGGCGCGCGCCAGGCGGGGGGGGGGGGGCGAGGGGGGGGGGGG<br>CGAGGCGGAGAGGTGCGGCGGCAGCCAATCAGAGCGGCGCGCTCCGAA<br>AGTTTCCTTTTATGGCGAGGCGGCGGCGGCGGCGGCCCTATAAAAAGCG<br>AAGCGCGCGGCGGGCGGGAGTCGCTGCGCGCTGCCTTCGCCCCGTGCC<br>CCGCTCCGCCGCCGCCTCGCGCCGCCCGCCCCGGCTCTGACTGACCGC<br>GTTACTCCCACAGGTGAGCGGGCGGGACGGCCCTTCTCCTCCGGGCTGT<br>AATTAGCGCTTGGTTTAATGACGGCTTGTTTCTTTTCTGTGGCTGCGTGAA<br>AGCCTTGAGGGGCTCCGGGAGGGCCCTTTGTGGGGGGGGAGCGGCTCG<br>GGGGGTGCGTGCGTGTGTGTGTGCGTGGGGAGCGCCGCGTGCGGCTCC<br>GCGCTGCCCGGCGGCTGTGAGCGCTGCGGGCGCGGCGCGGGGCTTTGT<br>GCGCTCCGCAGTGTGCGCGAGGGGAGCGCGGCCGGGGGGGGTGCCCC<br>GCGGTGCGGGGGGGGCTGCGAGGGGAACAAAGGCTGCGTGCGGGGTG<br>TGTGCGTGGGGGGGTGAGCAGGGGGTGTGGGCGCGTCGGTCGGGCTG<br>CAACCCCCCCTGCACCCCCCTCCCCGAGTTGCTGAGCACGGCCCGGCTT<br>CGGGTGCGGGGCTCCGTACGGGGCGTGGCGCGGGGCTCGCCGTGCCG<br>GGCGGGGGGTGGCGGCAGGTGGGGGTGCCGGGGGGGGGGGGGCCGC<br>CTCGGGCCGGGGAGGGCTCGGGGGAGGGGCGCGGCGGCCCCCGGAGC<br>GCCGGCGGCTGTCGAGGCGCGGCGAGCCGCAGCCATTGCCTTTTATGGT<br>AATCGTGCGAGAGGGCGCAGGGACTTCCTTTGTCCCAAATCTGTGCGGA<br>GCCGAAATCTGGGAGGCGCCGCCGCACCCCCTCTAGCGGGCGCGGGGC<br>GAAGCGGTGCGGCGCCGGCAGGAAGGAAATGGGGGGGGAGGGCCTTC<br>GTGCGTCGCCGCGCCGCCGTCCCCTTCTCCCTCTCCAGCCTCGGGGCTG<br>TCCGCGGGGGGACGGCTGCCTTCGGGGGGGACGGGGCAGGGGGGGGT<br>TCGGCTTCTGGCGTGTGACCGGCGGCTCTAGAGCCTCTGCTAACCATGTT<br>CATGCCTTCTTCTTTTTCCTACAGCTCCTGGGCAACGTGCTGGTTATTGTG<br>CTGTCTCATCATTTTGGCAAAGAATTG | 30 |
| CMV | TAGTTATTAATAGTAATCAATTACGGGGTCATTAGTTCATAGCCCATATATG<br>GAGTTCCGCGTTACATAACTTACGGTAAATGGCCCGCCTGGCTGACCGCC<br>CAACGACCCCCGCCCATTGACGTCAATAATGACGTATGTTCCCATAGTAA<br>CGCCAATAGGGACTTTCCATTGACGTCAATGGGTGGAGTATTTACGGTAA<br>ACTGCCCACTTGGCAGTACATCAAGTGTATCATATGCCAAGTACGCCCCC<br>TATTGACGTCAATGACGGTAAATGGCCCGCCTGGCATTATGCCCAGTACA<br>TGACCTTATGGGACTTTCCTACTTGGCAGTACATCTACGTATTAGTCATCG | 31 |

-continued

| Promoter | Sequence | SEQ ID NO: |
|---|---|---|
| | CTATTACCATGGTGATGCGGTTTTGGCAGTACATCAATGGGCGTGGATAG<br>CGGTTTGACTCACGGGGATTTCCAAGTCTCCACCCCATTGACGTCAATGG<br>GAGTTTGTTTTGGCACCAAAATCAACGGGACTTTCCAAAATGTCGTAACAA<br>CTCCGCCCCATTGACGCAAATGGGGGGTAGGCGTGTACGGTGGGAGGTC<br>TATATAAGCAGAGCTGGTTTAGTGAACCGTCAGATC | |
| SP-B | GTATAGGGCTGTCTGGGAGCCACTCCAGGGCCACAGAAATCTTGTCTCTG<br>ACTCAGGGTATTTTGTTTTCTGTTTTGTGTAAATGCTCTTCTGACTAATGCA<br>AACCATGTGTCCATAGAACCAGAAGATTTTTCCAGGGGAAAAGGTAAGGA<br>GGTGGTGAGAGTGTCCTGGGTCTGCCCTTCCAGGGCTTGCCCTGGGTTA<br>AGAGCCAGGCAGGAAGCTCTCAAGAGCATTGCTCAAGAGTAGAGGGGGC<br>CTGGGAGGCCCAGGGAGGGGATGGGAGGGGAACACCCAGGCTGCCCCC<br>AACCAGATGCCCTCCACCCTCCTCAACCTCCCTCCCACGGCCTGGAGAG<br>GTGGGACCAGGTATGGAGGCTTGAGAGCCCCTGGTTGGAGGAAGCCACA<br>AGTCCAGGAACATGGGAGTCTGGGCAGGGGGCAAAGGAGGCAGGAACA<br>GGCCATCAGCCAGGACAGGTGGTAAGGCAGGCAGGAGTGTTCCTGCTGG<br>GAAAAGGTGGGATCAAGCACCTGGAGGGCTCTTCAGAGCAAAGACAAAC<br>ACTGAGGTCGCTGCCACTCCTACAGAGCCCCCACGCCCCGCCCAGCTAT<br>AAGGGGCCATGCACCAAGCAGGGTACCCAGGCTGCAGAGGTGCC | 32 |
| CD144 | CATCCATGCCCATGGCCTCAGATGCCAGCCATAAGCTGTTGGGTTCCAAA<br>CCTCGACTCCAGGCTGGACTCACCCCTGTCTCCCCCACCAGCCTGACAC<br>CTCCACCTGGGTATCTAACGAGCATCTCAAACTCAACCTGCCTGAGACAG<br>AGGAATCACTATCCCCTCCTCCTCCAAAAATATCCTTCCATCACACTCCCC<br>ATCTTGTGCTCTGATTTACTAAACGGCCCTGGGCCCTCTCTTTCTCAGGGT<br>CTCTGCTTGCCCAGCTATATAATAAAACAAGTTTGGGACTTCCCAACCATT<br>CACCCATGGAAAAACAGAAGCAACTCTTCAAAGGACAGATTCCCAGGATC<br>TGCCCTGGGAGATTCCAAATCAGTTGATCTGGGGTGAGCCCAGTCCTCTG<br>TAGTTTTTAGAAGCTCCTCCTATGTCTCTCCTGGTCAGCAGAATCTTGGCC<br>CCTCCCTTCCCCCCAGCCTCTTGGTTCTTCTGGGCTCTGATCCAGCCTCA<br>GCGTCACTGTCTTCCACGCCCCTCTTTGATTCTCGTTTATGTCAAAAGCCT<br>TGTGAGGATGAGGCTGTGATTATCCCCATTTTACAGATGAGGAAACTGTG<br>GCTCCAGGATGACACAACTGGCCAGAGGTCACATCAGAAGCAGAGCTGG<br>GTCACTTGACTCCACCCAATATCCCTAAATGCAAACATCCCCTACAGACC<br>GAGGCTGGCACCTTAGAGCTGGAGTCCATGCCCGCTCTGACCAGGAGAA<br>GCCAACCTGGTCCTCCAGAGCCAAGAGCTTCTGTCCCTTTCCCATCTCCT<br>GAAGCCTCCCTGTCACCTTTAAAGTCCATTCCCACAAAGACATCATGGGA<br>TCACCACAGAAAATCAAGCTCTGGGGCTAGGCTGACCCCAGCTAGATTTT<br>TGGCTCTTTTATACCCCAGCTGGGTGGACAAGCACCTTAAACCCGCTGAG<br>CCTCAGCTTCCCGGGCTATAAAATGGGGGTGATGACACCTGCCTGTAGCA<br>TTCCAAGGAGGGTTAAATGTGATGCTGCAGCCAAGGGTCCCCACAGCCA<br>GGCTCTTTGCAGGTGCTGGGTTCAGAGTCCCAGAGCTGAGGCCGGGAGT<br>AGGGGTTCAAGTGGGGTGCCCCAGGCAGGGTCCAGTGCCAGCCCTCTGT<br>GGAGACAGCCATCCGGGGCCGAGGCAGCCGCCCACCGCAGGGCCTGCC<br>TATCTGCAGCCAGCCCAGCCCTCACAAAGGAACAATAACAGGAAACCATC<br>CCAGGGGGAAGTGGGCCAGGGCCAGCTGGAAAACCTGAAGGGGAGGCA<br>GCCAGGCCTCCCTCGCCAGCGGGGTGTGGCTCCCCTCCAAAGACGGTC<br>GGCTGACAGGCTCCACAGAGCTCCACTCACGCTCAGCCCTGGACGGACA<br>GGCAGTCCAACGGAACAGAAACATCCCTCAGCCCACAGGCACGGTGAGT<br>GGGGGCTCCCACACTCCCCTCCACCCCAAACCCGCCACCCTGCGCCCAA<br>GATGGGAGGGTCCTCAGCTTCCCCATCTGTAGAATGGGCATCGTCCCACT<br>CCCATGACAGAGAGGCTCC | 33 |
| wild type<br>native<br>leader<br>sequence | ATGTTCGTGTTCCTGGTGCTGCTGCCCCTGGTGAGCAGC | 34 |

In certain embodiments, the T cell attracting chemokine and the composition that promotes T cell proliferation are driven by the same promoter (e.g., the T cell attracting chemokine and the composition that promotes T cell proliferation are synthesized as a peptide). In certain embodiments, the T cell attracting chemokine and the composition that promotes T cell proliferation are driven by different promoters. In certain embodiments, the antigen, the T cell attracting chemokine, and the composition that promotes T cell proliferation are driven by the same promoter. In certain embodiments, the antigen, the T cell attracting chemokine, and the composition that promotes T cell proliferation are driven by the different promoters. In certain embodiments, the T cell attracting chemokine and the composition that promotes T cell proliferation are driven by the same promoter, and the one or more large sequences are driven by a different promoter.

In some embodiments, the antigen delivery system comprises one or more linkers between the T cell attracting chemokine and the composition that promotes T cell proliferation. In certain embodiments, linkers are used between one or more of the large sequences. The linkers may allow for cleavage of the separate molecules (e.g., chemokine). For example, in some embodiments, a linker is positioned between IL-7 (or IL-2) and CCL5, CXCL9, CXCL10, CXCL11, CCL25, CCL28, CXCL14, CXCL17, etc. In some embodiments, a linker is positioned between IL-15 and CCL5, CXCL9, CXCL10, CXCL11, CCL25, CCL28, CXCL14, CXCL17, etc. In some embodiments, a linker is positioned between the antigen or large sequence and another composition, e.g., IL-15, IL-7, CCL5, CXCL9, CXCL10, CXCL11, CCL25, CCL28, CXCL14, CXCL17, etc. A non-limiting example of a linker is T2A, E2A, P2A (see Table 6), or the like. The composition may feature a different linker between each open reading frame.

TABLE 6

Shows non-limiting examples of linkers that may be used in accordance with the present invention.

| Linker | Sequence | SEQ ID NO: |
|---|---|---|
| T2A Linker | GGAAGCGGAGAGGGCAGGGGAAGTCTTCTAACATGCG GGGACGTGGAGGAAAATCCCGGCCCC | 35 |
| E2A Linker | GGAAGCGGACAGTGTACTAATTATGCTCTCTTGAAAT TGGCTGGAGATGTTGAGAGCAACCCAGGTCCC | 36 |
| P2A Linker | GGAAGCGGAGCCACGAACTTCTCTCTGTTAAAGCAAG CAGGAGATGTTGAAGAAACCCCGGGCCT | 37 |
| | GCCGCCTAC | – |
| | GGCCCCGGCCCCGGC | 38 |
| 6-His Tag | CATCACCATCACCATCAC | 39 |

The present invention includes mRNA sequences encoding any of the vaccine compositions or portions thereof herein, e.g., a molecular adjuvant, a T cell enhancement, etc. The present invention also includes modified mRNA sequences encoding any of the vaccine compositions or portions thereof herein. The present invention also includes DNA sequence encoding any of the vaccine compositions or portions thereof herein.

In some embodiments, the mRNA sequence encodes at least two (preferably different) antigen. In certain embodiments, the mRNA sequence encodes at least three (preferably different) antigens. For example, the mRNA sequence may encode an NSP2 protein (or a portion thereof); an NSP3 protein (or a portion thereof); and a Nucleoprotein (Nucleoprotein) (or a portion thereof). Additionally, a separate mRNA sequence may encode a Spike protein (or portion thereof). In other embodiments, the mRNA sequence encodes at least four (preferably different) antigens; e.g., an NSP2 protein (or a portion thereof); an NSP3 protein (or a portion thereof); a Nucleoprotein (Nucleoprotein) (or a portion thereof); and a Spike protein (or a portion thereof).

In certain embodiments, nucleic acids of a vaccine composition herein are chemically modified. In some embodiments, the nucleic acids of a vaccine composition therein are unmodified. In some embodiments, all or a portion of the uracil in the open reading frame has a chemical modification. In some embodiments, a chemical modification is in the 5-position of the uracil. In some embodiments, a chemical modification is an N1-methyl pseudouridine. In some embodiments, all or a portion of the uracil in the open reading frame has an N1-methyl pseudouridine in the 5-position of the uracil.

In certain embodiments, an open reading frame of a vaccine composition herein encodes one antigen or epitopes. In some embodiments, an open reading frame of a vaccine composition herein encodes two or more antigens or epitopes. In some embodiments, an open reading frame of a vaccine composition herein encodes three antigens or epitopes. In some embodiments, an open reading frame of a vaccine composition herein encodes five or more antigens or epitopes. In some embodiments, an open reading frame of a vaccine composition herein encodes ten or more antigens or epitopes. In some embodiments, an open reading frame of a vaccine composition herein encodes 50 or more antigens or epitopes.

The mRNAs may further comprise a 5' untranslated region (UTR) and a 3' UTR. In some embodiments, the mRNAs further comprise a 3' poly(A) tail and/or a 5' cap or cap analog.

For example, the present invention may further feature a composition comprising two (or more) ribonucleic acids (mRNAs) comprising an open reading frame encoding at least a portion of a Coronavirus protein selected from a group comprising, consisting essentially or consisting of: an NSP2 protein, an NSP14 protein, and a Nucleoprotein protein. In some embodiments, the composition comprising three (or more) ribonucleic acids (mRNAs) comprising an open reading frame encoding at least a portion of a Coronavirus protein selected from a group comprising, consisting essentially or consisting of: an NSP2 protein, an NSP14 protein, and a Nucleoprotein protein. The two or three mRNAs may be formulated in a lipid nanoparticle. Alternatively, the composition may comprise two (or more) mRNAs comprising an open reading frame encoding an entire Coronavirus protein selected from a group comprising, consisting essentially, or consisting of: an NSP2 protein, an NSP14 protein, and a Nucleoprotein protein. In other embodiments, the composition may comprise three (or more) mRNAs comprising an open reading frame encoding an entire Coronavirus protein selected from a group comprising, consisting essentially, or consisting of: an NSP2 protein, an NSP14 protein, and a Nucleoprotein protein.

The composition may further comprise an mRNA comprising an open reading frame encoding a Coronavirus Spike protein or portion thereof formulated in a lipid nanoparticle. For example, the composition may comprise two (or more) mRNAs comprising an open reading frame encoding at least a portion of a Coronavirus protein selected from a group comprising, consisting essentially or consisting of: an NSP2 protein, an NSP14 protein, a Nucleoprotein protein; and a Spike protein. In other embodiments, the composition may comprise three (or more) mRNAs comprising an open reading frame encoding at least a portion of a Coronavirus protein selected from a group comprising, consisting essentially or consisting of: an NSP2 protein, an NSP14 protein, a Nucleoprotein protein; and a Spike protein. Alternatively, the composition may comprise two (or more) mRNAs comprising an open reading frame encoding an entire Coronavirus protein selected from a group comprising, consisting essentially, or consisting of: an NSP2 protein, an NSP14 protein, a Nucleoprotein protein; and a Spike protein. In some embodiments, the composition may comprise three (or more) mRNAs comprising an open reading frame encoding an entire Coronavirus protein selected from a group comprising, consisting essentially, or consisting of: an NSP2 protein, an NSP14 protein, a Nucleoprotein protein; and a Spike protein. The two or three (or more) mRNAs are formulated in a lipid nanoparticle.

Methods

As previously discussed, the compositions described herein, e.g., the antigens, the vaccine compositions, the antigen delivery systems, the chemokines, the adjuvants, etc., may be used to prevent a coronavirus disease in a subject. In some embodiments, the compositions described herein, e.g., the antigens, the vaccine compositions, the antigen delivery systems, the chemokines, the adjuvants, etc., may be used to prevent a coronavirus infection prophylactically in a subject. In some embodiments, the compositions described herein, e.g., the antigens, the vaccine compositions, the antigen delivery systems, the chemokines, the adjuvants, etc., may elicit an immune response in a subject. In some embodiments, the compositions described herein, e.g., the antigens, the vaccine compositions, the antigen delivery systems, the chemokines, the adjuvants, etc., may prolong an immune response induced by the universal pre-emptive pan-coronavirus vaccine composition and increase T-cell migration to the lungs.

Methods for preventing a coronavirus disease in a subject may comprise administering to the subject a therapeutically effective amount of a pre-emptive pan-coronavirus vaccine composition according to the present invention. In some embodiments, the composition elicits an immune response in the subject.

In some embodiments, the composition induces memory B and T cells. In some embodiments, the composition induces resident memory T cells (Trm). In some embodiments, the composition prevents virus replication, e.g., in the areas where the virus normally replicates, such as the lungs, brain, heart, and kidney. In some embodiments, the composition prevents a cytokine storm, e.g., in the areas where the virus normally replicates, such as the lungs, brain, heart, and kidney. In some embodiments, the composition prevents inflammation or an inflammatory response, e.g., in the areas where the virus normally replicates, such as the lungs, brain, heart, and kidney. In some embodiments, the composition improves the homing and retention of T cells, e.g., in the areas where the virus normally replicates, such as the lungs, brain, heart, and kidney.

Methods for preventing a coronavirus infection prophylactically in a subject may comprise administering to the subject a prophylactically effective amount of a pan-coronavirus vaccine composition according to the present invention. In some embodiments, the composition elicits an immune response in the subject. In some embodiments, the composition induces memory B and T cells. In some embodiments, the composition induces resident memory T cells (Trm). In some embodiments, the composition prevents virus replication, e.g., in the areas where the virus normally replicates, such as the lungs, brain, heart, and kidney. In some embodiments, the composition prevents a cytokine storm, e.g., in the areas where the virus normally replicates, such as the lungs, brain, heart, and kidney. In some embodiments, the composition prevents inflammation or an inflammatory response, e.g., in the areas where the virus normally replicates, such as the lungs, brain, heart, and kidney. In some embodiments, the composition improves the homing and retention of T cells, e.g., in the areas where the virus normally replicates, such as the lungs, brain, heart, and kidney.

Methods for eliciting an immune response in a subject may comprise administering to the subject a vaccine composition according to the present invention, wherein the composition elicits an immune response in the subject. In some embodiments, the composition induces memory B and T cells. In some embodiments, the composition induces resident memory T cells (Trm). In some embodiments, the composition prevents virus replication, e.g., in the areas where the virus normally replicates, such as the lungs, brain, heart, and kidney. In some embodiments, the composition prevents a cytokine storm, e.g., in the areas where the virus normally replicates, such as the lungs, brain, heart, and kidney. In some embodiments, the composition prevents inflammation or an inflammatory response, e.g., in the areas where the virus normally replicates, such as the lungs, brain, heart, and kidney. In some embodiments, the composition improves the homing and retention of T cells, e.g., in the areas where the virus normally replicates, such as the lungs, brain, heart, and kidney.

Methods for prolonging an immune response induced by a vaccine composition of the present invention and increasing T cell migration to particular tissues (e.g., lung, brain, heart, kidney, etc.) may comprise co-expressing a T-cell attracting chemokine, a composition that promotes T cell proliferation, and a vaccine composition (e.g., antigen) according to the present invention.

Methods for prolonging the retention of memory T cells into the lungs induced by a vaccine composition of the present invention and increasing virus-specific tissue-resident memory T-cells (TRM cells) may comprise co-expressing a T-cell attracting chemokine, a composition that promotes T cell proliferation, and a vaccine composition (e.g., antigen) according to the present invention.

The vaccine composition may be administered through standard means, e.g., through an intravenous route (i.v.), an intranasal route (i.n.), or a sublingual route (s.l.) route.

In certain embodiments, the method comprises administering to the subject a second (e.g., booster) dose. The second dose may comprise the same vaccine composition or a different vaccine composition. Additional doses of one or more vaccine compositions may be administered.

Sequential Vaccine Delivery Methodology

In some embodiments, the present invention features a method of delivering the vaccine to induce heterologous immunity in a subject (e.g., prime/boost). In some embodiments, the method comprises administering a first pan-coronavirus vaccine composition dose using a first delivery system. In further embodiments, the method comprises administering a second vaccine composition dose using a second delivery system. In some embodiments, the second composition is administered 8 days after administration of the first composition. In some embodiments, the second composition is administered 9 days after administration of the first composition. In some embodiments, the second composition is administered 10 days after administration of the first composition. In some embodiments, the second composition is administered 11 days after administration of the first composition. In some embodiments, the second composition is administered 12 days after administration of the first composition. In some embodiments, the second composition is administered 13 days after administration of the first composition. In some embodiments, the second composition is administered 14 days after administration of the first composition. In some embodiments, the second composition is administered from 14 to 30 days after administration of the first composition. In some embodiments, the second composition is administered from 30 to 60 days after administration of the first composition. In other embodiments, the first delivery system and the second delivery system are different. In some embodiments, the peptide vaccine composition is administered 14 days after the administration of the first vaccine composition dose. In some embodiments, the peptide vaccine composition is administered 30 or 60 days after the administration of the first vaccine composition dose.

In some embodiments, the first delivery system or the second delivery system comprises an mRNA, a modified mRNA, or a peptide vector. In other embodiments, the peptide vector comprises an adenovirus or an adeno-associated virus vector.

In some embodiments, the present invention features a method of delivering the vaccine to induce heterologous immunity in a subject (i.e., prime/pull). In some embodiments, the method comprises administering a pan-coronavirus vaccine composition. In further embodiments, the method comprises administering at least one T-cell attracting chemokine after administering the pan-coronavirus vaccine composition. In some embodiments, the T-cell attracting chemokine is administered 8 days after the vaccine composition is administered. In some embodiments, the T-cell attracting chemokine is administered 9 days after the vaccine composition is administered. In some embodiments, the T-cell attracting chemokine is administered 10 days after the vaccine composition is administered. In some embodiments, the T-cell attracting chemokine is administered 11 days after the vaccine composition is administered. In some embodiments, the T-cell attracting chemokine is administered 12 days after the vaccine composition is administered. In some embodiments, the T-cell attracting chemokine is administered 13 days after the vaccine composition is administered. In some embodiments, the T-cell attracting chemokine is administered 14 days after the vaccine composition is administered. In some embodiments, the T-cell attracting chemokine is administered from 14 to 30 days after administration of the vaccine composition. In some embodiments, the T-cell attracting chemokine is administered from 30 to 60 days after administration of the vaccine composition. In some embodiments, the T cell-attracting chemokine composition is administered 8 to 14 days after the administration of the final vaccine composition dose. In some embodiments, the cell-attracting chemokine composition is administered 30 or 60 days after the administration of the final vaccine composition dose.

The present invention also features a novel "prime, pull, and boost" strategy. In other embodiments, the present invention features a method to increase the size and maintenance of lung-resident B-cells, CD4+ T cells, and CD8+ T cells to protect against SARS-CoV-2. In some embodiments, the method comprises administering a pan-coronavirus vaccine composition. In other embodiments, the method comprises administering at least one T-cell attracting chemokine after administering the pan-coronavirus vaccine composition. In further embodiments, the method comprises administering at least one cytokine after administering the T-cell attracting chemokine. In some embodiments, the T-cell attracting chemokine is administered 14 days after administering the pan-coronavirus composition. In other embodiments, the cytokine is administered 10 days after administering the T-cell attracting chemokine. In some embodiments, the T-cell attracting chemokine is administered 8 days after the vaccine composition is administered. In some embodiments, the T-cell attracting chemokine is administered 9 days after the vaccine composition is administered. In some embodiments, the T-cell attracting chemokine is administered 10 days after the vaccine composition is administered. In some embodiments, the T-cell attracting chemokine is administered 11 days after the vaccine composition is administered. In some embodiments, the T-cell attracting chemokine is administered 12 days after the vaccine composition is administered. In some embodiments, the T-cell attracting chemokine is administered 13 days after the vaccine composition is administered. In some embodiments, the T-cell attracting chemokine is administered 14 days after the vaccine composition is administered. In some embodiments, the T-cell attracting chemokine is administered from 14 to 30 days after administration of the vaccine composition. In some embodiments, the T-cell attracting chemokine is administered from 30 to 60 days after administration of the vaccine composition. In some embodiments, the cytokine is administered 8 days after administering the T-cell attracting chemokine. In some embodiments, the cytokine is administered 9 days after administering the T-cell attracting chemokine. In some embodiments, the cytokine is administered 10 days after administering the T-cell attracting chemokine. In some embodiments, the cytokine is administered 11 days after administering the T-cell attracting chemokine. In some embodiments, the cytokine is administered 12 days after administering the T-cell attracting chemokine. In some embodiments, the cytokine is administered 13 days after administering the T-cell attracting chemokine. In some embodiments, the cytokine is administered 14 days after administering the T-cell attracting chemokine. In some embodiments, the cytokine is administered from 14 to 30 days after administering the T-cell attracting chemokine. In some embodiments, the cytokine is administered from 30 to 60 days after administering the T-cell attracting chemokine. In some embodiments, the cytokine composition is administered 8 to 14 days after the administration of the T cell-attracting chemokine. In some embodiments, the cytokine composition is administered 30 or 60 days after the administration of the T cell-attracting chemokine.

The present invention further features a novel "prime, pull, and keep" strategy. In further embodiments, the present invention features a method to increase the size and maintenance of lung-resident B-cells, CD4+ T cells, and CD8+ T cells to protect against SARS-CoV-2. In some embodiments, the method comprises administering a pan-coronavirus vaccine composition. In other embodiments, the method comprises administering at least one T-cell attracting chemokine after administering the pan-coronavirus vaccine composition. In further embodiments, the method comprises administering at least one mucosal chemokine after administering the T-cell attracting chemokine. In some embodiments, the T-cell attracting chemokine is administered 14 days after administering the pan-coronavirus composition. In other embodiments, the mucosal chemokines are administered 10 days after administering the T-cell attracting chemokine. In some embodiments, the T-cell attracting chemokine is administered 8 days after the vaccine composition is administered. In some embodiments, the T-cell attracting chemokine is administered 9 days after the vaccine composition is administered. In some embodiments, the T-cell attracting chemokine is administered 10 days after the vaccine composition is administered. In some embodiments, the T-cell attracting chemokine is administered 11 days after the vaccine composition is administered. In some embodiments, the T-cell attracting chemokine is administered 12 days after the vaccine composition is administered. In some embodiments, the T-cell attracting chemokine is administered 13 days after the vaccine composition is administered. In some embodiments, the T-cell attracting chemokine is administered 14 days after the vaccine composition is administered. In some embodiments, the T-cell attracting chemokine is administered from 14 to 30 days after administration of the vaccine composition. In some embodiments, the T-cell attracting chemokine is administered from 30 to 60 days after administration of the vaccine composition. In some embodiments, the mucosal chemokine is administered 8 days after administering the T-cell attracting chemokine. In some embodiments, the mucosal chemokine is administered 9 days after administering the T-cell attracting chemokine. In some embodiments, the mucosal chemokine is administered 10 days after administering the T-cell attracting chemokine. In some embodiments, the mucosal chemokine is administered 11 days after administering the T-cell attracting chemokine. In some embodiments, the mucosal chemokine is administered 12 days after administering the T-cell attracting chemokine. In some embodiments, the mucosal chemokine is administered 13 days after administering the T-cell attracting chemokine. In some embodiments, the mucosal chemokine is administered 14 days after administering the T-cell attracting chemokine. In some embodiments, the mucosal chemokine is administered from 14 to 30 days after administering the T-cell attracting chemokine.

In some embodiments, the mucosal chemokine is administered from 30 to 60 days after administering the T-cell attracting chemokine. In some embodiments, the mucosal chemokine composition is administered 8 to 14 days after the administration of the T cell-attracting chemokine. In some embodiments, the mucosal cytokine composition is administered 30 or 60 days after the administration of the T cell-attracting chemokine.

In some embodiments, the mucosal chemokines may comprise CCL25, CCL28, CXCL14, CXCL17, or a combination thereof. In some embodiments, the T-cell attracting chemokines may comprise CCL5, CXCL9, CXCL10, CXCL11, or a combination thereof. In some embodiments, the cytokines may comprise IL-15, IL-2, IL-7, or a combination thereof.

In some embodiments, the efficacy (or effectiveness) of a vaccine composition herein is greater than 60%. In some embodiments, the efficacy (or effectiveness) of a vaccine composition herein is greater than 70%. In some embodiments, the efficacy (or effectiveness) of a vaccine composition herein is greater than 80%. In some embodiments, the efficacy (or effectiveness) of a vaccine composition herein is greater than 90%. In some embodiments, the efficacy (or effectiveness) of a vaccine composition herein is greater than 95%.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with the use of the following formulas: Efficacy=(ARU−ARV)/ARU×100; and Efficacy=(1−RR)× 100.

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with the use of the odds ratio (OR) for developing infection despite vaccination: Effectiveness=(1−OR)×100.

In some embodiments, the vaccine immunizes the subject against a coronavirus for up to 1 year. In some embodiments, the vaccine immunizes the subject against a coronavirus for up to 2 years. In some embodiments, the vaccine immunizes the subject against a coronavirus for more than 1 year, more than 2 years, more than 3 years, more than 4 years, or for 5-10 years.

In some embodiments, the subject is a young adult between the ages of about 20 years and about 50 years (e.g., about 20, 25, 30, 35, 40, 45, or 50 years old).

In some embodiments, the subject is an elderly subject about 60 years old, about 70 years old, or older (e.g., about 60, 65, 70, 75, 80, 85, or 90 years old).

In some embodiments, the subject is about 5 years old or younger. For example, the subject may be between the ages of about 1 year and about 5 years (e.g., about 1, 2, 3, 5, or 5 years) or between the ages of about 6 months and about 1 year (e.g., about 6, 7, 8, 9, 10, 11 or 12 months). In some embodiments, the subject is about 12 months or younger (e.g., 12, 11, 10, 9, 8, 7, 6, 5, 4, 3, 2 months or 1 month). In some embodiments, the subject is about 6 months or younger.

In some embodiments, the subject was born full term (e.g., about 37-42 weeks). In some embodiments, the subject was born prematurely, for example, at about 36 weeks of gestation or earlier (e.g., about 36, 35, 34, 33, 32, 31, 30, 29, 28, 27, 26, or 25 weeks). For example, the subject may have been born at about 32 weeks of gestation or earlier. In some embodiments, the subject was born prematurely between about 32 weeks and about 36 weeks of gestation. In such subjects, a vaccine may be administered later in life, for example, at the age of about 6 months to about 5 years or older.

In some embodiments, the subject is pregnant (e.g., in the first, second, or third trimester) when administered a vaccine.

In some embodiments, the subject has a chronic pulmonary disease (e.g., chronic obstructive pulmonary disease (COPD) or asthma) or is at risk thereof. Two forms of COPD include chronic bronchitis, which involves a long-term cough with mucus, and emphysema, which involves damage to the lungs over time. Thus, a subject administered a vaccine may have chronic bronchitis or emphysema.

In some embodiments, the subject has been exposed to a coronavirus. In some embodiments, the subject is infected with a coronavirus. In some embodiments, the subject is at risk of infection by a coronavirus.

In some embodiments, the subject is immunocompromised (has an impaired immune system, e.g., has an immune disorder or autoimmune disorder).

Pharmaceutical Carriers

In certain embodiments, the vaccine composition further comprises a pharmaceutical carrier.

Pharmaceutical carriers are well known to one of ordinary skill in the art. For example, in certain embodiments, the pharmaceutical carrier is selected from the group consisting of water, an alcohol, a natural or hardened oil, a natural or hardened wax, a calcium carbonate, a sodium carbonate, a calcium phosphate, kaolin, talc, lactose and combinations thereof. In some embodiments, the pharmaceutical carrier may comprise a lipid nanoparticle, an adenovirus vector, or an adeno-associated virus vector. In some embodiments, the vaccine composition is constructed using an adeno-associated virus vectors-based antigen delivery system.

Also provided herein is a vaccine of any one of the foregoing paragraphs, formulated in a nanoparticle (e.g., a lipid nanoparticle). In some embodiments, the nanoparticle has a mean diameter of 50-200 nm. In some embodiments, the nanoparticle is a lipid nanoparticle. In some embodiments, the lipid nanoparticle comprises a cationic lipid, a PEG-modified lipid, a sterol, and a non-cationic lipid. In some embodiments, the lipid nanoparticle comprises a molar ratio of about 20-60% cationic lipid, 0.5-15% PEG-modified lipid, 25-55% sterol, and 25% non-cationic lipid. In some embodiments, the cationic lipid is an ionizable cationic lipid, the non-cationic lipid is a neutral lipid, and the sterol is a cholesterol. In some embodiments, the cationic lipid is selected from 2,2-dilinoleyl-4-dimethylaminoethyl-[1,3]-di-oxolane (DLin-KC2-DMA), dilinoleyl-methyl-4-dimethyl-aminobutyrate (DLin-MC3-DMA), and di((Z)-non-2-en-1-yl) 9-((4-(dimethylamino)butanoyl)oxy)heptadecanedioate (L319).

For example, the present invention may feature a pharmaceutical composition. In some embodiments, the pharmaceutical composition may comprise a plurality of lipid nanoparticles; where a first lipid nanoparticle comprises three messenger ribonucleic acids (mRNAs) encapsulated therein, and each mRNA comprises an open reading frame encoding a Coronavirus protein selected from a group comprising, consisting essentially, or consisting of: an NSP2 protein, an NSP14 protein, and a Nucleoprotein, and a second lipid nanoparticle comprising an mRNA comprising an open reading frame encoding a Coronavirus Spike protein or portion thereof encapsulated therein. Likewise, the pharmaceutical composition may comprise a plurality of lipid nanoparticles; where a first lipid nanoparticle comprises three messenger ribonucleic acids (mRNAs) encapsulated therein, and each mRNA comprises an open reading frame encoding an entire Coronavirus protein selected from a group comprising, consisting essentially, or consisting of: an NSP2 protein, an NSP14 protein, and a Nucleoprotein, and a second lipid nanoparticle comprising an mRNA comprising an open reading frame encoding a Coronavirus Spike protein or portion thereof encapsulated therein.

In some embodiments, the first lipid nanoparticle comprises two mRNAs (preferably different) encapsulated therein. In some embodiments, the first lipid nanoparticle comprises two or more mRNAs (preferably different) encapsulated therein. In some embodiments, the first lipid nanoparticle comprises three mRNAs (preferably different) encapsulated therein. In some embodiments, the first lipid nanoparticle comprises three or more mRNAs (preferably different) encapsulated therein. In some embodiments, the first lipid nanoparticle comprises four mRNAs (preferably different) encapsulated therein. In some embodiments, the first lipid nanoparticle comprises four or more mRNAs (preferably different) encapsulated therein.

In some embodiments, the second lipid nanoparticle comprises one mRNA encapsulated therein. In some embodiments, the second lipid nanoparticle comprises two or more mRNAs (preferably different) encapsulated therein. In some embodiments, the second lipid nanoparticle comprises three mRNAs (preferably different) encapsulated therein. In some embodiments, the second lipid nanoparticle comprises three or more mRNAs (preferably different) encapsulated therein. In some embodiments, the second lipid nanoparticle comprises four mRNAs (preferably different) encapsulated therein. In some embodiments, the second lipid nanoparticle comprises four or more mRNAs (preferably different) encapsulated therein.

The pharmaceutical composition described herein may comprise a single lipid nanoparticle (e.g., a first nanoparticle).

Example 1

The following is a non-limiting example of the present invention. It is to be understood that said example is not intended to limit the present invention in any way. Equivalents or substitutes are within the scope of the present invention.

Five highly conserved regions that encode ten common structural, non-structural, and accessory protein antigens, were identified in the SARS-CoV-2 single-stranded RNA genome.

The SARS-CoV-2 single-stranded genome is comprised of 29903 bp that encodes 29 proteins, including 4 structural, 16 nonstructural, and 9 accessory regulatory proteins. Using several in-silico bioinformatic approaches and alignments of 8.7 million genome sequences of SARS-CoV-2 strains that circulated worldwide throughout the pandemic, including twenty-one VOCs/Variants of Interest (VOI)/Variants being Monitored (VBM); SARS-CoV; MERS-CoV; Common Cold Coronaviruses (i.e., α-CCC-229E, α-CCC-NL63, pi-CCC-HKU1, and β-CCC-OC43 strains); and twenty-five animal's SARS-like Coronaviruses (SL-CoVs) genome sequences isolated from bats, pangolins, civet cats, and camels, 5 highly conserved regions were identified in the SARS-CoV-2 single-stranded RNA genome (1-1580 bp, 3547-12830 bp, 1772-21156 bp, 22585-24682 bp, and 26660-27421 bp, FIG. 1A). Further Sequence Homology Analysis confirmed that the five SARS-CoV-2 genome regions encode for ten highly conserved non-Spike T cell antigens (NSP-2 (Size: 1914 bp, Nucleotide Range: 540 bp-2454 bp), NSP-3 (Size: 4485 bp, Nucleotide Range: 3804 bp-8289 bp), NSP-4 (Size: 1500 bp, Nucleotide Range: 8290 bp-9790 bp), NSP-5-10 (Size: 3378 bp, Nucleotide Range: 9791 bp-13169 bp), NSP-12 (Size: 2796 bp, Nucleotide Range: 13170 bp-15966 bp), NSP-14 (Size: 1581 bp, Nucleotide Range: 17766 bp-19347 bp), ORF7a/b (Size: 492 bp, Nucleotide Range: 27327 bp-27819 bp), Membrane (Size: 666 bp, Nucleotide Range: 26455 bp-27121 bp), Envelope (Size: 225 bp, Nucleotide Range: 26177 bp-26402 bp), and Nucleoprotein (Size: 1248 bp, Nucleotide Range: 28206 bp-29454 bp) (FIG. 1B). The sequences of the ten highly conserved antigens were then used to design and construct N1-methylpseudouridine (m1ψ)-modified mRNAs encapsulated in lipid nanoparticles (mRNA/LNP vaccines) that are subsequently preclinically tested for safety, immunogenicity, and protective efficacy against several SARS-CoV-2 variants and sub-variants of concern in the golden Syrian hamster model (FIG. 1C).

Mutations screened against twelve major SARS-CoV-2 variants of concern and sequence homology analysis confirmed the sequences representing the ten non-Spike antigens are highly conserved in the currently highly mutated BA.2.86 and JN.1 Omicron sub-variants (FIG. 2). As expected, with 346 cumulative mutations, the sequence of the Spike is heavily mutated in the latest Omicron sub-variants compared to the non-Spike antigens. The sequences of Spike protein have 42 and 43 new mutations in the current highly transmissible and most immune-evasive Omicron sub-variants, BA.2.86 and JN.1 (FIG. 2). In contrast, compared to Spike, the sequences of the three non-Spike antigens (NSP-2, NSP-14, and Nucleoprotein) remain relatively conserved in these sub-variants BA.2.86 and JN.1 (21, 0, 57 mutations respectively). Of significant interest, the sequence of NSP-12 and NSP-14 antigens are fully conserved (100%) in all variants and sub-variants, including the recent BA.2.86 and JN.1, supporting the vital role of these two antigens in the life cycle of SARS-CoV-2. Of the ten non-Spike antigens, NSP3 (58 cumulative mutations) and Nucleoprotein (57 cumulative mutations) are the less conserved in all variants and sub-variants. Nevertheless, the Nucleoprotein was considered in the combined vaccine since it is the most abundant viral protein and one of the most predominantly targeted antigens by T cells in individuals with less severe COVID-19 disease.

Enriched cross-reactive memory CD4+ and CD8+ T cells, preferentially target seven of the ten highly conserved SARS-CoV-2 antigens and correlated with improved disease outcome in unvaccinated asymptomatic COVID-19 patients.

Next, whether the ten highly conserved non-Spike antigens are targeted by CD4$^+$ and CD8$^+$ T cells from "naturally protected" unvaccinated COVID-19 patients was determined. Peripheral blood-derived T cells were used from unvaccinated COVID-19 patients who were enrolled throughout the COVID-19 pandemic, irrespective of which SARS-CoV-2 variants were of concern they were exposed to (FIG. 3A).

CD4$^+$ and CD8$^+$ T cell responses specific to highly conserved epitopes, selected from these non-Spike antigens, were compared in unvaccinated asymptomatic individuals (those individuals who never develop any COVID-19 symptoms despite being infected with SARS-CoV-2) versus unvaccinated symptomatic COVID-19 patients (those patients who developed severe to fatal COVID-19 symptoms) (FIG. 4A). Unvaccinated HLA-DRB1*01:01$^+$ and HLA-A*0201 COVID-19 patients (n=71) enrolled throughout the COVID-19 pandemic (January 2020 to December 2023), irrespective of variants of concern infection, and divided into six groups, based on the level of severity of their COVID-19 symptoms (from severity 5 to severity 0, assessed at discharge-FIG. 4A). The clinical, and demographic characteristics of this cohort of COVID-19 patients are detailed in FIG. 2. Fresh PBMCs were isolated from these COVID-19 patients, on average, within five days after reporting a first COVID-19 symptom or a first PCR-positive test. PBMCs were then stimulated in vitro for 72 hours using recently identified highly conserved 13 HLA-DR-restricted CD4$^+$ or 16 HLA-A*0201-restricted CD8$^+$ T cell peptide epitopes derived from the non-structural proteins (NSPs), the ORF7a/b, Membrane, and Envelope, and Nucleoprotein, as detailed in Materials & Methods. The number of responding IFN-γ-producing CD4$^+$ T cells and IFN-γ-producing CD4$^+$ and CD8$^+$ T cells specific to epitopes from all the ten selected conserved antigens (FIG. 4B), 13 individual cross-reactive CD4$^+$ T cell epitopes (FIG. 4C); and 16 individual cross-reactive CD8$^+$ T cell epitopes (FIG. 4D) from the selected ten highly conserved antigens were quantified, in each of the six groups of COVID-19 patients, using ELISpot assay (i.e., number of IFN-γ-spot forming T cells or "SFCs"). A Pearson correlation analysis was then performed to determine the linear correlation between the magnitude of CD4$^+$ and CD8$^+$ T cell responses directed toward each of the conserved SARS-CoV-2 epitopes and the severity of COVID-19 symptoms. A negative correlation is considered strong when the coefficient R-value is between −0.7 and −1.

Overall, the highest frequencies of cross-reactive epitopes-specific IFN-γ-producing CD4$^+$ and CD8$^+$ T cells (determined as mean SFCs>50 per $0.5\times10^6$ PBMCs fixed as threshold) were detected in the unvaccinated COVID-19 patients with less severe disease (i.e., severity 0, 1, and 2, FIGS. 4B, 4C and 4D). In contrast, the lowest frequencies of cross-reactive IFN-γ-producing CD4$^+$ and CD8$^+$ T cells were detected in unvaccinated severely ill COVID-19 patients (severity scores 3 and 4, mean SFCs<50) and in unvaccinated COVID-19 patients with fatal outcomes (severity score 5, mean SFCs<25). A strong positive linear correlation was found between the high magnitude of IFN-γ-producing CD4$^+$ and CD8$^+$ T cells specific to seven out of ten common T cell antigens and the "natural protection" observed in unvaccinated asymptomatic COVID-19 patients (FIGS. 4B, 4C and 4D). This positive correlation existed regardless of whether CD4$^+$ and CD8$^+$ T cells target structural, non-structural, or accessory regulatory SARS-CoV-2 antigens.

Taken together, these results: (i) Demonstrate an overall higher magnitude of CD4$^+$ and CD8$^+$ T cell responses specific to seven out of ten highly conserved non-Spike antigens present in unvaccinated asymptomatic COVID-19 patients irrespective of SARS-CoV-2 variants of concern they were exposed to; (ii) Suggest a crucial role of these seven highly conserved structural, non-structural, and accessory regulatory T cell antigens, in protection from symptomatic and fatal Infections caused by multiple variants; and (iii) Validates the conserved non-Spike Coronavirus antigens as potential targets for a pan-Coronavirus vaccine.

Conserved SARS-CoV-2 NSP-2, NSP-14, and Nucleoprotein-based mRNA/LNP vaccines confer protection against the highly pathogenic Delta variants (B.1.617.2).

Methyl-pseudouridine-modified (m1Ψ) mRNA that encodes each of the ten highly conserved T cell antigens (i.e., NSP-2, NSP-3, NSP-4, NSP-5-10, NSP-12, NSP-14, ORF7a/b, Membrane, Envelope, and Nucleoprotein) were constructed, based on the Omicron sub-variant BA.2.75, that are capped using CleanCap technology (i.e., ten T cell antigen mRNA vaccines). The modified mRNA vaccines expressing the prefusion Spike proteins, stabilized by either two (Spike 2P) or six (Spike 6P) prolines, were constructed as B cell antigen mRNA vaccines. The 12 B- and T-cell mRNA vaccines were then encapsulated in the lipid nanoparticles (LNPs) as the delivery system (FIGS. 1B, 1C, and 5A). The "plug-and-play" mRNA/LNP platform, was selected as an antigen delivery technology over other platforms, as over one billion doses of the clinically proven Spike mRNA/LNP-based vaccines being already distributed around the world showed a high level of safety. The mRNA/LNP platform responds to current goals of the next-generation pan-CoV vaccines: (i) the ability to safely confer durable, cross-protective T cell responses; and (ii) the ability to be manufactured at a large scale to support a rapid and a global mass vaccination.

To downselect the 10 T-cell antigens mRNA/LNP-based vaccines, the protective efficacy of each T-cell antigen mRNA/LNP-based vaccine, delivered individually by intramuscular route, was compared against the highly pathogenic Delta variant (B.1.617.2) in the outbred golden Syrian hamster model (FIG. 5B). The Golden Syrian hamsters are naturally susceptible to SARS-CoV-2 infection, owing to the high degree of similarity between hamster ACE2 and human ACE2 (hACE2), and develop symptoms of COVID-19-like disease that closely mimic the COVID-19 pathogenesis in humans. Female golden Syrian hamsters (n=5 per group) were immunized intramuscularly twice on day 0 (prime) and day 21 (boost) with individual mRNA/LNP based vaccine expressing each of the 10 highly conserved non-Spike T-cell antigens and delivered using 2 doses (1 µg/dose (n=5) and 10 µg/dose (n=5), FIG. 5B)). The initial 1 µg and 10 µg doses were selected based on previous similar mRNA-LNP vaccine studies in mice and hamsters. Hamsters that received phosphate-buffered saline alone were used as mock-immunized controls (Saline, Mock, n=5). Power analysis demonstrated 5 hamsters per group was enough to produce significant results with a power>80%. Three weeks after the second immunization, all animals were challenged intranasally with the SARS-CoV-2 Delta variant (B.1.617.2) ($1\times10^5$ pfu total in both nostrils). In early $LD_{50}$ experiments, three different doses of the delta B.1.617.2 variant, $5\times10^4$ pfu, $1\times10^5$ pfu, and $5\times10^5$ pfu were compared and determined the middle dose of $1\times10^5$ pfu as the optimal $LD_{50}$ in hamsters (data not shown).

Following intranasal inoculation of hamsters with $1\times10^5$ pfu of the highly pathogenic Delta variant B.1.617.2, hamsters progressively lose up to 10% of their body weight within the first week after infection before gradually returning to their original weight by about 10 days after infection. Hamsters that received the mRNA/LNP vaccine expressing Spike 2P or Spike 6P were both protected against weight loss following the challenge with the highly pathogenic Delta variant B.1.617.2. (P<0.001, FIG. 5C). At a low dose of 1 μg/dose, the Spike 6P mRNA/LNP was slightly better in preventing weight loss compared to Spike 2P mRNA/LNP. Three out of ten highly conserved T-cell antigens mRNA/LNP-based vaccines, NSP-2, NSP-14, and Nucleoprotein prevented weight loss of the hamsters at a dose of as low as 1 μg/dose (P<0.05, FIG. 5D). At the 1 μg/dose, following intranasal inoculation with $1\times10^5$ pfu of the highly pathogenic Delta variant B.1.617.2, the NSP-2 antigen was the most protective antigen with only 2% of body weight loss, followed by 4% of body weight loss for the Nucleoprotein and 6% of body weight loss for the NSP-14 (Black arrows). The hamsters that were vaccinated with NSP-2, NSP-14, or Nucleoprotein mRNA/LNP vaccine gradually reversed their lost body weight as early as 4-5 days after challenge (Black arrows, FIG. 5D). In contrast, the mock-vaccinated hamsters gradually reversed their lost body weight late starting 6 to 9 days after being challenged (Red circles, FIG. 5D). At the high 10 μg/dose, two conserved T-cell antigens mRNA/LNP-based vaccines (i.e., NSP-3 and, ORF-7a/b) produced moderate protection against weight loss starting 6 days post-challenge. The remaining 5 T-cell antigens mRNA/LNP-based vaccines (i.e., NSP-4, NSP-5-10, NSP-12, Membrane, and Envelope) did not produce any significant protection against weight loss (P>0.05, FIG. 5D). As expected, the mock-vaccinated hamsters were not protected and started losing weight as early as two days following a challenge with the highly pathogenic Delta variant B.1.617.2.

Infectious virus titers are retrieved from the respiratory tract of infected hamsters and are approximately 1-2 logs higher in the nasal turbinate than in the lung, peaking at 2-4 days after infection. The modified mRNA/LNP vaccine expressing T cell NSP-2, NSP-14, and Nucleoprotein, at a dose as low as 1 μg/dose, produced a strong 20- to 40-fold reduction in median nasal viral titer two- and six-days following challenge with the highly pathogenic Delta variant B.1.617.2 (P<0.05).

Next, the protective efficacy of NSP-2, NSP-14, and Nucleoprotein mRNA/LNP-based vaccines (FIGS. 6A and 6B) delivered at an intermediate dose of 5 μg/dose was tested against lung pathology (FIG. 6C) and weight loss (FIG. 6D), viral replication (FIG. 6E) caused by a highly pathogenic Delta variant (B.1.617.2) in the golden Syrian hamster model.

Sars-CoV-2 infected hamsters developed lung pathologies, including alveolar destruction, proteinaceous exudation, hyaline membrane formation, marked mononuclear cell infiltration, cell debris-filled bronchiolar lumen, alveolar collapse, lung consolidation, and pulmonary hemorrhage. These lung pathologies are largely resolved by day 14 after infection, with air-exchange structures being restored to normal. In contrast, vaccination with individual NSP-2, NSP-14, and Nucleoprotein mRNA/LNP-based vaccines significantly reduced lung pathology (P<0.05, FIG. 6C), following a challenge with the highly pathogenic Delta variant B.1.617.2. The lungs of hamsters vaccinated with NSP-14 mRNA/LNP show peri bronchiolitis (arrow, perivasculitis (asterisk), and multifocal interstitial pneumonia (arrowhead). Lungs of hamsters that received NSP-2 or Nucleoprotein mRNA/LNP vaccine demonstrate normal bronchial, bronchiolar (arrows), and alveolar architecture (FIG. 6C). In contrast, the lungs of mock-vaccinated hamsters demonstrated bronchi with bronchiolitis (arrows) and adjacent marked interstitial pneumonia (asterisks). No serious local or systemic unwanted side effects were noticed in the mRNA/LNP vaccinated hamsters confirming the safety mRNA/LNP delivery system.

At an intermediate dose of 5 μg/dose, the NSP-2, NSP-14, and Nucleoprotein mRNA/LNP-based vaccines prevented weight loss of the hamsters, gradually reversing the lost body weight as early as 4-5 days after the challenge (Black arrows, FIG. 6D). At 5 μg/dose, the Nucleoprotein was the most protective antigen when it comes to prevention of body weight, followed by NSP-14 and NSP-2, respectively. Following intranasal inoculation of mock-vaccinated hamsters with $1\times10^5$ pfu of the highly pathogenic Delta variant B.1.617.2, the Nucleoprotein-vaccinated hamsters progressively lose their body weight declining by only 2% within the first 4 days after infection, before gradually and reversing the lost body weight starting on day 4 after challenge (black arrow, FIG. 6D). The NSP14-vaccinated hamsters progressively lose their body weight declining by only 6% within the first 5 days after infection, before reversing the lost body weight starting on day 6 after challenge (black arrow, FIG. 6D). The NSP2-vaccinated hamsters progressively lose their body weight declining by only 3% within the first 4 days after infection, before gradually and reversing the lost body weight starting on day 4 after challenge (black arrow, FIG. 6D). In contrast, following intranasal inoculation of mock-vaccinated hamsters with $1\times10^5$ pfu of the highly pathogenic Delta variant B.1.617.2, animals progressively lose their body weight declining by greater than 10% within the first week after infection, before gradually and spontaneously reversing the lost body weight starting on day 7 after challenge (red circles, FIG. 6D).

Infectious virus titers retrieved on days 2 and 6 post-challenge from the nasal turbinate of mock-vaccinated hamsters are approximately 20- to 40-fold logs higher compared to hamsters that received modified mRNA/LNP vaccine expressing T cell NSP-2, NSP-14, and Nucleoprotein, at the dose of 5 μg/dose, suggesting a fast and strong reduction in median nasal viral titer in the NSP-2, NSP-14, and Nucleoprotein mRNA/LNP vaccinated animals following challenge with the highly pathogenic Delta variant B.1.617.2 (P<0.05, FIG. 6E).

These results indicate that mRNA/LNP vaccines based on three out of ten highly conserved RTC T-cell antigens, NSP-2, NSP-14, and Nucleoprotein, safely confer protection against infection and COVID-19-like disease caused by the highly pathogenic Delta variant (B.1.617.2).

A combined NSP-2, NSP-14, and Nucleoprotein-based mRNA/LNP vaccine confers robust and broad protection against multiple SARS-CoV-2 variants and sub-variants of concern.

Next, the protective efficacy of a combined T cell antigens mRNA/LNP-based Coronavirus vaccine, that incorporates the highly conserved NSP-2, NSP-14, and Nucleoprotein T cell antigens (FIG. 7A) was determined, against VOCs with various characteristics, including the ancestral wild-type Washington variant (WA1/2020), the highly pathogenic Delta variant (B.1.617.2), and the heavily Spike-mutated and most immune-evasive Omicron sub-variant (XBB.1.5).

Female golden Syrian hamsters were immunized intramuscularly twice on day 0 and day 21 with 2 doses of the combination T-cell antigens mRNA/LNP-based vaccine at either 1 µg/dose (n=20 per group) or 10 µg/dose (n=20) or mock-immunized (n=15 per group) (FIG. 7B). Three weeks after the second immunization, animals were divided into groups of 5 hamsters each and challenged intranasally, in both nostrils, with $2\times10^5$ pfu of the wild-type Washington variant (WA1/2020) (n=5 per group), the $1\times10^5$ pfu of Delta variant (B.1.617.2) (n=5 per group) or $2\times10^5$ pfu of Omicron sub-variant (XBB1.5) (n=5 per group). In an earlier experiment, three different doses were tested for each variant and sub-variant and determined the dose of $2\times10^5$ pfu as the optimal $LD_{50}$ for the wild-type Washington variant (WA1/2020), $1\times10^5$ pfu as the optimal $LD_{50}$ for the Delta variant (B.1.617.2), and $2\times10^5$ pfu as the optimal $LD_{50}$ for the Omicron sub-variant (XBB1.5) in hamsters (data not shown).

Vaccination with the combined NSP-2, NSP-14, and Nucleoprotein-based mRNA/LNP vaccine, at 5 µg/dose, significantly reduced lung pathology (FIG. 7C), fast prevented weight loss of the hamsters (P<0.05) (FIG. 7D), and elicited a 20- to 40-fold reduction in median lung viral titer two- and six-days (FIG. 7E) following wild-type Washington variant (WA1/2020), Delta variant (B.1.617.2), and Omicron sub-variant (XBB1.5) in hamsters. Of interest, 5 out of 5 hamsters that received the combined NSP-2, NSP-14, and Nucleoprotein-based mRNA/LNP vaccine and challenged with the heavily Spike-mutated and most immune-evasive Omicron sub-variant (XBB.1.5) did not lose any weight (Black arrow, FIG. 7D, right panel). The combined mRNA/LNP vaccine fast prevented weight loss in 5 out of 5 five hamsters, starting as early as 2 days post-challenge with the ancestral wild-type Washington variant (WA1/2020) and the highly pathogenic Delta variant (B.1.617.2) (Black arrow, FIG. 7D, right and middle panels). As expected, the mock-vaccinated mice did not show a significant reduction in lung pathology, weight loss, and lung viral replication (FIGS. 7C, 7D, and 7E). The mock-vaccinated mice started losing weight as early as 1-2 days post-challenge and did not reverse the weight loss until late, 7-8-days post-challenge with Washington, Delta, and Omicron variants (red circles, FIGS. 7C, 7D, and 7E).

Fourteen days post-challenge, lung tissues were collected and fixed, and 5-µm sections were cut from hamsters and stained with hematoxylin and eosin. The lungs of hamsters that received the combined NSP-2, NSP-14, and Nucleoprotein-based mRNA/LNP vaccine demonstrated normal bronchial, bronchiolar (arrows), and alveolar architecture (FIG. 7C). In contrast, the lungs of mock-immunized hamsters have acute bronchi with bronchiolitis (arrows) and adjacent marked interstitial pneumonia (arrowheads).

Altogether, these results demonstrate that compared to individual mRNA/LNP vaccines, the combined NSP-2, NSP-14, and Nucleoprotein-based mRNA/LNP vaccine provided a synergetic or additive beneficial effect by inducing fast, robust, and broad protection against infection and disease-caused multiple SARS-CoV-2 variants and sub-variants of concern.

A combined Spike, NSP-2, NSP-14, and Nucleoprotein-based mRNA/LNP vaccine confers a more potent and rapid protection against the highly pathogenic Delta SARS-CoV-2 variant (B.1.617.2).

Next, whether the combination of NSP-2, NSP-14, and Nucleoprotein-based mRNA/LNP vaccines with the clinically proven Spike-alone mRNA/LNP-based vaccine would result in a beneficial additive or synergistic effect that translates into increased level of protection was investigated (FIG. 8A). For this experiment, the prefusion Spike proteins stabilized by two (Spike 2P) over six (Spike 6P) prolines was chosen. Although the mRNA/LNP Spike 6P provided slightly better protection than the mRNA/LNP Spike 2P (FIG. 5C), the latter was selected as it is safe with over one billion doses of the clinically proven Spike-alone mRNA/LNP-based vaccines that were already administered around the world. Given that most of the human population already received one to four doses of the first generation of Spike 2P-based COVID-19 vaccine, given the combined Spike 2P, NSP-2, NSP-14, and Nucleoprotein-based mRNA/LNP vaccine as boosters in humans with pre-existing Spike 2P immunity may boost the protective efficacy 46.

The expression of the four proteins, Spike, NSP-2, NSP-14, and Nucleoprotein, was ascertained after in vitro mRNA transfection into human epithelial HEK293T cells. The expression of each protein was detected, with a slight increase of Spike, NSP-2, and Nucleoprotein expression over NSP-14 protein (white arrows, FIG. 8B). The co-transfection of the 4 mRNA together did not result in competition as all the four antigens were equally expressed in vitro in human epithelial HEK293T cells (data not shown).

The efficacy of the combined Spike, NSP-2, NSP-14, and Nucleoprotein-based mRNA/LNP vaccine was compared to the Spike-alone-based mRNA/LNP vaccine against the highly pathogenic Delta SARS-CoV-2 variant (B.1.617.2) at an equimolar low amount of 1 µg/dose (FIG. 8C). Three groups of hamsters (n=5) were then vaccinated with mRNA/LNP-S (1 µg), or mRNA/LNP-S+mRNA/LNP-T cell Ag (1 µg for each mRNA/LNP) or with empty LNP (Mock), at weeks 0 and 3 (FIG. 8C). Three weeks after the booster (week 6), all hamsters were intranasally challenged with the SARS-CoV-2 Delta variant (B.1.617.2) ($1\times10^5$ pfu).

The combined Spike, NSP-2, NSP-14, and Nucleoprotein-based mRNA/LNP vaccine significantly reversed the weight loss in hamsters as early as 2 days post-challenge with SARS-CoV-2 Delta variant (B.1.617.2) (black arrow, FIG. 8D). In contrast, the Spike-alone-based mRNA/LNP vaccine reversed the weight loss starting 5 days post-challenge with SARS-CoV-2 Delta variant (B.1.617.2) (grey arrow, FIG. 8D). As expected, the mock-vaccinated hamsters lost weight as early as 2 days post-infection and did not reverse the weight loss until late 7 days post-challenge with SARS-CoV-2 Delta variant (B.1.617.2) (red circle, FIG. 8D).

On day 4 post-challenge, protection was analyzed based on viral loads (n=5) (FIG. 8E). Compared to the mock-vaccinated control hamsters, the combined Spike, NSP-2, NSP-14, and Nucleoprotein-based mRNA/LNP vaccine significantly reduced the viral load (5-log reduction of viral RNA copies) (FIG. 8E). In contrast, Spike-alone-based mRNA/LNP vaccine modestly reduced the viral load (3-log reduction of viral RNA copies) (FIG. 8E). These data indicate that at a low dose of 1 µg/dose, the combined Spike, NSP-2, NSP-14, and Nucleoprotein-based mRNA/LNP vaccine provided stronger protection against a highly pathogenic Delta variant (B.1.617.2) compared to an equimolar amount of the of Spike-alone-based mRNA/LNP vaccine.

These results indicate that, compared to the Spike-alone-based mRNA/LNP vaccine, combined Spike, NSP-2, NSP-14, and Nucleoprotein-based mRNA/LNP vaccine induced faster and stronger protection against the highly pathogenic Delta SARS-CoV-2 variant (B.1.617.2).

The combined Spike, NSP-2, NSP-14, and Nucleoprotein-based mRNA/LNP vaccine induces stronger, faster, and broader protection against multiple variants and sub-variants compared to Spike-alone-based mRNA/LNP vaccine.

Next, whether a combined Spike, NSP-2, NSP-14, and Nucleoprotein-based mRNA/LNP vaccine (FIG. 9A), would induce broader and stronger protection against the wild-type Washington variant (WA1/2020) and the heavily Spike-mutated and most immune-evasive Omicron sub-variant (XBB.1.5) (in addition to the highly pathogenic Delta variant (B.1.617.2), shown above) was investigated.

The hamsters that received the combined Spike, NSP-2, NSP-14, and Nucleoprotein-based mRNA/LNP vaccine significantly reversed the weight loss as early as 2 days post-challenge with the wild-type Washington variant (WA1/2020) (black arrow, FIG. 9B). In contrast, the hamsters that received the Spike-alone-based mRNA/LNP vaccine reversed the weight loss late 6 days post-challenge with the wild-type Washington variant (WA1/2020) (grey arrow, FIG. 9B). Moreover, the hamsters that received the combined Spike, NSP-2, NSP-14, and Nucleoprotein-based mRNA/LNP vaccine significantly reversed the weight loss as early as the first-day post-challenge with the heavily Spike-mutated and most immune-evasive Omicron sub-variant (XBB.1.5) (black arrow, FIG. 9C). In contrast, the hamsters that received the Spike-alone-based mRNA/LNP vaccine reversed the weight loss late 6 days post-challenge with the Omicron sub-variant (XBB.1.5) (grey arrow, FIG. 9C). As expected, the mock-vaccinated hamsters lost weight fast as early as the first day post-challenge and did not reverse the weight loss until late 7 to 8 days post-challenge with the wild-type Washington variant (WA1/2020) and the Omicron sub-variant (XBB.1.5) (red circle, FIGS. 9B and 9C).

Histopathological analysis showed that compared to lungs of mock-vaccinated controls, the lungs of hamsters that received the combination of Spike, NSP-2, NSP-14, and Nucleoprotein-based mRNA/LNP vaccine were fully protected from all lesions with normal bronchial, bronchiolar, and alveolar architecture (FIG. 9D). In contrast, the lungs of hamsters that received the Spike-alone-based mRNA/LNP vaccine developed small lesions, including interstitial pneumonia and peribronchitis (FIG. 9D). As expected, considerable pathological changes, including bronchitis and interstitial pneumonia, are evident in the lungs of mock-immunized hamsters on 4 days post-challenge (FIG. 9D). The higher lung pathology and lower virus titers detected in the lungs of hamsters that received the Spike-alone-based mRNA/LNP vaccine suggest an immune escape by the highly pathogenic the heavily Spike-mutated and most immune-evasive Omicron sub-variant (XBB.1.5). In contrast, lack of lung pathology and higher virus titers detected in the lungs of hamsters that received the combined spike, NSP-2, NSP-14, and Nucleoprotein-based mRNA/LNP vaccines likely indicates a lack of immune escape by the heavily Spike-mutated and most immune-evasive Omicron sub-variant (XBB.1.5).

The virus titers determined on days 2 and 6 post-challenge, confirmed the significant reduction of the lung viral burden by up to 5 logs by the combined Spike, NSP-2, NSP-14, and Nucleoprotein-based mRNA/LNP vaccine following a challenge by wild-type Washington variant (WA1/2020) or the Omicron sub-variant (XBB.1.5) (FIGS. 9E and 9F).

Together the results (i) demonstrated that the combined Spike, NSP-2, NSP-14, and Nucleoprotein-based mRNA/LNP vaccine induces stronger and broader protection against multiple variants and sub-variants; and (ii) suggest that the combined Spike, NSP-2, NSP-14, and Nucleoprotein-based mRNA/LNP vaccine that include T cell antigens likely induced stronger Spike-specific neutralizing antibodies that prevented immune escape by the heavily Spike-mutated variants, compared to Spike-alone-based mRNA/LNP vaccine.

Enriched lungs-resident Non-Spike antigen-specific CD4+ and CD8+ T cells and Spike-specific neutralizing antibodies induced by the combined Spike, NSP-2, NSP-14, and Nucleoprotein-based mRNA/LNP vaccine.

Finally, whether the observed rapid and broad clearance of SARS-CoV-2 infections in hamsters vaccinated with the combined Spike, NSP-2, NSP-14, and Nucleoprotein-based mRNA/LNP vaccine would be associated with anti-viral lung-resident NSP-2, NSP-14, and Nucleoprotein-specific $CD4^+$ and $CD8^+$ T cell responses were determined. After all, the protective NSP-2 and NSP-14 and Nucleoprotein T cell antigens in the combined vaccine all belong to the early-transcribed RTC region and are selectively targeted by human lung-resident enriched memory $CD4^+$ and $CD8^+$ T cells from "SARS-CoV-2 aborters" (i.e., those SARS-CoV-2 exposed seronegative healthcare workers and in household contacts who were able to rapidly abort the virus replication). Correlation of the frequencies of lung-enriched NSP-2, NSP-14, and Nucleoprotein-specific-specific $CD4^+$ and $CD8^+$ T cells with protection from virus load after challenge with various variants and sub-variants were compared in the hamsters that received the combined Spike, NSP-2, NSP-14, and Nucleoprotein-based mRNA/LNP vaccine vs. mock-vaccine.

Lungs from vaccinated and mock-vaccinated hamsters were collected 2 weeks after the SARS-CoV-2 challenge, and cell suspensions were stimulated with pools of 15-mer overlapping NSP-2, NSP-14, or Nucleoprotein (FIG. 8C). The frequency and function of lung-resident NSP-2-, NSP-14-, and Nucleoprotein-specific $CD8^+$ and $CD4^+$ T cells were compared in vaccinated protected hamsters versus mock-vaccinated unprotected hamsters.

The data showed that the combined Spike, NSP-2, NSP-14, and Nucleoprotein-based mRNA/LNP vaccines elicited robust NSP-2, NSP-14, Nucleoprotein-specific and Spike-specific $CD4^+$ and $CD8^+$ T cell responses. While there seem to be more $CD4^+$ T cell responses than $CD8^+$ T cell responses in the lungs, overall, NSP-2, NSP-14, and Nucleoprotein appeared to be targeted by the same frequencies of functional $CD4^+$ and $CD8^+$ T cells.

Among the cytokines examined, IFN-$\gamma$ and TNF-$\alpha$ were highly expressed by NSP-2-, NSP-14-, and Nucleoprotein-specific $CD4^+$ and $CD8^+$ T cells. The combined vaccine appeared to induce higher NSP-2- and Nucleoprotein-specific IFN-$\gamma^+$TNF-$\alpha^+$$CD4^+$ and IFN-$\gamma^+$TNF-$\alpha^+$$CD8^+$ T cell responses compared to NSP-14-specific IFN-$\gamma^+$TNF$\alpha^+$$CD4^+$ and IFN-$\gamma^+$TNF$\alpha^+$$CD8^+$ T cell responses (P<0.001 for IFN-$\gamma$). The analyses of T cell responses in the lungs of protected and non-protected hamsters indicate that the combined Spike, NSP-2, NSP-14, and Nucleoprotein-based mRNA/LNP vaccine induced high frequencies of NSP-2, NSP-14, and Nucleoprotein-specific lung-resident CXCR5$^+$ $CD4^+$ T follicular helper cells (TFH cells), compared to Spike-alone-based mRNA/LNP vaccine. This suggests that these CXCR5$^+$$CD4^+$ TFH cells likely contribute to the augmentation in the Spike-specific neutralizing antibodies and protection observed in the combined Spike, NSP-2, NSP-14, and Nucleoprotein-based mRNA/LNP vaccine group compared to Spike-alone-based mRNA/LNP vaccine.

Analysis of CD4$^+$ and CD8$^+$ T cell responses in the peripheral blood of vaccinated hamsters after two doses of the combined mRNA vaccine, before challenge, and after challenge indicated the combined Spike, NSP-2, NSP-14, and Nucleoprotein-based mRNA/LNP vaccine-induced robust NSP-2-, NSP-14- and Nucleoprotein-specific CD4$^+$ and CD8$^+$ T cell responses subsequently boosted by the exposure to the virus after challenge with Washington variant (WA1/2020), Delta variant (B.1.617.2), and Omicron sub-variant (XBB.1.5). These results confirm the antigen specificity of the induced CD4$^+$ and CD8$^+$ T cell responses. Compared to SARS-CoV-2-specific T cells in peripheral blood and spleen, better correlations were found between protection and lung-resident SARS-CoV-2 specific T cells (not shown), confirming the importance of airways-resident T cells in protection.

Since the combined Spike, NSP-2, NSP-14, and Nucleoprotein-based mRNA/LNP vaccine induced strong NSP-2, NSP-14, and Nucleoprotein-specific CXCR5$^+$CD4$^+$ TFH cells compared to the Spike mRNA/LNP vaccine alone, next, whether the combined vaccine would induce better Spike-specific neutralizing antibody titers was determined. Serum samples were collected after vaccination and before the viral challenge and tested by ELISA and neutralization assays against Washington, Delta, and Omicron. Higher titers of IgG-specific antibodies were detected in 5 out of 5 hamsters that received the combined vaccines compared to hamsters that received the Spike-alone vaccine (FIG. 10, upper panel). Moreover, compared to the Spike-alone-based mRNA/LNP vaccine, the combined Spike, NSP-2, NSP-14, and Nucleoprotein-based mRNA/LNP vaccine elicited stronger serum neutralizing activity against the wild-type virus (P<0.005) the Delta variant (P<0.005) and the Omicron variants (P<0.005) (FIG. 10, lower panel). While serum from the mRNA/LNP-Spike alone vaccinated hamsters manifested strong neutralizing activity against the wild-type Washington variant but markedly reduced neutralizing activity (a 5-fold reduction) against the heavily Spike-mutated Delta and Omicron variants (FIG. 10). These results suggest that the combination of Spike, NSP-2, NSP-14, and Nucleoprotein-based mRNA/LNP vaccine induced stronger Spike-specific neutralizing antibodies that prevented immune escape by the heavily Spike-mutated variants.

All together, these results indicate that, at a dose as low as 1 μg/dose, the combined Spike, NSP-2, NSP-14, and Nucleoprotein-based mRNA/LNP vaccine elicited Spike-specific neutralizing antibodies and airway-resident NSP-2-, NSP-14-, and Nucleoprotein-specific GzmB$^+$CD4$^+$ T$_{CYT}$ and GzmB$^+$CD8$^+$ T$_{CYT}$ cells, CD69$^+$IFN-γ$^+$TNFα$^+$CD4$^+$ TEFF cells, CD69$^+$IFN-γ$^+$TNFα$^+$CD8$^+$ TEFF cells, and CXCR5$^+$CD4$^+$ TFH cells that correlated with protection against several VOCs, including the ancestral wild-type Washington variant (WA1/2020), the highly pathogenic Delta variant (B.1.617.2), and the heavily Spike-mutated and most immune-evasive Omicron sub-variant (XBB.1.5). Compared to animals that received the Spike alone, the high frequency of CXCR5$^+$CD4$^+$ TFH cells in the lungs of hamsters that received the combined vaccine likely contributed to stronger Spike-specific neutralizing antibody activities that cleared the virus in the lungs. The airway-resident B- and T cell immunity induced by combined Spike, NSP-2, NSP-14, and Nucleoprotein-based mRNA/LNP vaccine likely contribute collectively to the enhanced protection capable of conferring broad cross-strain protective immunity against infection and disease caused by multiple variants and sub-variants.

Human study population cohort and HLA genotyping: Between January 2020 and December 2023, over 1100 unvaccinated patients with mild to severe COVID-19 were enrolled at the University of California Irvine Medical Center. Written informed consent was obtained from all patients before inclusion. SARS-CoV-2 positivity was defined by a positive RT-PCR on a respiratory tract sample. The unvaccinated COVID-19 patients were enrolled throughout the pandemic irrespective of SARS-CoV-2 variants of concern they are exposed to: The ancestral Washington variant (WA1/2020), alpha, beta, gamma, the highly pathogenic Delta variant (B.1.617.2), or the omicron sub-variants B.1.1.529, BA.2.86, XBB1.5, EG.5, HV.1, and JN.1. Patients were genotyped by PCR for class I HLA-A*02:01 and class II HLA-DRB1*01:01; and ended up with 147 that were HLA-A*02:01$^+$ or/and HLA-DRB1*01:01$^+$. The average days between the report of their first symptoms and the blood sample drawing was ~5 days. The 147 patients were from mixed ethnicities (Hispanic (28%), Hispanic Latino (22%), Asian (16%), Caucasian (13%), mixed Afro-American and Hispanic (8%), Afro-American (5%), mixed Afro-American and Caucasian (2%), Native Hawaiian and Other Pacific Islander descent (1%). Six percent of the patients did not reveal their race/ethnicity (FIG. 11). Following patient discharge, they were divided into groups by medical practitioners depending on the severity of their symptoms and their intensive care unit (ICU) and intubation (mechanical ventilation) status. The following scoring criteria were used: Severity 5: patients who died from COVID-19 complications; Severity 4: infected COVID-19 patients with severe disease who were admitted to the intensive care unit (ICU) and required ventilation support; Severity 3: infected COVID-19 patients with severe disease that required enrollment in ICU, but without ventilation support; Severity 2: infected COVID-19 patients with moderate symptoms that involved a regular hospital admission; Severity 1: infected COVID-19 patients with mild symptoms; and Severity 0: infected individuals with no symptoms. Subsequently, 15 liquid-nitrogen frozen PBMCs samples (blood collected pre-COVID-19 in 2018) were used from HLA-A*02:01$^+$/HLA-DRB1*01:01$^+$ unexposed pre-pandemic healthy individuals—8 males, 7 females; median age: 54 (20-76) as controls.

Peptide synthesis: Peptide-epitopes from twelve SARS-CoV-2 proteins, including 16 9-mer long CD8$^+$ T cell epitopes (ORF1ab$_{84-92}$, ORF1ab$_{1675-1683}$, ORF1ab$_{2210-2218}$, ORF1ab$_{2363-2371}$, ORF1ab$_{3013-3021}$, ORF1ab$_{3183-3191}$, ORF1ab$_{3732-3740}$, ORF1ab$_{4283-4291}$, ORF1ab$_{5470-5478}$, ORF1ab$_{6419-6427}$, ORF1ab$_{6749-6757}$, E$_{20-28}$, E$_{26-34}$, M$_{52-60}$, M$_{89-97}$, and ORF7b$_{26-34}$) and 13 13-mer long CD4$^+$ T cell epitopes (ORF1a$_{1350-1355}$, ORF1a$_{1801-1815}$, ORF1ab$_{5019-5033}$, ORF1ab$_{6088-6102}$, ORF1ab$_{6420-6434}$, E$_{20-34}$, E$_{26-40}$, M$_{176-190}$, ORF7a$_{1-15}$, ORF7a$_{3-17}$, ORF7a$_{98-112}$, ORF7b$_{8-22}$, and N$_{388-403}$) that were formerly identified were selected as described previously. The Epitope Conservancy Analysis tool was used to compute the degree of identity of CD8$^+$ T cell and CD4$^+$ T cell epitopes within a given protein sequence of SARS-CoV-2 set at 100% identity level. Peptides were synthesized (21$^{st}$ Century Biochemicals, Inc, Marlborough, MA) and the purity of peptides determined by both reversed-phase high-performance liquid chromatography and mass spectroscopy was over 95%.

Human Peripheral Blood Mononuclear Cells and T cell Stimulation: Peripheral blood mononuclear cells (PBMCs) from COVID-19 patients were isolated from the blood using Ficoll (GE Healthcare) density gradient media and transferred into 96-well plates at a concentration of $2.5 \times 10^6$ viable cells per ml in 200 µl ($0.5 \times 10^6$ cells per well) of RPMI-1640 media (Hyclone) supplemented with 10% (v/v) FBS (HyClone), Sodium Pyruvate (Lonza), L-Glutamine, Nonessential Amino Acids, and antibiotics (Corning). A fraction of the blood was kept separated to perform HLA genotyping of only the HLA-A*02:01 and DRB1*01:01 positive individuals. Subsequently, cells were stimulated with 10 µg/ml of each one of the 29 individual T cell peptide-epitopes (16 CD8$^+$ T cell peptides and 13 CD4$^+$ T cell peptides) and incubated in a humidified chamber with 5% $CO_2$ at 37° C. Post-incubation, cells were stained for flow cytometry, or transferred in IFN-γ ELISpot plates (FIG. 3A). The same isolation protocol was followed for HD samples obtained in 2018. Ficoll was kept frozen in liquid nitrogen in FBS DMSO 10%; after thawing, HD PBMCs were stimulated similarly for the IFN-γ ELISpot technique.

Human ELISpot assay: CD4$^+$ and CD8$^+$ T-cell response was assessed against conserved SARS-CoV-2-derived class-II restricted epitopes by IFN-γ ELISpot in COVID-19 patients representing different disease severity categories (FIG. 11 and FIG. 3A). All ELISpot reagents were filtered through a 0.22 µm filter. Wells of 96-well Multiscreen HTS Plates (Millipore, Billerica, MA) were pre-wet with 30% ethanol for 60 seconds and then coated with 100 µl primary anti-IFN-γ antibody solution (10 µg/ml of 1-D1K coating antibody from Mabtech, Cincinnati, OH) OVN at 4° C. After washing, the plate was blocked with 200 µl of RPMI media plus 10% (v/v) FBS for two hours at room temperature to prevent nonspecific binding. Twenty-four hours following the blockade, the peptide-stimulated cells from the patient's PBMCs ($0.5 \times 10^6$ cells/well) were transferred into the ELISpot-coated plates. PHA-stimulated or non-stimulated cells (DMSO) were used as positive or negative controls of T cell activation, respectively. Upon incubation in a humidified chamber with 5% $CO_2$ at 37° C. for an additional 48 hours, cells were washed using PBS and PBS-Tween 0.02% solution. Next, 100 µl of biotinylated secondary anti-IFN-γ antibody (1 µg/ml, clone 7-B6-1, Mabtech) in blocking buffer (PBS 0.5% FBS) was added to each well. After a two-hour incubation and wash, wells were incubated with 100 µl of HRP-conjugated streptavidin (1:1000) for 1 hour at room temperature. Lastly, wells were incubated for 15-30 minutes with 100 µl of TMB detection reagent at room temperature, and spots were counted both manually and by an automated ELISpot reader counter (ImmunoSpot Reader, Cellular Technology, Shaker Heights, OH).

Flow cytometry analysis: Surface markers detection and flow cytometry analysis were performed on 147 patients after 72 hours of stimulation with each SARS-CoV-2 class-I or class-II restricted peptide, and PBMCs ($0.5 \times 10^6$ cells) were stained. First, the cells were stained with a live/dead fixable dye (Zombie Red dye, 1/800 dilution—BioLegend, San Diego, CA) for 20 minutes at room temperature, to exclude dying/apoptotic cells. Cells were then stained for 45 minutes at room temperature with five different HLA-A*02*01 restricted tetramers and/or five HLA-DRB1*01:01 restricted tetramers (PE-labelled) specific toward the SARS-CoV-2 CD8$^+$ T cell epitopes Orf1 ab$_{2210-2218}$, and Orf1 ab$_{4283-4291}$ and the CD4$^+$ T cell epitopes ORF1a$_{1350-1365}$, E$_{26-40}$, and M$_{176-190}$ respectively (FIG. 3A). Cells were alternatively stained with the EBV BMLF-1$_{280-288}$-specific tetramer for control of specificity. HLA-A*02*01-HLA- DRB1*01:01-negative patients were stained with our 10 tetramers as a negative control aiming to assess tetramers staining specificity. Subsequently, anti-human antibodies were used for surface-marker staining: anti-CD45 (BV785, clone HI30—BioLegend), anti-CD3 (Alexa700, clone OKT3—BioLegend), anti-CD4 (BUV395, clone SK3-BD), anti-CD8 (BV510, clone SK1—BioLegend), anti-TIGIT (PercP-Cy5.5, clone A15153G—BioLegend), anti-TIM-3 (BV 711, clone F38-2E2—BioLegend), anti-PD1 (PE-Cy7, clone EH12.1—BD), anti-CTLA-4 (APC, clone BNI3—BioLegend), anti-CD137 (APC-Cy-7, clone 4B4-1—BioLegend) and anti-CD134 (BV650, clone ACT35—BD). mAbs against these various cell markers were added to the cells in phosphate-buffered saline (PBS) containing 1% FBS and 0.1% sodium azide (fluorescence-activated cell sorter [FACS] buffer) and incubated for 30 minutes at 4° C. Subsequently, cells were washed twice with FACS buffer and fixed with 4% paraformaldehyde (PFA, Affymetrix, Santa Clara, CA). A total of ~200,000 lymphocyte-gated PBMCs (140,000 alive CD45$^+$) were acquired by Fortessa X20 (Becton Dickinson, Mountain View, CA) and analyzed using FlowJo software (TreeStar, Ashland, OR). The gating strategy is detailed in FIG. 3B.

Viruses: SARS-CoV-2 viruses specific to six variants, namely (i) SARS-CoV-2-USA/WA/2020 (Batch Number: G2027B); (v) Delta (B.1.617.2) (isolate h-CoV-19/USA/MA29189; Batch number: G87167), and Omicron (XBB1.5) (isolate h-CoV-19/USA/FL17829; Batch number: G76172) were procured from Microbiologics (St. Cloud, MN). The initial batches of viral stocks were propagated to generate high-titer virus stocks. Vero E6 (ATCC-CRL1586) cells were used for this purpose. Procedures were completed after appropriate safety training was obtained using an aseptic technique under BSL-3 containment.

TaqMan quantitative polymerase reaction assay: A laboratory-developed modification of the CDC SARS-CoV-2 RT-PCR assay was used for the screening of SARS-CoV-2 Variants in COVID-19 patients, which received Emergency Use Authorization by the FDA on Apr. 17, 2020.

Briefly, 5 ml of the total nucleic acid eluate was added to a 20-ml total-volume reaction mixture (1× TaqPath 1-Step RT-qPCR Master Mix, CG; Thermo Fisher Scientific, Waltham, MA), with 0.9 mM each primer and 0.2 mM each probe). RT-PCR was carried out using the ABI StepOnePlus thermocycler (Life Technologies, Grand Island, NY). The S-N501Y, S-E484K, and S-L452R assays were carried out under the following running conditions: 25° C. for 2 minutes, then 50° C. for 15 minutes, followed by 10 minutes at 95° C. and 45 cycles of 95° C. for 15 seconds and 65° C. for 1 minute. The $\Delta_{69-70}/\Delta_{242-244}$ assays were run under the following conditions: 25° C. for 2 minutes, then 50° C. for 15 minutes, followed by 10 minutes at 95° C. and 45 cycles of 95° C. for 15 seconds and 60° C. for 1 minute. Samples displaying typical amplification curves above the threshold were considered positive. Samples that yielded a negative result or results in the S-Δ69-70/Δ242-244 assays or were positive for S-501Y P2, S-484K P2, and S-452R P2 were considered screen positive and assigned to VOCs.

Human Enzyme-linked immunosorbent assay (ELISA): Serum antibodies specific for epitope peptides and SARS-CoV-2 proteins were detected by ELISA. 96-well plates (Dynex Technologies, Chantilly, VA) were used and coated them with 0.5 µg peptides, 100 ng S or N protein per well at 4° C. overnight, respectively, and then washed three times with PBS and blocked with 3% BSA (in 0.1% PBST) for 2 hours at 37° C. After blocking, the plates were incubated with serial dilutions of the sera (100 µl/well, in two-fold dilution) for 2 hours at 37° C. The bound serum antibodies were detected with HRP-conjugated goat anti-mouse IgG and chromogenic substrate TMB (ThermoFisher, Waltham, MA). The cut-off for seropositivity was set as the mean value plus three standard deviations (3SD) in HBc-S control sera. The binding of the epitopes to the sera of SARS-CoV-2 infected samples was detected by ELISA using the same procedure; 96-well plates were coated with 0.5 μg peptides, and sera were diluted at 1:50.

Data and Code Availability: Human-specific SARS-CoV-2 complete genome sequences were retrieved from the GISAID database, whereas the SARS-CoV-2 sequences for bats, pangolin, civet cats, and camels were retrieved from the NCBI GenBank. Genome sequences of previous strains of SARS-CoV for humans (B.1.177, B.1.160, B.1.1.7, B.1.351, P.1, B.1.427/B.1.429, B.1.258, B.1.221, B.1.367, B.1.1.277, B.1.1.302, B.1.525, B.1.526, S:677H.Robin1, S:677P.Pelican, B.1.617.1, B.1.617.2, B.1.1.529) and common cold SARS-CoV strains (SARS-CoV-2-Wuhan-Hu-1 (MN908947.3), SARS-CoV-Urbani (AY278741.1), HKU1-Genotype B (AY884001), CoV-OC43 (KF923903), CoV-NL63 (NC_005831), CoV-229E (KY983587)) and MERS (NC_019843)), bats (RATG13 (MN996532.2), ZXC21 (MG772934.1), YN01 (EPI_ISL_412976), YN02 (EPI-_ISL_412977), WIV16 (KT444582.1), WIV1 (KF367457.1), YNLF_31C (KP886808.1), Rs672 (FJ588686.1)), pangolin (GX-P2V (MT072864.1), GX-P5E (MT040336.1), GX-P5L (MT040335.1), GX-P1E (MT040334.1), GX-P4L (MT040333.1), GX-P3B (MT072865.1), MP789 (MT121216.1), Guangdong-P2S (EPI_ISL_410544)), civet cats (Civet007, A022, B039)), and camels (KT368891.1, MN514967.1, KF917527.1, NC_028752.1) were retrieved from the NCBI GenBank.

mRNA synthesis and LNP formulation: Sequences of Spike and 10 T cell non-Spike antigens were derived from the SARS-CoV-2 Omicron sub-variant BA.2 (NCBI GenBank accession number OM617939) Nucleoside-modified mRNAs expressing SARS-CoV-2 full-length of prefusion-stabilized Spike protein with two or 6 proline mutations (mRNA-S-2P and mRNA-S-6P (Size: 3804 bp, Nucleotide Range: 21504 bp-25308 bp)) and part or full-length ten highly conserved non-Spike T cell antigens (NSP-2 (Size: 1914 bp, Nucleotide Range: 540 bp-2454 bp), NSP-3 (Size: 4485 bp, Nucleotide Range: 3804 bp-8289 bp), NSP-4 (Size: 1500 bp, Nucleotide Range: 8290 bp-9790 bp), NSP-5-10 (Size: 3378 bp, Nucleotide Range: 9791 bp-13169 bp), NSP-12 (Size: 2796 bp, Nucleotide Range: 13170 bp-15966 bp), NSP-14 (Size: 1581 bp, Nucleotide Range: 17766 bp-19347 bp), ORF7a/b (Size: 492 bp, Nucleotide Range: 27327 bp-27819 bp), Membrane (Size: 666 bp, Nucleotide Range: 26455 bp-27121 bp), Envelope (Size: 225 bp, Nucleotide Range: 26177 bp-26402 bp), and Nucleoprotein (Size: 1248 bp, Nucleotide Range: 28206 bp-29454 bp) were synthesized by in vitro transcription using T7 RNA polymerase (MegaScript, Thermo Fisher Scientific, Waltham, MA) on linearized plasmid templates, as previously reported. Modified mRNA transcript with full substitution of Pseudo-U was synthesized by TriLink Biotechnologies using proprietary CleanCap® technology. The synthesized polyadenylated (80A) mRNAs were subjected to DNase and phosphatase treatment, followed by Silica membrane purification. Finally, the synthesized mRNA was packaged as a 1.00±6% mg/mL solution in 1 mM Sodium Citrate, pH 6.4. Purified mRNAs were analyzed by agarose gel electrophoresis and were kept frozen at −20° C. The mRNAs were formulated into LNPs using an ethanolic lipid mixture of ionizable cationic lipid and an aqueous buffer system. Formulated mRNA-LNPs were prepared according to RNA concentrations (1 μg/μl) and were stored at −80° C. for animal immunizations.

Confirmation of protein expression by mRNAs. The expression of target viral protein by the vaccines was confirmed in HEK293T [American Type Culture Collection (ATCC), CRL-3216] cells before testing in animal experiments and plated 10ˆ6 cells in 500 μl culture medium in a 6-well plate on Day 0. Once the cells reached confluency, HEK293T cells in six-well plates were directly transfected with 2 μg of mRNA-LNP or only transfected with LNP. A transfection mix for mRNA was prepared and cells were transfected as described by the Lipofectamine™ MessengerMAX™ Transfection Reagent-specific protocol (Thermo Fisher Scientific, Catalog #LMRNA001).

Hamster immunization and SARS-CoV-2 variants challenge: The mRNA/LNP vaccines were evaluated in the outbred golden Syrian hamster model for protection against three SARS-CoV-2 variants and subvariants (Washington, Delta, and Omicron). The Institutional Animal Care and Use Committee approved animal model usage experiments at the University of California, Irvine (Protocol number AUP-22-086). The recommendations in the Guide for the Care and Use of Laboratory Animals of the National Institutes of Health performed animal experiments. The sample size for each animal study (n=5 per group) was calculated by power analysis, demonstrating that 5 hamsters per group were enough to produce significant results with a power>80%. Animals were randomly assigned to each group, and the study design was not blinded to researchers and animal facility staff.

Example 2

The following is a non-limiting example of the present invention. It is to be understood that said example is not intended to limit the present invention in any way. Equivalents or substitutes are within the scope of the present invention.

Pre-Clinical Protective Superiority of the TechImmune mRNA-LNP Encoding Spike+T Cell Antigens Combination Vaccine Against SARS-CoV-2 Delta (B.1.617.2) Variant is Mediated by T-Cells in hACE2 Mice.

To study the pre-clinical protective superiority of the TechImmune mRNA-LNP encoding Spike+T Cell Antigens vaccine versus mRNA-LNP encoding spike protein alone against intranasal infection with SARS-CoV-2 Delta (B.1.617.2), we have compared the body weight loss in hACE2 mice vaccinated with TechImmune mRNA-LNP encoding Spike 2P+T cell Ag (Nucleoprotein, NSP2 and NSP14) vaccine versus hACE2 mice vaccinated with mRNA-LNP encoding spike 2P protein alone, or encoding T cell Ag (Nucleoprotein, NSP2 and NSP14) combination or unvaccinated. Then all the mice were challenged with SARS-CoV-2 Delta (B.1.617.2) Variant. Although all the mice challenged with SARS-Cov-2 start losing weight 2-3 days post infection, unvaccinated mice start gaining weight only by days 11 and 12. Similarly but very less pronounced body weight loss, Spike alone and T cell antigen encoding mRNA-LNP start regaining weight by day 5-6. Importantly mice vaccinated with the combination Spike2P+T-cell Ag show no weight loss and keep regaining weight throughout all the experiment (FIG. 12A). Demonstrating that TechImmune mRNA-LNP encoding spike 2P and T cell Antigens (Nucleoprotein, NSP2 and NSP14) vaccine provide a superior protection against SARS-CoV-2 Delta (B.1.617.2) challenge when compared to mRNA-LNP encoding for spike 2P alone or T-cell Ag combination. To study the role of CD4+ and CD8+ T-cells in the protection of TechImmune mRNA-LNP encoding spike 2P and T cell Antigens (Nucleoprotein, NSP2 and NSP14) against the Delta challenge, we analyzed the effect of CD4+ and/or CD8+ T cells depletion on TechImmune mRNA-LNP encoding spike 2P and T cell Antigens (Nucleoprotein, NSP2 and NSP14) vaccine protection against SARS-CoV-2 Delta (B.1.617.2) variant in hACE2 mice. The results show that, in the mice immunized with Spike 2P+ T-cell Ags, CD4+ and CD8+ T-cells depletion have little impact on weight loss. However, depletion of both CD4+ and CD8+ T cells abrogate (to the levels of unvaccinated mice) the protective efficacy of TechImmune mRNA-LNP encoding spike 2P and T cell Antigens (Nucleoprotein, NSP2 and NSP14) against challenge with SARS-CoV-2 Delta virus (FIG. 12B).

Depletion of CD4+ and CD8+ T-cell subsets. Rat IgG2b monoclonal antibodies (mAbs) Gk1.5 specific for mouse CD4 and 2.43 specific for mouse CD8 were used for in vivo depletion as described previously [Ref]. hACE2 transgenic B57 mice were injected with 300 μg of anti-mouse CD4 and/or anti-mouse CD8α mAbs for each dose, given intraperitoneally (i.p.) 4 and 2 days before the challenge with SARS-CoV-2 B.617.2 variant (Delta).

EMBODIMENTS

The following embodiments are intended to be illustrative only and not to be limiting in any way.

Embodiment 1: A universal pre-emptive pan-Coronavirus vaccine composition, the composition comprising a sequence encoding, or comprising: two or more Coronavirus antigens derived from: a) at least a portion of an NSP2 protein, b) at least a portion of an NSP14 protein, and c) at least a portion of a Nucleoprotein protein.

Embodiment 2: A universal pre-emptive pan-Coronavirus vaccine composition, the composition comprising a sequence encoding, or comprising: three or more Coronavirus antigens derived from: a) at least a portion of an NSP2 protein, b) at least a portion of an NSP14 protein, and c) at least a portion of a Nucleoprotein protein.

Embodiment 3: The composition of embodiment 1 or embodiment 2 further comprising at least a portion of a Spike protein.

Embodiment 4: A universal pre-emptive pan-Coronavirus vaccine composition, the composition comprising a sequence encoding, or comprising: two or more Coronavirus antigens derived from: a) at least a portion of an NSP2 protein b) at least a portion of an NSP14 protein c) at least a portion of a Nucleoprotein protein, and d) at least a portion of a Spike protein.

Embodiment 5: A universal pre-emptive pan-Coronavirus vaccine composition, the composition comprising a sequence encoding, or comprising: three or more Coronavirus antigens derived from: a) at least a portion of an NSP2 protein, b) at least a portion of an NSP14 protein, c) at least a portion of a Nucleoprotein protein, and d) at least a portion of a Spike protein.

Embodiment 6: The composition of any one of embodiments 1-5, wherein the Coronavirus antigens are: the Spike protein or a portion thereof and the NSP2 protein or a portion thereof.

Embodiment 7: The composition of any one of embodiments 1-5, wherein the Coronavirus antigens are: the Spike protein or a portion thereof and the NSP14 protein or a portion thereof.

Embodiment 8: The composition of any one of embodiments 1-5, wherein the Coronavirus antigens are the Spike protein or a portion thereof and the Nucleoprotein or a portion thereof.

Embodiment 9: The composition of any one of embodiments 1-5, wherein the Coronavirus antigens are the Spike protein or a portion thereof, the NSP2 protein or a portion thereof, and the NSP14 protein or a portion thereof.

Embodiment 10: The composition of any one of embodiments 1-5, wherein the Coronavirus antigens are the Spike protein or a portion thereof, the NSP2 protein or a portion thereof, and the Nucleoprotein or a portion thereof.

Embodiment 11: The composition of any one of embodiments 1-5, wherein the Coronavirus antigens are the Spike protein or a portion thereof, the NSP14 protein or a portion thereof, and the Nucleoprotein or a portion thereof.

Embodiment 12: The composition of any one of embodiments 1-5, wherein the Coronavirus antigens are: the Spike protein; the NSP2 protein or a portion thereof; the NSP14 protein or a portion thereof; and the Nucleoprotein or a portion thereof.

Embodiment 13: The composition of any one of embodiments 1-12, wherein the portion of the NSP2 protein comprises at least a portion of SEQ ID NO: 3; or wherein the portion of the NSP2 protein is encoded by a sequence according to SEQ ID NO: 1 or SEQ ID NO: 2.

Embodiment 14: The composition of any one of embodiments 1-12, wherein the portion of the NSP14 protein comprises at least a portion of SEQ ID NO: 6; or wherein the portion of the NSP14 protein is encoded by a sequence according to SEQ ID NO: 4 or SEQ ID NO: 5.

Embodiment 15: The composition of any one of embodiments 1-12, wherein the portion of the Nucleoprotein comprises at least a portion of SEQ ID NO: 9, or wherein the portion of the Nucleoprotein is encoded by a sequence according to SEQ ID NO: 7 or SEQ ID NO: 8.

Embodiment 16: The composition of any one of embodiments 1-12, wherein the portion of the spike protein comprises at least a portion of either SEQ ID NO: 11 or SEQ ID NO: 12.

Embodiment 17: The composition of any one of embodiments 1-16, further comprising one or more Coronavirus antigens derived from: at least a portion of NSP3 protein, at least a portion of NSP12 protein, or at least a portion of a protein encoded by ORF7a/b.

Embodiment 18: The composition of embodiment 17, wherein the portion of NSP3 protein is encoded by a sequence according to SEQ ID NO: 13 or SEQ ID NO: 14.

Embodiment 19: The composition of embodiment 17, wherein the portion of NSP12 is encoded by a sequence according to SEQ ID NO: 15 or SEQ ID NO: 16.

Embodiment 20: The composition of embodiment 17, wherein the portion of the protein encoded by ORF7a/b is encoded by a sequence according to SEQ ID NO: 17 or SEQ ID NO: 18.

Embodiment 21: A universal pre-emptive pan-Coronavirus vaccine composition, the composition comprising, or comprising a sequence encoding: two or more Coronavirus antigens derived from: a) an NSP2 protein; b) an NSP14 protein; and c) a Nucleoprotein protein.

Embodiment 22: A universal pre-emptive pan-Coronavirus vaccine composition, the composition comprising, or comprising a sequence encoding: three or more Coronavirus antigens derived from: a) an NSP2 protein; b) an NSP14 protein; and c) a Nucleoprotein protein.

Embodiment 23: The composition of embodiment 21 or embodiment 22, further comprising a Spike protein.

Embodiment 24: A universal pre-emptive pan-Coronavirus vaccine composition, the composition comprising, or comprising a sequence encoding: two or more Coronavirus antigens derived from: a) an NSP2 protein; b) an NSP14 protein; c) a Nucleoprotein protein; and d) a Spike protein.

Embodiment 25: A universal pre-emptive pan-Coronavirus vaccine composition, the composition comprising, or comprising a sequence encoding: three or more Coronavirus antigens derived from: a) an NSP2 protein; b) an NSP14 protein; c) a Nucleoprotein protein; and d) a Spike protein.

Embodiment 26: The composition of any one of embodiments 20-25, wherein the Coronavirus antigens are: the Spike protein and the NSP2 protein.

Embodiment 27: The composition of any one of embodiments 20-25, wherein the Coronavirus antigens are: the Spike protein and the NSP14 protein.

Embodiment 28: The composition of any one of embodiments 20-25, wherein the Coronavirus antigens are the Spike protein and the Nucleoprotein.

Embodiment 29: The composition of any one of embodiments 20-25, wherein the Coronavirus antigens are the Spike protein, the NSP2 protein, and the NSP14 protein.

Embodiment 30: The composition of any one of embodiments 20-25, wherein the Coronavirus antigens are the Spike protein, the NSP2 protein, and the Nucleoprotein.

Embodiment 31: The composition of any one of embodiments 20-25, wherein the Coronavirus antigens are: the Spike protein, the NSP14 protein, and the Nucleoprotein.

Embodiment 32: The composition of any one of embodiments 20-25, wherein the Coronavirus antigens are the Spike protein, the NSP2 protein, the NSP14 protein, and the Nucleoprotein.

Embodiment 33: The composition of any one of embodiments 20-32, wherein the NSP2 protein comprises a sequences according to SEQ ID NO: 3, or wherein the NSP2 protein is encoded by a sequence according to SEQ ID NO: 1 or SEQ ID NO: 2.

Embodiment 34: The composition of any one of embodiments 20-32, wherein the NSP14 protein comprises a sequences according to SEQ ID NO: 6, or wherein the NSP14 protein is encoded by a sequence according to SEQ ID NO: 4 or SEQ ID NO: 5.

Embodiment 35: The composition of any one of embodiments 20-32, wherein the Nucleoprotein protein comprises a sequences according to SEQ ID NO: 9, or wherein the Nucleoprotein is encoded by a sequence according to SEQ ID NO: 7 or SEQ ID NO: 8.

Embodiment 36: The composition of any one of embodiments 20-32, wherein the spike protein is encoded by a sequence according to either SEQ ID NO: 11 or SEQ ID NO: 12.

Embodiment 37: The composition of any one of embodiments 20-36, further comprising one or more Coronavirus antigens derived from: an NSP3 protein, an NSP12 protein, or a protein encoded by ORF7a/b.

Embodiment 38: The composition of embodiment 37, wherein the NSP3 protein is encoded by a sequence according to either SEQ ID NO: 13 or SEQ ID NO: 14.

Embodiment 39: The composition of embodiment 37, wherein the NSP12 protein is encoded by a sequence according to either SEQ ID NO: 15 or SEQ ID NO: 16.

Embodiment 40: The composition of embodiment 37, wherein the protein encoded by ORF7a/b is encoded by a sequence according to either SEQ ID NO: 17 or SEQ ID NO: 18.

Embodiment 41: The composition of any one of embodiments 1-40 further comprising a T cell attracting chemokine, wherein the T cell attracting chemokine is CCL5, CXCL9, CXCL10, CXCL11, or a combination thereof.

Embodiment 42: The composition of any one of embodiments 1-40 further comprising a composition that promotes T cell proliferation and T-cell memory, wherein the composition that promotes T cell proliferation and memory is IL-7, IL-2, or IL-15.

Embodiment 43: The composition of any one of embodiments 1-42, wherein the vaccine composition protects against disease caused by one or more coronavirus variants or coronavirus subvariants.

Embodiment 44: The composition of embodiment 43, wherein the coronavirus variants or coronavirus subvariants comprise past or currently circulating coronavirus variants or coronavirus subvariants wherein the coronavirus variants comprise alpha, beta, gamma, delta, and omicron.

Embodiment 45: The composition of embodiment 43, wherein the coronavirus variants or coronavirus subvariants comprise future variants or future subvariants of human and animal coronavirus.

Embodiment 46: The composition of any one of embodiments 1-45, wherein the vaccine composition protects against infection and re-infection of coronavirus variants or coronavirus subvariants.

Embodiment 47: The composition of embodiment 46, wherein the coronavirus variants or coronavirus subvariants comprise past or currently circulating coronavirus variants or coronavirus subvariants, wherein the coronavirus variants comprise alpha, beta, gamma, delta, and omicron.

Embodiment 48: The composition of embodiment 46, wherein the coronavirus variants or coronavirus subvariants comprise future variants or future subvariants of human and animal coronavirus.

Embodiment 49: The composition of embodiment 46, wherein the vaccine composition protects against infection or reinfection of one or more coronavirus variant or coronavirus subvariant.

Embodiment 50: The composition of embodiment 49, wherein the vaccine composition protects against infection or reinfection of multiple coronavirus variants or coronavirus subvariants.

Embodiment 51: The composition of embodiment 49, wherein the vaccine composition protects against infection or re-infection of one coronavirus variants or coronavirus subvariants.

Embodiment 52: The composition of any one of embodiments 1-51, wherein the vaccine composition induces strong and long-lasting protection mediated by antibodies (Abs), CD4+ T helper (Th1) cells, and/or CD8+ cytotoxic T-cells (CTL).

Embodiment 53: The composition of any one of embodiments 1-52, wherein the composition protects against Sarbecoviruses, wherein sarbecoviruses comprise SARS-CoV1 or SARS-CoV2.

Embodiment 54: A pan-Coronavirus recombinant vaccine composition, the composition comprising a delivery system encoding two or more Coronavirus antigens derived from: a) at least a portion of an NSP2 protein; b) at least a portion of an NSP14 protein; and c) at least a portion of a Nucleoprotein protein.

Embodiment 55: A pan-Coronavirus recombinant vaccine composition, the composition comprising a delivery system encoding three or more Coronavirus antigens derived from: a) at least a portion of an NSP2 protein; b) at least a portion of an NSP14 protein; and c) at least a portion of a Nucleoprotein protein.

Embodiment 56: The composition of embodiments 54 or 55, wherein the delivery system further encodes a Coronavirus antigen derived from at least a portion of a Spike protein.

Embodiment 57: The composition of embodiments 54 or 55, further comprising a delivery system (e.g., a second delivery system) encoding a Coronavirus antigens derived from at least a portion of a Spike protein.

Embodiment 58: A pan-Coronavirus recombinant vaccine composition, the composition comprising an delivery system encoding two or more Coronavirus antigens derived from: a) at least a portion of an NSP2 protein; b) at least a portion of an NSP14 protein; c) at least a portion of a Nucleoprotein protein; and d) at least a portion of a Spike protein.

Embodiment 59: A pan-Coronavirus recombinant vaccine composition, the composition comprising an delivery system encoding three or more Coronavirus antigens derived from: a) at least a portion of an NSP2 protein; b) at least a portion of an NSP14 protein; c) at least a portion of a Nucleoprotein protein; and d) at least a portion of a Spike protein.

Embodiment 60: The composition of any one of embodiments 54-59, wherein the Coronavirus antigens are the Spike protein or a portion thereof and the NSP2 protein or a portion thereof.

Embodiment 61: The composition of any one of embodiments 54-59, wherein the Coronavirus antigens are the Spike protein or a portion thereof and the NSP14 protein or a portion thereof.

Embodiment 62: The composition of any one of embodiments 54-59, wherein the Coronavirus antigens are the Spike protein or a portion thereof and the Nucleoprotein or portion thereof.

Embodiment 63: The composition of any one of embodiments 54-59, wherein the Coronavirus antigens are the Spike protein or a portion thereof, the NSP2 protein or a portion thereof, and the NSP14 protein or portion thereof.

Embodiment 64: The composition of any one of embodiments 54-59, wherein the Coronavirus antigens are the Spike protein or a portion thereof, the NSP2 protein or portion thereof, and the Nucleoprotein or portion thereof.

Embodiment 65: The composition of any one of embodiments 54-59, wherein the Coronavirus antigens are the Spike protein or a portion thereof, the NSP14 protein or portion thereof; and the Nucleoprotein or portion thereof.

Embodiment 66: The composition of any one of embodiments 54-59, wherein the Coronavirus antigens are the Spike protein or a portion thereof, the NSP2 protein or portion thereof, the NSP14 protein or portion thereof; and the Nucleoprotein or portion thereof.

Embodiment 67: The composition of any one of embodiments 54-66, wherein the portion of the NSP2 protein comprises at least a portion of SEQ ID NO: 3; or wherein the portion of the NSP2 protein is encoded by a sequence according to SEQ ID NO: 1 or SEQ ID NO: 2.

Embodiment 68: The composition of any one of embodiments 54-66, wherein the portion of the NSP14 protein comprises at least a portion of SEQ ID NO: 6; or wherein the portion of the NSP14 protein is encoded by a sequence according to SEQ ID NO: 4 or SEQ ID NO: 5.

Embodiment 69: The composition of any one of embodiments 54-66, wherein the portion of the Nucleoprotein protein comprises at least a portion of SEQ ID NO: 9; or wherein the portion of the Nucleoprotein is encoded by a sequence according to SEQ ID NO: 7 or SEQ ID NO: 8.

Embodiment 70: The composition of any one of embodiments 54-66, wherein the portion of the spike protein comprises at least a portion of either SEQ ID NO: 11 or SEQ ID NO: 12.

Embodiment 71: The composition of any one of embodiments 54-70, further comprising one or more Coronavirus antigens derived from: at least a portion of NSP3 protein, at least a portion of NSP12 protein, or at least a portion of a protein encoded by ORF7a/b.

Embodiment 72: The composition of embodiment 71, wherein the portion of NSP3 protein is encoded by a sequence according to either SEQ ID NO: 13 or SEQ ID NO: 14.

Embodiment 73: The composition of embodiment 71, wherein the portion of NSP12 protein is encoded by a sequence according to either SEQ ID NO: 15 or SEQ ID NO: 16.

Embodiment 74: The composition of embodiment 71, wherein the portion of the protein encoded by ORF7a/b is encoded by a sequence according to either SEQ ID NO: 17 or SEQ ID NO: 18.

Embodiment 75: The composition of any of embodiments 54-74, wherein the delivery system in a single delivery system.

Embodiment 76: The composition of any of embodiments 54-74, wherein the delivery system comprises two or more delivery systems.

Embodiment 77: The composition of any of embodiments 54-76, wherein the delivery system is an adeno-associated viral vector-based antigen delivery system.

Embodiment 78: The composition of embodiment 77, wherein the adeno-associated viral vector is an adeno-associated virus vector type 8 (AAV8 serotype) or an adeno-associated virus vector type 9 (AAV9 serotype).

Embodiment 79: The composition of embodiment any of embodiments 54-78, wherein the delivery system is a vesicular stomatitis virus (VSV) vector.

Embodiment 80: The composition of any of embodiments 54-79, wherein antigens are operatively linked to a generic promoter.

Embodiment 81: The composition of embodiment 54-80, wherein the generic promoter is a CMV or a CAG promoter.

Embodiment 82: The composition of any of embodiments 54-81, wherein antigens and the at least a portion of the spike protein are operatively linked to a lung-specific promoter.

Embodiment 83: The composition of embodiment 82, wherein the lung-specific promoter is SpB or CD144.

Embodiment 84: The composition of any of embodiments 54-83, wherein the delivery system further encodes a T cell attracting chemokine.

Embodiment 85: The composition of embodiment 84, wherein the T cell attracting chemokine is CCL5, CXCL9, CXCL10, CXCL11, or a combination thereof.

Embodiment 86: The composition of any of embodiments 54-85, wherein the T cell attracting chemokine is operatively linked to a lung-specific promoter.

Embodiment 87: The composition of any of embodiments 54-86, wherein the T cell attracting chemokine is operatively linked to a generic promoter.

Embodiment 88: The composition of any of embodiments 54-87, wherein the delivery system further encodes a composition that promotes T cell proliferation.

Embodiment 89: The composition of embodiment 88, wherein the composition that promotes T cell proliferation is IL-7, IL-2, or IL-15.

Embodiment 90: The composition of any of embodiments 54-89, wherein the composition that promotes T cell proliferation is operatively linked to a lung-specific promoter.

Embodiment 91: The composition of any of embodiments 54-90, wherein the composition that promotes T cell proliferation is operatively linked to a generic promoter.

Embodiment 92: The composition of any of embodiments 54-91, wherein the T cell attracting chemokine and the composition that promotes T cell proliferation are driven by the same promoter.

Embodiment 93: The composition of any of embodiments 54-92, wherein the composition encodes a peptide comprising a T cell attracting chemokine and a composition that promotes T cell proliferation.

Embodiment 94: The composition of embodiment 93, wherein the peptide is operatively linked to a lung-specific promoter.

Embodiment 95: The composition of embodiment 93 wherein the peptide is operatively linked to a generic promoter.

Embodiment 96: A pan-Coronavirus recombinant vaccine composition, the composition comprising a delivery system encoding two or more Coronavirus antigens derived from: a) an NSP2 protein; b) an NSP14 protein; and c) a Nucleoprotein protein.

Embodiment 97: A pan-Coronavirus recombinant vaccine composition, the composition comprising a delivery system encoding three or more Coronavirus antigens derived from: a) an NSP2 protein; b) an NSP14 protein; and c) a Nucleoprotein protein.

Embodiment 98: The composition of embodiments 96 or 97, wherein the delivery system further encodes a Coronavirus antigens derived from a Spike protein.

Embodiment 99: The composition of embodiments 96 or 97, further comprising a delivery system (e.g., a second delivery system) encoding a Coronavirus antigens derived from a Spike protein.

Embodiment 100: A pan-Coronavirus recombinant vaccine composition, the composition comprising an delivery system encoding two or more Coronavirus antigens derived from: a) an NSP2 protein; b) an NSP14 protein; c) a Nucleoprotein protein; and d) a Spike protein.

Embodiment 101: A pan-Coronavirus recombinant vaccine composition, the composition comprising a delivery system encoding three or more Coronavirus antigens derived from: a) an NSP2 protein; b) an NSP14 protein; c) a Nucleoprotein protein; and d) a Spike protein.

Embodiment 102: The composition of any one of embodiments 96-101, wherein the Coronavirus antigens are the Spike protein and the NSP2 protein Embodiment 103: The composition of any one of embodiments 96-101, wherein the Coronavirus antigens are the Spike protein and the NSP14 protein.

Embodiment 104: The composition of any one of embodiments 96-101, wherein the Coronavirus antigens are the Spike protein and the Nucleoprotein.

Embodiment 105: The composition of any one of embodiments 96-101, wherein the Coronavirus antigens are the Spike protein, the NSP2 protein, and the NSP14 protein.

Embodiment 106: The composition of any one of embodiments 96-101, wherein the Coronavirus antigens are the Spike protein, the NSP2 protein, and the Nucleoprotein.

Embodiment 107: The composition of any one of embodiments 96-101, wherein the Coronavirus antigens are the Spike protein, the NSP14 protein, and the Nucleoprotein.

Embodiment 108: The composition of any one of embodiments 96-101, wherein the Coronavirus antigens are the Spike protein, the NSP2 protein, the NSP14 protein, and the Nucleoprotein.

Embodiment 109: The composition of any one of embodiments 96-101, wherein the NSP2 protein comprises according to SEQ ID NO: 3; or where the NSP2 protein is encoded by a sequence according to SEQ ID NO: 1 or SEQ ID NO: 2.

Embodiment 110: The composition of any one of embodiments 96-109, wherein the NSP14 protein comprises sequence according to SEQ ID NO: 6; or wherein the portion of the NSP14 protein is encoded by a sequence according to SEQ ID NO: 4 or SEQ ID NO: 5.

Embodiment 111: The composition of any one of embodiments 96-109, wherein the Nucleoprotein comprises a sequence according to SEQ ID NO: 9; or wherein the portion of the Nucleoprotein is encoded by a sequence according to SEQ ID NO: 7 or SEQ ID NO: 8.

Embodiment 112: The composition of any one of embodiments 96-109, wherein the spike protein comprises a sequence according to either SEQ ID NO: 11 or SEQ ID NO: 12.

Embodiment 113: The composition of any one of embodiments 96-112, further comprising one or more Coronavirus antigens derived from: an NSP3 protein, an NSP12 protein, or a protein encoded by ORF7a/b.

Embodiment 114: The composition of any one of embodiments 96-113, wherein the antigen delivery system in a single delivery system.

Embodiment 115: The composition of any one of embodiments 96-113, wherein the antigen delivery system comprises two or more delivery systems.

Embodiment 116: The composition of any one of embodiments 96-115, wherein the vaccine composition protects against disease caused by one or more coronavirus variants or coronavirus subvariants.

Embodiment 117: The composition of embodiment 116, wherein the coronavirus variants or coronavirus subvariants comprise past or currently circulating coronavirus variants or coronavirus subvariants wherein the coronavirus variants comprise alpha, beta, gamma, delta, and omicron.

Embodiment 118: The composition of embodiment 116, wherein the coronavirus variants or coronavirus subvariants comprise future variants or future subvariants of human and animal coronavirus.

Embodiment 119: The composition of any one of embodiments 96-118, wherein the vaccine composition protects against infection and re-infection of coronavirus variants or coronavirus subvariants.

Embodiment 120: The composition of embodiment 119, wherein the coronavirus variants or coronavirus subvariants comprise past or currently circulating coronavirus variants or coronavirus subvariants, wherein the coronavirus variants comprise alpha, beta, gamma, delta, and omicron.

Embodiment 121: The composition of embodiment 120, wherein the coronavirus variants or coronavirus subvariants comprise future variants or future subvariants of human and animal coronavirus.

Embodiment 122: The composition of embodiment 120, wherein the vaccine composition protects against infection or reinfection of one or more coronavirus variant or coronavirus subvariant.

Embodiment 123: The composition of embodiment 122, wherein the vaccine composition protects against infection or reinfection of multiple coronavirus variants or coronavirus subvariants.

Embodiment 124: The composition of embodiment 122, wherein the vaccine composition protects against infection or re-infection of one coronavirus variants or coronavirus subvariants.

Embodiment 125: The composition of any one of embodiments 96-124, wherein the vaccine composition induces strong and long-lasting protection mediated by antibodies (Abs), CD4+ T helper (Th1) cells, and/or CD8+ cytotoxic T-cells (CTL).

Embodiment 126: The composition of any one of embodiments 96-125, wherein the composition protects against Sarbecoviruses, wherein sarbecoviruses comprise SARS-CoV1 or SARS-CoV2.

Embodiment 127: A composition, comprising: two or more messenger ribonucleic acids (mRNAs) comprising an open reading frame encoding at least a portion of a Coronavirus protein selected from a group consisting of: an NSP2 protein, an NSP14 protein, a Nucleoprotein protein; and a Spike protein; wherein the two or more mRNAs are formulated in a lipid nanoparticle.

Embodiment 128: A composition, comprising: two or more messenger ribonucleic acids (mRNAs) comprising an open reading frame encoding an entire Coronavirus protein selected from a group consisting of: an NSP2 protein, an NSP14 protein, a Nucleoprotein protein; and a Spike protein; wherein the two or more mRNAs are formulated in a lipid nanoparticle.

Embodiment 129: A composition, comprising: three messenger ribonucleic acids (mRNAs) comprising an open reading frame encoding at least a portion of a Coronavirus protein selected from a group consisting of: an NSP2 protein, an NSP14 protein, and a Nucleoprotein protein; wherein the three mRNAs are formulated in a lipid nanoparticle.

Embodiment 130: A composition, comprising: three messenger ribonucleic acids (mRNAs) comprising an open reading frame encoding an entire Coronavirus protein selected from a group consisting of: an NSP2 protein, an NSP14 protein, and a Nucleoprotein protein; wherein the three mRNAs are formulated in a lipid nanoparticle.

Embodiment 131: The composition of embodiment 129 or embodiment 130, further comprising an mRNA comprising an open reading frame encoding a Coronavirus Spike protein or portion thereof formulated in a lipid nanoparticle.

Embodiment 132: The composition of any one of embodiments 127-131, wherein the mRNA further comprises a 5' untranslated region (UTR) and a 3' UTR.

Embodiment 133: The composition of any one of embodiments 127-132, wherein the mRNA further comprises a poly(A) tail.

Embodiment 134: The composition of any one of embodiments 127-133, wherein the mRNA further comprises a 5' cap or a 5' cap analog.

Embodiment 135: The composition of any one of embodiments 127-134, wherein the mRNAs comprise N1-methylpseudouridine (m1ψ) modified mRNAs.

Embodiment 136: The composition of any one of embodiments 127-135, wherein the lipid nanoparticles comprise ionizable catatonic lipid, neutral lipid, a sterol, a PEG modified lipid, or a combination thereof.

Embodiment 137: A pharmaceutical composition comprising: a plurality of lipid nanoparticles; wherein a first lipid nanoparticle comprises three messenger ribonucleic acids (mRNAs) encapsulated therein, wherein each mRNA comprises an open reading frame encoding a Coronavirus protein selected from a group consisting of: an NSP2 protein, an NSP14 protein, and a Nucleoprotein, and a second lipid nanoparticle comprising an mRNA comprising an open reading frame encoding a Coronavirus Spike protein or portion thereof encapsulated therein.

Embodiment 138: A pharmaceutical composition comprising: a plurality of lipid nanoparticles; wherein a first lipid nanoparticle comprises three messenger ribonucleic acids (mRNAs) encapsulated therein, wherein each mRNA comprises an open reading frame encoding at least a portion a Coronavirus protein selected from a group consisting of: an NSP2 protein, an NSP14 protein, and a Nucleoprotein, and a second lipid nanoparticle comprising an mRNA comprising an open reading frame encoding a Coronavirus Spike protein or portion thereof encapsulated therein.

Embodiment 139: The composition of embodiment 137 or embodiment 138, wherein the mRNA further comprises a 5' untranslated region (UTR) and a 3' UTR.

Embodiment 140: The composition of any one of embodiments 137-139, wherein the mRNA further comprises a poly(A) tail.

Embodiment 140: The composition of any one of embodiments 136-139, wherein the mRNA further comprises a 5' cap or 5' cap analog.

Embodiment 141: The composition of any one of embodiments 137-140, wherein the mRNAs comprise N1-methylpseudouridine (m1ψ) modified mRNAs.

Embodiment 142: The composition of any one of embodiments 137-141, wherein the lipid nanoparticles comprise ionizable catatonic lipid, neutral lipid, a sterol, a PEG modified lipid, or a combination thereof.

Embodiment 143: The composition of any one of embodiments 127-142, wherein the vaccine composition protects against disease caused by one or more coronavirus variants or coronavirus subvariants.

Embodiment 144: The composition of embodiment 143, wherein the coronavirus variants or coronavirus subvariants comprise past or currently circulating coronavirus variants or coronavirus subvariants wherein the coronavirus variants comprise alpha, beta, gamma, delta, and omicron.

Embodiment 145: The composition of embodiment 143, wherein the coronavirus variants or coronavirus subvariants comprise future variants or future subvariants of human and animal coronavirus.

Embodiment 146: The composition of any one of embodiments 127-145, wherein the vaccine composition protects against infection and re-infection of coronavirus variants or coronavirus subvariants.

Embodiment 147: The composition of embodiment 146, wherein the coronavirus variants or coronavirus subvariants comprise past or currently circulating coronavirus variants or coronavirus subvariants, wherein the coronavirus variants comprise alpha, beta, gamma, delta, and omicron.

Embodiment 148: The composition of embodiment 147, wherein the coronavirus variants or coronavirus subvariants comprise future variants or future subvariants of human and animal coronavirus.

Embodiment 149: The composition of embodiment 147, wherein the vaccine composition protects against infection or reinfection of one or more coronavirus variant or coronavirus subvariant.

Embodiment 150: The composition of embodiment 149, wherein the vaccine composition protects against infection or reinfection of multiple coronavirus variants or coronavirus subvariants.

Embodiment 151: The composition of embodiment 149, wherein the vaccine composition protects against infection or re-infection of one coronavirus variants or coronavirus subvariants.

Embodiment 152: The composition of any one of embodiments 127-151, wherein the vaccine composition induces strong and long-lasting protection mediated by antibodies (Abs), CD4+ T helper (Th1) cells, and/or CD8+ cytotoxic T-cells (CTL).

Embodiment 153: The composition of any one of embodiments 127-152, wherein the composition protects against Sarbecoviruses, wherein sarbecoviruses comprise SARS-CoV1 or SARS-CoV2.

Embodiment 154: A universal pre-emptive pan-Coronavirus vaccine composition, the composition comprising a sequence encoding or comprising: a B cell antigen or two or more T cell antigens.

Embodiment 155: A universal pre-emptive pan-Coronavirus vaccine composition, the composition comprising a sequence encoding or comprising: a B cell antigen and three T-cell antigens.

Embodiment 156: The composition of embodiment 154 and embodiment 155, wherein the B cell antigen is derived from a Coronavirus Spike protein or portion thereof.

Embodiment 157: The composition of embodiment 154 and embodiment 155, wherein the T cell antigens are derived from at least a portion of: an NSP2 protein, an NSP14 protein, a Nucleoprotein, or a combination thereof.

Embodiment 158: A method of inducing an immune response in a subject, the method comprising administering to the subject a composition (e.g., a vaccine composition, a pharmaceutical composition, etc.) according to any one of the preceding embodiments.

Embodiment 159: Use of a composition (e.g., a vaccine composition, a pharmaceutical composition, etc.) according to any one of embodiments 1-157 to induce an immune response in a subject.

Embodiment 160: A composition (e.g., a vaccine composition, a pharmaceutical composition, etc.) according to any one of embodiments 1-157 for use in a method of inducing an immune response in a subject.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

SEQUENCE LISTING

```
Sequence total quantity: 40
SEQ ID NO: 1            moltype = DNA  length = 1923
FEATURE                 Location/Qualifiers
source                  1..1923
                        mol_type = genomic DNA
                        organism = unidentified
SEQUENCE: 1
atggcataca ctcgctatgt cgataacaac ttctgtggcc ctgatggcta ccctcttgag   60
tgcattaaag accttctagc acgtgctggt aaagcttcat gcactttgtc cgaacaactg  120
gactttattg acactaagag gggtgtatac tgctgccgtg aacatgagca tgaaattgct  180
tggtacacgg aacgttctga aaagagctat gaattgcaga cacctttttga aattaaattg  240
gcaaagaaat ttgacacctt caatggggaa tgtccaaatt ttgtatttcc cttaaattcc  300
ataatcaaga ctattcaacc aagggttgaa aagaaaaagc ttgatggctt tatgggtaga  360
attcgatctg tctatccagt tgcgtcacca aatgaatgca accaaatgtg cctttcaact  420
ctcatgaagt gtgatcattg tggtgaaact tcatggcaga cgggcgattt tgttaaagcc  480
acttgcgaat tttgtggcac tgagaatttg actaaagaag gtgccactac ttgtggttac  540
ttaccccaaa atgctgttgt taaaatttat tgtccagcat gtcacaattc agaagtagga  600
cctgagcata gtcttgccga ataccataat gaatctggct tgaaaaccat tcttcgtaag  660
ggtggtcgca ctattgcctt tggaggctgt gtgttctctt atgttggttg ccataacaag  720
tgtgcctatt gggttccacg tgctagcgct aacatagggtt gtaaccatac aggtgttgtt  780
ggagaaggtt ccgaaggtct taatgacaac cttcttgaaa tactccaaaa agagaaagtc  840
aacatcaata ttgttggtga ctttaaactt aatgaagaga tcgccattat tttggcatct  900
ttttctgctt ccacaagtgc ttttgtggaa actgtgaaag gtttggatta taaagcattc  960
aaacaaattg ttgaatcctg tggtaatttt aaagttacaa aaggaaaagc taaaaaaggt  1020
gcctggaata ttggtgaaca gaaatcaata ctgagtcctc tttatgcatt tgcatcagag  1080
gctgctcgtg ttgtacgatc aattttctcc cgcactcttg aaactgctca aaattctgtg  1140
cgtgtttac agaaggccgc tataacaata ctagatggaa tttcacagta ttcactgaga  1200
ctcattgatg ctatgatgtt cacatctgat ttggctacta acaatctagt tgtaatggcc  1260
tacattacag gtggtgttgt tcagttgact tcgcagtggc taactaacat ctttggcact  1320
gtttatgaaa aactcaaacc cgtccttgat tggcttgaag agaagtttaa ggaaggtgta  1380
gagtttctta gagacggttg ggaaattgtt aaatttatct caacctgtgc ttgtgaaatt  1440
gtcggtggac aaattgtcac ctgtgcaaag gaaattaagg agagtgttca gacattcttt  1500
aagcttgtaa ataaatttttt ggctttgtgt gctgactcta tcattattgg tggagctaaa  1560
cttaaagcct tgaatttagg tgaaacattt gtcacgcact caaagggatt gtacagaaag  1620
tgtgttaaat ccagagaaga aactggccta ctcatgcctc taaaagcccc aaaagaaatt  1680
atcttcttag agggagaaac acttcccaca gaagtgttaa cagaggaagt tgtcttgaaa  1740
actggtgatt tacaaccatt agaacaacct actagtgaag ctgttgaagc tccattggtt  1800
ggtacaccag tttgtattaa cgggcttatg ttgctcgaaa tcaaagacac agaaaagtac  1860
tgtgcccttg cacctaatat gatggtaaca aacaatacct tcacactcaa aggcggttga  1920
tga                                                                  1923

SEQ ID NO: 2            moltype = DNA  length = 1923
```

```
FEATURE              Location/Qualifiers
source               1..1923
                     mol_type = other DNA
                     organism = synthetic construct
SEQUENCE: 2
atggcctata ccaggtacgt ggataataat ttctgtgggc ctgacggcta ccctctggaa   60
tgcatcaaag acctgttggc tagggcagga aaagcttcat gcaccctgtc tgagcaactt  120
gacttcattg acacaaagcg gggagtctac tgctgccgcg aacatgagca cgagattgct  180
tggtacacag agcgaagcga aaaatcttat gaactgcaga caccctttga aatcaagtta  240
gcaaagaagt tcgacacctt taatggcgag tgcccaaact ttgtgttccc tctgaattcg  300
atcattaaaa ccatccagcc tagagtagaa aaaaaaaagc tcgatggttt catgggccgc  360
ataagatctg tgtatcctgt ggctagcccc aacgagtgta accagatgtg tttgtcaacc  420
ctgatgaaat gtgatcactg tggagaaacg agttggcaga ctggagactt tgttaaagct  480
acttgcgcat tctgcgggac agagaacctc accaaggagg gagcaaccac gtgcggttac  540
ctgccccaaa atgctgtagt caaaatctac tgtccggcat gccataactc agaggttggg  600
ccagagcata gcttggcaga gtaccataat gaatcgggac ttaaaacaat cctgcggaag  660
ggtggccgta cgattgcctt tggagggtgc gttttcagct atgtgggctg ccacaacaag  720
tgcgcctact gggtgcccag agccagtgcc aacattggat gtaaccacac aggcgtcgtt  780
ggggagggca gtgagggctt gaatgacaat cttctggaga ttctacaaaa ggaaaaggtc  840
aacatcaaca tagttgggga tttcaagctg aacgaggaga ttgccatcat tttagcgtcc  900
tttttctgcct caacaagtgc cttcgtggaa actgtgaaag ggcttgacta caaggcattt  960
aagcagatcg tggagtcctg tggcaacttt aaagtgacta agggcaaggc caaaaagggg 1020
gcctggaata taggcgaaca gaagtccatc ctgagccctc tctatgcttt tgctagtgaa 1080
gctgccgcg ttgtccggtc tatcttcagc cgaactttgg agactgctca gaactctgtc 1140
agagtcctgc agaaggcagc cattaccata cttgatggga tatctcaata cagcctccgt 1200
ctgattgatg ccatgatgtt tacttcagat ctcgcaacca acaatctcgt tgtgatggct 1260
tatatcactg ggggtgtggt acagctgacg tcccagtggc tgactaatat attcgggacc 1320
gtatatgaga agctcaagcc agtgctggac tggctggaag agaaattcaa ggaaggtgtg 1380
gaatttttga gggacggctg ggagattgtg aagtttatta gcacctgtgc atgtgagatt 1440
gttggcggac agatcgtgac atgtgctaag gaaataaaag agagtgtaca aacgttcttc 1500
aaactcgtga ataaattttt agcgctatgt gctgactcca tcataattgg cggagccaag 1560
ttaaaagcgc tcaacttggg agagacattt gtcacccact ccaaaggtct gtataggaag 1620
tgtgtaaagt ccagagagga gactggacta ctaatgccac tgaaggctcc caaagagatc 1680
atcttcttag aaggagagac acttccgact gaggtcctta cagaagaagt ggtcctcaaa 1740
actggtgatc tccagcccct agagcagccc acatccgagg cagtcgaagc cccactggtg 1800
ggcacacctg tgtgcatcaa tggactcatg ttactcgaaa tcaaggatac cgagaagtac 1860
tgcgcactgg ccctaacat gatggtaacc aataacacat tcaccctgaa aggtggttga 1920
taa                                                                 1923

SEQ ID NO: 3           moltype = AA  length = 638
FEATURE                Location/Qualifiers
source                 1..638
                       mol_type = protein
                       organism = synthetic construct
SEQUENCE: 3
AYTRYVDNNF CGPDGYPLEC IKDLLARAGK ASCTLSEQLD FIDTKRGVYC CREHEHEIAW   60
YTERSEKSYE LQTPFEIKLA KKFDTFNGEC PNFVFPLNSI IKTIQPRVEK KKLDGFMGRI  120
RSVYPVASPN ECNQMCLSTL MKCDHCGETS WQTGDFVKAT CEFCGTENLT KEGATTCGYL  180
PQNAVVKIYC PACHNSEVGP EHSLAEYHNE SGLKTILRKG GRTIAFGGCV FSYVGCHNKC  240
AYWVPRASAN IGCNHTGVVG EGSEGLNDNL LEILQKEKVN INIVGDFKLN EEIAIILASF  300
SASTSAFVET VKGLDYKAFK QIVESCGNFK VTKGKAKKGA WNIGEQKSIL SPLYAFASEA  360
ARVVRSIFSR TLETAQNSVR VLQKAAITIL DGISQYSLRL IDAMMFTSDL ATNNLVVMAY  420
ITGGVVQLTS QWLTNIFGTV YEKLKPVLDW LEEKFKEGVE FLRDGWEIVK FISTCACEIV  480
GGQIVTCAKE IKESVQTFFK LVNKFLALCA DSIIIGGAKL KALNLGETFV THSKGLYRKC  540
VKSREETGLL MPLKAPKEII FLEGETLPTE VLTEEVVLKT GDLQPLEQPT SEAVEAPLVG  600
TPVCINGLML LEIKDTEKYC ALAPNMMVTN NTFTLKGG                          638

SEQ ID NO: 4           moltype = DNA  length = 1590
FEATURE                Location/Qualifiers
source                 1..1590
                       mol_type = genomic DNA
                       organism = unidentified
SEQUENCE: 4
atggctgaaa atgtaacagg actctttaaa gattgtagta aggtaatcac tgggttacat   60
cctacacagg cacctacaca cctcagtgtt gacactaaat caaaactga aggtttatgt   120
gttgacgtac ctggcatacc taaggacatg acctatagaa gactcatctc tatgatgggg  180
tttaaaatga attatcaagt taatggttac cctaacatgt ttatcacccg cgaagaagct  240
ataagacatg tacgtgcatg gattggcttc gatgtcgagg ggtgtcatgc tactagagaa  300
gctgttggta ccaatttacc tttacagcta ggttttcta caggtgttaa cctagttgct  360
gtacctacag gttatgttga tacctaat aatacagatt tttccagagt tagtgctaaa  420
ccaccgcctg gagatcaatt taaacacctc ataccactta tgtacaaagg acttccttgg  480
aatgtagtgc gtataaagat tgtacaaatg ttaagtgaca cacttaaaaa tctctctgac  540
agagtcgtat ttgtcttatg ggcacatggc tttgagttga catctatgaa gtattttgtg  600
aaaataggac ctgagcgcac ctgttgtcta tgtgataagc gtgccacatg cttttccact  660
gcttcagaca cttatgcctg ttggcatcat tctattggat ttgattacgt ctataatccg  720
tttatgatta atgttcaaca atggggtttt acaggtaacc tacaaagcaa ccatgatctg  780
tattgtcaag tccatggtaa tgcacatgta gctagttgtg atgcaatcat gactaggtgt  840
ctagctgtcc acgagtgctt tgttaagcgt gttgactgga ctattgaata tcctataatt  900
ggtgatgaac tgaagattaa tgcggcttgt agaaaggttc aacacatggt tgttaaagct  960
```

```
gcattattag cagacaaatt cccagttctt cacgacattg gtaaccctaa agctattaag   1020
tgtgtacctc aagctgatgt agaatggaag ttctatgatg cacagccttg tagtgacaaa   1080
gcttataaaa tagaagaatt attctattct tatgccacac attctgacaa attcacagat   1140
ggtgtatgcc tattttggaa ttgcaatgtc gatagatatc ctgctaattc cattgtttgt   1200
agatttgaca ctagagtgct atctaacctt aacttgcctg gttgtgatgg tggcagtttg   1260
tatgtaaata aacatgcatt ccacacacca gcttttgata aaagtgcttt tgttaattta   1320
aaacaattac cattttttcta ttactctgac agtccatgtg agtctcatgg aaaacaagta   1380
gtgtcagata tagattatgt accactaaag tctgctacgt gtataacacg ttgcaattta   1440
ggtggtgctg tctgtagaca tcatgctaat gagtacagat tgtatctcga tgcttataac   1500
atgatgatct cagctggctt tagcttgtgg gtttacaaac aatttgatac ttataacctc   1560
tggaacactt ttacaagact tcagtgatga                                    1590
```

SEQ ID NO: 5          moltype = DNA   length = 1590
FEATURE               Location/Qualifiers
source                1..1590
                      mol_type = other DNA
                      organism = synthetic construct
SEQUENCE: 5

```
atggctgaga atgtcacagg gctgtttaag gactgttcca aggtgataac aggactgcac   60
ccaacacagg cccctacgca cttgtctgtt gacacaaaat tcaaaacaga aggactctgt   120
gtggatgtac ccggcatccc taaagacatg acctatcgca ggctcatcag tatgatgggc   180
ttcaagatga actaccaggt caatggctac ccaaatatgt tcatcaccag ggaggaagct   240
attaggcatg tgagggcctg gattggtttt gacgtggaag gctgtcatgc aacaagagaa   300
gcagtgggga ccaacttacc tctgcagctg gggttcagca ctggggtcaa cctggttgct   360
gtcccaactg gatatgttga tacccccaac aacacagact tctcacgggt ctctgcaaag   420
cctccacctg gggatcagtt caagcacctg atcccattaa tgtataaagg tctgccctgt   480
aatgtggtaa ggatcaaaat tgttcagatg ctgagtgaca ctctgaagaa cttgagtgac   540
agagttgtgt ttgtcctgtg ggctcatggc tttgagctga ccagcatgaa gtactttgtg   600
aaaattggac cagagagaac gtgctgcctg tgtgaccgac gggcaacttg ttttttctacc   660
gcatcagata cttacgcctg ctggcaccat agtatcggtt ttgactatgt ctacaaccct   720
ttcatgattg atgtccagca atggggcttc acaggaaatt tgcagtccaa ccacgacctg   780
tactgccagg tccatgggaa tgctcacgtg gcctcctgcg atgctatcat gacacgatgt   840
ctggctgtgc atgagtgctt tgtgaagcgt gtcgactgga ccatcgaata ccccattatt   900
ggcgacgagc taaaaataaa tgcagcgtgt agaaaagtgc agcacatggt ggtcaaggca   960
gcactccttg ctgacaagtt tccagtatta catgacatcg gcaacccaaa ggccattaag   1020
tgtgttcctc aagcggatgt ggagtggaag ttctatgatg cccagccgtg ctctgataaa   1080
gcctacaaga tagaagaact ctttttattct tacgctactc acagcgacaa atttacagat   1140
ggagtttgcc tcttctggaa ctgcaatgtc gatagatatc cggccaacag catagtgtgc   1200
cgctttgtat cgcgcgtgct atccaacttg aacctcccgg gttgtgatgg cggttcgctt   1260
tatgtaaata aacatgcttt ccacacacct gccttcgaca gtccgcctt tgtgaatctg   1320
aaacaacttc ccttcttcta ctacagcgac agccctgcg agtcccacgg gaagcaggtg   1380
gtgagtgata ttgactatgt cccccttaag tcagcgactt gcatcactcg ctgtaacctt   1440
ggaggagctg tttgtcggca ccacgcgaat gagtaccgac tctacctgga cgcctataac   1500
atgatgatct ctgccggttt ctcactatgg gtatataagc agtttgatac ctacaatttg   1560
tggaacacct tcacccggct ccaatgataa                                    1590
```

SEQ ID NO: 6          moltype = AA   length = 527
FEATURE               Location/Qualifiers
source                1..527
                      mol_type = protein
                      organism = synthetic construct
SEQUENCE: 6

```
AENVTGLFKD CSKVITGLHP TQAPTHLSVD TKFKTEGLCV DVPGIPKDMT YRRLISMMGF   60
KMNYQVNGYP NMFITREEAI RHVRAWIGFD VEGCHATREA VGTNLPLQLG FSTGVNLVAV   120
PTGYVDTPNN TDFSRVSAKP PPGDQFKHLI PLMYKGLPWN VVRIKVQML SDTLKNLSDR   180
VVFVLWAHGF ELTSMKYFVK IGPERTCCLC DRRATCFSTA SDTYACWHHS IGFDYVYNPF   240
MIDVQWGFT GNLQSNHDLY CQVHGNAHVA SCDAIMTRCL AVHECFVKRV DWTIEYPIIG   300
DELKINAACR KVQHMVVKAA LLADKFPVLH DIGNPKAIKC VPQADVEWKF YDAQPCSDKA   360
YKIEELFYSY ATHSDKFTDG VCLFWNCNVD RYPANSIVCR FDTRVLSNLN LPGCDGGSLY   420
VNKHAFHTPA FDKSAFVNLK QLPFFYYSDS PCESHGKQVV SDIDYVPLKS ATCITRCNLG   480
GAVCRHHANE YRLYLDAYNM MISAGFSLWV YKQFDTYNLW NTFTRLQ              527
```

SEQ ID NO: 7          moltype = DNA   length = 1257
FEATURE               Location/Qualifiers
source                1..1257
                      mol_type = other DNA
                      organism = synthetic construct
SEQUENCE: 7

```
atgtctgata atggacccca aaatcagcga aatgcactcc gcattacgtt tggtggaccc   60
tcagattcaa ctggcagtaa ccagaatggt ggggcgcgat caaaacaacg tcggccccaa   120
ggtttaccca ataatactgc gtcttggttc accgctctca ctcaacatgg caaggaagac   180
cttaaattcc ctcgaggaca aggcgttcca attaacacca atagcagtcc agatgaccaa   240
attggctact accgaagagc taccagacga attcgtggtg gtgacggtaa aatgaaagat   300
ctcagtccaa gatggtattt ctactaccta ggaactgggc cagaagctgg acttccctat   360
ggtgctaaca aagacggcat catatgggtt gcaactgagg gagccttgaa tacaccaaaa   420
gatcacattg gcacccgcaa tcctgctaac aatgctgcaa tcgtgctaca acttcctcaa   480
ggaacaacat tgccaaaagg cttctacgca gaagggagca gaggcggcag tcaagcctct   540
tctcgttcct catcacgtag tcgcaacagt tcaagaaatt caactccagg cagcagtaaa   600
cgaacttctc ctgctagaat ggctggcaat ggcggtgatg ctgctcttgc tttgctgctg   660
```

```
cttgacagat tgaaccagct tgagagcaaa atgtctggta aaggccaaca acaacaaggc   720
caaactgtca ctaagaaatc tgctgctgag gcttctaaga agcctcggca aaaacgtact   780
gccactaaag catacaatgt aacacaagct ttcggcagac gtggtccaga acaaacccaa   840
ggaaattttg gggaccagga actaatcaga caaggaactg attacaaaca ttggccgcaa   900
attgcacaat ttgcccccag cgcttcagcg ttcttcggca tgtcgcgcat tggcatggaa   960
gtcacacctt cgggaacgtg gttgacctac acaggtgcca tcaaattgga tgacaaagat   1020
ccaaatttca aagatcaagt cattttgctt aataagcata ttgacgcata caaaacattc   1080
ccaccaacag agcctaaaaa ggacaaaaag aagaaggctg atgaaactca gccttaccg   1140
cagagacaga agaaacagca aactgtgact cttcttcctg ctgcagattt ggatgatttc   1200
tccaaacaat tgcaacaatc catgagccgt gctgactcaa ctcaggccta atgatga     1257
```

SEQ ID NO: 8             moltype = DNA   length = 1257
FEATURE                  Location/Qualifiers
source                   1..1257
                         mol_type = other DNA
                         organism = synthetic construct
SEQUENCE: 8

```
atgtcagaca atgggcccca gaaccagaga aatgcccttc gcatcacgtt tggtggccct   60
agtgacagca ccggcagcaa tcagaatgga ggtgcccgca gtaaacaaag gagaccacag   120
ggactgccaa acaacacagc atcctggttt actgcactta cgcagcatgg taaggaggac   180
ctgaagttcc caagaggaca gggagtcccc atcaacacca cagctcacc agatgatcag   240
atcggctatt accggcgggc tactcgccgc atacgaggtg gcgatggcaa gatgaaggat   300
ctaagtccgc gttggtactt ctactatctg ggcacagggc ctgaagctgg cctgccttat   360
ggggccaata aggatggcat catctgggtg gccactgagg gggctttgaa taccccaaaa   420
gaccacatcg ggactcgaaa ccctgccaac aatgcagcca ttgtccttca gctcccacaa   480
gggacaaacat tacccaaggg cttctatgca gagggctcca ggggaggttc tcaagccgat   540
agccggagca gctcgcggtc ccggaactca agccgaaatt ccactcctgg cagctccaag   600
agaacatcac ctgcgaggat ggctggaaat ggaggcgatg ctgctctggc cctcctttg   660
ctggacaggc tcaaccagct ggagagtaaa atgagtggaa aggggcagca gcaacagggc   720
cagactgtga ccaagaagtc tgcagcagaa gcgtccaaca aacccaggca gaaaaggaca   780
gccacaaaag cctataatgt gacacaagcc tttgggagaa gagggccaga gcagaccag   840
ggaaactttg gagaccagga gctgattcgt caaggtacag actacaagca ctggccacag   900
attgctcagt ttgctccctc tgcatcagcc ttcttcggca tgagcaggat aggtatggag   960
gtgactccga gcgggaacctg gctgacctac accggagcca tcaagctgga tgacaaggat   1020
cccaacttca aggaccaggt aattctctta aacaagcata ttgatgccta caaaaccttt   1080
cctccaacag aacccaaaaa ggacaaaaaa aaaaaagctg atgaaactca ggccctacct   1140
cagcggcaaa agaaacaaca gacggttacc ctactcccgg ctgcagattt ggacgacttc   1200
tctaagcagc tgcagcagtc catgtccaga gctgactcta cccaagcatg ataatga     1257
```

SEQ ID NO: 9             moltype = AA   length = 416
FEATURE                  Location/Qualifiers
source                   1..416
                         mol_type = protein
                         organism = synthetic construct
SEQUENCE: 9

```
MSDNGPQNQR NALRITFGGP SDSTGSNQNG GARSKQRRPQ GLPNNTASWF TALTQHGKED   60
LKFPRGQGVP INTNSSPDDQ IGYYRRATRR IRGGDGKMKD LSPRWYFYYL GTGPEAGLPY   120
GANKDGIIWV ATEGALNTPK DHIGTRNPAN NAAIVLQLPQ GTTLPKGFYA EGSRGGSQAS   180
SRSSSRSRNS SRNSTPGSSK RTSPARMAGN GGDAALALLL LDRLNQLESK MSGKGQQQQG   240
QTVTKKSAAE ASKKPRQKRT ATKAYNVTQA FGRRGPEQTQ GNFGDQELIR QGTDYKHWPQ   300
IAQFAPSASA FFGMSRIGME VTPSGTWLTY TGAIKLDDKD PNFKDQVILL NKHIDAYKTF   360
PPTEPKKDKK KKADETQALP QRQKKQQTVT LLPAADLDDF SKLQQSMSR ADSTQA        416
```

SEQ ID NO: 10            moltype = DNA   length = 2099
FEATURE                  Location/Qualifiers
source                   1..2099
                         mol_type = genomic DNA
                         organism = unidentified
SEQUENCE: 10

```
taccaagcta ctagagtagt ggtactttca tttgagcttc taaatgcacc tgccacagtg   60
tgtggaccaa aattgtccac atcactaatt aagaaccagt gtgtcaattt taatttcaat   120
ggactcaagg gtactggtgt gttgactgac tcgtccaaaa agtttcagtc ttttcaacaa   180
tttggaaggg atgcatctga tttttactga ctcagtacgcg accctcagac acttcaaata   240
cttgacattt caccatgttc atttggtggt gtgagtgtaa taaccaccagg aacaaatgct   300
tcatctgaag tagccgttct ataccaagat gtaaactgca ctgatgttcc cacggccata   360
cgtgctgacc aactcacacc tgcttggcgt gtttactctg ctggagtaaa tgtgtttcaa   420
actcaggctg gctgtttaat aggagcggaa catgtcaatg cttcatatga gtgtgacatt   480
cccattggtg caggcatttg tgctagttac catacagctc ccttttacg taatacaggc   540
cagaaatcaa ttgtggccta tactatgtca cttggtgcta aaaactcaat tgcttatgct   600
aataactcaa ttgccatacc tacaaatttt tcaatcagtg tcacaactga agtgatgcct   660
gtttcaatgg ctaagacatc agtagattgt acaatgtaca tctgtggtga ctctcaggag   720
tgcagcaact actacttca gtatggtagc ttttgcacac aattaaatcg tgcccttttca   780
ggcattgcta ttgaacagga caaaaacact caagaggttt ttgcccaagt aaacaaatg    840
tataagacac cagccataaa agattttggt ggctttaatt tctcacaaat attgcctgac   900
ccttctaagc caacaaaaag atcatttatt gaggatttac tcttcaacaa agtgactctc   960
gctgatgctg ctttatgaa gcaatacggc gaatgcctag cgatattag tgctagagat   1020
ctcatttgtg cgcagaagtt caatggactc actgtccttc cacctctact cacggatgaa   1080
atgattgctg cttacaccgc cgctcttgtc agcggtactg ctactgctgg ttggacattt   1140
ggtgcaggtg ctgctctaca ataccttttt gctatgcaaa tggcttatag gttcaatggc   1200
```

-continued

```
attggagtta ctcaaaatgt tctctatgag aaccagaagc agatcgctaa ccaatttaac   1260
aaggcgatca gtcaaattca agaatcactt actactactt caactgcatt gggcaagctg   1320
caagacgtcg tcaaccagaa tgctcaagca ttgaacacac ttgttaaaca actaagttct   1380
aactttggtg caatttcaag tgttttaaat gacattctgt ctcgactyga caaagttgag   1440
gctgaagtgc aaattgatag gttgattact ggcagattac aaagccttca gacctatgta   1500
acacaacaac taatcagagc tgctgaaatc agagcttctg ccaatcttgc tgccactaag   1560
atgtccgagt gtgttcttgg acaatcaaaa agagttgact tttgtggaaa aggctatcat   1620
cttatgtctt tccctcaagc agccccacat ggtgtcgtct tcttacatgt cacatacgtg   1680
ccatcgcaag aaagaaactt caccactgcc ccagcaatct gccatcaagg caaggcacac   1740
ttccctcgtg aaggtgtttt tgtatctaat ggcacttctt ggtttatcac acagaggaac   1800
ttcttttcac cacaaataat tacaacagac aatacatttg tctctggaaa ttgtgatgtc   1860
gttattggca tcatcaacaa tactgtttat gatcctctgc aacctgagct tgactcattt   1920
aaagaagagc tggacaagta cttcaaaaac cacacgtcac ctgatgtrga tcttggcgac   1980
atctcaggca ttaatgcttc agtcgtcaat attcaaaaag aaattgaccg cctcaatgag   2040
gttgccaaaa atctaaatga atcgctcatc gatcttcaag aacttggaaa atatgagca    2099

SEQ ID NO: 11        moltype = AA   length = 1273
FEATURE              Location/Qualifiers
source               1..1273
                     mol_type = protein
                     organism = synthetic construct
SEQUENCE: 11
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDPPEAE VQIDRLITGR LQSLQTYVTQ QLIRAAEIRA   1020
SANLAATKMS ECVLGQSKRV DFCGKGYHLM SFPQSAPHGV VFLHVTYVPA QEKNFTTAPA   1080
ICHDGKAHFP REGVFVSNGT HWFVTQRNFY EPQIITTDNT FVSGNCDVVI GIVNNTVYDP   1140
LQPELDSFKE ELDKYFKNHT SPDVDLGDIS GINASVVNIQ KEIDRLNEVA KNLNESLIDL   1200
QELGKYEQYI KWPWYIWLGF IAGLIAIVMV TIMLCCMTSC CSCLKGCCSC GSCCKFDEDD   1260
SEPVLKGVKL HYT                                                     1273

SEQ ID NO: 12        moltype = AA   length = 1273
FEATURE              Location/Qualifiers
source               1..1273
                     mol_type = protein
                     organism = synthetic construct
SEQUENCE: 12
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRAG CLIGAEHVNN SYECDIPIGA   600
GICASYQTQT NRDPQTLEIL DITPCSFGGV SVITPGTNTS NQVAVLYQDV NCTEVPVAIH   660
ADQLTPTWRV YSTGSNVFQS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSPIED LLFNKVTLAD AGFIKQYGDC   840
LGDIAARDLI CAQKFNGLTV LPPLLTDEMI AQYTSALLAG TITSGWTFGA GPALQIPFPM   900
QMAYRFNGIG VTQNVLYENQ KLIANQFNSA IGKIQDSLSS TPSALGKLQD VVNQNAQALN   960
TLVKQLSSNF GAISSVLNDI LSRLDPPEAE VQIDRLITGR LQSLQTYVTQ QLIRAAEIRA   1020
SANLAATKMS ECVLGQSKRV DFCGKGYHLM SFPQSAPHGV VFLHVTYVPA QEKNFTTAPA   1080
ICHDGKAHFP REGVFVSNGT HWFVTQRNFY EPQIITTDNT FVSGNCDVVI GIVNNTVYDP   1140
LQPELDSFKE ELDKYFKNHT SPDVDLGDIS GINASVVNIQ KEIDRLNEVA KNLNESLIDL   1200
QELGKYEQYI KWPWYIWLGF IAGLIAIVMV TIMLCCMTSC CSCLKGCCSC GSCCKFDEDD   1260
SEPVLKGVKL HYT                                                     1273

SEQ ID NO: 13        moltype = DNA   length = 4493
FEATURE              Location/Qualifiers
source               1..4493
                     mol_type = genomic DNA
                     organism = unidentified
```

```
SEQUENCE: 13
atgctcttgt tagtgacatt gacatcactt tcttaaagaa agatgctcca tatatagtgg   60
gtgatgttgt tcaagagggt gttttaactg ctgtggttat acctactaaa aaggctagtg  120
gcactactga aatgctagcg aaagctttga gaaaagtgcc aacagacaat tatataacca  180
cttacccggg tcagggttta aatggttaca ctgtagaggga ggcaaagaca gtgcttaaaa  240
agtgtaaaag tgcttttttac attctaccat ctattatctc taatgagaag caagaaattc  300
ttggaactgt ttcttggaat ttgcgagaaa tgcttgcaca tgcagaagaa acacgcaaat  360
taatgcctgt ctgtgtggaa actaaagcca tagtttcaac tatacagcgt aaatataagg  420
gtattaaaat acaagagggt gtggttgatt atggtgctag attttacttt tacaccagta  480
aaacaactgt agcgtcactt atcaacacac ttaacgatct aaatgaaact cttgttacaa  540
tgccacttgg ctatgtaaca catggcttaa atttggaaga agctgctcgg tatatgagat  600
ctctcaaagt gccagctaca gtttctgttt cttcacctga tgctgttaca gcgtataatg  660
gttatcttac ttcttcttct aaaacacctg aagaacattt tattgaaacc atctcacttg  720
ctggttccta taaagattgg tcctattctg gacaatctac acaactaggt atagaatttc  780
ttaagagagg tgataaaagt gtatattaca ctagtaatcc taccacattc cacctagatg  840
gtgaagttat cacctttgac aatcttaaga cacttctttc tttgagagaa gtgaggacta  900
ttaaggtgtt tacaacagta gacaacatta acctccacac gcaagttgtg gacatgtcaa  960
tgacatatgg acaacagttt ggtccaactt atttggatgg agctgatgtt actaaaataa 1020
aacctcataa ttcacatgaa ggtaaaacat tttatgtttt acctaatgat gacactctac 1080
gtgttgaggc ttttgagtac taccacacaa ctgatcctag ttttctgggt aggtacatgt 1140
cagcattaaa tcacactaaa aagtggaaat acccacaagt taatggttta acttctatta 1200
aatgggcaga taacaactgt tatcttgcca ctgcattgtt aacactccaa caaatagagt 1260
tgaagtttaa tccacctgct ctacaagatg cttattacag agcaagggct ggtgaagctg 1320
ctaacttttg tgcacttatc ttagcctact gtaataagac agtaggtgag ttaggtgatg 1380
ttagagaaac aatgagttac ttgtttcaac atgccaattt agattcttgc aaaagagtct 1440
tgaacgtggt gtgtaaaact tgtggacaac agcagacaac cctaagggt gtagaagctg 1500
ttatgtacat gggcacactt tcttatgaac aatttaagaa aggtgttcag ataccttgta 1560
cgtgtggtaa acaagctaca aaatatctag tacaacagga gtcaccttt gttatgatgt 1620
cagcaccacc tgctcagtat gaacttaagc atggtacatt tacttgtgct agtgagtaca 1680
ctggtaatta ccagtgtggt cactataaac atataacttc taaagaaact ttgtattgca 1740
tagacggtgc tttacttaca aagtcctcag aatacaaagg tcctattacg gatgtttttct 1800
acaaagaaaa cagttacaca acaaccataa aaccagttac ttataaattg gatggtgttg 1860
tttgtacaga aattgaccct aagttggaca attattataa gaaagacaat tcttatttca 1920
cagagcaacc aattgatctt gtaccaaacc aaccatatcc aaacgcaagc ttcgataatt 1980
ttaagtttgt atgtgataat atcaaatttg ctgatgattt aaaccagtta actggttata 2040
agaaacctgc ttcaagagag cttaaagtta catttttccc tgacttaaat ggtgatgtgg 2100
tggctattga ttataaacac tacacaccct cttttaagaa aggagctaaa ttgttacata 2160
aacctattgt ttggcatgtt aacaatgcaa ctaataaagc cacgtataaa ccaaatacct 2220
ggtgtatacg ttgtctttgg agcacaaaac cagttgaaac atcaaattcg tttgatgtac 2280
tgaagtcaga ggacgcgcag ggaatggata atcttgcctg cgaagatcta aaaccagtct 2340
ctgaagaagt agtggaaaat cctaccacac agaaagacgt tcttgagtgt aatgtgaaaa 2400
ctaccgaagt tgtaggagac attatactta aaccagcaaa taatagttta aaaattacag 2460
aagaggttgg ccacacagat ctaatggctg cttatgtaga caattctagt cttactatta 2520
agaaacctaa tgaattatct agagtattag gtttgaaaac ccttgctact catggtttag 2580
ctgctgttaa tagtgtccct tgggatacta tagctaatta tgctaagcct tttcttaaca 2640
aagttgttag tacaactact aacatagtta cacggtgttt aaaccgtgtt tgtactaatt 2700
atatgcctta tttctttact ttattgctac aattgtgtac ttttactaga agtacaaatt 2760
ctagaattaa agcatctatg ccgactacta gcaaagaa tactgttaag agtgtcggta 2820
aattttgtct agaggcttca tttaattatt tgaagtcacc taattttct aaaactgataa 2880
atattataat ttggttttta ctattaagtg tttgcctagg ttctttaatc tactcaaccg 2940
ctgctttagg tgtttttaatg tctaaattag gcatgccttc ttactgtact ggttacagag 3000
aaggctattt gaactctact aatgtcacta ttgcaaccta ctgtactggt tctatacctt 3060
gtagtgtttg tcttagtggt ttagattctt tagacaccta tccttcttta gaaactatac 3120
aaattaccat ttcatctttt aaatgggatt taactgcttt tggcttagtt gcagagtggt 3180
ttttggcata tattcttttc actaggtttt tctatgtact tggattggct gcaatcatgc 3240
aattgttttt cagctatttt gcagtacatt ttattagtaa ttcttggctt atgtggttaa 3300
taattaatct tgtacaaatg gccccgattt cagctatggt tagaatgtac atcttctttg 3360
catcatttta ttatgtatgg aaaagttatg tgcatgttgt agacgggtgt aattcatcaa 3420
cttgtatgat gtgttacaaa cgtaatagag caacaagagt cgaatgtaca actattgtta 3480
atggtgttag aaggtccttt tatgtctatg ctaatggagg taaaggcttt tgcaaaactac 3540
acaattggaa ttgtgttaat tgtgatacat tctgtgctgg tagtacattt attagtgatg 3600
aagttgcgag agacttgtca ctacagttta aaagaccaat aaatcctact gaccagtctt 3660
cttacatcgt tgatagtgtt acagtgaaga atggttccat ccatcttttac tttgataaag 3720
ctggtcaaaa gacttatgaa agacattctc tctctcattt tgttaactta gacaacctga 3780
gagctaataa cactaaaggt tcattgccta ttaatgttat agttttttgat ggtaaatcaa 3840
aatgtgaaga atcatctgca aaatcagcgt ctgtttacta cagtcagctt atgtgtcaac 3900
ctatactgtt actagatcag gcattagtgt ctgatgttgg tgatagtgcg gaagttcag 3960
ttaaaatgtt tgatgcttac gttaatacgt tttcatcaac ttttaacgta ccaatggaaa 4020
aactcaaaac actagttgca actgcagaag ctgaacttgc aaagaatgtg tccttagaca 4080
atgtcttatc tactttttatt tcagcagctc ggcaagggtt tgttgattca gatgtagaaa 4140
ctaaagatgt tgttgaatgt cttaaattgt cacatcaatc tgacatagaa gttactggcg 4200
atagttgtaa taactatatg ctcacctata acaaagttga aaacatgaca ccccgtgacc 4260
ttggtgcttg tattgactgt agtgcgcgtc atattaatgc gcaggtagca aaaagtcaca 4320
acattgcttg gatatggaac gttaaagatt tcatgtcatt gtctgaacaa ctacgaaaac 4380
aaatacgtag tgctgctaaa aagaataact accttttaa gttgacatgt gcaactacta 4440
gacaagttgt taatgttgta acaacaaaga tagcacttaa gggtggttga tga          4493

SEQ ID NO: 14          moltype = DNA  length = 4491
FEATURE                Location/Qualifiers
```

```
source                  1..4491
                        mol_type = other DNA
                        organism = synthetic construct
SEQUENCE: 14
atgctcttac ttgttattga catcaccttt ctaaagaaag atgcccctta tattgtggga   60
gacgttgtcc aggagggagt ccttacggcc gtggtgattc caacaaagaa ggctagtggc  120
accacagaaa tgctggccaa ggccttgcgc aaggtgccga cagacaacta catcactaca  180
tatcctggac aaggcctgaa cggatataca gtggaagagg caaagactgt gctaaagaag  240
tgcaagtctg ccttttacat ccttccaagc attattagca acgagaagca ggaaatactc  300
ggaaccgtaa gctggaacct tagagagatg cttgcgcatg ctgaggaaac ccgaaaactg  360
atgcctgtgt gtgttgaaac caaagccatc gtttctacca tccagcgaaa gtataagggt  420
atcaagatcc aagagggagt ggtagactat ggcgctagat tctacttcta tacctctaaa  480
acaactgtcg cctctcttat caatactctg aatgacctga atgagactct tgtgaccatg  540
cccctgggat acgtaaccca tgggcttaac ttggaagaag ccgctcgcta catgcgtagc  600
ctgaaggtcc ctgctactgt tagtgtctct tcccccgatg ccgtcacagc ttacaacggg  660
tatctgacgt caagctccaa aactcctgaa gagcacttca tcgagaccat tagtctagca  720
ggatcctata aagactggag ttactcaggc cagagcaccc agctggggat agagttcttg  780
aaacgtggag acaagtccgt ctactacaca tcaaatccca cgacgttcca cctggatggg  840
gaagtgataa cctttgataa cttaaaaacc ctgctgagcc tgagggaagt ccggactatc  900
aaggttttta ctacagtgga taatattaac cttcacacac aggtggtgga catgtccatg  960
acctatgggc agcagttcgg tcctacctac ctggacggag ctgacgttac caaaatcaaa  1020
ccccacaact ctcatgaggg aaagacgttc tacgtgctgc caatgatga caccttgcga  1080
gtggaggcat ttgagtatta ccacactacc gatccgtctt tcttaggccg ctatatgtcc  1140
gctttaaatc atacaaagaa gtggaagtac cctcaggtaa acggcctgac atctattaaa  1200
tgggccgaca caactgcta tctggcaact gctttgctca cacttcagca gattgagttg  1260
aaatttaacc ctcccgcact gcaggacgct tattatcggg tgaggcggct gaggcggct  1320
aacttctgtg ctctcatcct tgcttactgt aacaaaacag tgggcgagct aggagatgtc  1380
agggagacaa tgtcttactt gtttcagcac gccaacttag actcctgcaa aagagtgctc  1440
aatgtagtct gcaaaacctg cggtcagcag cagactacct tgaagggggt cgaagcagtg  1500
atgtacatgg gtacactatc ctatgagcaa tttaaaaagg gtgttcagat ccctgcaca  1560
tgtggcaagc aggcaacaaa atacctcgtg cagcaagaat ccccatttgt tatgatgagc  1620
gcacctccag cccagtacga actgaaacat ggaacattta cctgcgcttc ggagtacact  1680
ggcaattacc agtgtgggca ttacaagcac atcacgtcca aagaaacact ctactgcata  1740
gatggagccc tgttgaccaa gtccagcgaa tataaaggcc ctatcacaga tgtttctac  1800
aaggagaatt catatacaac caccatcaag cccgtgacat acaagttaga cggcgtgta  1860
tgtacagaaa ttgaccccaa gctggacaat tactacaaaa aagacaatag ctattttact  1920
gaacaaccaa tcgatcttgt ccctaatcag ccctacccca atgcgtcatt tgataacttt  1980
aagtttgtgt gtgataatat taaatttgca gatgatctaa accagttgac gggatacaag  2040
aaacccgcct cgcgcgaact gaaagtgact tttttccag atctgaatgg ggatgtcgtg  2100
gccatagatt ataagcatta tactccaagt ttcaagaaag gcgctaagtt attacataag  2160
cctattgtct ggcatgtcaa caatgctaca aataaagcca cttataagcc aaacacatgg  2220
tgtattaggt gcctgtggag cacaaaacca gtggagacta gcaattcctt tgacgtcctg  2280
aagagtgaag atgcacaagg catggataac ttggcctgta ggacctgaa accagtctca  2340
gaggaagtgg tggaaaatcc aaccatccag aaagacgtac tggagtgtaa cgtgaaaacc  2400
actgaggttg tggggacat tatcttaaaa cctgctaaca acagcctgaa gattaccgag  2460
gaggtaggac acactgattt aatggcagct tacgtagata actccagtct gaccatcaag  2520
aagcctaacg agctgagtcg ggtgctaggc ctcaaaactc tggccaccca cggcctagcg  2580
gccgttaatt ctgtaccgtg ggatacaatc gctaattatg ccaagccctt cctcaacaag  2640
gttgtcagca cgaccaccaa catcgtgacc cgatgcttga accgtgtgtg cacgaactat  2700
atgccctatt tctttaccct tctactccag ctgtgtactt tcaccoggtc tacaaacagt  2760
cggatcaagg ccagcatgcc aaccacaatt gccaagaaca ccgttaaatc cgttgggaag  2820
ttctgccttg aggctagctt caactacctg aaatcaccaa acttctcgaa gctgattaac  2880
attataatat ggttcctgct cctgtccgtg tgtcttggaa gccttatcta ctccacagct  2940
gccctgggcg tcctcatgtc taatctgggt atgcctagtt actgcacagg ctaccgggaa  3000
ggttatttga atagcactaa cgttacaatc gccacatact gcacagggaa cattccttgc  3060
tccgtttgtt tgtcaggttt ggattctctc gatacttatc cctctctgga aactattcag  3120
atcacgattt ctagtttcaa atgggacctc acggcatttg ggctcgtggc cgagtggttc  3180
ctggcctata tactcttcac taggttcttc tatgtcctgg ggctggctgc catcatgcag  3240
ctcttttca gttatttcgc agtccatttt atcagcaata gctggctcat gtggctcata  3300
ataaatttag tacagatggc accaatctcg gccatggtga ggatgtatat cttttcgca  3360
tcctttttact atgtgtggaa atcatatgc cacgtggtgg acggatgcaa tagtagcacg  3420
tgcatgatgt gctacaaacg gaatagacg acccgcgtgg aatgtaccac cattgtgaat  3480
ggggttcgca gatcattcta cgtatatgcc aacgcggca agggcttctg caagctccat  3540
aactggaact gtgtcaattg tgacacattt cagtgcagat caactttcat cagtgacgag  3600
gtcgcgcggg acctcagtct gcaattcaag agaccgatca accctaccga ccagtcatct  3660
tacatcgtgg attcagttac cgtcaagaat ggatccattc acttatactt cgataaagca  3720
ggccaaaaga cttacgagag gcactctctc agccactttg tgaacctgga caatctgagg  3780
gcaaataaca ccaaggggtc tcttcccatt aatgtgatag tgtttgacgg gaagagcaag  3840
tgtgaggaga gcagcgccaa atctgcctca gtgtcaacca gccagctcat gtgtcaacca  3900
atactccttc tagaccaagc cctggtctca gacgttgggg acagtgctga agtggctgtg  3960
aagatgttcg atgcttatgt gaacacattt tcttccactt tcaacgtccc tatggagaaa  4020
ctaaagacgc tggtggcaac ggccgaggcc gagctggcca agaacgtttc attggacaat  4080
gtgctctcga cattcatctc cgctgcaaga cagggctttg tggactcaga tgtagaaacc  4140
aaggatgtgg tcgagtgctt gaagttgtcg caccagagcg acatcgaagt cacaggtgac  4200
agctgcaata attacatgct gacctataac aaggtagaga acatgacacc acgcgattg  4260
ggagcctgca tagactgtag tgctaggcac attaatgcac aggtcgcaaa atctcataac  4320
atcgcgctaa tctggaatgt caaagatttc atgagcctgt ctgagcaatt gagaaagcaa  4380
atcaggagtc cagctaaaaa aaataacctc ccgttcaagc taacatgtgc cacaactaga  4440
caggtggtga acgtggtaac tactaaaatt gcgctgaagg gtggttgata a            4491
```

```
SEQ ID NO: 15          moltype = DNA  length = 2802
FEATURE                Location/Qualifiers
source                 1..2802
                       mol_type = genomic DNA
                       organism = unidentified
SEQUENCE: 15
atgtcagctt gcacaatcgt tttttaaacgg gtttgcggtg taagtgcagc ccgtcttaca   60
ccgtgcggca caggcactag tactgatgtc gtatacaggg cttttgacat ctacaatgat  120
aaagtagctg gttttgctaa attcctaaaa actaattgtt gtcgcttcca agaaaaggac  180
gaagatgaca atttaattga ttcttacttt gtagttaaga gacacacttt ctctaactac  240
caacatgaag aaacaattta taatttactt aaggattgtc cagctgttgc taaacatgac  300
ttctttaagt ttagaataga cggtgacatg gtaccacata tatcacgtca acgtcttact  360
aaatacacaa tggcagacct cgtctatgct ttaaggcatt ttgatgaagg taattgtgac  420
acattaaaag aaatacttgt cacatacaat tgttgtgatg atgattattt caataaaaag  480
gactggtatg attttgtaga aaacccagat atattacgcg tatacgccaa cttaggtgaa  540
cgtgtacgcc aagctttgtt aaaaacagta caattctgtg atgccatgcg aaatgctggt  600
attgttggtg tactgacatt agataatcaa gatctcaatg gtaactggta tgatttcggt  660
gatttcatac aaaccacgcc aggtagtgga gttcctgttg tagattctta ttattcattg  720
ttaatgccta tattaacctt gaccagggct ttaactgcag agtcacatgt tgacactgac  780
ttaacaaagc cttacattaa gtgggatttg ttaaaatatg acttcacgga agagaggtta  840
aaactctttg accgttattt taaatattgg gatcagacat accacccaaa ttgtgttaac  900
tgtttggatg acagatgcat tctgcattgt gcaaacttta atgtttatt ctctacagtg  960
ttcccactta caagttttgg accactagtg agaaaaatat ttgttgatgg tgttccattt 1020
gtagtttcaa ctggatacca cttcagagag ctaggtgttg tacataatca ggatgtaaac 1080
ttacatagct ctagacttag tttttaaggaa ttacttgtgt atgctgctga ccctgctatg 1140
cacgctgctt ctggtaatct attactagat aaacgcacta cgtgcttttc agtagctgca 1200
cttactaaca atgttgcttt tcaaactgtc aaacccggta attttaacaa agacttctat 1260
gactttgctg tgtctaaggg tttctttaag gaaggaagtt ctgttgaatt aaaacacttc 1320
ttctttgctc aggatggtaa tgctgctatc agcgattatg actactatcg ttataatcta 1380
ccaacaatgt gtgatatcag acaactacta tttgtagttg aagttgttga taagtacttt 1440
gattgttacg atggtggctg tattaatgct aaccaagtca tcgtcaacaa cctagacaaa 1500
tcagctggtt ttccatttaa taaatggggt aaggctagac tttattatga ttcaatgagt 1560
tatgaggatc aagatgcact tttcgcatat acaaaacgta atgtcatccc tactataact 1620
caaatgaatc ttaagtatgc cattagtgca aagaatagag ctcgcaccgt agctggtgtc 1680
tctatctgta gtactatgac caatagacag tttcatcaaa aattattgaa atcaatagcc 1740
gccactagag gagctactgt agtaattgga acaagcaaat tctatggtgg ttggcacaac 1800
atgttaaaaa ctgtttatag tgatgtagaa aaccctcacc ttatgggttg ggattatcct 1860
aaatgtgata gagccatgcc taacatgctt agaattatgg cctcacttgt tcttgctcgc 1920
aaacatacaa cgtgttgtag cttgtcacac cgtttctata gattagctaa tgagtgtgct 1980
caagtattga gtgaaatggt catgtgtggc ggttcactat atgttaaacc aggtggaacc 2040
tcatcaggag atgccacaac tgcttatgct aatagtgttt ttaacatttg tcaagctgtc 2100
acggccaaatg ttaatgcact tttatctact gatggtacac ttatgattga cggttcgtg 2160
cgcaatttac aacacagact ttatgagtgt ctctatagaa atagagatgt tgacacagac 2220
tttgtgaatg agtttttacgc atatttgcgt aaacatttct caatgatgat actttctgac 2280
gatgctgttg tgtgtttcaa tagcacttat gcatctcaag gtcagtggc tagcataaag 2340
aactttaagt cagttctta ttatcaaaac aatgtttttta tgtctgaagc aaaatgttgg 2400
actgagactg accttactaa aggacctcat gaatttttgct ctcaacatac aatgctagtt 2460
aaacagggtg atgattatgt gtaccttcct tacccagatc catcaagaat cctagggggcc 2520
ggctgttttg tagatgatat cgtaaaaaca gatggtacac ttatgattga cggttcgtg 2580
tctttagcta tagatgctta cccacttact aaacatccta tcaggagta tgctgatgtc 2640
tttcatttgt acttacaata cataagaaag ctacatgatg agttaacagg acacatgtta 2700
gacatgtatt ctgttatgct tactaatgat aacacttcaa ggtattggga acctgagttt 2760
tatgaggcta tgtacacacc gcatacagtc ttacagtgat ga                     2802

SEQ ID NO: 16          moltype = DNA  length = 2802
FEATURE                Location/Qualifiers
source                 1..2802
                       mol_type = other DNA
                       organism = synthetic construct
SEQUENCE: 16
atgtctgcct gcacaattgt gttcaagcgg gtgtgtggag tgtctgcagc gcgattaact   60
ccctgtggaa ccggcacctc aacagacgta gtgtaccgtg ccttcgatat ttacaatgat  120
aaggtggccg ggttcgcgaa attcctaaag acgaactgtt gcaggttcca ggagaaggat  180
gaagatgaca atctcataga ttcttatttc gtggttaaac ggcatacatt agtaattac  240
caacatgaag aaacaatcta caacctcctc aaagactgtc ctgctgtggc aaaacatgac  300
ttcttcaagt tccggattga cggcgacatg gttccacaca tctctcggca gagattaaca  360
aagtacacca tggctgacct tgtatatgca ctgcgcacct ttgatgaagg aaattgcgat  420
actctgaaag agattcttgt tacctacaac tgctgtgatg acgactactt caacaagaaa  480
gactggtacg actttgtaga aaacccagat atcctcagag tttacgccaa cttaggagag  540
cgcgtaagac aagccctgtt aaaaacagtt cagttctgtg atgccatgag gaatgcagga  600
atcgtggag tcttgaccct ggacaaccag gacttgaatg ggaactggta tgacttcggg  660
gatttcatca gactacacc cggcagcgga gtgccagtg tggatagcta ttactccttg  720
ctgatgccaa tccttacgtt gacaagagcc ctgacagcag agagccatgt tgacactgac  780
cttaccaaac cctacatcaa gtgggactta tcaagtatg acttcacaga gagcggcta  840
aagttgttcg atcgctactt taaatattgg gatcagacct atcatccaa ctgtgtgaat  900
tgtctggatg acaggtgcat attgcactgt gcaaacttca acgttctttt ttccacggtt  960
ttcccccctga ccagctttgg gcctctggtg agaaagatct ttgtcgacgg ggtaccattt 1020
gttgtcagta ccggctacca tttcaggggaa ctcggtgtcg tgcacaatca ggatgtaaac 1080
```

```
ctgcacagca gccggctaag ctttaaagaa ctgcttgttt atgctgctga tccagccatg   1140
cacgctgcca gcggaaattt actcctggac aagcgtacta cctgtttcag tgtggcagcc   1200
ctcaccaaca acgtagcctt ccaaaccgtg aaaccaggca actttaacaa agatttctac   1260
gactttgccg tttcaaaggg gttttttaag gagggggagtt ccgtggaact gaagcattt   1320
ttctttgcac aagacggtaa tgctgctata agcgactatg attattaccg gtataatctg   1380
ccaacgatgt gtgatattag gcaactgctc ttcgtggtag aggtcgtgga caaatacttt   1440
gactgctacg atggcggctg catcaatgct aatcaggtga ttgtcaacaa tctcgacaag   1500
agtgcgggct ttcctttcaa taaatggggc aaggcccgcc tctactatga cagcatgagc   1560
tacgaggacc aagatgctct gtttgcttat acaaagagaa atgtgatccc taccatcaca   1620
cagatgaacc ttaaatatgc catctccgcg aagaaccgtg cccgaacagt tgctggtgtc   1680
tccatttgtt ctaccatgac aaaccgccag ttccaccaga agctgttgaa gagcatagca   1740
gctactaggg gcgccaccgt cgtaatcggg acatccaagt tttatggagg gtggcacaac   1800
atgcttaaaa cggtttactc agatgtggag aatccccacc taatgggctg ggactacccc   1860
aagtgtgacc gagcaatgcc gaacatgctc cgcattatgg caagtctggt cctcgcccaga  1920
aaacacacga cttgctgctc attgtcacac aggttttatc gtctggccaa tgaatgtgcc   1980
caggtcctgt cagagatggt catgtgcgga ggatccttat atgtgaagcc aggtggcact   2040
agttctggtg atgccacaac tgcgtacgca aatagtgtgt tcaacatctg ccaggctgtc   2100
actgcgaatg ttaatgcgtt gctgtccact gatggaaaca aaattgcaga caaatacgtg   2160
cgcaacctgc agcatcgttt atatgagtgc ctatacagaa acagagatgt ggacaccgat   2220
tttgtgaacg agttctatgc ctacctgagg aagcatttct caatgatgat cctgtcggat   2280
gatgccgttg tctgctttaa ttctacttat gcttcacagg gcctggtggc ttccataaaa   2340
aacttcaagt ctgtgctgta ttaccagaac aatgtgttta tgtctgaagc taagtgctgg   2400
accgagacgg acctcaccaa gggtcccat gagttctgct cccagcacac aatgcttgtg    2460
aagcaggggg acgattatgt gtatctccct tacctgacc cttcgaggat actgggcgcc    2520
gggtgttttg tagacgacat tgtcaaaact gacggtactc taatgatcga gcggttcgtg   2580
agcctggcta ttgatgctta cccactgacc aagcacccga atcaagagta cgcagatgtc   2640
tttcacctt acctcagta cattcggaag cttcatgatg agctgaccgg ccacatgctg     2700
gacatgtatt cagtgatgct gacaaatgac aatacatcta ggtactggga gcctgaattt   2760
tatgaagcta tgtatactcc tcataccgtg ttgcagtgat aa                      2802
```

```
SEQ ID NO: 17          moltype = DNA  length = 498
FEATURE                Location/Qualifiers
source                 1..498
                       mol_type = genomic DNA
                       organism = unidentified
SEQUENCE: 17
atgaaaatta ttctttttctt ggcactgata acactcgcta cttgtgagct ttatcactac   60
caagagtgtg ttagaggtac aacagtactt ttaaaagaac cttgctcttc tggaacatac   120
gagggcaatt caccatttca tcctctagct gataacaaat ttgcactgac ttgctttagc   180
actcaatttg cttttgcttg tcctgacggc gtaaaacacg tctatcagtt acgtgccaga   240
tcagtttcac ctaaactgtt catcagacaa gaggaagttc aagaacttta ctctccaatt   300
tttcttattg ttgcggcaat agtgtttata acactttgct tcacactcaa aagaaagaca   360
gaatgtgaac tttcattaat tgacttctat ttgtgctttt tagcctttct gttattcctt   420
gttttaatta tgcttattat cttttggttc tcacttgaac tgcaagatca taatgaaact   480
tgtcacgcct aatgatga                                                  498
```

```
SEQ ID NO: 18          moltype = DNA  length = 498
FEATURE                Location/Qualifiers
source                 1..498
                       mol_type = other DNA
                       organism = synthetic construct
SEQUENCE: 18
atgaagatca ttttgtttct agcattaata actctagcca cctgtgagct ctaccactac   60
caggagtgtg tgaggggtac cactgtactg ctgaaggagc cctgcagctc tggaacatat   120
gaaggcaaca gccctttcca cccttttggct gataacaaat ttgctcttac gtgcttttct   180
actcagtttg catttgcctg cccagatggg gtgaagcatg tgtatcagct gcgagcgcgc   240
agtgtttccc caaaactctt cattcggcaa gaagaggtcc aagaactgta tagtcccatc   300
tttctcattg tggctgccat cgtgttcatc acactatgtt tcaccctgaa aagaaaaaca   360
gaatgtgaac tttcattgat tgacttctac ctgtgcttcc tggccttcct cttatttctt   420
gttctcatca tgctgatcat cttctggttc tccctggagc tgcaggacca caatgagacc   480
tgccatgcat gataatga                                                  498
```

```
SEQ ID NO: 19          moltype = DNA  length = 303
FEATURE                Location/Qualifiers
source                 1..303
                       mol_type = genomic DNA
                       organism = Homo sapiens
SEQUENCE: 19
atgaacagga aggtgaccgc catcgccctg gccgccatca tctgggccac cgccgcccag   60
ggcttcctga tgttcaagca gggcaggtgc ctgtgcatcg gccccggcat gaaggccgtg   120
aagatggccg agatcgagaa ggccagcgtg atctacccca gcaacggctg cgacaaggtg   180
gaggtgatcg tgaccatgaa ggcccacaag aggcagaggt gcctggaccc caggagcaag   240
caggccaggc tgatcatgca ggccatcgag aagaagaact cctgaggag gcagaacatg    300
tga                                                                 303
```

```
SEQ ID NO: 20          moltype = DNA  length = 465
FEATURE                Location/Qualifiers
source                 1..465
                       mol_type = genomic DNA
```

```
                        organism = Homo sapiens
SEQUENCE: 20
atgaaggtct ccgcggcagc cctcgctgtc atcctcattg ctactgccct ctgcgctcct    60
gcatctgcct ccccatattc ctcggacacc acacctgct gctttgccta cattgcccgc   120
ccactgcccc gtgcccacat caaggagtat ttctacacca gtggcaagtg ctccaaccca   180
gcagtcgtcc acaggtcaag gatgccaaag agagagggac agcaagtctg ccaggatttc   240
ctgtatgact cccggctgaa caagggcaag ctttgtcacc cgaaagaacc gccaagtgtg   300
tgccaaccca gagaagaaat gggttcggga gtacatcaac tctttggaga tgagctagga   360
tggagagtcc ttgaacctga acttacacaa atttgcctgt ttctgcttgc tcttgtccta   420
gcttgggagg cttcccctca ctatcctacc ccaccgctc cttga                   465

SEQ ID NO: 21          moltype = DNA   length = 378
FEATURE                Location/Qualifiers
source                 1..378
                       mol_type = genomic DNA
                       organism = Homo sapiens
SEQUENCE: 21
atgaagaaaa gtggtgttct tttcctcttg ggcatcatct tgctggttct gattggagtg    60
caaggaaccc cagtagtgag aaagggtcgc tgttcctgca tcagcaccaa ccaagggact   120
atccacctac aatccttgaa agaccttaaa caatttgccc caagcccttc ctgcgagaaa   180
attgaaatca ttgctacact gaagaatgga gttcaaacat gtctaaaccc agattcagca   240
gatgtgaagg aactgattaa aaagtgggag aaacaggtca gccaaaagaa aaagcaaaag   300
aatgggaaaa aacatcaaaa aaagaaagtt ctgaaagttc gaaaatctca acgttctcgt   360
caaaagaaga ctacataa                                                378

SEQ ID NO: 22          moltype = DNA   length = 297
FEATURE                Location/Qualifiers
source                 1..297
                       mol_type = genomic DNA
                       organism = Homo sapiens
SEQUENCE: 22
atgaatcaaa ctgccattct gatttgctgc cttatctttc tgactctaag tggcattcaa    60
ggagtacctc tctctagaac tgtacgctgt acctgcatca gcattagtaa tcaacctgtt   120
aatccaaggt ctttagaaaa acttgaaatt attcctgcaa gccaattttg tccacgtgtt   180
gagatcattg ctacaatgaa aaagaagggt gagaagagat gtctgaatcc agaatcgaag   240
gccatcaaga atttactgaa agcagttagc aaggaaaggt ctaaaagatc tccttaa       297

SEQ ID NO: 23          moltype = DNA   length = 300
FEATURE                Location/Qualifiers
source                 1..300
                       mol_type = genomic DNA
                       organism = Homo sapiens
SEQUENCE: 23
atgaggctcc tggcggccgc gctgctcctg ctgctgctgg cgctgtacac cgcgcgtgtg    60
gacgggtcca aatgcaagtg ctcccggaag ggacccaaga tccgctacag cgacgtgaag   120
aagctggaaa tgaagccaaa gtacccgcac tgcgaggaga agatggttat catcaccacc   180
aagagcgtgt ccaggtaccg aggtcaggag cactgcctgc accccaagct gcagagcacc   240
aagcgcttca tcaagtggta caacgcctgg aacgagaagc gcagggtcta cgaagaatag   300

SEQ ID NO: 24          moltype = DNA   length = 360
FEATURE                Location/Qualifiers
source                 1..360
                       mol_type = genomic DNA
                       organism = Homo sapiens
SEQUENCE: 24
atgaaagttc taatctcttc cctcctcctg ttgctgccac taatgctgat gtccatggtc    60
tctagcagcc tgaatccagg ggtcgccaga ggccacaggg accgaggcca ggcttctagg   120
agatggctcc aggaaggcgg ccaagaatgt gagtgcaaag attggttcct gagagccccg   180
agaagaaaat tcatgacagt gtctgggctg ccaaagaagc agtgcccctg tgatcatttc   240
aagggcaatg tgaagaaaac aagacaccaa aggcaccaca gaaagccaaa caagcattcc   300
agagcctgcc agcaatttct caaacaatgt cagctaagaa gctttgctct gcctttgtag   360

SEQ ID NO: 25          moltype = DNA   length = 453
FEATURE                Location/Qualifiers
source                 1..453
                       mol_type = genomic DNA
                       organism = Homo sapiens
SEQUENCE: 25
atgaacctgt ggctcctggc ctgcctggtg gccggcttcc tgggagcctg ggccccgct     60
gtccacaccc aaggtgtctt tgaggactgc tgcctggcct accactaccc cattgggtgg   120
gctgtgctcc ggcgcgcctg gacttaccgg atccaggagg tgagcgggag ctgcaatctg   180
cctgctgcga tattctacct ccccaagaga cacaggaagg tgtgtgggaa ccccaaaagc   240
agggaggtgc agagagccat gaagctcctg gatgctcgaa ataaggtttt tgcaaagctc   300
caccacaaca cgcagacctt ccaagcaggc cctcatgctg taaagaagtt gagttctgga   360
aactccaagt tatcatcgtc caagtttagc aatcccatca gcagcagtaa gaggaatgtc   420
tccctcctga tatcagctaa ttcaggactg tga                               453

SEQ ID NO: 26          moltype = DNA   length = 384
FEATURE                Location/Qualifiers
```

-continued

```
source                    1..384
                          mol_type = genomic DNA
                          organism = Homo sapiens
SEQUENCE: 26
atgcagcaga gaggactcgc catcgtggcc ttggctgtct gtgcggccct acatgcctca   60
gaagccatac ttcccattgc ctccagctgt tgcacggagg tttcacatca tatttccaga   120
aggctcctgg aaagagtgaa tatgtgtcgc atccagagag ctgatgggga ttgtgacttg   180
gctgctgtca tccttcatgt caagcgcaga agaatctgtg tcagcccgca caaccatact   240
gttaagcagt ggatgaaagt gcaagctgcc aagaaaaatg gtaaaggaaa tgtttgccac   300
aggaagaaac accatggcaa gaggaacagt aacagggcac atcaggggaa acacgaaaca   360
tacggccata aaactcctta ttag                                         384

SEQ ID NO: 27              moltype = DNA   length = 465
FEATURE                    Location/Qualifiers
source                    1..465
                          mol_type = genomic DNA
                          organism = Homo sapiens
SEQUENCE: 27
atgttccacg tgagcttcag gtacatcttc ggcatccccc ccctgatcct ggtgctgctg   60
cccgtgacca gcagcgagtg ccacatcaag gacaaggagg gcaaggccta cgagagcgtg   120
ctgatgatca gcatcgacga gctggacaag atgaccggca ccgacagcaa ctgccccaac   180
aacgagccca acttcttcag gaagcacgtg tgcgacgaca ccaaggaggc cgccttcctg   240
aacagggccg ccaggaagct gaagcagttc ctgaagatga acatcagcga ggagttcaac   300
gtgcacctgc tgaccgtgag ccagggcacc cagaccctgg tgaactgcac cagcaaggag   360
gagaagaacg tgaaggagca gaagaagaac gacgcctgct tcctgaagag gctgctgagg   420
gagatcaaga cctgctggaa caagatcctg aagggcagca tctga                 465

SEQ ID NO: 28              moltype = DNA   length = 489
FEATURE                    Location/Qualifiers
source                    1..489
                          mol_type = genomic DNA
                          organism = Homo sapiens
SEQUENCE: 28
atgagaattt cgaaaccaca tttgagaagt atttccatcc agtgctactt gtgtttactt   60
ctaaacagtc attttctaac tgaagctggc attcatgtct tcattttggg ctgtttcagt   120
gcagggcttc ctaaaacaga agccaactgg gtgaatgtaa taagtgattt gaaaaaaatt   180
gaagatctta ttcaatctat gcatattgat gctactttat atacggaaag tgatgttcac   240
cccagttgca aagtaacagc aatgaagtgc tttctcttgg agttacaagt tatttcactt   300
gagtccggag atgcaagtat tcatgataca gtagaaaatc tgatcatcct agcaaacaac   360
agtttgtctt ctaatgggaa tgtaacagaa tctggatgca aagaatgtga ggaactggag   420
gaaaaaaata ttaaagaatt tttgcagagt tttgtacata ttgtccaaat gttcatcaac   480
acttcttga                                                          489

SEQ ID NO: 29              moltype = DNA   length = 462
FEATURE                    Location/Qualifiers
source                    1..462
                          mol_type = genomic DNA
                          organism = Homo sapiens
SEQUENCE: 29
atgtacagga tgcaactcct gtcttgcatt gcactaagtc ttgcacttgt cacaaacagt   60
gcacctactt caagttctac aaagaaaaca cagctacaac tggagcattt actgctggat   120
ttacagatga ttttgaatgg aattaataat tacaagaatc ccaaactcac caggatgctc   180
acatttaagt tttacatgcc caagaaggcc acagaactga aacatcttca gtgtctagaa   240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca gttagtaatt ctgaacaga   420
tggattacct tttgtcaaag catcatctca acactgactt ga                    462

SEQ ID NO: 30              moltype = DNA   length = 1733
FEATURE                    Location/Qualifiers
source                    1..1733
                          mol_type = other DNA
                          organism = synthetic construct
SEQUENCE: 30
ctcgacattg attattgact agttattaat agtaatcaat tacggggtca ttagttcata   60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattacc atggtcgagg tgagccccac gttctgcttc actctcccca   420
tctcccccc ctccccaccc ccaattttgt atttattta ttttttaatta ttttgtgcag   480
cgatggggg gggggggggg gggggcgcg cgccaggcgg ggcggggcgg ggcgaggggc   540
gggcgggggc gaggcggaga ggtgcggcgg cagccaatca gagcggcgcg ctccgaaagt   600
ttcctttat ggcgaggcgg cggcggcggc ggccctataa aaagcgaagc gcgcggcggg   660
cgggagtcgc tgcgcgctgc cttcgccccg tgccccgctc cgccgccgcc tcgcgccgcc   720
cgccccggct ctgactgacc gcgttactcc cacaggtgag cgggcgggac ggcccttctc   780
ctccgggctg taattagcgc ttggtttaat gacggcttgt ttcttttctg tggctgcgtg   840
aaagccttga ggggctccgg gagggccctt tgtgcggggg gagcggctcg ggggtgcgt   900
```

-continued

```
gcgtgtgtgt gtgcgtgggg agcgccgcgt gcggctccgc gctgcccggc ggctgtgagc  960
gctgcgggcg cggcgcgggg ctttgtgcgc tccgcagtgt gcgcgagggg agcgcggccg  1020
ggggcggtgc cccgcggtgc gggggggggct gcgaggggaa caaaggctgc gtgcggggtg  1080
tgtgcgtggg ggggtgagca gggggtgtgg gcgcgtcggt cgggctgcaa ccccccctgc  1140
accccctcc ccgagttgct gagcacggcc cggcttcggg tgcgggggctc cgtacggggc  1200
gtggcgcggg gctcgccgtg ccgggcgggg ggtggcggca ggtggggggtg ccgggcgggg  1260
cggggccgcc tcgggccggg gagggctcgg gggaggggcg cggcggcccc cggagcgccg  1320
gcggctgtcg aggcgcggcg agccgcagcc attgccttt atggtaatcg tgcgagaggg  1380
cgcagggact tcctttgtcc caaatctgtg cggagccgaa atctgggagg cgccgccgca  1440
ccccctctag cgggcgcggg gcgaagcggt gcggcgccgg caggaaggaa atgggcgggg  1500
aggggccttcg tgcgtcgccg cgccgccgtc cccttctccc tctccagcct cggggctgtc  1560
cgcgggggga cggctgcctt cgggggggac ggggcagggc ggggttcggc ttctggcgtg  1620
tgaccggcgg ctctagagcc tctgctaacc atgttcatgc cttcttcttt ttcctacagc  1680
tcctgggcaa cgtgctggtt attgtgctgt ctcatcattt tggcaaagaa ttg  1733
```

```
SEQ ID NO: 31              moltype = DNA   length = 589
FEATURE                    Location/Qualifiers
source                     1..589
                           mol_type = other DNA
                           organism = synthetic construct
SEQUENCE: 31
tagttattaa tagtaatcaa ttacgggggtc attagttcat agcccatata tggagttccg  60
cgttacataa cttacggtaa atggcccgcc tggctgaccg cccaacgacc cccgcccatt  120
gacgtcaata atgacgtatg ttcccatagt aacgccaata gggactttcc attgacgtca  180
atgggtggag tatttacggt aaactgccca cttggcagta catcaagtgt atcatatgcc  240
aagtacgccc cctattgacg tcaatgacgg taaatggccc gcctggcatt atgcccagta  300
catgacctta tgggactttc ctacttggca gtacatctac gtattagtca tcgctattac  360
catggtgatg cggttttggc agtacatcaa tgggcgtgga tagcggtttg actcacgggg  420
atttccaagt ctccacccca ttgacgtcaa tgggagtttg ttttggcacc aaaatcaacg  480
ggactttcca aaatgtcgta acaactccgc cccattgacg caaatgggcg gtaggcgtgt  540
acggtgggag gtctatataa gcagagctgg tttagtgaac cgtcagatc  589
```

```
SEQ ID NO: 32              moltype = DNA   length = 635
FEATURE                    Location/Qualifiers
source                     1..635
                           mol_type = genomic DNA
                           organism = Homo sapiens
SEQUENCE: 32
gtatagggct gtctgggagc cactccaggg ccacagaaat cttgtctctg actcagggta  60
tttttgttttc tgtttttgtgt aaatgctctt ctgactaatg caaaccatgt gtccatagaa  120
ccagaagatt tttccagggg aaaaggtaag gaggtggtga gagtgtcctg ggtctgccct  180
tccagggctt gccctgggtt aagagccagg caggaagctc tcaagagcat tgctcaagag  240
tagaggggcc ctgggaggcc cagggagggg atgggagggg aacacccagg ctgcccccaa  300
ccagatgccc tccaccctcc tcaacctccc tcccacgggc tggagaggtg ggaccaggta  360
tggaggcttg agagccctg gttggaggaa gccacaagtc caggaacatg ggagtctggg  420
caggggggcaa aggaggcagg aacaggccat cagccaggac aggtggtaag gcaggcagga  480
gtgttcctgc tgggaaaagg tgggatcaag cacctggagg gctcttcaga gcaaagacaa  540
acactgaggt cgctgccact cctacagagc ccccacgccc cgcccagcta taaggggcca  600
tgcaccaagc agggtaccca ggctgcagag gtgcc  635
```

```
SEQ ID NO: 33              moltype = DNA   length = 1559
FEATURE                    Location/Qualifiers
source                     1..1559
                           mol_type = genomic DNA
                           organism = Homo sapiens
SEQUENCE: 33
catccatgcc catggcctca gatgccagcc ataagctgtt gggttccaaa cctcgactcc  60
aggctggact caccctgtc tcccccacca gcctgacacc tccacctggg tatctaacga  120
gcatctcaaa ctcaacctgc ctgagacaga ggaatcacta tccctcctc ctccaaaaat  180
atccttccat cacactcccc atcttgtgct ctgatttact aaacggccct gggccctctc  240
tttctcaggg tctctgcttg cccagctata taataaaaca agtttgggac ttcccaacca  300
ttcacccatg gaaaaacaga agcaactctt caaaggacag attcccagga tctgccctgg  360
gagattccaa atcagttgat ctggggtgag cccagtcctc tgtagttttt agaagctcct  420
cctatgtctc tcctggtcag cagaatcttg gcccctccct tcccccagc ctcttggttc  480
ttctgggctc tgatccagcc tcagcgtcac tgtcttccac gccctctttt gattctcgtt  540
tatgtcaaaa gccttgtgag gatgaggctg tgattatccc cattttacag atgaggaaac  600
tgtggctcca ggatgacaca actggccaga ggtcacatca gaagcagagc tgggtcactt  660
gactccacc aatatcccta aatgcaaaca tcccctacag accgaggctg gcaccttaga  720
gctggagtcc atgcccgctc tgaccaggag aagccaacct ggtcctccag agccaagagc  780
ttctgtccct ttcccatctc ctgaagcctc cctgtcacct ttaaagtcca ttcccacaaa  840
gacatcatgg gatcaccaca gaaaatcaag ctctgggggct aggctgaccc cagctagatt  900
tttggctctt ttatacccca gctgggtgga caagcacctt aaacccgctg agcctcagct  960
tcccgggcta taaaatgggg gtgatgacac ctgcctgtag cattccaagg agggttaaat  1020
gtgatgctgc agccaagggt ccccacagcc aggctctttg caggtgctgg gttcagagtc  1080
ccagagctga ggccgggagt aggggttcaa gtggggtgcc ccaggcaggg tccagtgcca  1140
gccctctgtg gagacagcca tccgggggccg aggcagccgc ccaccgcagg gcctgcctat  1200
ctgcagccag cccagccctc acaaaggaac aataacagga aaccatccca ggggggaagtg  1260
ggccagggcc agctggaaaa cctgaagggg aggcagccag gcctccctcg ccagcggggt  1320
gtggctcccc tccaaagacg gtcggctgac aggtccaca gagctccact cacgctcagc  1380
```

-continued

```
cctggacgga caggcagtcc aacggaacag aaacatccct cagcccacag gcacggtgag   1440
tgggggctcc cacactcccc tccacccaa acccgccacc ctgcgcccaa gatgggaggg   1500
tcctcagctt ccccatctgt agaatgggca tcgtcccact cccatgacag agaggctcc    1559

SEQ ID NO: 34             moltype = DNA   length = 39
FEATURE                   Location/Qualifiers
source                    1..39
                          mol_type = other DNA
                          organism = synthetic construct
SEQUENCE: 34
atgttcgtgt tcctggtgct gctgcccctg gtgagcagc                          39

SEQ ID NO: 35             moltype = DNA   length = 63
FEATURE                   Location/Qualifiers
source                    1..63
                          mol_type = other DNA
                          organism = synthetic construct
SEQUENCE: 35
ggaagcggag agggcagggg aagtcttcta acatgcgggg acgtggagga aaatcccggc    60
ccc                                                                 63

SEQ ID NO: 36             moltype = DNA   length = 69
FEATURE                   Location/Qualifiers
source                    1..69
                          mol_type = other DNA
                          organism = synthetic construct
SEQUENCE: 36
ggaagcggac agtgtactaa ttatgctctc ttgaaattgg ctggagatgt tgagagcaac    60
ccaggtccc                                                           69

SEQ ID NO: 37             moltype = DNA   length = 66
FEATURE                   Location/Qualifiers
source                    1..66
                          mol_type = other DNA
                          organism = synthetic construct
SEQUENCE: 37
ggaagcggag ccacgaactt ctctctgtta aagcaagcag gagatgttga agaaaacccc    60
gggcct                                                              66

SEQ ID NO: 38             moltype = DNA   length = 15
FEATURE                   Location/Qualifiers
source                    1..15
                          mol_type = other DNA
                          organism = synthetic construct
SEQUENCE: 38
ggccccggcc ccggc                                                    15

SEQ ID NO: 39             moltype = DNA   length = 18
FEATURE                   Location/Qualifiers
source                    1..18
                          mol_type = other DNA
                          organism = synthetic construct
SEQUENCE: 39
catcaccatc accatcac                                                 18

SEQ ID NO: 40             moltype = AA   length = 5
FEATURE                   Location/Qualifiers
source                    1..5
                          mol_type = protein
                          organism = synthetic construct
SEQUENCE: 40
GPGPG                                                               5
```

What is claimed is:

1. A Coronavirus vaccine composition: the Coronavirus vaccine composition comprising a nucleic acid, wherein the nucleic acid comprises a nucleic acid sequence encoding different Coronavirus antigens, wherein the nucleic acid sequence comprises SEQ ID NO: 4 or SEQ ID NO: 5, the nucleic acid sequence comprises SEQ ID NO: 10, and the nucleic acid sequence comprises SEQ ID NO: 7 or SEQ ID NO: 8; or the Coronavirus vaccine composition comprising different proteins wherein the different proteins are different Coronavirus antigens, wherein the different Coronavirus antigens comprise a Coronavirus NSP14 protein encoded by SEQ ID NO: 4 or SEQ ID NO: 5, a Coronavirus Spike protein encoded by SEQ ID NO: 10, and a Coronavirus Nucleoprotein encoded by SEQ ID NO: 7 or SEQ ID NO: 8; and wherein the sequence nucleic acid or different proteins are formulated in a lipid nanoparticle comprising a cationic lipid, a PEG-modified lipid, a sterol, and a non-cationic lipid.

2. The Coronavirus vaccine composition of claim 1, wherein the cationic lipid is an ionizable cationic lipid, the non-cationic lipid is a neutral lipid, and the sterol is a cholesterol.

3. The Coronavirus vaccine composition of claim 2, wherein the cationic lipid is selected from 2,2-dilinoleyl-4-dimethylaminoethyl-[1,3]-dioxolane, dilinoleyl-methyl-4- dimethylaminobutyrate, or di((Z)-non-2-en-1-yl) 9-((4-(di-methylamino)butanoyl)oxy)heptadecanedioate.

4. The Coronavirus vaccine composition of claim 1, wherein: the nucleic acid sequence comprises SEQ ID NO: 4 or SEQ ID NO: 5, the nucleic acid sequence comprises SEQ ID NO: 10, the nucleic acid sequence comprises SEQ ID NO: 7 or SEQ ID NO: 8, and the nucleic acid sequence comprises SEQ ID NO: 1 or SEQ ID NO: 2; and wherein the different proteins are different Coronavirus antigens, wherein the different Coronavirus antigens comprise the Coronavirus NSP14 protein encoded by SEQ ID NO: 4 or SEQ ID NO: 5, the Coronavirus Spike protein encoded by SEQ ID NO: 10, a Coronavirus NSP2 protein encoded by SEQ ID NO: 1 or SEQ ID NO: 2, and the Coronavirus Nucleoprotein encoded by SEQ ID NO: 7 or SEQ ID NO: 8.

5. A Coronavirus recombinant vaccine composition comprising a pharmaceutical carrier, an adjuvant, and a delivery system;

wherein the delivery system comprises an adeno-associated viral vector based antigen delivery system, wherein the adeno-associated viral vector is an adeno-associated virus vector type 8 (AAV8) serotype or an adeno-associated virus vector type 9 (AAV9) serotype; and wherein the adeno-associated viral vector comprises a nucleic acid sequence encoding different Coronavirus antigens, wherein the nucleic acid sequence comprises SEQ ID NO: 4 or SEQ ID NO:5, the nucleic acid sequence comprises SEQ ID NO: 10, and the nucleic acid sequence comprises SEQ ID NO:7 or SEQ ID NO:8.

6. The Coronavirus recombinant vaccine composition of claim 5, wherein the nucleic acid sequence comprises SEQ ID NO:4 or SEQ ID NO:5, the nucleic acid sequence comprises SEQ ID NO:10, the nucleic acid sequence comprises SEQ ID NO:7 or SEQ ID NO:8, and the nucleic acid sequence comprises SEQ ID NO:1 or SEQ ID NO:2.

7. The Coronavirus recombinant vaccine composition of claim 5, wherein the adeno-associated viral vector is an AAV8 serotype.

8. The Coronavirus recombinant vaccine composition of claim 5, wherein the adeno-associated viral vector is an AAV9 serotype.

9. A composition, comprising:

a messenger ribonucleic acid (mRNA) comprising an open reading frame encoding a single Coronavirus NSP14 protein encoded by SEQ ID NO:4 or SEQ ID NO: 5;

an mRNA comprising an open reading frame encoding a single Coronavirus Nucleoprotein encoded by SEQ ID NO:7 or SEQ ID NO: 8; and an mRNA comprising an open reading frame encoding a single Coronavirus Spike protein encoded by SEQ ID NO: 10;

wherein the mRNAs are formulated in a lipid nanoparticle, and wherein the lipid nanoparticle comprises a cationic lipid, a PEG-modified lipid, a sterol, and a non-cationic lipid.

10. The composition of claim 9, wherein each of the mRNAs further comprise a 5' untranslated region (UTR) and a 3' UTR.

11. The composition of claim 10, wherein each of the mRNAs further comprise a poly(A) tail and a 5' cap.

12. A pharmaceutical composition comprising a first lipid nanoparticle and a second lipid nanoparticle, wherein each lipid nanoparticle comprises a cationic lipid, a PEG-modified lipid, a sterol, and a non-cationic lipid, wherein the first lipid nanoparticle comprises a first messenger ribonucleic acid (mRNA) encapsulated therein, a second mRNA encapsulated therein, and a third mRNA encapsulated therein, wherein the first mRNA comprises an open reading frame encoding a single Coronavirus NSP2 protein encoded by SEQ ID NO: 1 or SEQ ID NO:2, wherein the second mRNA comprises an open reading frame encoding a single Coronavirus NSP14 protein encoded by SEQ ID NO:4 or SEQ ID NO:5, wherein the third mRNA comprises an open reading frame encoding a single Coronavirus Nucleoprotein encoded by SEQ ID NO:7 or SEQ ID NO:8, and wherein the second lipid nanoparticle comprises an mRNA encapsulated therein, wherein the mRNA comprises an open reading frame encoding a single Coronavirus Spike protein encoded by SEQ ID NO:10.

13. The pharmaceutical composition of claim 12, wherein each mRNA further comprises a 5' untranslated region (UTR) and a 3' UTR.

14. The pharmaceutical composition of claim 13, wherein each mRNA further comprises a poly(A) tail and a 5' cap.

15. The composition of claim 9, comprising: the mRNA comprising the open reading frame encoding the single Coronavirus NSP14 protein encoded by SEQ ID NO: 4 or SEQ ID NO: 5; an mRNA comprising an open reading frame encoding a single Coronavirus NSP2 protein encoded by SEQ ID NO: 1 or SEQ ID NO: 2; the mRNA comprising the open reading frame encoding the single Coronavirus Nucleoprotein encoded by SEQ ID NO: 7 or SEQ ID NO: 8; and the mRNA comprising the open reading frame encoding the single Coronavirus Spike protein encoded by SEQ ID NO: 10; wherein the mRNAs are formulated in the lipid nanoparticle, and wherein the lipid nanoparticle comprises the cationic lipid, the PEG-modified lipid, the sterol, and the non-cationic lipid.

* * * * *